(12) United States Patent
Collins et al.

(10) Patent No.: US 7,622,108 B2
(45) Date of Patent: Nov. 24, 2009

(54) MULTI-LINEAGE PROGENITOR CELLS

(75) Inventors: Daniel P. Collins, Lino Lakes, MN (US); Stacey L. Sprague, West Lakeland, MN (US); Barbara M. Tigges, Hudson, WI (US)

(73) Assignee: BioE, Inc., St. Paul, MN (US)

( * ) Notice: Subject to any disclaimer, the term of this patent is extended or adjusted under 35 U.S.C. 154(b) by 0 days.

(21) Appl. No.: 11/208,873

(22) Filed: Aug. 22, 2005

(65) Prior Publication Data

US 2006/0040392 A1    Feb. 23, 2006

Related U.S. Application Data

(63) Continuation-in-part of application No. 11/110,299, filed on Apr. 20, 2005.

(60) Provisional application No. 60/564,687, filed on Apr. 23, 2004.

(51) Int. Cl.
A01N 63/00 (2006.01)
A61K 8/18 (2006.01)
A01N 1/02 (2006.01)
C12Q 1/37 (2006.01)
C12N 5/00 (2006.01)

(52) U.S. Cl. ............... 424/93.1; 424/93.71; 435/2; 435/7.23; 435/7.24; 435/7.25; 435/325; 435/355; 436/523

(58) Field of Classification Search ............... 424/93.1, 424/93.7; 435/2, 7.23, 7.24, 7.25, 325, 355; 436/523

See application file for complete search history.

(56) References Cited

U.S. PATENT DOCUMENTS

| | | | |
|---|---|---|---|
| 5,004,681 A | 4/1991 | Boyse et al. | |
| 5,130,144 A | 7/1992 | Civin | |
| 5,192,553 A | 3/1993 | Boyse et al. | |
| 5,453,357 A | 9/1995 | Hogan | |
| 5,486,359 A | 1/1996 | Caplan et al. | |
| 5,580,714 A | 12/1996 | Polovina | |
| 5,624,840 A | 4/1997 | Naughton et al. | |
| 5,744,347 A | 4/1998 | Wagner et al. | |
| 5,750,397 A | 5/1998 | Tsukamoto et al. | |
| 5,789,147 A | 8/1998 | Rubinstein et al. | |
| 5,827,735 A | 10/1998 | Young et al. | |
| 5,827,740 A | 10/1998 | Pittenger | |
| 5,830,651 A | 11/1998 | Cauley et al. | |
| 5,843,780 A | 12/1998 | Thomson | |
| 5,877,299 A | 3/1999 | Thomas et al. | |
| 5,908,782 A | 6/1999 | Marshak et al. | |
| 5,928,214 A | 7/1999 | Rubinstein et al. | |
| 5,942,225 A | 8/1999 | Bruder et al. | |
| 5,965,436 A | 10/1999 | Thiede et al. | |
| 5,968,829 A | 10/1999 | Carpenter | |
| 6,030,836 A | 2/2000 | Thiede et al. | |
| 6,103,530 A | 8/2000 | Carpenter | |
| 6,140,121 A | 10/2000 | Ellington et al. | |
| 6,200,806 B1 | 3/2001 | Thomson | |
| 6,251,669 B1 | 6/2001 | Luskin | |
| 6,280,718 B1 | 8/2001 | Kaufman et al. | |
| 6,306,575 B1 | 10/2001 | Thomas et al. | |
| 6,322,784 B1 | 11/2001 | Pittenger et al. | |
| 6,328,960 B1 | 12/2001 | McIntosh et al. | |
| 6,387,367 B1 | 5/2002 | Davis-Sproul et al. | |
| 6,432,711 B1 | 8/2002 | Dinsmore et al. | |
| 6,436,704 B1 | 8/2002 | Roberts et al. | |
| 6,448,075 B1 | 9/2002 | Thomas et al. | |
| 6,461,645 B1 | 10/2002 | Boyse et al. | |
| 6,465,247 B1 | 10/2002 | Weissman et al. | |
| 6,477,090 B2 | 11/2002 | Yamaki et al. | |
| 6,482,926 B1 | 11/2002 | Thomas et al. | |
| 6,491,917 B1 | 12/2002 | Thomas et al. | |
| 6,491,918 B1 | 12/2002 | Thomas et al. | |
| 6,498,034 B1 | 12/2002 | Strobl | |
| 6,569,427 B1 | 5/2003 | Boyse et al. | |
| 6,605,275 B1 | 8/2003 | Boyse et al. | |
| 6,645,727 B2 | 11/2003 | Thomas et al. | |
| 6,680,198 B1 | 1/2004 | Snyder et al. | |
| 6,709,864 B1 | 3/2004 | Pittenger et al. | |
| 6,740,493 B1 | 5/2004 | Long et al. | |
| 6,750,326 B2 | 6/2004 | Thomas et al. | |
| 6,761,883 B2 | 7/2004 | Weissman et al. | |
| 6,767,737 B1 | 7/2004 | Wilson et al. | |
| 6,777,231 B1 | 8/2004 | Katz et al. | |
| 6,777,233 B2 | 8/2004 | Carpenter | |
| 6,800,480 B1 | 10/2004 | Bodnar et al. | |
| 6,835,377 B2 | 12/2004 | Goldberg et al. | |
| 6,852,533 B1 | 2/2005 | Rafii et al. | |
| 6,875,430 B2 | 4/2005 | McIntosh et al. | |
| 6,887,704 B2 | 5/2005 | Peled et al. | |
| 6,911,201 B1 | 6/2005 | Merchav et al. | |
| 6,946,293 B1 | 9/2005 | Lu et al. | |
| 6,962,698 B1 | 11/2005 | Peled et al. | |
| 6,967,086 B2 | 11/2005 | Guarino et al. | |
| 6,986,887 B2 | 1/2006 | Lawman et al. | |
| 6,991,897 B2 | 1/2006 | Smith et al. | |
| 7,015,037 B1 | 3/2006 | Furcht et al. | |
| 7,045,148 B2 | 5/2006 | Hariri | |
| 7,160,723 B2 * | 1/2007 | Collins et al. | ......... 435/372 |
| 7,399,632 B2 | 7/2008 | Simmons et al. | |
| 7,413,734 B2 | 8/2008 | Mistry et al. | |

(Continued)

FOREIGN PATENT DOCUMENTS

EP    03 01 7676.2    8/2004

(Continued)

OTHER PUBLICATIONS

Madlambayan GJ, Rogers I, Casper RF, Zandstra PW. Controlling culture dynamics for the expansion of hematopoietic stem cells. J Hematother Stem Cell Res. Aug. 2001;10(4):481-92.*

(Continued)

Primary Examiner—Maria Leavitt
(74) Attorney, Agent, or Firm—Fish & Richardson P.C.

(57) ABSTRACT

Fetal blood multi-lineage progenitor cells that are capable of a wide spectrum of transdifferentiation are described.

6 Claims, 56 Drawing Sheets

U.S. PATENT DOCUMENTS

| | | |
|---|---|---|
| 2001/0034061 A1 | 10/2001 | Csete et al. |
| 2001/0046489 A1 | 11/2001 | Habener et al. |
| 2002/0012903 A1 | 1/2002 | Goldman et al. |
| 2002/0028510 A1 | 3/2002 | Sanberg et al. |
| 2002/0045196 A1 | 4/2002 | Mahoney et al. |
| 2002/0064519 A1 | 5/2002 | Bruder et al. |
| 2002/0068045 A1 | 6/2002 | Reubinoff et al. |
| 2002/0132987 A1 | 9/2002 | Anderson |
| 2002/0164308 A1 | 11/2002 | Reubinoff et al. |
| 2002/0164790 A1 | 11/2002 | Warburton et al. |
| 2002/0164794 A1 | 11/2002 | Wernet |
| 2002/0168763 A1 | 11/2002 | Yan et al. |
| 2002/0177227 A1 | 11/2002 | Kraus et al. |
| 2002/0192816 A1 | 12/2002 | Roberts et al. |
| 2003/0003084 A1 | 1/2003 | Seshi |
| 2003/0027233 A1 | 2/2003 | Collins et al. |
| 2003/0032179 A1 | 2/2003 | Hariri |
| 2003/0092078 A1 | 5/2003 | Thomas et al. |
| 2003/0113910 A1 | 6/2003 | Levanduski |
| 2003/0134416 A1 | 7/2003 | Yamanishi et al. |
| 2003/0157078 A1 | 8/2003 | Hall et al. |
| 2003/0161818 A1 | 8/2003 | Weiss et al. |
| 2003/0165852 A1 | 9/2003 | Schueler et al. |
| 2003/0180269 A1* | 9/2003 | Hariri ..................... 424/93.21 |
| 2003/0203483 A1 | 10/2003 | Seshi |
| 2003/0235563 A1* | 12/2003 | Strom et al. ............. 424/93.21 |
| 2003/0235909 A1 | 12/2003 | Hariri et al. |
| 2004/0018621 A1 | 1/2004 | Reid et al. |
| 2004/0028660 A1 | 2/2004 | Hariri et al. |
| 2004/0058398 A1 | 3/2004 | Sarvetnick et al. |
| 2004/0058412 A1 | 3/2004 | Ho et al. |
| 2004/0107453 A1 | 6/2004 | Furcht et al. |
| 2004/0121464 A1 | 6/2004 | Rathjen et al. |
| 2004/0137612 A1 | 7/2004 | Baksh et al. |
| 2004/0142463 A1 | 7/2004 | Walker et al. |
| 2004/0161419 A1 | 8/2004 | Strom et al. |
| 2004/0171147 A1 | 9/2004 | Hariri |
| 2004/0203142 A1 | 10/2004 | Rai |
| 2004/0219136 A1 | 11/2004 | Hariri |
| 2004/0228847 A1 | 11/2004 | Goldschmidt-Clermont et al. |
| 2004/0259254 A1 | 12/2004 | Honmou et al. |
| 2005/0019865 A1 | 1/2005 | Kihm et al. |
| 2005/0019908 A1 | 1/2005 | Hariri |
| 2005/0019911 A1 | 1/2005 | Gronthos et al. |
| 2005/0032209 A1 | 2/2005 | Messina et al. |
| 2005/0037493 A1 | 2/2005 | Mandalam et al. |
| 2005/0048035 A1 | 3/2005 | Fraser et al. |
| 2005/0053588 A1 | 3/2005 | Yin |
| 2005/0054098 A1 | 3/2005 | Mistry et al. |
| 2005/0058629 A1 | 3/2005 | Harmon et al. |
| 2005/0058630 A1 | 3/2005 | Harris et al. |
| 2005/0058631 A1 | 3/2005 | Kihm et al. |
| 2005/0059147 A1 | 3/2005 | Seshi |
| 2005/0063961 A1 | 3/2005 | Friedlander et al. |
| 2005/0074435 A1 | 4/2005 | Casper et al. |
| 2005/0095703 A1 | 5/2005 | Semb et al. |
| 2005/0106554 A1 | 5/2005 | Palecek et al. |
| 2005/0118715 A1 | 6/2005 | Hariri |
| 2005/0124003 A1 | 6/2005 | Atala et al. |
| 2005/0142118 A1 | 6/2005 | Wernet |
| 2005/0158289 A1 | 7/2005 | Simmons et al. |
| 2005/0176139 A1 | 8/2005 | Chen et al. |
| 2005/0181502 A1 | 8/2005 | Furcht et al. |
| 2005/0255592 A1 | 11/2005 | Collins et al. |
| 2005/0260748 A1 | 11/2005 | Chang et al. |
| 2005/0260751 A1 | 11/2005 | Lucas et al. |
| 2006/0008450 A1 | 1/2006 | Verfaillie et al. |
| 2006/0030039 A1* | 2/2006 | Chen et al. ................ 435/325 |
| 2006/0037092 A1 | 2/2006 | Lawman et al. |
| 2006/0040392 A1 | 2/2006 | Collins et al. |
| 2006/0078993 A1 | 4/2006 | Phan et al. |
| 2006/0134636 A1 | 6/2006 | Stanton |
| 2006/0141493 A1* | 6/2006 | West et al. ..................... 435/6 |
| 2006/0154366 A1 | 7/2006 | Brown et al. |
| 2006/0182724 A1 | 8/2006 | Riordan |
| 2006/0206953 A1 | 9/2006 | Lanza et al. |
| 2007/0249047 A1 | 10/2007 | McKenna |
| 2007/0292398 A1 | 12/2007 | Collins et al. |

FOREIGN PATENT DOCUMENTS

| | | |
|---|---|---|
| WO | WO 90/11354 | 10/1990 |
| WO | WO 91/01140 | 2/1991 |
| WO | WO 93/04169 | 3/1993 |
| WO | 02/36751 | 5/2002 |
| WO | WO 02/083262 | 10/2002 |
| WO | WO 03/55989 | 7/2003 |
| WO | WO 03/68937 | 8/2003 |
| WO | 03/078610 | 9/2003 |
| WO | 2004/024875 | 3/2004 |
| WO | 2004/029208 | 4/2004 |
| WO | WO 2005/017132 | 2/2005 |

OTHER PUBLICATIONS

Belov et al., Immunophenotyping of leukemias using a cluster of differentiation antibody microarray Cancer Res. Jun. 1, 2001;61(11):4483-9.*

Bigbee et al., "Monoclonal antibodies specific for the M- and N-forms of human glycophorin A," *Mol. Immunol.*, 1983, 20(12):1353-1362.

Bradley, "Modifying the mammalian genome by gene targeting," *Curr. Opin. Biotechnol.*, 1991, 2:823-829.

Cole et al., "The EBV-Hybridoma Technique and its Application to Human Lung Cancer" *Monoclonal Antibodies and Cancer Therapy*, 1985, pp. 77-96.

Cote et al., "Generation of human monoclonal antibodies reactive with cellular antigens." *Proc. Natl. Acad. Sci. USA*, 1983, 80:2026-2030.

Eggens et al., "Specific Interaction between $Le^x$ and $Le^x$ Determinants. A Possible Basis for Cell Recognition in Preimplantation Embryos and in Embryonal Carcinoma Cells," *J. Biol. Chem.*, 1989, 264(16):9476-9484.

Forraz et al., "$AC133^+$ umbilical cord blood progenitors demonstrate rapid self-renewal and low apoptosis," *British Journal of Haematology*, 2002, 119:516-524.

Forraz et al., "Characterization of a lineage-negative stem-progenitor cell population optimized for ex vivo expansion and enriched for LTC-IC," *Stem Cells*, 2004, 22:100-108.

Forraz et al., "Haemopoietic and neuroglial progenitors are promoted during cord blood ex vivo expansion," *British Journal of Haematology*, 2002, 119:888.

Fowler and Greenspan, "Application of Nile Red, a Fluorescent Hydrophobic Probe, for the Detection of Neutral Lipid Deposits in Tissue Sections: Comparison with Oil Red O," *J. Histochem. Cytochem.*, 1985, 33(8):833-836.

Jaiswal et al., "Osteogenic Differentiation of Purified, Culture-Expanded Human Mesenchymal Stem Cells In Vitro," *J. Cell. Biochem.*, 1997, 64:295-312.

Jennings et al., "CD9 cluster workshop report: cell surface binding and functional analysis," *Leucocyte Typing V*, 1995, Schlossmann et al. (eds.), Oxford University Press, Oxford, pp. 1249-1251.

Johnson et al., "Bone marrow may be source of new egg-cell generation in adult mammals," [online] 2005, [retrieved on Jul. 29, 2005]. Retrieved from the Internet: <URL: www.eurekalert.org/pub_releases/2005-07/mgh-bmm071505.php>, 3 pages.

Kannagi et al., "A Series of Human Erythrocyte Glycosphingolipids Reacting to the Monoclonal Antibody Directed to a Developmentally Regulated Antigen, SSEA-1," *J. Biol. Chem.*, 1982, 257(24):14865-14874.

Kay et al., "Gene therapy," *Proc. Natl. Acad. Sci. USA*, 1997,94:12744-12746.

Kögler et al., "A new human somatic stem cell from placental cord blood with intrinsic pluripotent differentiation potential," *J. Exp. Med.*, 2004, 200(2):123-135.

Lanza et al., "cDNA cloning and expression of platelet p24/CD9. Evidence for a new family of multiple membrane-spanning proteins," *J. Biol. Chem.*, 1991, 266(16):10638-10645.

Magnani et al., "Monoclonal Antibodies PMN 6, PMN 29, and PM-81 Bind Differently to Glycolipids Containing a Sugar Sequence Occurring in Lacto-*N*-Fucopentaose III," *Arch. Biochem. Biophys.*, 1984, 233(2):501-506.

McGuckin et al., "Colocalization analysis of sialomucins CD34 and CD164," *Stem Cells*, 2003, 21:162-170.

McGuckin et al., "Multiparametric analysis of immature cell populations in umbilical cord blood and bone marrow," *Eur. J. Haematol.*, 2003, 71:341-350.

McGuckin et al., "Production of stem cells with embryonic characteristics from human umbilical cord blood," *Cell Prolif.*, 2005, 38:245-255.

McGuckin et al., "Thrombopoietin, flt3-ligand and c-kit-ligand modulate *HOX* gene expression in expanding cord blood $CD133^+$ cells," *Cell Prolif.*, 2004, 37:295-306.

McGuckin et al., "Umbilical cord blood stem cells can expand hematopoietic and neuroglial progenitors in vitro," *Experimental Cell Research*, 2004, 295:350-359.

Outram et al., "Erythromyeloid Lineage Fidelity is Conserved in Erythroleukaemia," *Leukemia Research*, 1988, 12(8):651-657.

Pittenger et al., "Multilineage Potential of Adult Human Mesenchymal Stem Cells," *Science*, 1999, 284:143-147.

Reinberg, "Banking on Stem Cells," [online]. The Scientist, 2005, [retrieved on Jul. 28, 2005]. Retrieved from the Internet: <URL: www.the-scientist.com>, 5 pages.

Rubinstein et al., "Anti-Platelet Antibody Interactions with Fcγ Receptor," *Semin. Thromb Hemost.*, 1995, 21(1):10-22.

Solter and Knowles, "Monoclonal antibody defining a stage-specific mouse embryonic antigen (SSEA-1)," *Proc. Natl. Acad. Sci. USA*, 1978, 75(11):5565-5569.

Telen and Bolk, "Human red cell antigens. IV. The abnormal sialoglycoprotein of Gerbich-negative red cells," *Transfusion*, 1987, 27(4):309-314.

Von dem Borne and Modderman, "P2.1 Cluster Report: CD9" *Leucocyte Typing IV*, 1989, Knapp et al. (eds.), Oxford University Press, Oxford, pp. 989-992.

Whiting et al., "Three-dimensional analysis of CD34 sialomucin distribution on cord blood and bone marrow," *British Journal of Haematology*, 2003, 122:771-777.

Wright and Tomlinson, "The ins and outs of the transmembrane 4 superfamily," *Immunology Today*, 1994, 15(12):588-594.

Xiao et al., "Transplantation of a novel cell line population of umbilical cord blood stem cells ameliorates neurological deficits associated with ischemic brain injury," *Stem Cells and Development*, 2005, 14:722-733.

Terai et al., "Immortalization of Human Fetal Cells: The Life Span of Umbilical Cord Blood-derived Cells Can Be Prolonged without Manipulating $p16^{INK4a}$/RB Braking Pathway," *Mol. Biol. Cell*, 2005, 16:1491-1499.

Madlambayan et al., "Controlling Culture Dynamics for the Expansion of Hematopoietic Stem Cells," *J. Hematother. Stem Cell Res.*, 2001, 10(4):481-492.

Pittenger et al. "Adult Mesenchymal Stem Cells: Potential for Muscle and Tendon Regeneration and use in Gene Therapy." *Journal of Musculoskeletal Interactions*. 2002, 2 (4) 309-320.

Rosada et al. "The human umbilical cord blood: A potential source for osteoblast progenitor cells." *Calcified Tissue International*. 2003, 72 (2) 135-142.

BDTM Biosciences Technical Bulletin BDTM Three Dimensional Collagen Composite and OPLA Scaffolds, 2002.

Abe et al., "Cells Derived from the Circulation Contribute to the Repair of Lung Injury," *Am. J. Respir. Crit. Care Med.*, 2004, 170(11):1158-1163.

Baksh et al., "Adult mesenchymal stem cells: characterization, differentiation, and application in cell and gene therapy," *J. Cell. Mol. Med.*, 2004, 8(3):301-316.

Belov et al., "Immunophenotyping of leukemias using a cluster of differentiation antibody microarray," *Cancer Res.*, 2001, 61(11):4483-4489.

Bensidhoum et al., "Homing of in vitro expanded Stro-1⁻ or Stro-1⁺ human mesenchymal stem cells into the NOD/SCID mouse and their role in supporting human CD34 cell engraftment," *Blood*, 2004, 103:3313-3319.

Berger et al., "Differentiation of umbilical cord blood-derived multilineage progenitor cells into respiratory epithelial cells," *Cytotherapy*, 2006, 8(5):480-487.

Cadet et al., "A Functionally Coupled µ3-Like Opiate Receptor/Nitric Oxide Regulatory Pathway in Human Multi-Lineage Progenitor Cells," *J. Immunol.*, 2007, 179:5839-5844.

Choi et al., "Chondrogenic differentiation of human umbilical cord blood-derived multilineage progenitor cells in atelocollagen," *Cytotherapy*, 2008, 0:1-9.

D'Ippolito et al., "Marrow-isolated adult multilineage inducible (MIAMI) cells, a unique population of postnatal young and old human cells with extensive expansion and differentiation potential," *J. Cell Sci.*, 2004, 117:2971-2981.

Erices et al., "Mesenchymal progenitor cells in human umbilical cord blood," *Br. J. Haematol.*, 2000, 109:235-242.

Goodwin et al., "Multilineage Differentiation Activity by Cells Isolated from Umbilical Cord Blood: Expression of Bone, Fat, and Neural Markers," *Biol. Blood Marrow Transplant.*, 2001, 7:581-588.

Hou et al., "Study of in vitro expansion and differentiation into neuron-like cells of human umbilical cord blood mesenchymal stem cells," *Chin. J. Hematol.*, 2002, 23(8):414-419 (English Abstract only).

Jäger and Krauspe, "Antigen expression of cord blood derived stem cells under osteogenic stimulation in vitro," *Cell Biology International*, 2007, 31:950-957.

Jiang et al., "Pluripotency of mesenchymal stem cells derived from adult marrow," *Nature*, 2002, 418:41-49.

Jones et al., "Isolation and Characterization of Bone Marrow Multipotential Mesenchymal Progenitor Cells," *Arth. Rheum.*, 2002, 46(12):3349-3360.

Kern et al., "Comparative Analysis of Mesenchymal Stem Cells from Bone Marrow, Umbilical Cord Blood, or Adipose Tissue," *Stem Cells*, 2006, 24:1294-1301.

Kobune et al., "Telomerized human multipotent mesenchymal cells can differentiate into hematopoietic and cobblestone area—supporting cells," *Exp. Hematol.*, 2003, 31:715-722.

Kögler et al., "Cytokine production and hematopoiesis supporting activity of cord blood—derived unrestricted somatic stem cells," *Exp. Hematol.*, 2005, 33:573-583.

Krause et al., "Multi-Organ, Multi-Lineage Engraftment by a Single Bone Marrow-Derived Stem Cell," *Cell*, 2001, 105:369-377.

Lakshmipathy et al., "Efficient Transfection of Embryonic and Adult Stem Cells," *Stem Cells*, 2004, 22:531-543.

Lam et al., "Preclinical ex vivo expansion of cord blood hematopoietic stem and progenitor cells: duration of culture; the media, serum supplements, and growth factors used; and engraftment in NOD/SCID mice," *Transfusion*, 2001, 41:1567-1576.

Lee et al., "Isolation of multipotent mesenchymal stem cells from umbilical cord blood," *Blood*, 2004, 103(5):1669-1675.

Lodie et al., "Systematic analysis of reportedly distinct populations of multipotent bone marrow-derived stem cells reveals a lack of distinction," *Tissue Eng.*, 2002, 8(5):739-751.

Meng et al., "Endometrial regenerative cells: A novel stem cell population," *J. Translational Med.*, 2007, 5:57.

Perez et al., "Human Cord Blood derived Stem Cells Differentiated into Hormone-Expressing Islet Cell-like Aggregates to Produce Insulin as an Alternative to Pancreatic transplant for diabetic and pancreatic Cancer Patients," http://www.eliondiagnostics.com/pdf/news/Celprogen_Stem_Cell_Abstract.pdf#search=%22perez%20pancreatic%20cord%20blood%22, Stem Cells Research and Therapeutics Conference, San Diego, CA, Apr. 11-12, 2005, 4 pages.

Phinney and Prockop, "Concise Review: Mesenchymal Stem/Multipotent Stromal Cells: The State of Transdifferentiation and Modes of Tissue Repair—Current Views," *Stem Cells*, 2007, 25:2896-2902.

Rutella et al., "Identification of a Novel Subpopulation of Human Cord Blood CD34-CD133-CD7-CD45+Lineage- Cells Capable of Lymphoid/NK Cell Differentiation After In Vitro Exposure to IL-15," *J. Immunol.*, 2003, 171:2977-2988.

Sakaguchi et al., "Comparison of Human Stem Cells Derived from Various Mesenchymal Tissues," *Arth. Rheum.*, 2005, 52(8):2521-2529.

Simonsen et al., "Telomerase expression extends the proliferative life-span and maintains the osteogenic potential of human bone marrow stromal cells," *Nat. Biotechnol.*, 2002, 20:592-596.

Stefano et al., "Endogenous morphine/nitric oxide-coupled regulation of cellular physiology and gene expression: Implications for cancer biology," *Semin. Cancer Biol.*, 2008, 18(3):199-210.

Tocci and Forte, "Mesenchymal stem cell: use and perspectives," *Hematol. J.*, 2003, 4(2):92-96.

Wagner et al., "Comparative characteristics of mesenchymal stem cells from human bone marrow, adipose tissue, and umbilical cord blood," *Exp. Hematol.*, 2005, 33:1402-1416.

Yoon et al., "Clonally expanded novel multipotent stem cells from human bone marrow regenerate myocardium after myocardial infarction," *J. Clin. Invest.*, 2005, 115:326-338.

International Search Report/Written Opinion mailed Apr. 27, 2007 in PCT/US06/33129, 9 pages.

Supplementary Search Report mailed Nov. 28, 2007 in EP 05 73 6785, 6 pages.

International Search Report/Written Opinion mailed Dec. 12, 2006 in PCT/US2005/13244, 7 pages.

Lechner et al., "Clonal growth of epithelial cells from normal adult human bronchus," *Cancer Res.*, 1981, 41:2294-2304.

Authorized Officer Michael A. Belyavski, International Search Report/Written Opinion, PCT/US05/13244, mailed Dec. 12, 2006, 7 pages.

Authorized Officer Yoshiko Kuwahara, International Preliminary Report on Patentability, PCT/US05/13244, mailed Jan. 11, 2007, 5 pages.

Examiner Donata Paresce, Supplementary European Search Report, EP Application No. 05 73 6785, mailed Nov. 28, 2007, 6 pages.

Examiner Donata Paresce, Examination Report, EP Application No. 05 73 6785, mailed Mar. 3, 2008, 6 pages.

The Patent Office of the State Intellectual Property Office of the People's Republic of China, Examination Report, Chinese Application No. 200580012739.3, mailed Mar. 9, 2009, 10 pages.

Examiner Christine Hall, Examination Report, Australian Application No. 2005241008, mailed Mar. 25, 2009, 5 pages.

Examiner Maria Gomez Leavitt, Office Action, U.S. Appl. No. 11/110,299, mailed Apr. 29, 2008, 14 pages.

Examiner Maria Gomez Leavitt, Office Action, U.S. Appl. No. 11/110,299, mailed Oct. 27, 2008, 13 pages.

Examiner Maria Gomez Leavitt, Office Action, U.S. Appl. No. 11/110,299, mailed Apr. 1, 2009, 9 pages.

Examiner Fereydoun Ghotb Sajjadi, Office Action, U.S. Appl. No. 11/452,502, mailed Jul. 31, 2008, 12 pages.

Examiner Fereydoun Ghotb Sajjadi, Office Action, U.S. Appl. No. 11/452,502, mailed Jan. 14, 2009, 13 pages.

Authorized Officer Q. Janice Li, International Search Report/Written Opinion, PCT/US07/66797, mailed Sep. 23, 2008, 9 pages.

Authorized Officer Philippe Becamel, International Preliminary Report on Patentability, PCT/US07/66797, mailed Oct. 30, 2008, 6 pages.

Examiner Qian Janice Li, Office Action, U.S. Appl. No. 11/736,273, mailed Apr. 28, 2009, 12 pages.

Authorized Officer Jung Hee Han, International Search Report/Written Opinion, PCT/US2008/71207, mailed Jul. 25, 2008, 10 pages.

Authorized Officer Beate Giffo-Schmitt, International Preliminary Report on Patentability, PCT/US06/33129, mailed Mar. 6, 2008, 8 pages.

Examiner Donata Paresce, Communication pursuant to Article 94(3) EPC, EP Application No. 05 736 785, mailed Jul. 22, 2009, 4 pages.

* cited by examiner

FIG 2
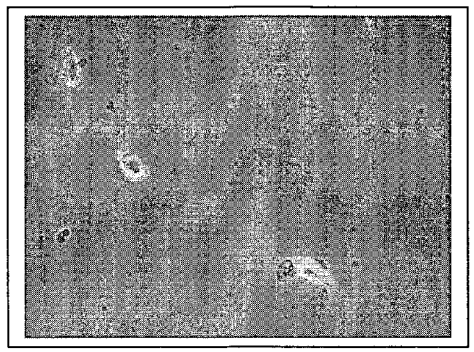
FIG 2A
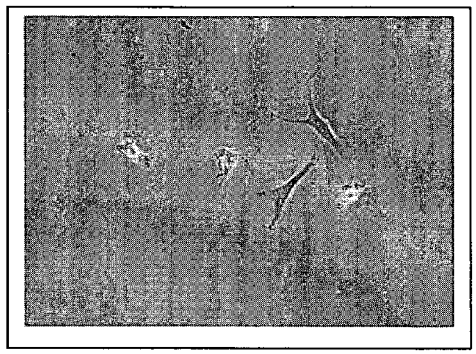
FIG 2B
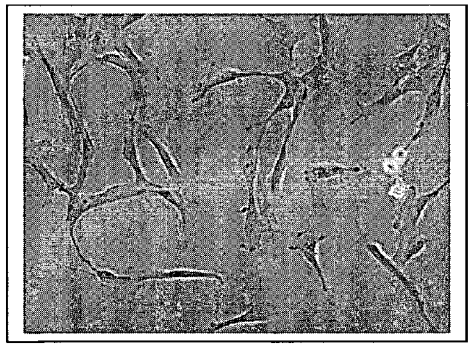
FIG 2C
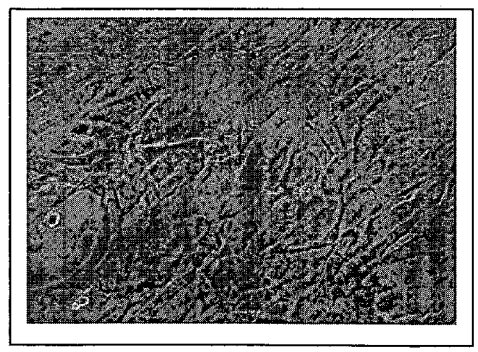
FIG 2D

Fig 3-1

| UNIQ ID | NAME | B | C | D | E | F |
|---|---|---|---|---|---|---|
| 43 | TNFR1: (TNFRSF1A OR TNFR1 OR TNFAR OR TNFR-1) TUMOR NECROSIS FACTOR RECEPTOR SUPERFAMILY MEMBER 1A PRECURSOR (TUMOR NECROSIS FACTOR RECEPTOR 1) (TUMOR NECROSIS FACTOR BINDING PROTEIN 1) (TBP1) (P60) (TNF-R1) (TNF-RI) (P55) (CD120A). | 0.68 | 0.78 | 0.75 | 0.81 | 0.77 |
| 47 | ACTA2: (ACTA2 OR ACTSA OR ACTVS) AORTIC SMOOTH MUSCLE (ALPHA-ACTIN 2). | 0.57 | 0.52 | 0.5 | 33.17 | 0.4 |
| 49 | TUBA_HUMAN: (TUBA3) (TUBA6) TUBULIN ALPHA-UBIQUITOUS CHAIN (ALPHA-TUBULIN UBIQUITOUS) (TUBULIN K-ALPHA-1) (TUBULIN ALPHA-6 CHAIN) (ALPHA-TUBULIN 6) (TUBULIN ALPHA-3 CHAIN) (ALPHA-TUBULIN 3) (TUBULIN B-ALPHA-1). | 0.93 | 1.07 | 1.74 | 1.31 | 1.28 |
| 55 | TUBB1-TUBB5_HUMAN: (TUBB1) TUBULIN BETA-1 CHAIN. (TUBB5) TUBULIN BETA-5 CHAIN. | 1.41 | 0.84 | 3.04 | 2.27 | 2.18 |
| 87 | CDKN1A: (CDKN1A OR CDKN1 OR CIP1 OR WAF1 OR MDA6 OR SDI1 OR PIC1 OR CAP20) CYCLIN-DEPENDENT KINASE INHIBITOR 1 (MELANOMA DIFFERENTIATION ASSOCIATED PROTEIN 6) (MDA-6) (P21) (CDK-INTERACTING PROTEIN 1). | 0.49 | 0.49 | 0.15 | 1.9 | 0.44 |
| 89 | CDKN1B: (CDKN1B OR KIP1) CYCLIN-DEPENDENT KINASE INHIBITOR 1B (CYCLIN-DEPENDENT KINASE INHIBITOR P27) (P27KIP1). | 1.58 | 1.12 | 0.67 | 0.51 | 0.41 |
| 91 | P53: (TP53 OR P53) CELLULAR TUMOR ANTIGEN P53 (TUMOR SUPPRESSOR P53) (PHOSPHOPROTEIN P53). | 1.49 | 1.47 | 1.71 | 1.06 | 0.96 |
| 106 | TNFSF11: (TNFSF11 OR RANKL OR TRANCE OR OPGL) TNF-RELATED ACTIVATION-INDUCED CYTOKINE (RANKL) (TRANCE) (OPGL) (OSTEOPROTEGERIN LIGAND) (TUMOR NECROSIS FACTOR LIGAND). |  | 1.46 | 1.67 | 1.38 | 0.93 |
| 118 | CCNB2: (CCNB2) CYCLIN B2 G2/MITOTIC SPECIFIC CYCLIN B2. | 1.07 | 1.19 | 3.54 | 0.8 | 2.32 |
| 134 | CCNG2: (CCNG2) CYCLIN G2. | 1.13 | 1.3 | 0.69 | 1.21 | 0.87 |
| 138 | CCNE2: (CCNE2) G1/S-SPECIFIC CYCLIN E2. | 2.1 | 1.97 | 2.99 |  | 0.75 |
| 139 | MAPK3: (MAPK3 OR PRKM3 OR ERK1) MITOGEN-ACTIVATED PROTEIN KINASE 3 (EC 2.7.1.-) (EXTRACELLULAR SIGNAL-REGULATED KINASE 1) (ERK-1) (INSULIN-STIMULATED MAP2 KINASE) (MAP KINASE 1) (MAPK 1) (P44-ERK1) (ERT2) (P44-MAPK) (MICROTUBULE-ASSOCIATED PROTEIN-2 KINAS | 1.11 | 1.17 | 0.71 | 0.94 | 0.91 |
| 143 | MAPK6: (MAPK6 OR PRKM6 OR ERK3) MITOGEN-ACTIVATED PROTEIN KINASE 6 (EC 2.7.1.-) (EXTRACELLULAR SIGNAL-REGULATED KINASE 3) (ERK3) (P55-MAPK). | 1.01 | 0.93 | 1.22 | 5.72 | 1.63 |
| 163 | MAPK14: (MAPK14 OR CSBP1 OR CSBP2 OR MXI2) MITOGEN-ACTIVATED PROTEIN KINASE 14 (EC 2.7.1.37) (MITOGEN-ACTIVATED PROTEIN KINASE P38ALPHA) (MAP KINASE P38ALPHA) (CYTOKINE SUPPRESSIVE ANTI-INFLAMMATORY DRUG BINDING PROTEIN) (CSAID BINDING PROTEIN) (C | 0.83 | 0.99 | 1.03 | 0.68 | 1.15 |

Fig 3-2

| | | | | | | | |
|---|---|---|---|---|---|---|---|
| 211 | CASP8_1: (MCH5 OR CASP8) CASPASE 8 PRECURSOR (EC 3.4.22.-) (ICE-LIKE APOPTOTIC PROTEASE 5) (MORT1-ASSOCIATED CED-3 HOMOLOG) (MACH) (FADD HOMOLOGOUS ICE/CED-3-LIKE PROTEASE) (FLICE) (APOPTOTIC CYSTEINE PROTEASE) (APOPTOTIC PROTEASE MCH-5) (CAP4). | 1 | 1.36 | 0.83 | 0.71 | 1 |
| 241 | TNFSF4: (TNFSF4 OR TXGP1) OX40 LIGAND (OX40L) (GLYCOPROTEIN GP34) (TAX-TRANSCRIPTIONALLY ACTIVATED GLYCOPROTEIN 1). | 1.17 | 1.78 | 1.42 | 1.35 | 1.12 |
| 251 | TNFRSF1B: (TNFRSF1B OR TNFR2 OR TNFBR OR TNFR-2) TUMOR NECROSIS FACTOR RECEPTOR SUPERFAMILY MEMBER 1B PRECURSOR (TUMOR NECROSIS FACTOR RECEPTOR 2) (TUMOR NECROSIS FACTOR BINDING PROTEIN 2) (TBPII) (P80) (TNF-R2) (P75) (CD120B) (ETANERCEPT). | 0.63 | 0.95 | 0.61 | 0.36 | 0.53 |
| 301 | CYPA: (PPIA OR CYPA) CYCLOPHILIN 1 PEPTIDYL-PROLYL CIS-TRANS ISOMERASE A (EC 5.2.1.8) (PPIASE) (ROTAMASE) (CYCLOPHILIN A) (CYCLOSPORIN A-BINDING PROTEIN). | 1.4 | 1.09 | 1.87 | 1.49 | 1.98 |
| 303 | ICAM2: (ICAM2 OR ICAM-2) INTERCELLULAR ADHESION MOLECULE-2 PRECURSOR (ICAM-2) (CD102) (LYMPHOCYTE FUNCTION-ASSOCIATED AG-1 COUNTER-RECEPTOR). | 1.47 | 1.08 | 1 | 0.48 | 0.76 |
| 309 | ENG: (ENG OR END) ENDOGLIN PRECURSOR (CD105 ANTIGEN) (CELL SURFACE MJ7/18 ANTIGEN). | 0.88 | 0.68 | 1.22 | 2.07 | 1.28 |
| 311 | VCAM1: (VCAM1 OR L1CAM OR VCAM-1) VASCULAR CELL ADHESION PROTEIN 1 PRECURSOR (V-CAM 1) (CD106 ANTIGEN) (INCAM-100). | 0.63 | 0.31 | 0.45 | 1.02 | 0.86 |
| 322 | KIT: (KIT OR SL) MAST/STEM CELL GROWTH FACTOR RECEPTOR PRECURSOR (EC 2.7.1.112) (SCFR) (PROTO-ONCOGENE TYROSINE-PROTEIN KINASE KIT) (C-KIT) (CD117 ANTIGEN) (C-KIT RECEPTOR TYROSINE KINASE). | 0.96 | 1.46 | 0.78 | 0.71 | 1.09 |
| 324 | IFNGR1: (IFNGR1 OR IFNGR) INTERFERON-GAMMA RECEPTOR ALPHA CHAIN PRECURSOR (CDW119) (CD119). | 0.28 | 0.7 | 0.39 | 0.52 | 0.67 |
| 326 | IL1R1: (IL1R1 OR IL1RA OR IL1R) INTERLEUKIN-1 RECEPTOR, TYPE I PRECURSOR (IL-1R-1) (IL-1R-ALPHA) (P80) (ANTIGEN CD121A). | 1.14 | 0.87 | 2.12 | 1.81 | |
| 328 | IL1R2: (IL1R2 OR IL1RB) INTERLEUKIN-1 RECEPTOR, TYPE II PRECURSOR (IL-1R-2) (IL-1R-BETA) (ANTIGEN CDW121B). | 0.95 | 8.66 | 1.14 | 0.82 | 0.62 |
| 332 | IL3RA: ((IL3RAX OR IL3RA OR IL3R OR IL3RX) AND (IL3RAY OR IL3RA OR IL3R OR IL3RY)) INTERLEUKIN-3 RECEPTOR ALPHA CHAIN PRECURSOR (IL-3R-ALPHA) (CD123 ANTIGEN). | 0.8 | 1.19 | 1.19 | 0.87 | 5.58 |
| 333 | IL4R: (IL4R OR IL4RA OR 582J2.1) INTERLEUKIN-4 RECEPTOR ALPHA CHAIN PRECURSOR (IL-4R-ALPHA) (CD124 ANTIGEN) [CONTAINS: SOLUBLE INTERLEUKIN-4 RECEPTOR ALPHA CHAIN (SIL4RALPHA/PROT) (IL-4-BINDING PROTEIN) (IL4-BP)]. | 1.4 | 2.19 | 0.71 | 0.95 | 0.95 |
| 337 | IL6R: (IL6RA OR IL6R) INTERLEUKIN-6 RECEPTOR ALPHA CHAIN PRECURSOR (IL-6R-ALPHA) (CD126 ANTIGEN) (IL-6R 1). | 0.88 | 1.45 | 1.04 | 0.54 | 0.96 |
| 339 | IL7R: (IL7R) INTERLEUKIN-7 RECEPTOR ALPHA CHAIN PRECURSOR (IL-7R-ALPHA) | 10.09 | 3.89 | 0.36 | 0.08 | 2.62 |

Fig 3-3

| | | | | | | |
|---|---|---|---|---|---|---|
| 343 | (CDW127) (CD127 ANTIGEN). | | | | | 0.84 |
| | IL6ST: (IL6ST) INTERLEUKIN-6 RECEPTOR BETA CHAIN PRECURSOR (IL-6R-BETA) (INTERLEUKIN 6 SIGNAL TRANSDUCER) (MEMBRANE GLYCOPROTEIN 130) (GP130) (ONCOSTATIN M RECEPTOR) (CDW130) (CD130 ANTIGEN). | 1.13 | 0.96 | 0.79 | 1.58 | |
| 349 | FLT3: (FLT3 OR STK1 OR FLT-3 OR FLK-2) FL CYTOKINE RECEPTOR PRECURSOR (EC 2.7.1.112) (TYROSINE-PROTEIN KINASE RECEPTOR FLT3) (STEM CELL TYROSINE KINASE 1) (STK-1) (CD135 ANTIGEN) (TYROSINE-PROTEIN KINASE RECEPTOR FLK-2) (FETAL LIVER KINASE 2). | 0.56 | 0.62 | 1.14 | 0.44 | 0.53 |
| 355 | PDGFRA: (PDGFRA) ALPHA PLATELET-DERIVED GROWTH FACTOR RECEPTOR PRECURSOR (EC 2.7.1.112) (PDGF-R-ALPHA) (CD140A ANTIGEN). | 0.73 | 1.32 | 0.52 | 1.46 | 0.58 |
| 357 | PDGFRB: (PDGFRB OR PDGFR) BETA PLATELET-DERIVED GROWTH FACTOR RECEPTOR PRECURSOR (EC 2.7.1.112) (PDGF-R-BETA) (CD140B ANTIGEN). | 0.98 | 1.06 | 0.72 | 0.5 | 0.75 |
| 359 | THBD: (THBD OR THRM) THROMBOMODULIN PRECURSOR (FETOMODULIN) (TM) (CD141 ANTIGEN). | 0.83 | 1.59 | 0.86 | | 2.63 |
| 365 | CDH5: (CDH5) VASCULAR ENDOTHELIAL-CADHERIN PRECURSOR (VE-CADHERIN) (CADHERIN-5) (7B4 ANTIGEN) (CD144 ANTIGEN) (CDH5). | 1.02 | 1.51 | 0.72 | 0.83 | 0.93 |
| 367 | MCAM: (MCAM OR MUC18) CELL SURFACE GLYCOPROTEIN MUC18 PRECURSOR (MELANOMA-ASSOCIATED ANTIGEN MUC18) (MELANOMA-ASSOCIATED ANTIGEN A32) (S-ENDO 1 ENDOTHELIAL-ASSOCIATED ANTIGEN) (CD146 ANTIGEN) (MELANOMA ADHESION MOLECULE) (S-GICERIN/MUC18) (L-GICERIN/MUC18 | 0.9 | 1.01 | 1.17 | 7.53 | 1.09 |
| 385 | SELPLG: (SELPLG) P-SELECTIN GLYCOPROTEIN LIGAND 1 PRECURSOR (PSGL-1) (SELECTIN P LIGAND) (CD162 ANTIGEN). | 1.27 | 0.97 | 1.93 | 1.04 | 1.01 |
| 387 | ALCAM: (ALCAM) CD166 ANTIGEN PRECURSOR (ACTIVATED LEUKOCYTE-CELL ADHESION MOLECULE) (ALCAM) (MEMD PROTEIN) (HB2) (KG-CAM) (MEMD PROTEIN) (HB2) (KG-CAM). | 1.96 | 0.86 | 0.39 | 1.38 | 0.8 |
| 399 | CD58_HUMAN: (CD58 OR LFA3) LYMPHOCYTE FUNCTION-ASSOCIATED ANTIGEN 3 PRECURSOR (AG3) (ANTIGEN CD58) (SURFACE GLYCOPROTEIN LFA-3). | 0.66 | 0.83 | 1.02 | 0.62 | 1.48 |
| 401 | ITGB3: (ITGB3 OR GP3A) INTEGRIN BETA-3 PRECURSOR (PLATELET MEMBRANE GLYCOPROTEIN IIIA) (GPIIIA) (CD61 ANTIGEN). | 0.77 | 1.13 | 0.69 | 0.79 | 0.83 |
| 403 | SELE: (SELE OR ELAM1 OR ELAM-1) E-SELECTIN PRECURSOR (ENDOTHELIAL LEUKOCYTE ADHESION MOLECULE 1) (ELAM-1) (LEUKOCYTE-ENDOTHELIAL CELL ADHESION MOLECULE 2) (LECAM2) (CD62E). | 3 | 1.09 | 2.54 | 0.83 | |
| 405 | SELL: (SELL OR LYAM1 OR LNHR OR LY-22) L-SELECTIN PRECURSOR (LYMPH NODE HOMING RECEPTOR) (LEUKOCYTE ADHESION MOLECULE-1) (LAM-1) (LEUKOCYTE SURFACE ANTIGEN LEU-8) (TQ1) (GP90-MEL) (LEUKOCYTE-ENDOTHELIAL CELL ADHESION MOLECULE 1) (LECAM1) (CD62L) (LY-22). | 2.59 | 2.2 | 0.31 | 0.18 | 0.24 |
| 416 | CD68: (CD68) MACROSIALIN PRECURSOR (CD68 ANTIGEN) (GP110). | 0.24 | 0.34 | 0.57 | 0.22 | 2.11 |
| 422 | TFRC_MIDDLE: (TFRC) TRANSFERRIN RECEPTOR PROTEIN (TFR1) (TR) (TFR) (TRFR). | 1.3 | 4.22 | 10.66 | 0.86 | 2.9 |

Fig 3-4

| | | | | | | |
|---|---|---|---|---|---|---|
| 426 | (CD71 ANTIGEN) (T9) (P90). | | 0.87 | 0.95 | 0.71 | 0.81 | 0.87 |
| 438 | NT5: (NT5E OR NT5 OR NTE) 5'-NUCLEOTIDASE PRECURSOR (EC 3.1.3.5) (ECTO-NUCLEOTIDASE) (5'-NT) (CD73 ANTIGEN). | 1.44 | 1.99 | 2.65 | 1.01 | 4.17 |
| 446 | KAI1: (KAI1 OR CD82 OR SAR2) CD82 ANTIGEN (INDUCIBLE MEMBRANE PROTEIN R2) (C33 ANTIGEN) (IA4) (METASTASIS SUPPRESSOR KANGAI 1) (SUPPRESSOR OF TUMORIGENICITY-6). | 0.66 | 1.71 | 0.71 | 0.66 | 1.57 |
| 451 | PLAUR: (PLAUR OR UPAR OR MO3) UROKINASE PLASMINOGEN ACTIVATOR SURFACE RECEPTOR, GPI-ANCHORED FORM PRECURSOR (U-PAR) (UPAR) (MONOCYTE ACTIVATION ANTIGEN MO3) (CD87 ANTIGEN). | 0.78 | 0.67 | 0.61 | 1.9 | 0.68 |
| 466 | THY1: (THY1) THY-1 MEMBRANE GLYCOPROTEIN PRECURSOR (THY-1 ANTIGEN) (CDW90) (CD90 ANTIGEN). | 3.05 | 1.73 | 0.77 | 0.61 | 1.17 |
| 469 | ITGAL: (ITGAL OR CD11A OR LFA-1) INTEGRIN ALPHA-L PRECURSOR (LEUKOCYTE ADHESION GLYCOPROTEIN LFA-1 ALPHA CHAIN) (LEUKOCYTE FUNCTION ASSOCIATED MOLECULE 1, ALPHA CHAIN) (CD11A) (INTEGRIN ALPHA-L). | 0.4 | 0.58 | 1.67 | 0.79 | 1.99 |
| 475 | ANPEP: (ANPEP OR PEPN OR APN OR CD13 OR LAP1 OR LAP-1) AMINOPEPTIDASE N (EC 3.4.11.2) (MICROSOMAL AMINOPEPTIDASE) (GP150) (MYELOID PLASMA MEMBRANE GLYCOPROTEIN CD13) (P161 MEMBRANE PROTEIN) (MAPN) (RAPN) (ALANYL AMINOPEPTIDASE) (AMINOPEPTIDASE M) (APM) ( | 0.42 | 0.76 | 0.26 | 0.02 | 0.93 |
| 489 | ITGB2: (ITGB2 OR CD18) INTEGRIN BETA-2 PRECURSOR (CELL SURFACE ADHESION GLYCOPROTEINS LFA-1/CR3/P150,95 BETA-SUBUNIT) (CD18) (COMPLEMENT RECEPTOR C3 BETA-SUBUNIT). | 0.45 | 1.27 | 0.38 | 0.18 | 1.39 |
| 499 | CD24: (CD24 OR CD24A) SIGNAL TRANSDUCER CD24 PRECURSOR (M1/69-J11D HEAT STABLE ANTIGEN) (HSA) (NECTADRIN) (LY-52) (X62 HEAT STABLE ANTIGEN) (R13-AG). | 0.74 | 0.18 | 0.3 | 2.92 | 0.2 |
| 501 | ITGB1: (ITGB1 OR FNRB) INTEGRIN BETA-1 PRECURSOR (FIBRONECTIN RECEPTOR BETA SUBUNIT) (CD29 ANTIGEN) (INTEGRIN VLA-4 BETA SUBUNIT). | 0.57 | 0.83 | 0.57 | 0.1 | 0.56 |
| 505 | PECAM1: (PECAM1 OR PECAM-1 OR PECAM) PLATELET ENDOTHELIAL CELL ADHESION MOLECULE PRECURSOR (PECAM-1) (CD31 ANTIGEN) (ENDOCAM) (GPIIA'). | 0.17 | 0.31 | 0.64 | 0.15 | 0.73 |
| 506 | CD33: (CD33) MYELOID CELL SURFACE ANTIGEN CD33 PRECURSOR (GP67) (SIGLEC-3). | 0.89 | 1.08 | 0.86 | 0.65 | 1.09 |
| 512 | CD34: (CD34) HEMATOPOIETIC PROGENITOR CELL ANTIGEN CD34 PRECURSOR. | 0.7 | 0.91 | 0.23 | 0.08 | 0.36 |
| 514 | CD38: (CD38) ADP-RIBOSYL CYCLASE 1 (EC 3.2.2.5) (CYCLIC ADP-RIBOSE HYDROLASE 1) (CADPR HYDROLASE 1) (LYMPHOCYTE DIFFERENTIATION ANTIGEN CD38) (T10) (ACUTE LYMPHOBLASTIC LEUKEMIA CELLS ANTIGEN CD38) (NIM-R5 ANTIGEN) (I-19) (CD38 HOMOLOG) (CD38H). | 4.78 | 2.14 | 0.88 | 0.49 | 2.01 |
| 526 | ITGA2B: (ITGA2B OR ITGAB OR GP2B) PLATELET MEMBRANE GLYCOPROTEIN IIB | 2.68 | 2.67 | 1.02 | 0.61 | 0.84 |

Fig 3-5

| | | | | | | | |
|---|---|---|---|---|---|---|---|
| 538 | PRECURSOR (GPIIB) (GPALPHA IIB) (INTEGRIN ALPHA-IIB) (CD41). | 0.53 | 1.2 | 0.96 | 0.86 | | 1.29 |
| 543 | CD44_EX10-12_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTE | 1.13 | 0.92 | 1.17 | 0.99 | | 1.44 |
| 549 | CD47: (CD47 OR IAP) LEUKOCYTE SURFACE ANTIGEN CD47 PRECURSOR (ANTIGENIC SURFACE DETERMINANT PROTEIN OA3) (INTEGRIN ASSOCIATED PROTEIN) (IAP) (MER6) (ITGP) (INTEGRIN-ASSOCIATED PROTEIN PRECURSOR). | 0.71 | 0.54 | 0.43 | 3.42 | | 0.74 |
| 552 | ITGA1_2: (ITGA1) INTEGRIN ALPHA-1 (LAMININ AND COLLAGEN RECEPTOR) (VLA-1) (CD49A). | 1.03 | 1.46 | 0.83 | 0.82 | | 1 |
| 554 | ITGA3: (ITGA3) INTEGRIN ALPHA-3 PRECURSOR (GALACTOPROTEIN B3) (GAPB3) (VLA-3 ALPHA CHAIN) (CD49C). | 0.67 | 0.81 | 0.81 | 0.45 | | 1.63 |
| 556 | ITGA4: (ITGA4 OR VLA-4) INTEGRIN ALPHA-4 PRECURSOR (INTEGRIN ALPHA-IV) (VLA-4) (CD49D) (LYMPHOCYTE-PEYER'S PATCH ADHESION MOLECULES ALPHA SUBUNIT) (LPAM ALPHA SUBUNIT) | 1.01 | 0.43 | 0.88 | 3.01 | | 0.77 |
| 558 | ITGA5: (ITGA5 OR FNRA) INTEGRIN ALPHA-5 PRECURSOR (FIBRONECTIN RECEPTOR ALPHA SUBUNIT) (INTEGRIN ALPHA-F) (VLA-5) (CD49E). | 1.53 | 1.43 | 1.84 | 0.78 | | 1.21 |
| 563 | ITGA6: (ITGA6) INTEGRIN ALPHA-6 PRECURSOR (VLA-6) (CD49F) (INTA6) (INTEGRIN ALPHA 6 SUBCHAIN). | 0.7 | 0.67 | 0.76 | 0.34 | | 0.95 |
| 567 | ICAM1: (ICAM1 OR ICAM-1) INTERCELLULAR ADHESION MOLECULE 1 PRECURSOR (ICAM-1) (MAJOR GROUP RHINOVIRUS RECEPTOR) (CD54) (MALA-2). | 5.59 | 2.69 | 0.66 | 0.89 | | 0.75 |
| 573 | CD7: (CD7) T-CELL ANTIGEN CD7 PRECURSOR (GP40) (T-CELL LEUKEMIA ANTIGEN) (TP41) (LEU-9). | 0.85 | 0.59 | 0.38 | 0.75 | | 0.66 |
| 595 | CD9: (CD9 OR MIC3) CD9 ANTIGEN (P24) (LEUKOCYTE ANTIGEN MIC3) (MOTILITY-RELATED PROTEIN) (MRP-1). | 0.75 | 0.89 | 0.84 | 0.68 | | 1.12 |
| 598 | HTR1D_1: (HTR1D OR HTR1DA) 5-HYDROXYTRYPTAMINE 1D RECEPTOR (5-HT-1D) (SEROTONIN RECEPTOR) (5-HT-1D-ALPHA) (GPCR14) 5-HYDROXYTRYPTAMINE 1D RECEPTOR (5-HT-1D) (SEROTONIN RECEPTOR) (GPCR14) (HTR1DB) (5-HYDROXYTRYPTAMINE 1D BETA RECEPTOR) (SEROTONIN RECEPTOR) | 0.99 | 0.81 | 0.89 | 0.6 | | 1.1 |
| 606 | HTR1F: (HTR1F OR HTR1EL) 5-HYDROXYTRYPTAMINE 1F RECEPTOR (5-HT-1F) (SEROTONIN RECEPTOR). | 0.72 | 1.18 | | 0.43 | | 1.77 |
| 614 | HTR4: (HTR4) 5-HYDROXYTRYPTAMINE 4 RECEPTOR (5-HT-4) (SEROTONIN RECEPTOR) (5-HT4) (FRAGMENT). | 1.37 | 1.63 | 1.55 | 1.62 | | 1.32 |
| 616 | HTR6: (HTR6) 5-HYDROXYTRYPTAMINE 6 RECEPTOR (5-HT-6) (SEROTONIN RECEPTOR). | | 1.23 | 2.17 | 0.85 | | 1.04 |
| 632 | HTR7: (HTR7) 5-HYDROXYTRYPTAMINE 7 RECEPTOR (5-HT-7) (5-HT-X) (SEROTONIN RECEPTOR) (5HT7). CHRM1: (CHRM1) MUSCARINIC ACETYLCHOLINE RECEPTOR M1. | 0.79 | 0.86 | 0.43 | 0.26 | | 0.55 |

Fig 3-6

| | | | | | | |
|---|---|---|---|---|---|---|
| 705 | DRD3: (DRD3) D(3) DOPAMINE RECEPTOR. | 4.97 | 2.45 | 0.82 | 0.9 | 1.84 |
| 713 | EDNRA: (EDNRA OR ETRA) ENDOTHELIN-1 RECEPTOR PRECURSOR (ET-A). | 0.48 | 1.11 | 0.32 | 0.74 | 0.46 |
| 818 | GJA5: (GJA5) GAP JUNCTION ALPHA-5 PROTEIN (CONNEXIN 40) (CX40). | 0.7 | 0.93 | 0.78 | 0.66 | 1.13 |
| 820 | GJA7: (GJA7 OR CXN-45) GAP JUNCTION ALPHA-7 PROTEIN (CONNEXIN 45) (CX45). | 0.77 | 1 | 0.59 | 0.48 | 0.67 |
| 829 | GJB5: (GJB5 OR CXN-31.1) GAP JUNCTION BETA-5 PROTEIN (CONNEXIN 31.1) (CX31.1). | 0.51 | 0.77 | 0.81 | 0.48 | 1.84 |
| 845 | EAAT4: (SLC1A6 OR EAAT4) EXCITATORY AMINO ACID TRANSPORTER 4 (SODIUM-DEPENDENT GLUTAMATE/ASPARTATE TRANSPORTER). | | 2.47 | 2.55 | 0.65 | 1.5 |
| 1088 | PTHR2: (PTHR2) PARATHYROID HORMONE RECEPTOR PRECURSOR (PTH2 RECEPTOR). | 0.89 | 0.92 | 0.76 | 0.43 | 1.14 |
| 1089 | PTHR1: (PTHR1 OR PTHR) PARATHYROID HORMONE/PARATHYROID HORMONE-RELATED PEPTIDE RECEPTOR PRECURSOR (PTH/PTHR RECEPTOR). | 1.21 | 1.28 | 0.77 | 0.63 | 0.92 |
| 1191 | COL18A1_1: (COL18A1) COLLAGEN ALPHA 1(XVIII) CHAIN [CONTAINS: ENDOSTATIN]. | 1.57 | 1.74 | 9.98 | | 1.61 |
| 1201 | FZD3: (FZD3) FRIZZLED 3 PRECURSOR (FRIZZLED-3) (FZ-3) (HFZ3) (MFZ3) (RFZ3). | | | | | 1.55 |
| 1210 | FZD4: (FZD4) WNT RECEPTOR FRIZZLED-4, FRIZZLED 4 PRECURSOR (FRIZZLED-4) (FZ-4) (HFZ4) (FZE4) (MFZ4) (RFZ4). | 1.22 | | 0.83 | 5.56 | 0.55 |
| 1284 | BMP3: (BMP3 OR BMP-3) BONE MORPHOGENETIC PROTEIN 3 PRECURSOR (BMP-3) (OSTEOGENIN) (BMP-3A). | 1.56 | 1.74 | 0.66 | 0.36 | 0.64 |
| 1287 | BMP6: (BMP6 OR BMP-6 OR VGR1) BONE MORPHOGENETIC PROTEIN 6 PRECURSOR (BMP 6). | 2.77 | 1.76 | 0.47 | 0.89 | 1.05 |
| 1294 | CTGF: (CTGF OR HCS24) CONNECTIVE TISSUE GROWTH FACTOR PRECURSOR (HYPERTROPHIC CHONDROCYTE-SPECIFIC PROTEIN 24). | 0.52 | 0.35 | 0.2 | 4.98 | 0.23 |
| 1316 | GDNF: (GDNF) GLIAL CELL LINE-DERIVED NEUROTROPHIC FACTOR PRECURSOR. | 1.22 | 1.1 | 1.15 | 1.18 | 1.69 |
| 1350 | PDGFB: (PDGFB OR C-SIS OR PDGF2 OR SIS) PLATELET-DERIVED GROWTH FACTOR, B CHAIN PRECURSOR (PDGF B-CHAIN) (PDGF-2) (BECAPLERMIN) (C-SIS). | 1.31 | 1.21 | 0.66 | 1.46 | 0.66 |
| 1430 | VEGFB: (VEGFB OR VRF) VASCULAR ENDOTHELIAL GROWTH FACTOR B PRECURSOR (VEGF-B) (VEGF RELATED FACTOR). | 1.58 | 0.67 | 0.9 | 1.39 | 1.22 |
| 1436 | VEGF 1: (VEGF OR VEGFA) VASCULAR ENDOTHELIAL GROWTH FACTOR PRECURSOR (VEGF) (VASCULAR PERMEABILITY FACTOR) (VPF) (VEGF A). | 0.71 | 0.91 | 0.73 | 1.39 | 0.89 |
| 1442 | WISP3: (WISP3 OR CCN6 OR DJ142L7.3 OR LIBC) WNT1 INDUCIBLE SIGNALING PATHWAY PROTEIN 3 PRECURSOR (WISP-3) (CONNECTIVE TISSUE GROWTH FACTOR (NOV, GIG) LIKE PROTEIN (WISP3) (CONNECTIVE TISSUE GROWTH FACTOR RELATED PROTEIN WISP-3) (LOST IN INFLAMMATORY BREAS | 0.7 | 0.72 | 0.51 | 1.67 | 0.65 |
| 1447 | SLIT-1: (SLIT-1) SLIT-1 PROTEIN (MEGF4) (SLIT1). | 1.15 | 1.67 | 0.77 | 0.92 | 1.21 |
| 1465 | VEGFD: (FIGF OR VEGF-D) VASCULAR ENDOTHELIAL GROWTH FACTOR D (C-FOS INDUCED GROWTH FACTOR). | 2.03 | 1.2 | 0.99 | 6.35 | |

Fig 3-7

| | | | | | | | |
|---|---|---|---|---|---|---|---|
| 1497 | PRKCB_1: (PRKCB1 OR PRKCB OR PKCB) PROTEIN KINASE C, BETA TYPE (EC 2.7.1.37) (PKC-BETA) (PKC-B). | 0.89 | 0.82 | 0.61 | 0.11 | 0.59 |
| 1499 | PRKCB_2: (PRKCB1 OR PRKCB OR PKCB) PROTEIN KINASE C, BETA TYPE (EC 2.7.1.37) (PKC-BETA) (PKC-B). | 1.2 | 1.35 | 0.65 | 0.23 | 0.63 |
| 1507 | PRKCH: (PRKCH OR PKCL) PROTEIN KINASE C, ETA TYPE (EC 2.7.1.-) (NPKC-ETA) (PKC-L). | 1.58 | 1.45 | 0.8 | 0.73 | 1.04 |
| 1691 | ACTB: (ACTB) BETA1, CYTOPLASMIC (BETA-ACTIN) ACTIN, CYTOPLASMIC 1. | 0.66 | 1.09 | 0.47 | 1.23 | 0.93 |
| 1710 | MAPT: (MAPT OR MTBT1 OR TAU) MICROTUBULE-ASSOCIATED PROTEIN TAU (NEUROFIBRILLARY TANGLE PROTEIN) (PAIRED HELICAL FILAMENT-TAU) (PHF-TAU). | 1.29 | 1.3 | 1.25 | 1.47 | 1.18 |
| 1743 | APOE: (APOE) APOLIPOPROTEIN E PRECURSOR (APO-E). | | | 183.19 | | 322.13 |
| 1761 | SNCA: (SNCA OR NACP) ALPHA-SYNUCLEIN (NON-A BETA COMPONENT OF AD AMYLOID) (NACP). | 7.07 | 46.35 | 0.75 | 0.44 | 0.76 |
| 1915 | CSK: (CSK) TYROSINE-PROTEIN KINASE CSK (EC 2.7.1.112) (C-SRC KINASE) (PROTEIN- TYROSINE KINASE CYL). | 0.94 | 1.02 | 0.63 | 0.4 | 0.65 |
| 1930 | PKCD: (PRKCD OR PKCD) PROTEIN KINASE C, DELTA TYPE (EC 2.7.1.-) (NPKC-DELTA). | 0.17 | 0.61 | 0.6 | 0.17 | 0.79 |
| 1953 | PIK3CG: (PIK3CG) PHOSPHATIDYLINOSITOL 3-KINASE CATALYTIC SUBUNIT, GAMMA ISOFORM (EC 2.7.1.137) (PI3-KINASE P110 SUBUNIT GAMMA) (PTDINS-3-KINASE P110) (PI3K). | | 2.72 | 1.86 | | 1.55 |
| 2009 | CXCR4: (CXCR4 OR LESTR OR CMKAR4 OR SDF1R) C-X-C CHEMOKINE RECEPTOR TYPE 4 (CXC-R4) (CXCR-4) (SDF-1 RECEPTOR) (STROMAL CELL-DERIVED FACTOR 1 RECEPTOR) (FUSIN) (LEUKOCYTE-DERIVED SEVEN TRANSMEMBRANE DOMAIN RECEPTOR) (LCR1) (FB22) (NPYRL) (HM89) CD184 ANTI | 2.95 | 4.16 | 0.4 | 0.04 | 0.33 |
| 2031 | GAD1_1: (GAD1 OR GAD) GLUTAMATE DECARBOXYLASE, 67 KDA ISOFORM (EC 4.1.1.15) (GAD-67) (67 KDA GLUTAMIC ACID DECARBOXYLASE). | 1.06 | 0.78 | 1.03 | 0.85 | 1.46 |
| 2035 | CALB1: (CALB1 OR CAB27) CALBINDIN (VITAMIN D-DEPENDENT CALCIUM-BINDING PROTEIN, AVIAN-TYPE) (CALBINDIN D28) (D-28K). | 0.97 | 1.09 | 0.84 | 0.79 | 3.36 |
| 2039 | EAAT1: (SLC1A3 OR EAAT1) EXCITATORY AMINO ACID TRANSPORTER 1 (SODIUM-DEPENDENT GLUTAMATE/ASPARTATE TRANSPORTER 1) (GLIAL GLUTAMATE TRANSPORTER) (GLAST1) | 1.13 | 1.09 | 1.1 | 2.36 | 1.04 |
| 2043 | EAAT2_1: (SLC1A2 OR EAAT2 OR GLT1) EXCITATORY AMINO ACID TRANSPORTER 2 (SODIUM-DEPENDENT GLUTAMATE/ASPARTATE TRANSPORTER 2). | 1.13 | 1.1 | 1.5 | 1.13 | 1.01 |
| 2047 | GRIK1: (GRIK1 OR GLUR5) GLUTAMATE RECEPTOR, IONOTROPIC KAINATE 1 PRECURSOR (GLUTAMATE RECEPTOR 5) (GLUR-5) (EXCITATORY AMINO ACID RECEPTOR 3) (EAA3). | 2.95 | 2.56 | 0.91 | 0.54 | 1.83 |

Fig 3-8

| | | | | | | |
|---|---|---|---|---|---|---|
| 2053 | GRIA1: (GRIA1 OR GLUR1 OR GLUH1) GLUTAMATE RECEPTOR 1 PRECURSOR (GLUR-1) (GLUR-A) (GLUTAMATE RECEPTOR IONOTROPIC, AMPA 1). | 0.97 | 0.56 | 1.23 | 0.87 | 1.09 |
| 2106 | GDF5: (GDF5 OR CDMP1) GROWTH/DIFFERENTIATION FACTOR 5 PRECURSOR (GDF-5) (CARTILAGE-DERIVED MORPHOGENETIC PROTEIN 1) (CDMP-1). | 1.07 | 1.46 | 0.68 | 0.65 | 0.92 |
| 2108 | INHBA: (INHBA) INHIBIN BETA A CHAIN PRECURSOR (ACTIVIN BETA-A CHAIN) (ERYTHROID DIFFERENTIATION PROTEIN) (EDF). | 0.9 | 0.17 | 0.13 | 16.04 | 0.21 |
| 2183 | VEGFC: (VEGFC) VASCULAR ENDOTHELIAL GROWTH FACTOR C PRECURSOR (VEGF-C) (VASCULAR ENDOTHELIAL GROWTH FACTOR RELATED PROTEIN) (VRP) (FLT4 LIGAND) (FLT4-L). | 1.33 | 0.54 | 0.58 | 5.76 | 0.57 |
| 2193 | PLCG1: (PLCG1 OR PLC1) 1-PHOSPHATIDYLINOSITOL-4,5-BISPHOSPHATE PHOSPHODIESTERASE GAMMA 1 (EC 3.1.4.11) (PLC-GAMMA-1) (PHOSPHOLIPASE C-GAMMA-1) (PLC-II) (PLC-148). | 2.1 | 1.58 | 0.91 | 1.21 | 1.11 |
| 2195 | PLCG2: (PLCG2) 1-PHOSPHATIDYLINOSITOL-4,5-BISPHOSPHATE PHOSPHODIESTERASE GAMMA 2 (EC 3.1.4.11) (PLC-GAMMA-2) (PHOSPHOLIPASE C-GAMMA-2) (PLC-IV). | 0.48 | 0.74 | 0.74 | | 0.64 |
| 2211 | GAPD: (GAPD) GLYCERALDEHYDE 3-PHOSPHATE DEHYDROGENASE, LIVER (EC 1.2.1.12) (GAPDH). | 0.71 | 0.8 | 1.09 | 2.05 | 1.89 |
| 2260 | COL1A1: (COL1A1) COLLAGEN ALPHA 1(I) CHAIN PRECURSOR. | 0.87 | 0.1 | 0.06 | 8.74 | 0.08 |
| 2262 | COL10A1: (COL10A1) COLLAGEN ALPHA 1(X) CHAIN PRECURSOR. | | 1.51 | | | 1.03 |
| 2264 | COL11A1: (COL11A1) COLLAGEN ALPHA 1(XI) CHAIN PRECURSOR. | 0.59 | 0.3 | 0.26 | 1.96 | 0.32 |
| 2266 | COL12A1: (COL12A1) COLLAGEN ALPHA 1(XII) CHAIN PRECURSOR. | | | | 26.69 | |
| 2271 | COL14A1: (COL14A1) EXTRACELLULAR MATRIX PROTEIN COLLAGEN TYPE XIV, C-TERMINUS (FRAGMENT) (UNDULIN). | 0.55 | 0.24 | 0.3 | 1.33 | 0.31 |
| 2275 | COL15A1: (COL15A1) COLLAGEN ALPHA 1(XV) CHAIN PRECURSOR. | 0.62 | 0.6 | 0.31 | 1.57 | 0.54 |
| 2277 | COL16A1: (COL16A1) COLLAGEN ALPHA 1(XVI) CHAIN PRECURSOR. | 0.65 | 0.33 | 0.25 | 21.47 | 0.26 |
| 2281 | COL18A1_2: (COL18A1) COLLAGEN ALPHA 1(XVIII) CHAIN [CONTAINS: ENDOSTATIN]. | 1.51 | 3.83 | 1.14 | 1.94 | 5.37 |
| 2289 | COL4A1: (COL4A1) COLLAGEN ALPHA 1(IV) CHAIN PRECURSOR (ARRESTEN). | 1.03 | 0.96 | 0.79 | 7.98 | 0.95 |
| 2293 | COL6A1: (COL6A1) COLLAGEN (VI) ALPHA-1 CHAIN (FRAGMENT) COLLAGEN ALPHA 1(VI) CHAIN PRECURSOR. | 0.42 | 0.2 | 0.2 | 4.83 | 0.22 |
| 2295 | COL7A1: (COL7A1) COLLAGEN ALPHA 1(VII) CHAIN PRECURSOR (LONG-CHAIN COLLAGEN) (LC COLLAGEN). | 0.9 | 0.99 | 0.54 | 4.24 | 1.08 |
| 2297 | COL8A1: (COL8A1) COLLAGEN ALPHA 1(VIII) CHAIN PRECURSOR (ENDOTHELIAL COLLAGEN). | 0.33 | 0.04 | 0.03 | 8.43 | 0.03 |
| 2299 | COL9A1_1: (COL9A1) COLLAGEN ALPHA 1(IX) CHAIN PRECURSOR. | 1.12 | 0.88 | 2.2 | 2.09 | 1.36 |
| 2301 | COL1A2: (COL1A2) COLLAGEN ALPHA 2(I) CHAIN PRECURSOR. | 0.65 | 0.03 | 0.02 | 12.07 | 0.02 |

Fig 3-9

| | | | | | | | |
|---|---|---|---|---|---|---|---|
| 2307 | COL5A2: (COL5A2) COLLAGEN ALPHA 2(V) CHAIN PRECURSOR. | 0.44 | 0.05 | 0.05 | 9.18 | 0.06 |
| 2309 | COL6A2_1: (COL6A2) COLLAGEN ALPHA 2(VI) CHAIN PRECURSOR. COLLAGEN VI ALPHA-2 C-TERMINAL GLOBULAR DOMAIN (FRAGMENT). (DKFZP586E1322). | 0.66 | 0.08 | 0.04 | 7.85 | 0.04 |
| 2315 | COL4A3_1: (COL4A3) COLLAGEN ALPHA 3(IV) CHAIN PRECURSOR. | 0.52 | 0.72 | 0.75 | 1.74 | 0.74 |
| 2324 | INTEGRINA7: (ITGA7) INTEGRIN ALPHA-7 (INTEGRIN ALPHA 7 CHAIN) (INTEGRIN ALPHA-7). | 0.72 | 0.6 | 0.75 | 5.6 | 0.54 |
| 2326 | INTEGRINA8: (ITGA8) INTEGRIN ALPHA-8. | 1.03 | 1.24 | 0.89 | 1.83 | 1.03 |
| 2330 | INTEGRINB5: (ITGB5) INTEGRIN BETA-5 PRECURSOR. | 1.19 | 0.05 | 0.06 | 15.04 | 0.46 |
| 2332 | INTEGRINB6: (ITGB6) INTEGRIN BETA-6 PRECURSOR. | 0.72 | 0.56 | 0.55 | 3.38 | 0.61 |
| 2334 | INTEGRINB7: (ITGB7) INTEGRIN BETA-7 PRECURSOR. | 3.39 | 1.52 | 1.06 | 0.14 | 1.6 |
| 2336 | ITGB8: (ITGB8) INTEGRIN BETA-8 PRECURSOR. | 0.67 | 0.16 | 0.1 | 9.96 | 0.09 |
| 2338 | PAI1: (SERPINE1 OR PAI1 OR PLANH1) PLASMINOGEN ACTIVATOR INHIBITOR-1 PRECURSOR (PAI-1) (ENDOTHELIAL PLASMINOGEN ACTIVATOR INHIBITOR) (PAI). | 1.08 | 0.08 | 0.07 | 8.83 | 0.09 |
| 2340 | PAI2: (SERPINB2 OR PAI2 OR PLANH2) PLASMINOGEN ACTIVATOR INHIBITOR-2 PRECURSOR (PAI-2) (PLACENTAL PLASMINOGEN ACTIVATOR INHIBITOR) (MONOCYTE ARG-SERPIN) (UROKINASE INHIBITOR). | 1.94 | 0.79 | 1.99 | | 1.35 |
| 2342 | TACE: (ADAM17 OR TACE OR CSVP) ADAM 17 PRECURSOR (EC 3.4.24.-) (A DISINTEGRIN AND METALLOPROTEINASE DOMAIN 17) (TNF-ALPHA CONVERTING ENZYME) (TNF-ALPHA CONVERTASE) (SNAKE VENOM-LIKE PROTEASE) (CD156B ANTIGEN). | 1.04 | 1.88 | 1.03 | 1.61 | 2.42 |
| 2344 | TIMP1: (TIMP1 OR TIMP OR CLGI) METALLOPROTEINASE INHIBITOR 1 PRECURSOR (TIMP-1) (ERYTHROID POTENTIATING ACTIVITY) (EPA) (TISSUE INHIBITOR OF METALLOPROTEINASES) (FIBROBLAST COLLAGENASE INHIBITOR) (COLLAGENASE INHIBITOR). | 0.57 | 0.15 | 0.33 | 5.67 | 3.86 |
| 2346 | TIMP2: (TIMP2) METALLOPROTEINASE INHIBITOR 2 PRECURSOR (TIMP-2) (TISSUE INHIBITOR OF METALLOPROTEINASES-2) (CSC-21K). | 0.22 | 0.37 | 0.36 | 1.09 | 1.24 |
| 2348 | TIMP3: (TIMP3) METALLOPROTEINASE INHIBITOR 3 PRECURSOR (TIMP-3) (TISSUE INHIBITOR OF METALLOPROTEINASES-3) (MIG-5 PROTEIN). | 0.97 | 0.35 | 0.51 | 14.51 | 0.34 |
| 2352 | TPA: (PLAT) TISSUE-TYPE PLASMINOGEN ACTIVATOR PRECURSOR (EC 3.4.21.68) (TPA) (T-PA) (T-PLASMINOGEN ACTIVATOR) (ALTEPLASE) (RETEPLASE). | 1.58 | 0.61 | 0.42 | 2.25 | 1.01 |
| 2354 | UPA: (PLAU) UROKINASE-TYPE PLASMINOGEN ACTIVATOR PRECURSOR (EC 3.4.21.73) (UPA) (U-PLASMINOGEN ACTIVATOR). | 0.72 | 0.15 | 0.59 | 0.74 | 1.43 |
| 2356 | BMP7: (BMP7 OR BMP-7 OR OP1) BONE MORPHOGENETIC PROTEIN 7 PRECURSOR (BMP-7) (OSTEOGENIC PROTEIN 1) (OP-1). | 1.05 | 1.13 | 1.38 | 1.69 | 1.18 |
| 2360 | LAMA1: (LAMA1 OR LAMA) LAMININ ALPHA-1 CHAIN PRECURSOR (LAMININ A CHAIN). | 0.7 | 0.21 | 0.18 | 7.44 | 0.15 |

Fig 3-10

| | | | | | | | |
|---|---|---|---|---|---|---|---|
| 2362 | LAMA2: (LAMA2 OR LAMM) LAMININ ALPHA-2 CHAIN PRECURSOR (LAMININ M CHAIN) (MEROSIN HEAVY CHAIN). | | | | 0.33 | 7.19 | 0.54 |
| 2364 | LAMA3: (LAMA3) LAMININ ALPHA-3 CHAIN PRECURSOR (EPILIGRIN 170 KDA SUBUNIT) (E170). | 0.74 | 0.79 | 0.52 | 0.77 | 1.07 |
| 2366 | LAMA4: (LAMA4) LAMININ ALPHA-4 CHAIN PRECURSOR. | 0.38 | 0.21 | 0.16 | 1.9 | 0.19 |
| 2368 | LAMA5: (KIAA0533 OR LAMA5) KIAA0533 PROTEIN (LAMININ ALPHA 5 CHAIN) (FRAGMENT). | 1.17 | 2.12 | 1.22 | 2.3 | 2.04 |
| 2370 | LAMB1: (LAMB1) LAMININ BETA-1 CHAIN PRECURSOR (LAMININ B1 CHAIN). | 0.53 | 0.18 | 0.26 | 3.23 | 0.81 |
| 2375 | LAMB3: (LAMB3) LAMININ BETA-3 CHAIN PRECURSOR (LAMININ B1K CHAIN) (KALININ B1 CHAIN). | 0.51 | 0.8 | 0.69 | 1.36 | 1.19 |
| 2377 | LAMG1: (LAMC1 OR LAMB2) LAMININ GAMMA-1 CHAIN PRECURSOR (LAMININ B2 CHAIN). | 0.6 | 0.09 | 0.19 | 6.3 | 0.32 |
| 2400 | COL4A6: (COL4A6) COLLAGEN TYPE IV A6 CHAIN. | 1.57 | 1.47 | 1.22 | 1.21 | 1.3 |
| 2403 | COL4A5: (COL4A5) COLLAGEN ALPHA 5(IV) CHAIN PRECURSOR. | 1.59 | 0.69 | 1.22 | 1.36 | 1.44 |
| 2423 | AGGRECAN1: (AGC1 OR CSPG1 OR AGC) AGGRECAN CORE PROTEIN PRECURSOR (CARTILAGE-SPECIFIC PROTEOGLYCAN CORE PROTEIN) (CSPCP) (CHONDROITIN SULFATE PROTEOGLYCAN CORE PROTEIN 1). | 0.87 | 1.18 | 0.81 | 2.34 | 1.07 |
| 2425 | AGRIN: (AGRN) AGRIN PRECURSOR. | 0.95 | 1.42 | 0.75 | 0.73 | 1.05 |
| 2429 | BAMACAN: (BAM OR SMCD OR HCAP OR CSPG6 OR SMC3 OR SMC3L1 OR BMH) STRUCTURAL MAINTENANCE OF CHROMOSOME 3 (CHONDROITIN SULFATE PROTEOGLYCAN 6) (CHROMOSOME SEGREGATION PROTEIN SMCD) (BAMACAN) BASEMENT MEMBRANE-ASSOCIATED CHONDROITIN PROTEOGLYCAN) (HCAP). | 0.99 | 0.65 | 2.39 | 1.27 | 1.09 |
| 2433 | BMP1_1: (BMP1 OR PCP-3) BONE MORPHOGENETIC PROTEIN 1 PRECURSOR (EC 3.4.24.-) (BMP-1) PROCOLLAGEN C-PROTEINASE 3. | 0.77 | 0.7 | 0.68 | 4.93 | 0.75 |
| 2439 | BCAN: (BCAN) BREVICAN CORE PROTEIN PRECURSOR (CHONDROITIN SULFATE PROTEOGLYCAN BEHAB/BREVICAN). | | 0.62 | 1.38 | 0.6 | 1.34 |
| 2451 | FIBROMODULIN: (FMOD OR FM) FIBROMODULIN PRECURSOR (FM) (COLLAGEN-BINDING 59 KDA PROTEIN). | 1.07 | 1.45 | 0.79 | 0.74 | 1.02 |
| 2453 | FN1: (FN1 OR FN) FIBRONECTIN PRECURSOR (FN) (COLD-INSOLUBLE GLOBULIN) (CIG). | 0.88 | 0.00838027 | 0.00811593 | 7.46 | 0.01 |
| 2473 | LUMICAN: (LDC) LUMICAN PRECURSOR (LUM) (KERATAN SULFATE PROTEOGLYCAN). | 0.56 | 0.16 | 0.14 | 18.39 | 0.14 |
| 2489 | MMP11: (MMP11 OR STMY3) STROMELYSIN-3 PRECURSOR (EC 3.4.24.-) (MATRIX METALLOPROTEINASE-11) (MMP-11) (ST3) (SL-3). | 0.71 | 1.03 | 1.13 | 1.83 | 0.91 |
| 2491 | MMP12: (MMP12 OR HME) MACROPHAGE METALLOELASTASE PRECURSOR (EC 3.4.24.65) (HME) (MATRIX METALLOPROTEINASE-12) (MMP-12). | 0.89 | 1.09 | 0.8 | 0.82 | 1.55 |

Fig 3-11

| | | | | | | |
|---|---|---|---|---|---|---|
| 2493 | MMP13: (MMP13) COLLAGENASE 3 PRECURSOR (EC 3.4.24.-) (MATRIX METALLOPROTEINASE-13) (MMP-13). | | | 1.42 | | 2.9 |
| 2501 | MMP2: (MMP2 OR CLG4A) 72 KDA TYPE IV COLLAGENASE PRECURSOR (EC 3.4.24.24) (72 KDA GELATINASE) (MATRIX METALLOPROTEINASE-2) (MMP-2) (GELATINASE A) (TBE-1). | 0.76 | | 0.33 | 0.31 | 2.09 | 0.51 |
| 2509 | MMP9: (MMP9 OR CLG4B) 92 KDA TYPE IV COLLAGENASE PRECURSOR (EC 3.4.24.35) (92 KDA GELATINASE) (MATRIX METALLOPROTEINASE-9) (MMP-9) (GELATINASE B) (GELB). | 0.76 | | 16.12 | 1.99 | 0.49 | 21.55 |
| 2517 | OPN: (SPP1 OR OPN) OSTEOPONTIN PRECURSOR (BONE SIALOPROTEIN 1) (URINARY STONE PROTEIN) (SECRETED PHOSPHOPROTEIN 1) (SPP-1) (NEPHROPONTIN) (UROPONTIN). | 0.95 | | 1.21 | 1.88 | 0.84 | 17.02 |
| 2519 | OSF: (OSTF1 OR SH3D3 OR SH3P2) OSTEOCLAST STIMULATING FACTOR 1 (SH3 DOMAIN PROTEIN 3). | 1.45 | | 0.89 | 1.44 | 0.52 | 1.08 |
| 2527 | DCN_1: (DCN) BONE PROTEOGLYCAN II PRECURSOR (PG-S2) (DECORIN) (PG40) (PGS2). | 0.33 | | 0.01 | 0.0087354 8 | 5.66 | 0.0086 1886 |
| 2531 | RYUDOCAN: (SDC4) SYNDECAN-4 PRECURSOR (AMPHIGLYCAN) (SYND4) (RYUDOCAN CORE PROTEIN). | 1.26 | | 1.51 | 1.68 | 1.77 | 1.23 |
| 2541 | TNC: (TNC OR HXB) TENASCIN PRECURSOR (TN) (HEXABRACHION) (CYTOTACTIN) (NEURONECTIN) (GMEM) (JI) (MIOTENDINOUS ANTIGEN) (GLIOMA-ASSOCIATED- EXTRACELLULAR MATRIX ANTIGEN) (GP 150-225) (TENASCIN-C) (TN-C). | | | 0.66 | 0.43 | 4.91 | 0.4 |
| 2545 | TENASCINX: (TNXB OR TNX OR XB OR HXBL) TENASCIN-X PRECURSOR (TN-X) (HEXABRACHION-LIKE) (TNXB ISOFORM 1) (TNXA). | 0.99 | | 1.51 | 1.12 | 1.12 | 0.97 |
| 2549 | THROMBOSPONDIN2: (THBS2 OR TSP2) THROMBOSPONDIN 2 PRECURSOR. | 0.71 | | 0.12 | 0.11 | 10.19 | 0.09 |
| 2555 | THROMBOSPONDIN1: (THBS1 OR TSP1 OR TSP) THROMBOSPONDIN 1 PRECURSOR. | 0.89 | | 0.99 | 0.53 | 3.94 | 0.8 |
| 2557 | THROMBOSPONDIN5: (COMP) CARTILAGE OLIGOMERIC MATRIX PROTEIN PRECURSOR (COMP). | | | 2.11 | 1.35 | 33.83 | 1.98 |
| 2560 | MMP19: (MMP19 OR MMP18 OR RASI) MATRIX METALLOPROTEINASE-19 PRECURSOR (EC 3.4.24.-) (MMP-19) (MATRIX METALLOPROTEINASE RASI) (MMP-18). | 0.39 | | 0.39 | 0.58 | 2.58 | 1.31 |
| 2936 | IL6: (IL6 OR IFNB2 OR IL-6) INTERLEUKIN-6 PRECURSOR (IL-6) (B-CELL STIMULATORY FACTOR 2) (BSF-2) (INTERFERON BETA-2) (HYBRIDOMA GROWTH FACTOR). | 1.05 | | 0.45 | 0.29 | 5.49 | 0.57 |
| 2965 | BMP4: (BMP4 OR BMP2B OR BMP-4 OR DVR4 OR BMP-4 OR DVR-4) BONE MORPHOGENETIC PROTEIN 4 PRECURSOR (BMP-4) (BMP-2B). | 1.37 | | 2.47 | 1.2 | 1.49 | 0.95 |
| 3018 | HPRT: (HPRT1 OR HPRT) HYPOXANTHINE-GUANINE PHOSPHORIBOSYLTRANSFERASE (EC 2.4.2.8) (HGPRT) (HGPRTASE). | 1.38 | | 1.18 | 1.81 | 0.98 | 1.26 |
| 3058 | PRDC: (PRDC) PRDC (FLJ21195). | | | | | 5.17 | |

Fig 3-12

| | | | | | | |
|---|---|---|---|---|---|---|
| 3385 | CSPG2_1: (CSPG2) VERSICAN CORE PROTEIN PRECURSOR (LARGE FIBROBLAST PROTEOGLYCAN) (CHONDROITIN SULFATE PROTEOGLYCAN CORE PROTEIN 2) (GLIAL HYALURONATE- BINDING PROTEIN) (GHAP). | 0.07 | 0.21 | 0.24 | 0.83 | 0.12 |
| 3454 | ITGAM: (ITGAM OR CR3A OR CD11B) INTEGRIN ALPHA-M PRECURSOR (CELL SURFACE GLYCOPROTEIN MAC-1 ALPHA SUBUNIT) (CR-3 ALPHA CHAIN) (CD11B) (LEUKOCYTE ADHESION RECEPTOR MO1) (INTEGRIN ALPHA-M) (NEUTROPHIL ADHERENCE RECEPTOR). | 0.61 | 0.97 | | | 0.93 |
| 3535 | JUN: (JUN) TRANSCRIPTION FACTOR AP-1 (ACTIVATOR PROTEIN 1) (AP1) (PROTO-ONCOGENE C-JUN) (V-JUN AVIAN SARCOMA VIRUS 17 ONCOGENE HOMOLOG) (P39). | 0.38 | 0.34 | 0.32 | 0.7 | 0.3 |
| 3540 | ATF2: (ATF2 OR CREB2 OR CREBP1) CYCLIC-AMP-DEPENDENT TRANSCRIPTION FACTOR ATF-2 (ACTIVATING TRANSCRIPTION FACTOR 2) (CAMP RESPONSE ELEMENT BINDING PROTEIN CRE- BP1) (HB16). | 1.07 | 0.64 | 1.29 | 4.19 | |
| 3562 | ATF4: (ATF4) CYCLIC-AMP-DEPENDENT TRANSCRIPTION FACTOR ATF-4 (DNA-BINDING PROTEIN TAXREB67) (CYCLIC AMP RESPONSE ELEMENT-BINDING PROTEIN 2) (CREB2). | 0.89 | 1.21 | 1.66 | 1.63 | 1.43 |
| 3591 | HSPA4_1: (HSPA4 OR HSP110 OR IRP94) HEAT SHOCK 70 KDA PROTEIN 4 (HEAT SHOCK 70-RELATED PROTEIN APG-2) (HSP70RY) (ISCHEMIA RESPONSIVE 94 KDA PROTEIN). | 0.8 | 0.35 | 1.98 | 1.28 | 1.32 |
| 3594 | HSPA9: (HSPA9B OR HSPA9 OR GRP75) MITOCHONDRIAL STRESS-70 PROTEIN PRECURSOR (75 KDA GLUCOSE REGULATED PROTEIN) (GRP 75) (PEPTIDE-BINDING PROTEIN 74) (PBP74) (MORTALIN) (MOT). | 0.94 | 0.45 | 2.41 | 2.35 | 1.2 |
| 3600 | ORP150: (HYOU1 OR ORP150) 150 KDA OXYGEN REGULATED HSP70 FAMILY PROTEIN (ORP150) (CAB140 OR GRP170) (HYPOXIA UP-REGULATED 1). | 0.8 | 0.85 | 1.73 | 2.26 | 1.4 |
| 3608 | CEBPB: (CEBPB OR TCF5) CCAAT/ENHANCER BINDING PROTEIN BETA (C/EBP BETA) (NUCLEAR FACTOR NF-IL6) (TRANSCRIPTION FACTOR 5). | 0.2 | 0.54 | 0.14 | 0.39 | 0.38 |
| 3614 | CEBPG: (CEBPG) CCAAT/ENHANCER BINDING PROTEIN GAMMA (C/EBP GAMMA). | 0.54 | 0.34 | 0.83 | 2.36 | 1.5 |
| 3644 | JUNB: (JUNB) TRANSCRIPTION FACTOR JUN-B (G0S3). | 0.81 | 0.74 | 0.17 | 0.33 | 0.15 |
| 3676 | FOXG1A-FOXG1B: (FOXG1B OR FKHL1) FORKHEAD PROTEIN G1B (FORKHEAD-RELATED PROTEIN FKHL1) (TRANSCRIPTION FACTOR BF-1) (BRAIN FACTOR 1) (BF1) (HFK1) (FOXG1A OR FKHL2) FORKHEAD BOX PROTEIN G1A (FORKHEAD-RELATED PROTEIN FKHL2) (TRANSCRIPTION FACTOR BF-2). | 1.69 | 1.13 | 0.82 | 0.85 | 1.27 |
| 3680 | FAST1: (FOXH1 OR FAST1) FORKHEAD BOX PROTEIN H1 (FORKHEAD ACTIVIN SIGNAL TRANSDUCER 1) (FAST-1). (FOXH1 OR FAST2) FORKHEAD ACTIVIN SIGNAL TRANSDUCER 2. TGF-BETA/ACTIVIN SIGNAL TRANSDUCER FAST-1P. | 1.6 | 1.46 | 1.22 | 1.12 | 1.04 |
| 3684 | FKHL16: (FOXM1 OR FKHL16 OR HFH11 OR WIN OR MPP2) FORKHEAD PROTEIN M1 (FORKHEAD-RELATED PROTEIN FKHL16) (HEPATOCYTE NUCLEAR FACTOR 3 FORKHEAD HOMOLOG 11) (HNF-3/FORK-HEAD HOMOLOG-3) (HFH-11) (WINGED | 0.67 | 0.25 | 0.92 | 9.9 | 0.37 |

Fig 3-13

| ID | Description | | | | | | |
|---|---|---|---|---|---|---|---|
| 3686 | HELIX FACTOR FROM INS-1 CELLS) (M-PHASE PHOSPHOPROTEIN 2 | | | | | | |
| 3707 | FKHR: (FOXO1A OR FKHR) FORKHEAD PROTEIN O1A (FORKHEAD IN RHABDOMYOSARCOMA). | 2.1 | 1.26 | 0.35 | 0.89 | | 0.35 |
| 3709 | HNF3A: (FOXA1 OR HNF3A OR TCF3A) HEPATOCYTE NUCLEAR FACTOR 3-ALPHA (HNF-3A). | 1.31 | 1.35 | 1.3 | | | 1.51 |
| 3711 | HNF3B: (FOXA2 OR HNF3B OR TCF3B) HEPATOCYTE NUCLEAR FACTOR 3-BETA (HNF-3B). | 0.78 | 0.87 | 1.13 | 3.25 | | 0.98 |
| 3719 | HNF3G: (FOXA3 OR TCF-3G OR HNF3G OR TCF3G) HEPATOCYTE NUCLEAR FACTOR 3-GAMMA (HNF-3G) (FORK HEAD-RELATED PROTEIN FKH H3). | 0.85 | 1.59 | 1.79 | 1.66 | | 1.46 |
| | MFH1: (FOXC2 OR FKHL14 OR MFH1) FORKHEAD BOX PROTEIN C2 (FORKHEAD-RELATED PROTEIN FKHL14) (MESENCHYME FORK HEAD PROTEIN 1) (MFH-1 PROTEIN) (TRANSCRIPTION FACTOR FKH-14). | 1.58 | | | | | |
| 3896 | CNP: (CNP) 2',3'-CYCLIC NUCLEOTIDE 3'-PHOSPHODIESTERASE (EC 3.1.4.37) (CNP) (CNPASE) (CNPI) (CNPII). | 0.88 | 0.82 | 1.11 | 1.65 | | 0.68 |
| 3919 | MAP-2: (MAP2) MICROTUBULE-ASSOCIATED PROTEIN 2 (MAP2B) [CONTAINS: MAP2C]. | 1.61 | 1.2 | 0.85 | 1.46 | | 1.22 |
| 3929 | MUSLAMR: (P40-8 OR LAMR1 OR RPSA OR LAMBR) LAMININ REZEPTOR 40S RIBOSOMAL PROTEIN SA (P40) (34/67 KD LAMININ RECEPTOR) (COLON CARCINOMA LAMININ-BINDING PROTEIN) (NEM/1CHD4). | 2.46 | 1.58 | 1.61 | 0.72 | | 1.15 |
| 3945 | OSP: (OTM OR OSP OR CLDN11) CLAUDIN-11 (OLIGODENDROCYTE SPECIFIC PROTEIN) (OLIGODENDROCYTE TRANSMEMBRANE PROTEIN). | 0.53 | 0.34 | 0.41 | 0.38 | | 0.42 |
| 3953 | S100B: (S100B) S-100 PROTEIN, BETA CHAIN. | 2.19 | 1.13 | 1.76 | 0.65 | | 2.71 |
| 4042 | IKKA: (IKK ALPHA OR CHUK) INHIBITOR OF NUCLEAR FACTOR KAPPA-B KINASE ALPHA SUBUNIT (EC 2.7.1.-) (I KAPPA-B KINASE ALPHA) (IKBKA) (IKK-ALPHA) (IKK-A) (IKAPPAB KINASE) (I-KAPPA-B KINASE 1) (IKK1) (CONSERVED HELIX-LOOP-HELIX UBIQUITOUS KINASE) (NUCLEAR FACTO | 1.07 | 1.47 | 0.99 | 0.89 | | 0.98 |
| 4045 | IKKB: (IKKB OR IKBKB) INHIBITOR OF NUCLEAR FACTOR KAPPA B KINASE BETA SUBUNIT (EC 2.7.1.-) (I-KAPPA-B-KINASE BETA) (IKBKB) (IKK-BETA) (IKK-B) (I-KAPPA-B KINASE 2) (IKK2) (NUCLEAR FACTOR NF-KAPPA-B INHIBITOR KINASE BETA) (NFKBIKB). | 0.95 | 0.65 | 0.83 | 0.43 | | 0.69 |
| 4064 | NFATCB_1: (NFATC1 OR NFATC OR NFAT2) NUCLEAR FACTOR OF ACTIVATED T-CELLS, CYTOPLASMIC 1 (NFAT TRANSCRIPTION COMPLEX CYTOSOLIC COMPONENT) (NF-ATC1) (NF-ATC). | 0.81 | 0.77 | 1.23 | 1.6 | | 1.02 |
| 4068 | NFKB1: (NFKB1) NUCLEAR FACTOR NF-KAPPA-B P105 SUBUNIT (DNA-BINDING FACTOR KBF1) (EBP-1) [CONTAINS: NUCLEAR FACTOR NF-KAPPA-B P50 SUBUNIT]. | 1.31 | 1.05 | 1.38 | 0.55 | | 0.8 |
| 4070 | NFKB2: (NFKB2) NUCLEAR FACTOR NF-KAPPA-B P100 SUBUNIT (H2TF1) (ONCOGENE LYT-10) (LYT10) [CONTAINS: NUCLEAR FACTOR NF-KAPPA-B P52 SUBUNIT]. | 1.22 | 1.14 | 0.68 | 0.68 | | 0.7 |
| 4072 | NFKB3: (RELA OR NFKB3) TRANSCRIPTION FACTOR P65 (NUCLEAR FACTOR NF- | 0.91 | 0.49 | 0.41 | 5.88 | | 0.26 |

Fig 3-14

| | | | | | | | |
|---|---|---|---|---|---|---|---|
| | KAPPA-B P65 SUBUNIT). | | | | | | |
| 4181 | ASCL1: (ASCL1 OR ASH1 OR MASH1 OR MASH-1) ACHAETE-SCUTE HOMOLOG 1 (MASH-1) (HASH1). | 1.82 | 1.63 | 0.58 | 3.34 | 0.6 | |
| 4197 | HIF1A: (HIF1A) HYPOXIA-INDUCIBLE FACTOR 1 ALPHA (HIF-1 ALPHA) (ARNT INTERACTING PROTEIN) (MEMBER OF PAS PROTEIN 1) (MOP1) (HIF1 ALPHA). | 0.73 | 0.47 | 0.42 | 1.67 | 0.37 | |
| 4199 | ID1: (ID1 OR ID) DNA-BINDING PROTEIN INHIBITOR ID-1 (ID) | 0.2 | 0.0067259 | 0.03 | 0.39 | 0.03 | |
| 4201 | ID2: (ID2) DNA-BINDING PROTEIN INHIBITOR ID-2. | 0.86 | 0.45 | 0.58 | 0.57 | 1.11 | |
| 4203 | ID3: (ID3 OR 1R21 OR HEIR-1) DNA-BINDING PROTEIN INHIBITOR ID-3 (ID-LIKE PROTEIN INHIBITOR HLH 1R21) (HELIX-LOOP-HELIX PROTEIN HEIR-1). | 0.42 | 0.07 | 0.07 | 2.17 | 0.19 | |
| 4233 | NEUROD1: (NEUROD1 OR NEUROD) NEUROGENIC DIFFERENTIATION FACTOR 1. | 1.33 | 1.61 | 1.36 | 1.43 | 1.82 | |
| 4237 | NEUROG1: (NEUROG1 OR NGN1 OR NEUROD3 OR NGN) NEUROGENIN 1 (NEUROGENIC DIFFERENTIATION FACTOR 3) (NEUROD3) (NEUROGENIC BASIC-HELIX-LOOP-HELIX PROTEIN). | 1.3 | 1.87 | | | 0.85 | |
| 4241 | NMYC: (MYCN OR NMYC) N-MYC PROTO-ONCOGENE PROTEIN. | | 0.99 | 1.63 | | | |
| 4251 | TAL1: (TAL1 OR SCL OR TCL5) T-CELL ACUTE LYMPHOCYTIC LEUKEMIA-1 PROTEIN (TAL-1 PROTEIN) (STEM CELL PROTEIN) (T-CELL LEUKEMIA/LYMPHOMA-5 PROTEIN). | 2.14 | 7.5 | 1.23 | 3.67 | 0.76 | |
| 4255 | TCF3: (TCF3 OR E2A OR ITF1 OR TCFE2A OR ALF2 OR ME2) TRANSCRIPTION FACTOR E2-ALPHA (IMMUNOGLOBULIN ENHANCER BINDING FACTOR E12/E47) (TRANSCRIPTION FACTOR-3) (TCF-3) (IMMUNOGLOBULIN TRANSCRIPTION FACTOR-1) (TRANSCRIPTION FACTOR ITF-1) (TRANSCRIPTIONAL REGU | 0.85 | 1.04 | 0.86 | 1.63 | 0.97 | |
| 4257 | TCF4: (TCF4 OR ITF2 OR SEF2) TRANSCRIPTION FACTOR 4 (IMMUNOGLOBULIN TRANSCRIPTION FACTOR 2) (RITF-2) (ITF-2) (SL3-3 ENHANCER FACTOR 2) (SEF-2) (CLASS A HELIX-LOOP-HELIX TRANSCRIPTION FACTOR ME2). | 0.46 | 0.39 | 1.07 | 1.05 | 0.31 | |
| 4275 | EBCTF: (EBF) EARLY B-CELL TRANSCRIPTION FACTOR (FRAGMENT). (COE1 OR OLF1) TRANSCRIPTION FACTOR COE1 (OE-1) (O/E-1) (OLFACTORY NEURONAL TRANSCRIPTION FACTOR) (OLF-1). | 0.6 | 0.32 | 0.22 | 1.32 | 0.13 | |
| 4279 | HAND1: (HAND1 OR EHAND) HEART- AND NEURAL CREST DERIVATIVES-EXPRESSED PROTEIN 1 (EXTRAEMBRYONIC TISSUES, HEART, AUTONOMIC NERVOUS SYTEM AND NEURAL CREST DERIVATIVES-EXPRESSED PROTEIN 1) (EHAND) (BASIC HELIX-LOOP-HELIX PROTEIN HAND1) (THING1). | 1.51 | 1.65 | 0.8 | 0.83 | 1.16 | |
| 4289 | HESR1: (HESR-1 OR CHF2 OR HEY1) HAIRY AND ENHANCER OF SPLIT RELATED-1 (HEY1 PROTEIN). | 0.7 | 0.43 | 0.29 | 6.68 | 0.26 | |
| 4321 | NGN3: (NEUROG3 OR NGN3 OR ATOH5 OR ATH4B) NEUROGENIN 3 (ATONAL PROTEIN HOMOLOG 5) (HELIX-LOOP-HELIX PROTEIN MATH-4B) (MATH4B) (RELAX). | 0.84 | 0.65 | 1.64 | 1.33 | 1.13 | |
| 4331 | RACK17: (OLIG2 OR BHLHB1 OR PRKCBP2 OR RACK17) OLIGODENDROCYTE | 0.96 | 1.18 | 1.41 | 1.73 | 1.08 | |

Fig 3-15

| | | | | | | | |
|---|---|---|---|---|---|---|---|
| 4398 | TRANSCRIPTION FACTOR 2 (BASIC HELIX-LOOP-HELIX PROTEIN CLASS B 1) (PROTEIN KINASE C-BINDING PROTEIN RACK17) (PROTEIN KINASE C BINDING PROTEIN 2). | | 0.99 | | 1.24 | 1.24 | 1.47 |
| 4418 | BRACHYURY: (T) BRACHYURY PROTEIN (T PROTEIN). | 0.54 | | 1.74 | 0.46 | 0.65 | 0.5 | 0.25 |
| 4446 | MEF-2C: (MEF2C) MYOCYTE-SPECIFIC ENHANCER FACTOR 2C. | 1.65 | 0.93 | 1.51 | 1.19 | 0.83 |
| 4528 | TBX3: (TBX3) T-BOX TRANSCRIPTION FACTOR TBX3 (T-BOX PROTEIN 3). | 0.83 | 0.75 | 0.56 | 5.62 | 0.54 |
| 4683 | CXCL12: (SDF1) STROMAL CELL-DERIVED FACTOR 1 PRECURSOR (SDF-1) (PRE-B CELL GROWTH STIMULATING FACTOR) (PBSF) | 1.14 | 1.06 | 0.97 | 2.15 | 0.82 |
| | BFGFR_1_HUMAN: (FGFR1 OR FLG OR FGFBR OR FLT2) BASIC FIBROBLAST GROWTH FACTOR RECEPTOR 1 PRECURSOR (BFGF-R) EC 2.7.1.112) (FMS-LIKE TYROSINE KINASE-2) (C-FGR). | | | | | |
| 4693 | EGFR-LONG: (EGFR OR ERBB1) EPIDERMAL GROWTH FACTOR RECEPTOR PRECURSOR (EC 2.7.1.112) (RECEPTOR PROTEIN-TYROSINE KINASE ERBB-1). | 0.94 | 0.82 | 0.59 | 3.27 | 0.51 |
| 4695 | FN1_EIIIA: (FN1 OR FN) FIBRONECTIN PRECURSOR (FIBRONECTIN EIIIA DOMAIN). | 0.64 | 0.08 | 0.04 | 1.72 | 0.03 |
| 4696 | ENOS: (NOS3) NITRIC-OXIDE SYNTHASE, ENDOTHELIAL (EC 1.14.13.39) (EC-NOS) (NOS, TYPE III) (NOSIII) (ENDOTHELIAL NOS) (ENOS) (CONSTITUTIVE NOS) (CNOS). | 1.43 | 1.1 | 2.41 | 1.3 | 1.49 |
| 4699 | EDN1: (EDN1) ENDOTHELIN-1 PRECURSOR (ET-1). | | 0.6 | | 2.47 | |
| 4701 | EDN2: (EDN2) ENDOTHELIN-2 PRECURSOR (ET-2) (VASOACTIVE INTESTINAL CONTRACTOR) (VIC). | | | | 2.88 | |
| 4705 | GFAP_1_HUMAN: (GFAP) GLIAL FIBRILLARY ACIDIC PROTEIN, ASTROCYTE (GFAP). | 0.98 | 0.5 | 1.61 | 1.62 | 1.3 |
| 4711 | HGF: (HGF OR HPTA) HEPATOCYTE GROWTH FACTOR PRECURSOR (SCATTER FACTOR) (SF) (HEPATOPOEITIN A). | 1.22 | 1.39 | 1.15 | 0.85 | 0.65 |
| 4715 | SERPINH1-SERPINH2: (SERPINH1 OR CBP1 OR HSP47) HEAT SHOCK PROTEIN 47 COLLAGEN BINDING PROTEIN 1 (CBP1) (COLLIGIN 1) (SERPINH2 OR CBP2) (COLLAGEN-BINDING PROTEIN 2 PRECURSOR) (COLLIGIN 2) (RHEUMATOID ARTHRITIS RELATED ANTIGEN RA-A47). | 0.69 | 0.05 | 0.22 | 8.25 | 0.12 |
| 4727 | IGF1R: (IGF1R) INSULIN-LIKE GROWTH FACTOR I RECEPTOR PRECURSOR (EC 2.7.1.112) (CD221 ANTIGEN). | 1.48 | 1.27 | 1.09 | 2.03 | 1.01 |
| 4736 | LIF: (LIF OR HILDA) LEUKEMIA INHIBITORY FACTOR PRECURSOR (LIF) (DIFFERENTIATION- STIMULATING FACTOR) (D FACTOR) (MELANOMA-DERIVED LPL INHIBITOR) (MLPLI) (CHOLINERGIC NEURONAL DIFFERENTIATION FACTOR). | 1.94 | 0.95 | 1.96 | 1.1 | 0.95 |
| 4739 | LIFRA: (LIFR) LEUKEMIA INHIBITORY FACTOR RECEPTOR PRECURSOR (LIF-R). | 2.07 | 1.24 | 1.34 | 1.02 | 3.22 |
| 4747 | M6PR_HUMAN: ((IGF2R OR MPRI) CATION-INDEPENDENT MANNOSE-6-PHOSPHATE RECEPTOR PRECURSOR (CI MAN-6-P RECEPTOR) (CI-MPR) (INSULIN-LIKE GROWTH FACTOR II RECEPTOR) (300 KDA MANNOSE 6-PHOSPHATE RECEPTOR) (MPR 300) (MPR300) (CD222 ANTIGEN). | 0.77 | 0.96 | 0.33 | 2.03 | 0.42 |
| 4764 | RARB2_1: (RARB OR NR1B2 OR HAP) RETINOIC ACID RECEPTOR BETA-2 (RAR-BETA- | 0.73 | 0.35 | 0.36 | 1.52 | 0.27 |

Fig 3-16

| ID | Description | | | | | | |
|---|---|---|---|---|---|---|---|
| | 2) (RAR-EPSILON). | | | | | | |
| 4765 | SMAD2: (MADH2 OR SMAD2 OR MADR2) MOTHERS AGAINST DECAPENTAPLEGIC HOMOLOG 2 (SMAD 2) (MOTHERS AGAINST DPP HOMOLOG 2) (MAD-RELATED PROTEIN 2) (HMAD-2) (JV18-1) (HSMAD2). | 1.13 | 0.66 | 0.92 | 0.85 | 0.93 |
| 4767 | SMAD3_HUMAN: (MADH3 OR SMAD3 OR MAD33) MOTHERS AGAINST DECAPENTAPLEGIC HOMOLOG 3 (SMAD 3) (MOTHERS AGAINST DPP HOMOLOG 3) (MAD3) (HMAD-3) (MMAD3) (JV15-2). | 0.81 | 0.47 | 0.54 | 1.15 | 0.33 |
| 4772 | SMAD7: (MADH7 OR SMAD7 OR MADH8) MOTHERS AGAINST DECAPENTAPLEGIC HOMOLOG 7 (SMAD 7) (MOTHERS AGAINST DPP HOMOLOG 7) (SMAD7) (HSMAD7). | 0.82 | 0.45 | 0.21 | 4.25 | 0.28 |
| 4775 | TGFBR1: (TGFBR1) TGF-BETA RECEPTOR TYPE I PRECURSOR (EC 2.7.1.37) (TGFR-1) (TGF-BETA TYPE I RECEPTOR) (SERINE/THREONINE-PROTEIN KINASE RECEPTOR R4) (SKR4) (ACTIVIN RECEPTOR-LIKE KINASE 5) (ALK-5). | 1.86 | 1.56 | 1.01 | | 1.66 |
| 4777 | TGFBR2: (TGFBR2) TGF-BETA RECEPTOR TYPE II PRECURSOR (EC 2.7.1.37) (TGFR-2) (TGF-BETA TYPE II RECEPTOR). | 0.78 | 0.53 | 0.52 | 0.51 | 0.52 |
| 4839 | HNF4A: (HNF4A OR NR2A1 OR TCF14 OR HNF4) HEPATOCYTE NUCLEAR FACTOR 4-ALPHA (HNF-4-ALPHA) (TRANSCRIPTION FACTOR HNF-4) (TRANSCRIPTION FACTOR 14). | 1.54 | 1.42 | 1.04 | 1.35 | 1.17 |
| 4841 | HNF4G: (HNF4G OR NR2A2) HEPATOCYTE NUCLEAR FACTOR 4-GAMMA (HNF4-GAMMA) | 2.19 | 0.93 | 2.13 | 0.87 | 1 |
| 4855 | LXR-ALPHA: (NR1H3 OR LXRA) OXYSTEROLS RECEPTOR LXR-ALPHA (LIVER X RECEPTOR ALPHA) (NUCLEAR ORPHAN RECEPTOR LXR-ALPHA). | 0.65 | 0.9 | 0.56 | 1.15 | 0.7 |
| 4893 | PPARG_HUMAN: (PPARG OR NR1C3) PEROXISOME PROLIFERATOR ACTIVATED RECEPTOR GAMMA (PPAR-GAMMA) (PPARG2). | | 1.24 | | | 3.24 |
| 4895 | RARG1: (RARG OR NR1B3) RETINOIC ACID RECEPTOR GAMMA-1 (RAR-GAMMA-1). | 1.01 | 0.44 | 0.86 | 4.77 | 0.54 |
| 4909 | RXRA: (RXRA OR NR2B1) RETINOIC ACID RECEPTOR RXR-ALPHA. | 0.63 | 2.31 | 0.35 | 0.95 | 0.45 |
| 4913 | RXRG: (RXRG OR NR2B3) RETINOIC ACID RECEPTOR RXR-GAMMA. | 0.81 | | | 1.66 | 0.24 |
| 4923 | TFCOUP1: (TFCOUP1 OR NR2F1 OR ERBAL3 OR EAR3) COUP TRANSCRIPTION FACTOR 1 (COUP-TF1) (COUP-TF 1) (V-ERBA RELATED PROTEIN EAR-3). | 0.77 | 0.54 | 0.92 | 1.85 | 0.78 |
| 4978 | CNTF-ZFP91_1: (CNTF) CILIARY NEUROTROPHIC FACTOR (ZFP91) (ZINC FINGER PROTEIN ZFP91) (PZF) (ZINK FINGER PROTEIN PZF). | 1.15 | 1.02 | 2.3 | 1.07 | 1.05 |
| 4982 | CTF1: (CTF1) CARDIOTROPHIN-1 (CT-1). | 1.22 | 1.7 | 1.17 | 1.7 | 1.02 |
| 4986 | HB-EGF: (DTR OR HEGFL) HEPARIN-BINDING EGF-LIKE GROWTH FACTOR PRECURSOR (HB-EGF) (HBEGF) (DIPHTERIA TOXIN RECEPTOR) (DT-R). | 0.33 | 0.58 | 0.32 | 0.57 | 1.18 |
| 4990 | NRG1: (NRG1 OR HGL OR NDF OR HRGA OR GGF OR SMDF) PRO-NEUREGULIN-1 PRECURSOR (PRO-NRG1) [CONTAINS: NEUREGULIN-1 (NEU DIFFERENTIATION FACTOR) (HEREGULIN) (HRG) (BREAST CANCER CELL DIFFERENTIATION FACTOR P45) (ACETYLCHOLINE RECEPTOR INDUCING ACTIVITY) (ARIA | 0.44 | | 0.63 | 1.35 | 0.38 |

Fig 3-17

| ID | Description | | | | | |
|---|---|---|---|---|---|---|
| 4995 | NRG3: (NRG3) PRO-NEUREGULIN-3 PRECURSOR (PRO-NRG3) [CONTAINS: NEUREGULIN-3 (NRG-3)]. | 2.01 | 1.03 | 2.02 | 0.91 | 0.99 |
| 5004 | SMAD1: (MADH1 OR SMAD1 OR MADR1 OR BSP1) MOTHERS AGAINST DECAPENTAPLEGIC HOMOLOG 1 (SMAD 1) (MOTHERS AGAINST DPP HOMOLOG 1) (MAD-RELATED PROTEIN 1) (TRANSFORMING GROWTH FACTOR-BETA SIGNALING PROTEIN-1) (BSP-1) (HSMAD1) (JV4-1). | 0.66 | 0.89 | 0.93 | 1.22 | 0.61 |
| 5006 | SMAD5: (MADH5 OR SMAD5) MOTHERS AGAINST DECAPENTAPLEGIC HOMOLOG 5 (SMAD 5) (MOTHERS AGAINST DPP HOMOLOG 5) (SMAD5) (HSMAD5) (JV5-1). | 0.74 | 0.74 | 0.33 | 1.68 | 0.34 |
| 5014 | AKT: (AKT1 OR RAC OR PKB) RAC-ALPHA SERINE/THREONINE KINASE (EC 2.7.1.-) (RAC-PK-ALPHA) (PROTEIN KINASE B) (PKB) (C-AKT). | 0.89 | 0.48 | 1.06 | 1.19 | 0.55 |
| 5016 | ATM: (ATM) SERINE-PROTEIN KINASE ATM (EC 2.7.1.37) (ATAXIA TELANGIECTASIA MUTATED) (A-T, MUTATED) (ATDC). | 1.94 | 1.62 | 0.51 | 0.99 | 0.46 |
| 5018 | CTNNB1: (CTNNB1 OR CTNNB) BETA-CATENIN. | | 0.62 | | | 1.96 |
| 5036 | MYB: (MYB) MYB PROTO-ONCOGENE PROTEIN (C-MYB). | 1.26 | 1.21 | 3.58 | | 2.15 |
| 5042 | PTEN1-PTEN2: (PTEN OR MMAC1 OR TEP1) PROTEIN-TYROSINE PHOSPHATASE PTEN (EC 3.1.3.48) (MUTATED IN MULTIPLE ADVANCED CANCERS 1). (PTEN2) HYPOTHETICAL 39.9 KDA PROTEIN (EC 3.1.3.48). | 0.89 | 1.47 | 0.71 | 0.62 | 0.64 |
| 5056 | IGF1: (IGF-1 OR IGF1) INSULIN-LIKE GROWTH FACTOR I PRECURSOR (SOMATOMEDIN). (IGF1 OR IBP1) INSULIN-LIKE GROWTH FACTOR IA PRECURSOR (IGF-IA) (SOMATOMEDIN C). INSULIN-LIKE GROWTH FACTOR IB PRECURSOR (IGF-IB) (SOMATOMEDIN C). | 0.91 | 0.63 | 2.98 | 3.97 | 1.88 |
| 5131 | CDC2: (CDC2) CELL DIVISION CONTROL PROTEIN 2 HOMOLOG (EC 2.7.1.-) (P34 PROTEIN KINASE) (CYCLIN-DEPENDENT KINASE 1) (CDK1). | 0.98 | 1.14 | 3.63 | 0.78 | 2.4 |
| 5137 | CDK4: (CDK4) CELL DIVISION PROTEIN KINASE 4 (EC 2.7.1.-) (CYCLIN-DEPENDENT KINASE4) (PSK-J3). | 1.35 | 0.42 | 4.75 | 1.68 | 1.85 |
| 5149 | CDKN2A_1_HUMAN: (CDKN2A OR CDKN2) CYCLIN-DEPENDENT KINASE 4 INHIBITOR A (CDK4I) (P16-INK4) (P16-INK4A) (MULTIPLE TUMOR SUPPRESSOR 1) (MTS1) (P14ARF OR ARF) (CELL CYCLE REGULATOR). | 0.74 | 0.55 | 0.3 | 1.68 | 0.44 |
| 5153 | CDKN2B: (CDKN2B OR MTS2) CYCLIN-DEPENDENT KINASE 4 INHIBITOR B (P14-INK4B) (P15-INK4B) (MULTIPLE TUMOR SUPPRESSOR 2) (MTS2). | 4.75 | 2.25 | | 2.86 | |
| 5159 | CDKN2D: (CDKN2D) CYCLIN-DEPENDENT KINASE 4 INHIBITOR D (P19-INK4D). | 1.74 | 6.36 | 0.28 | 0.17 | 0.34 |
| 5171 | ERBB2: (ERBB2 OR HER2 OR NGL OR NEU) RECEPTOR PROTEIN-TYROSINE KINASE ERBB-2 PRECURSOR (EC 2.7.1.112) (P185ERBB2) (NEU PROTO-ONCOGENE) (C-ERBB-2) (TYROSINE KINASE-TYPE CELL SURFACE RECEPTOR HER2) (MLN 19). | 2.92 | 2.25 | 1.36 | 1.23 | 0.71 |
| 5177 | FGF1: (FGF1 OR FGFA) HEPARIN-BINDING GROWTH FACTOR 1 PRECURSOR (HBGF-1) (ACIDIC FIBROBLAST GROWTH FACTOR) (AFGF) (BETA-ENDOTHELIAL CELL GROWTH FACTOR) (ECGF-BETA). | 0.97 | 1.07 | 1.05 | 1.52 | 1.07 |
| 5187 | FGF16: (FGF16) FIBROBLAST GROWTH FACTOR-16 (FGF-16). | | | 1.67 | | |

Fig 3-18

| | | | | | | | |
|---|---|---|---|---|---|---|---|
| 5193 | FGF19_HUMAN: (FGF19) FIBROBLAST GROWTH FACTOR-19 PRECURSOR (FGF-19). | 1.17 | 0.73 | 2.42 | 1.42 | 1.19 |
| 5199 | FGF5: (FGF5) FIBROBLAST GROWTH FACTOR-5 PRECURSOR (FGF-5) (HBGF-5). | 0.94 | 0.49 | 1.02 | 1.5 | 0.54 |
| 5201 | FGF6: (FGF6 OR HST2) FIBROBLAST GROWTH FACTOR-6 PRECURSOR (FGF-6) (HBGF-6) (HST-2). | | | | 1.61 | |
| 5203 | FGF7: (FGF7 OR KGF) KERATINOCYTE GROWTH FACTOR PRECURSOR (KGF) (FIBROBLAST GROWTH FACTOR-7) (FGF-7) (HBGF-7). | | 0.79 | | 20.18 | 1.06 |
| 5209 | FGFR2: (FGFR2 OR ECT1 OR BEK) FIBROBLAST GROWTH FACTOR RECEPTOR 2 PRECURSOR (FGFR-2) (EC 2.7.1.112) (KERATINOCYTE GROWTH FACTOR RECEPTOR) (K-SAM). (BFR2) FIBROBLAST GROWTH FACTOR RECEPTOR BFR-2 PRECURSOR (EC 2.7.1.112). | 1.36 | 1.5 | 1.34 | 1.15 | 1.09 |
| 5211 | IGF2_1: (IGF2) INSULIN-LIKE GROWTH FACTOR II PRECURSOR (IGF-II) (SOMATOMEDIN A). | 1.41 | 2.83 | 1.54 | 9.6 | 1.25 |
| 5213 | LEPR: (OBR OR LEPR OR DB OR FA) LEPTIN RECEPTOR PRECURSOR (LEP-R) (OB RECEPTOR) (OB-R) (B219RECEPTOR). | 1.09 | 1.15 | 1.59 | 2.51 | 1.27 |
| 5219 | NGFB: (NGFB) BETA-NERVE GROWTH FACTOR PRECURSOR (BETA-NGF). | | 1.02 | | 5.5 | 1.85 |
| 5221 | TRK-A: (NTRK1 OR TRK) HIGH AFFINITY NERVE GROWTH FACTOR RECEPTOR PRECURSOR (EC 2.7.1.112) (TRK1 TRANSFORMING TYROSINE KINASE PROTEIN) (P140-TRKA) (TRK-A). | | 1.5 | 1.6 | 1.22 | 2.69 |
| 5223 | TRK-B: (NTRK2 OR TRKB) BDNF/NT-3 GROWTH FACTORS RECEPTOR PRECURSOR (EC 2.7.1.112) (TRKB TYROSINE KINASE) (GP145-TRKB) (TRK-B). | 1.78 | 1.03 | 1.88 | 1.86 | 0.95 |
| 5225 | TRK-C: (NTRK3 OR TRKC) NT-3 GROWTH FACTOR RECEPTOR PRECURSOR (EC 2.7.1.112) (TRKC TYROSINE KINASE) (GP145-TRKC) (TRK-C). | 1.1 | 1.88 | 0.97 | 1.26 | 1.15 |
| 5231 | VGR3: (FLT4) VASCULAR ENDOTHELIAL GROWTH FACTOR RECEPTOR 3 PRECURSOR (EC 2.7.1.112) (VEGFR-3) (TYROSINE-PROTEIN KINASE RECEPTOR FLT4). | 0.94 | 1 | 1.31 | 1.57 | 1.4 |
| 5233 | CDH1: (CDH1 OR UVO OR CDHE) EPITHELIAL-CADHERIN PRECURSOR (E-CADHERIN) (UVOMORULIN) (CAM 120/80). | | | | 1.51 | |
| 5239 | MMP21-22-23: (MMP-23 OR MMP21/22 OR MIFR-1 OR MIFR OR DJ283E3.2) MMP-23 (MIFR/FEMALYSIN) (DJ283E3.2.1) (MATRIX METALLOPROTEINASE MMP21/22A (MIFR1)) (MATRIX METALLOPROTEINASE 23B) (MIFR-2 OR DJ283E3.2) MIFR-2 (DJ283E3.2.2) (MIFR2 MATRIX METALLOPROTEINASE I | 1.19 | 0.9 | 0.61 | 0.95 | 0.6 |
| 5241 | MPH6: (MPHOSPH6 OR MPP6) M-PHASE PHOSPHOPROTEIN 6. | 1.27 | 0.63 | 2.09 | 1.05 | 3.03 |
| 5366 | APC3: (APOC3) APOLIPOPROTEIN C-III PRECURSOR (APO-CIII). | 1.44 | 1.48 | | | 1.43 |
| 5434 | EDN3: (EDN3) ENDOTHELIN-3 PRECURSOR (ET-3). | 0.86 | 0.79 | 0.53 | 1.64 | 0.42 |
| 5439 | FABP4: (FABP4 OR AP2 OR FABA) FATTY ACID-BINDING PROTEIN, ADIPOCYTE (AFABP) (ADIPOCYTE LIPID-BINDING PROTEIN) (ALBP) (A-FABP) (P2 ADIPOCYTE PROTEIN) (MYELIN P2 PROTEIN HOMOLOG) (3T3-L1 LIPID BINDING PROTEIN) (422 PROTEIN) (P15). | 1.62 | | | | 2.87 |

Fig 3-19

| | | | | | | |
|---|---|---|---|---|---|---|
| 5442 | FABE: (FABP5 OR MAL1 OR KLBP OR FABPE) FATTY ACID-BINDING PROTEIN, EPIDERMAL (E-FABP) (PSORIASIS-ASSOCIATED FATTY ACID-BINDING PROTEIN HOMOLOG) (PA-FABP). | 0.64 | 0.28 | 6.9 | 0.3 | 4.21 |
| 5446 | FABI: (FABP2) FATTY ACID-BINDING PROTEIN, INTESTINAL (I-FABP) (FABPI). | 1.03 | 0.62 | 1.12 | 1.31 | 0.66 |
| 5456 | FGF2_1: (FGF2 OR FGFB) HEPARIN-BINDING GROWTH FACTOR 2 PRECURSOR (HBGF-2) (BASIC FIBROBLAST GROWTH FACTOR) (BFGF) (PROSTATROPIN). | 0.85 | 0.39 | 1.07 | 4.17 | 0.92 |
| 5498 | VLDLR: (VLDLR OR LDVR) VERY LOW-DENSITY LIPOPROTEIN RECEPTOR PRECURSOR (VLDL RECEPTOR). | 0.73 | | 1.09 | 6.45 | 0.83 |
| 5544 | OB 2: (LEP OR OB) LEPTIN PRECURSOR (OBESITY FACTOR) (OBESE PROTEIN). | 1.26 | 0.71 | 2.81 | 1.96 | 1.97 |
| 5574 | PGH2: (PTGS2 OR COX2) PROSTAGLANDIN G/H SYNTHASE 2 PRECURSOR (EC 1.14.99.1) (CYCLOOXYGENASE-2) (COX-2) (PROSTAGLANDIN-ENDOPEROXIDE SYNTHASE 2) (PROSTAGLANDIN H2SYNTHASE 2) (PGH SYNTHASE 2) (PGHS-2) (PHS II) (PTGS2). | 0.44 | | 0.55 | 1.11 | 0.41 |
| 6118 | COX7A2: (COX7A2 OR COX7AL) CYTOCHROME C OXIDASE POLYPEPTIDE VIIA-LIVER/HEART, MITOCHONDRIAL PRECURSOR (EC 1.9.3.1) (CYTOCHROME C OXIDASE SUBUNIT VIIA-L). | 1.29 | 1.31 | 1.82 | 0.98 | 1.96 |
| 6146 | GCK: (GCK) HEXOKINASE D, PANCREATIC ISOZYME (EC 2.7.1.1) (HEXOKINASE TYPE IV) (HK4) (GLUCOKINASE). | 0.77 | 1.16 | 0.7 | 0.87 | 2.08 |
| 6194 | MTHFD2: (MTGFD2 OR NMDMC) BIFUNCTIONAL METHYLENETETRAHYDROFOLATE DEHYDROGENASE/CYCLOHYDROLASE, MITOCHONDRIAL PRECURSOR [INCLUDES: NAD-DEPENDENT METHYLENETETRAHYDROFOLATE DEHYDROGENASE (EC 1.5.1.15); METHENYLTETRAHYDROFOLATE CYCLOHYDROLASE (EC 3.5.4.9)]. | 0.47 | 0.59 | 1.2 | 1.09 | 1.24 |
| 6204 | PCK2: (PCK2 OR PEPCK2) PHOSPHOENOLPYRUVATE CARBOXYKINASE, MITOCHONDRIAL PRECURSOR [GTP] (EC 4.1.1.32) (PHOSPHOENOLPYRUVATE CARBOXYLASE) (PEPCK-M). | 0.94 | 0.45 | 1.75 | 3.74 | 1.09 |
| 6515 | AMBP: (AMBP OR ITIL OR HCP) AMBP PROTEIN PRECURSOR [CONTAINS: ALPHA-1-MICROGLOBULIN (PROTEIN HC) (COMPLEX-FORMING GLYCOPROTEIN HETEROGENEOUS IN CHARGE); INTER-ALPHA-TRYPSIN INHIBITOR LIGHT CHAIN (ITI-LC) (BIKUNIN) (HI-30)]. | 0.97 | 1.42 | 0.99 | 1.57 | 1.54 |
| 6890 | F5: (F5) COAGULATION FACTOR V PRECURSOR (ACTIVATED PROTEIN C COFACTOR). | 0.38 | 0.98 | 0.38 | 0.3 | 0.47 |
| 7010 | TTR: (TTR OR PALB) TRANSTHYRETIN PRECURSOR (PREALBUMIN) (TBPA) (TTR) (ATTR). | 0.89 | 1.02 | 1.12 | 1.97 | 1.29 |
| 7043 | CYP3A4_HUMAN: (CYP3A4) CYTOCHROME P450 3A4 (EC 1.14.14.1) (CYPIIIA4) (NIFEDIPINE OXIDASE) (NF-25) (P450-PCN1). | 0.98 | 1.11 | 1.02 | 1.5 | 1.34 |
| 7082 | CCT8: (CCT8 OR CCTQ) T-COMPLEX PROTEIN 1, THETA SUBUNIT (TCP-1-THETA) (CCT-THETA) (KIAA0002). | 1.17 | 0.88 | 2.18 | 0.64 | 1.59 |
| 7088 | CDC25B: (CDC25B OR CDC25HU2) M-PHASE INDUCER PHOSPHATASE 2 (EC 3.1.3.48). | 1.52 | 2.37 | 1.5 | 1.54 | 0.79 |

Fig 3-20

| | | | | | | |
|---|---|---|---|---|---|---|
| 7091 | CDC25C: (CDC25C) M-PHASE INDUCER PHOSPHATASE 3 (EC 3.1.3.48). | 0.71 | 0.93 | 2.86 | 1.39 | 1.9 |
| 7346 | PSMA2: (PSMA2 OR PSC3) PROTEASOME SUBUNIT ALPHA TYPE 2 (EC 3.4.25.1) (PROTEASOME COMPONENT C3) (MACROPAIN SUBUNIT C3) (MULTICATALYTIC ENDOPEPTIDASE COMPLEX SUBUNIT C3). | 1.18 | 0.57 | 2.11 | 0.77 | 1.76 |
| 7352 | PSMA3: (PSMA3 OR PSC8) PROTEASOME SUBUNIT ALPHA TYPE 3 (EC 3.4.99.46) (PROTEASOME COMPONENT C8) (MACROPAIN SUBUNIT C8) (MULTICATALYTIC ENDOPEPTIDASE COMPLEX SUBUNIT C8) (INGENSIN). | 0.86 | 0.37 | 2.92 | 1.1 | 1.87 |
| 7382 | ABCC8: (ABCC8 OR SUR1 OR SUR) (ABC-TRANSPORTER) SULFONYLUREA RECEPTOR 1. | 1.9 | 1.23 | 0.96 | | 1.16 |
| 7523 | BCRP: (ABCG2 OR ABCP OR BCRP OR BCRP1) ATP-BINDING CASSETTE, SUB-FAMILY G, MEMBER 2 (PLACENTA-SPECIFIC ATP-BINDING CASSETTE TRANSPORTER) (BREAST CANCER RESISTANCE PROTEIN). | 1.17 | 2.17 | 1.95 | 1 | 1.73 |
| 7634 | EMX-2: (EMX2 OR EMX-2) HOMEOBOX PROTEIN EMX2 (FRAGMENT). | 1.32 | 1.06 | 1.19 | 1.49 | 1.13 |
| 7804 | KRT14: (KRT14) KERATIN, TYPE I CYTOSKELETAL 14 (CYTOKERATIN 14) (K14) (CK 14). | 0.75 | 0.25 | 0.53 | 14.76 | 1.47 |
| 7807 | KRT17: (KRT17) KERATIN, TYPE I CYTOSKELETAL 17 (CYTOKERATIN 17) (K17) (CK 17) (39.1) (VERSION 1). | 1.32 | 1 | 1.74 | 3.28 | 1.03 |
| 7837 | NCAD: (CDH2 OR CDHN OR NCAD) NEURAL-CADHERIN PRECURSOR (N-CADHERIN) (CADHERIN-2). | 0.8 | 0.68 | 0.7 | 6.5 | 0.58 |
| 7873 | ODC1: (ODC1) ORNITHINE DECARBOXYLASE (EC 4.1.1.17) (ODC). | 1.33 | 3.22 | 2.1 | 1.78 | 1.27 |
| 7924 | RAC1: (RAC1) RAS-RELATED C3 BOTULINUM TOXIN SUBSTRATE 1 (P21-RAC1) (RAS-LIKE PROTEIN TC25). | 0.48 | 0.5 | 0.61 | 0.69 | 0.8 |
| 7939 | RHOA: (ARHA OR ARH12 OR RHOA OR RHO12) TRANSFORMING PROTEIN RHOA (H12). | 0.99 | 0.94 | 0.85 | 1.42 | 1.2 |
| 7951 | RPL7A: (RPL7A OR SURF3 OR SURF-3) 60S RIBOSOMAL PROTEIN L7A (SURFEIT LOCUS PROTEIN 3) (PLA-X POLYPEPTIDE). | 1.41 | 0.81 | 1.14 | 0.44 | 0.79 |
| 7996 | TK1: (TK1) THYMIDINE KINASE, CYTOSOLIC (EC 2.7.1.21). | 1.97 | 2.79 | 20.45 | 1.22 | 11.18 |
| 8071 | CTNNA1: (CTNNA1) ALPHA-1 CATENIN (CADHERIN-ASSOCIATED PROTEIN) (ALPHA E-CATENIN). | 0.38 | 0.51 | 0.62 | 1.47 | 0.56 |
| 8080 | ENO2: (ENO2) GAMMA ENOLASE (EC 4.2.1.11) (2-PHOSPHO-D-GLYCERATE HYDRO-LYASE). | 0.66 | 0.65 | 0.98 | 1.85 | 0.84 |
| 8188 | RBL2: (RBL2 OR RB2) RETINOBLASTOMA-LIKE PROTEIN 2 (130 KDA RETINOBLASTOMA-ASSOCIATED PROTEIN) (PRB2) (P130) (RBR-2). | 2.9 | 1.32 | 0.8 | 0.52 | 0.52 |
| 8612 | TRF1: (TRF1 OR TRF) TELOMERIC REPEAT BINDING FACTOR 1. | 1.15 | | 1.38 | 1.59 | |
| 9037 | HJ1: (JAG1) JAGGED 1 PRECURSOR (JAGGED1) (HJ1) NOTCH LIGAND JAGGED 1). | 2.09 | 1.83 | 2.05 | 6.03 | |
| 9046 | NOTCH1: (NOTCH1 OR TAN1) NEUROGENIC LOCUS NOTCH PROTEIN HOMOLOG 1 PRECURSOR | 1.55 | 1.19 | 1.02 | 1.3 | 1.18 |
| 9060 | ACTG2: (ACTG2 OR ACTA3 OR ACTSG) ACTIN, GAMMA-ENTERIC SMOOTH MUSCLE | 1.34 | 1.19 | 1.38 | 7.15 | 0.95 |

Fig 3-21

| | | | | | | |
|---|---|---|---|---|---|---|
| 9099 | (ALPHA-ACTIN 3). FGFR3: (FGFR3 OR JTK4) FIBROBLAST GROWTH FACTOR RECEPTOR 3 PRECURSOR (FGFR-3) (EC 2.7.1.112). | 1.3 | | 1.34 | 1.3 | 1.3 |
| 9102 | FLN1: (FLNA OR FLN1 OR FLN) FILAMIN A (ALPHA-FILAMIN) (FILAMIN 1) (ENDOTHELIAL ACTIN-BINDING PROTEIN) (ABP-280) (NONMUSCLE FILAMIN). | 0.73 | 2.4 0.36 | 0.44 | 5.67 | 0.48 |
| 9132 | MYH11: (MYH11) MYOSIN HEAVY CHAIN, SMOOTH MUSCLE ISOFORM (SMMHC) (FRAGMENT). | | | | 1.53 | |
| 9144 | SERPINF1: (SERPINF1 OR PEDF OR SDF3) PIGMENT EPITHELIUM-DERIVED FACTOR PRECURSOR (PEDF) (EPC-1) (STROMAL CELL-DERIVED FACTOR 3) (SDF-3) (CASPIN). | 1.6 | 0.96 | 1.71 | 1.71 | 0.76 |
| 9165 | SLC2A1: (SLC2A1 OR GLUT1) GLUCOSE TRANSPORTER TYPE 1, ERYTHROCYTE/BRAIN. | 2.19 | 5.61 | 0.95 | 2.56 | 1.06 |
| 9261 | LDHB: (LDHB) L-LACTATE DEHYDROGENASE H CHAIN (EC 1.1.1.27) L-LACTATE DEHYDROGENASE B CHAIN (EC 1.1.1.27) (LDH-B) (LDH HEART SUBUNIT) (LDH-H). | 2.5 | 1.08 | 2.91 | 1.12 | 1.3 |
| 9314 | CRABP2: (CRABP2) RETINOIC ACID-BINDING PROTEIN II, CELLULAR (CRABP-II). | 0.48 | 0.68 | 0.62 | 1.82 | 0.68 |
| 9338 | HOXA2: (HOXA2) HOMEOBOX PROTEIN HOX-A2. | 1.09 | 1.14 | 2.77 | 1.19 | 1.86 |
| 9362 | PRRX1: (PRRX1 OR PMX1 OR PRX1) PAIRED MESODERM HOMEOBOX PROTEIN 1 (PRX-1) (PAIRED RELATED HOMEOBOX PROTEIN 1) (HOMEOBOX PROTEIN PHOX1). | 0.47 | 0.44 | 0.26 | 2.68 | 0.28 |
| 9386 | RBL1: (RBL1) RETINOBLASTOMA-LIKE PROTEIN 1 (107 KDA RETINOBLASTOMA-ASSOCIATED PROTEIN) (PRB1) (P107). | 1.25 | 1.13 | 2.21 | 1.05 | 1.77 |
| 9407 | SOX9: (SOX9) TRANSCRIPTION FACTOR SOX-9. | 1.16 | 0.43 | 0.39 | 3.26 | 0.45 |
| 9422 | WNT10B: (WNT10B OR WNT10 OR WNT12 OR WNT-10B) WNT-10B PROTEIN PRECURSOR (WNT-12). | | 1.76 | | 1.58 | |
| 9443 | WNT3: (WNT3 OR WNT-3 OR INT4) WNT-3 PROTO-ONCOGENE PROTEIN PRECURSOR. | | | | 4.13 | |
| 9452 | WNT5A: (WNT5A OR WNT-5A) WNT-5A PROTEIN PRECURSOR. | 1.13 | 0.87 | 0.97 | 4.5 | 1.18 |
| 9572 | ELOVL6: (ELOVL6 OR BALDSPOT OR FAE OR RELO2) LONG-CHAIN FATTY-ACYL ELONGASE (ELOVL6 PROTEIN) (FATTY ACID ELONGASE 2) (MYELINATION ASSOCIATED SUR4-LIKE PROTEIN) (FLJ23378). | 0.99 | 4.9 | 3.89 | | 4.1 |
| 9663 | HERMES: (HERMES OR RBPMS) RNA-BINDING PROTEIN WITH MULTIPLE SPLICING (RBP-MS). | 0.85 | 0.45 | 0.23 | 2.8 | 0.14 |
| 9713 | PAFAH1B1: (PAFAH1B1 OR PAFAHA OR LIS1 OR MDCR) PLATELET-ACTIVATING FACTOR ACETYLHYDROLASE IB ALPHA SUBUNIT (EC 3.1.1.47) (PAF ACETYLHYDROLASE 45 KDA SUBUNIT) (PAF-AH 45 KDA SUBUNIT) (PAF-AH ALPHA) (PAFAH ALPHA) (LISSENCEPHALY-1 PROTEIN) (LIS-1). | 0.99 | 1.32 | 1.26 | 1.63 | 1.32 |
| 9992 | MGST1: (MGST1 OR MGST OR GST12) GLUTATHIONE S-TRANSFERASE, MICROSOMAL (EC 2.5.1.18). | 0.53 | 0.36 | 3.09 | 1.39 | 1.71 |
| 10265 | ANXA2: (ANXA2 OR ANX2) ANNEXIN II (LIPOCORTIN II) (CALPACTIN I HEAVY CHAIN) (CHROMOBINDIN 8) (P36) (PROTEIN I) (PLACENTAL ANTICOAGULANT | 0.37 | 0.14 | 0.27 | 3.11 | 0.66 |

Fig 3-22

| ID | Description | | | | | | |
|---|---|---|---|---|---|---|---|
| 10455 | PROTEIN IV) (PAP-IV). | | | | | | |
| | PEG1-MEST: (PEG1/MEST) PEG1/MEST PROTEIN (MESODERM SPECIFIC TRANSCRIPT (MOUSE) HOMOLOG) (HYPOTHETICAL 38.8 KDA PROTEIN) (UNKNOWN) (PROTEIN FOR MGC:20321). | 1.36 | | 0.39 | 0.94 | | 0.62 |
| 10467 | PLCB4: (PLCB4) PHOSPHOLIPASE C BETA 4. | 2.99 | | | 6.11 | 5.46 | |
| 10470 | PLCE: (PLCE OR PLCE1 OR PLC-EPSILON) PHOSPHOINOSITIDE-SPECIFIC PHOSPHOLIPASE C PLC-EPSILON (KIAA1516) (PANCREAS-ENRICHED PHOSPHOLIPASE C) (FLJ12481). | | | | | 3.68 | |
| 10934 | CHEK1: (CHEK1 OR CHK1) SERINE/THREONINE-PROTEIN KINASE CHK1 (EC 2.7.1.-) CHECKPOINT KINASE 1. | 1.1 | | 1.26 | 1.69 | 1.52 | |
| 10937 | CHEK2: (CHEK2 OR CHK2) SERINE/THREONINE-PROTEIN KINASE CHK2 (EC 2.7.1.-) (CDS1). | 0.83 | | 1.03 | | 0.85 | 1.23 |
| 10970 | FZD1_2: (FZD1) FRIZZLED 1 PRECURSOR (FRIZZLED-1) (FZ-1) (HFZ1) (FZE1) (RFZ1) (MFZ1). | 0.84 | | 0.69 | 0.68 | 0.86 | 1.19 |
| 10985 | HMGB2: (HMGB2 OR HMG2) HIGH MOBILITY GROUP PROTEIN HMG2 (HMG-2). | 1.09 | | 1.32 | 3.76 | 1.97 | 0.58 |
| 11074 | TERT: (TERT OR TRT OR EST2 OR TCS1) TELOMERASE REVERSE TRANSCRIPTASE (EC 2.7.7.-) (TELOMERASE CATALYTIC SUBUNIT) (HEST2). | 1.2 | | 1.56 | | 0.58 | 1.98 |
| 11115 | ITGA3_5PRIME: (ITGA3) INTEGRIN ALPHA-3 PRECURSOR (GALACTOPROTEIN B3) (GAPB3) (VLA-3 ALPHA CHAIN) (CD49C). | 1.03 | | 1.53 | 1.03 | 0.89 | 1.03 |
| 11181 | KRT18: (KRT18 OR CYK18) KERATIN, TYPE I CYTOSKELETAL 18 (CYTOKERATIN 18) (K18) (CK 18). | 0.51 | | 0.18 | 1.25 | 1.43 | 1.29 |
| 11204 | KRT8: (KRT8 OR CYK8) KERATIN, TYPE II CYTOSKELETAL 8 (CYTOKERATIN 8) (K8) (CK 8) (KRT2-8). | 0.96 | | 0.95 | 0.28 | 1.82 | 0.31 |
| 11328 | TDGF1-TDGF3_2_HUMAN: (TDGF1 OR CRIPTO) TERATOCARCINOMA-DERIVED GROWTH FACTOR 1 (EPIDERMAL GROWTH FACTOR-LIKE CRIPTO PROTEIN CR1) (CRIPTO-1 GROWTH FACTOR) (CRGF) (TDGF3 OR TDGF2) TERATOCARCINOMA-DERIVED GROWTH FACTOR 2 (EPIDERMAL GROWTH FACTOR-LIKE CRIPTO | 1.24 | | 1.53 | 0.73 | 1.45 | 0.85 |
| 11334 | TPM1: (TPM1 OR TPMA OR TMSA) TROPOMYOSIN ALPHA CHAIN. | 0.82 | | 0.2 | 1.12 | 0.83 | 1 |
| 11389 | SCARB1: (SCARB1 OR CD36L1 OR CLA1) SCAVENGER RECEPTOR CLASS B MEMBER 1 (SRB1) (SR-BI) (CD36 ANTIGEN-LIKE 1) (CD36 AND LIMPII ANALOGOUS 1) (CLA-1) (COLLAGEN TYPE I RECEPTOR, THROMBOSPONDIN RECEPTOR-LIKE 1). | | | 1.09 | 0.22 | 13.76 | 0.13 |
| 11404 | CRABP1: (CRABP1 OR RBP5) RETINOIC ACID-BINDING PROTEIN I, CELLULAR (CRABP-I). | | | 1.31 | 2.05 | 1.13 | 1.87 |
| 11635 | ACVR1: (ACVR1 OR ACVRLK2) ACTIVIN RECEPTOR TYPE I PRECURSOR (EC 2.7.1.-) (ACTR-I) (SERINE/THREONINE-PROTEIN KINASE RECEPTOR R1) (SKR1) (ACTIVIN RECEPTOR-LIKE KINASE 2) (ALK-2) (TGF-B SUPERFAMILY RECEPTOR TYPE I) (TSR-I). | 0.71 | | 1.19 | 1.38 | 1.23 | 1.39 |
| | | 1.3 | | | 0.94 | 1.64 | 1.05 |

Fig 3-23

| | | | | | | |
|---|---|---|---|---|---|---|
| 11641 | ACVR2: (ACVR2) ACTIVIN RECEPTOR TYPE II PRECURSOR (EC 2.7.1.-) (ACTR-II) (ACTRIIA). | | 1.44 | 1.53 | 1.8 | |
| 11644 | ACVR2B: (ACVR2B) ACTIVIN RECEPTOR TYPE IIB PRECURSOR (EC 2.7.1.-) (ACTR-IIB). | 0.96 | 1.54 | 1.18 | 1.1 | 1.21 |
| 11647 | ACVRL1: (ACVRL1 OR ACVRLK1 OR ALK1) SERINE/THREONINE-PROTEIN KINASE RECEPTOR R3 PRECURSOR (EC 2.7.1.37) (SKR3) (ACTIVIN RECEPTOR-LIKE KINASE 1) (ALK-1) (TGF-B SUPERFAMILY RECEPTOR TYPE I) (TSR-I). | 1.74 | 2.68 | 1.02 | 1.7 | 1.27 |
| 11683 | BMP15: (BMP15 OR GDF9B) BONE MORPHOGENETIC PROTEIN 15 PRECURSOR (BMP-15) (GROWTH/DIFFERENTIATION FACTOR 9B) (GDF-9B). | | | | 2.26 | |
| 11686 | BMPR1A: (BMPR1A OR ACVRLK3) BONE MORPHOGENETIC PROTEIN RECEPTOR TYPE IA PRECURSOR (EC 2.7.1.-) (SERINE/THREONINE-PROTEIN KINASE RECEPTOR R5) (SKR5) (ACTIVIN RECEPTOR-LIKE KINASE 3) (ALK-3). | 0.73 | 1.03 | 0.91 | 1.88 | 0.99 |
| 11689 | BMPR1B: (BMPR1B) BONE MORPHOGENETIC PROTEIN RECEPTOR TYPE IB PRECURSOR (EC 2.7.1.-). | | 3.23 | | | |
| 11698 | CD164: (CD164 OR MMGC-24) PUTATIVE MUCIN CORE PROTEIN 24 PRECURSOR (MULTI-GLYCOSYLATED CORE PROTEIN 24) (MGC-24) (MUC-24) (CD164 ANTIGEN) (CELL-SURFACE SIALOMUCIN MGC-24) (ENDOLYN PRECURSOR). | 0.91 | 0.55 | 1.21 | 1.13 | 0.69 |
| 11701 | CD44_EX16-20_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTE | 0.86 | 0.75 | 0.57 | 0.55 | 1.01 |
| 11704 | CD44_EX13-15_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTE | 0.73 | 1.17 | 0.61 | 0.92 | 1.44 |
| 11707 | CD44_EX3-5_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOG | 1.04 | 1.14 | 0.68 | 0.6 | 1.15 |
| 11710 | CD44_EX7-9_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOG | 1.11 | 1.46 | 0.96 | 0.97 | 1 |
| 11725 | CDH3: (CDH3 OR CDHP) CADHERIN-3 PRECURSOR (PLACENTAL-CADHERIN) (P-CADHERIN). | 1.1 | 1.88 | 1.66 | 1.88 | |
| 11761 | EGR2: (EGR2 OR KROX20) EARLY GROWTH RESPONSE PROTEIN 2 (EGR-2) (KROX-20 PROTEIN) (AT591). | 1.44 | 3.11 | 1.07 | 0.94 | 1.69 |
| 11767 | EPHB2: (EPHB2 OR EPTH3 OR ERK OR DRT OR HEK5) EPHRIN TYPE-B RECEPTOR 2 | 1.79 | 2.14 | 0.97 | 0.95 | 0.99 |

Fig 3-24

| | | | | | | | |
|---|---|---|---|---|---|---|---|
| 11797 | PRECURSOR (EC 2.7.1.112) (TYROSINE-PROTEIN KINASE RECEPTOR EPH-3) (DRT) (RECEPTOR PROTEIN-TYROSINE KINASE HEK5) (ERK). | 1.22 | 1.33 | 1.67 | 0.84 | 1.81 | |
| 11804 | GATA2: (GATA2) ENDOTHELIAL TRANSCRIPTION FACTOR GATA-2. | 0.69 | 0.34 | 0.2 | 7.23 | 0.16 | |
| 11920 | GATA4_HUMAN: (GATA4) TRANSCRIPTION FACTOR GATA-4 (GATA BINDING FACTOR-4). | | | | | | |
| 11953 | LMO2: (LMO2 OR RBTN2 OR RHOM2 OR TTG2) RHOMBOTIN-2 (CYSTEINE RICH PROTEIN TTG-2) (T-CELL TRANSLOCATION PROTEIN 2) (LIM-ONLY PROTEIN 2). | 0.34 | 0.46 | 1.23 | 0.18 | 0.65 | |
| 11998 | MAP3K5: (MAP3K5 OR MAPKKK5 OR MEKK5 OR ASK1) MITOGEN-ACTIVATED PROTEIN KINASE KINASE KINASE 5 (EC 2.7.1.-) (MAPK/ERK KINASE KINASE 5) (MEK KINASE 5) (MEKK 5) (APOPTOSIS SIGNAL-REGULATING KINASE 1) (ASK-1). | | | 1.67 | | | |
| 12034 | PAX5: (PAX5) PAIRED BOX PROTEIN PAX-5 (B-CELL SPECIFIC TRANSCRIPTION FACTOR) (BSAP). | | 0.86 | | | | 1.46 |
| 12085 | PRKCZ: (PRKCZ OR PKC2) PROTEIN KINASE C, ZETA TYPE (EC 2.7.1.-) (NPKC-ZETA). | | 1.76 | | | | |
| 12088 | SEMA4D: (SEMA4D OR CD100) SEMAPHORIN 4D PRECURSOR (LEUKOCYTE ACTIVATION ANTIGEN CD100) (BB18) (A8) (GR3). (SEMA4D OR SEMAJ OR SEMACL2) SEMAPHORIN 4D PRECURSOR (SEMAPHORIN J) (SEMA J) (SEMAPHORIN C-LIKE 2) (M-SEMA G). | 1.22 | 1.41 | 0.99 | 0.8 | 0.96 | |
| 12091 | SEMAL: (SEMA7A OR SEMAL OR CD108) SEMAPHORIN 7A PRECURSOR (SEMAPHORIN L) (SEMA L) (SEMAPHORIN K1) (SEMA K1) (JOHN-MILTON-HARGEN HUMAN BLOOD GROUP AG) (JMH BLOOD GROUP ANTIGEN) (CD108 ANTIGEN) (CDW108). | | 2.23 | 1.14 | 2.11 | 1.67 | |
| 12386 | SHH: (SHH) SONIC HEDGEHOG PROTEIN PRECURSOR (SHH) (HHG-1). | 1.04 | 1.52 | 1.49 | 1.58 | 1.27 | |
| 12452 | SLC16A1: (SLC16A1 OR MCT1) MONOCARBOXYLATE TRANSPORTER 1 (MCT 1). | 1.16 | 1.76 | 1.15 | 1.05 | 0.94 | |
| 12627 | CD45_EX10-11: (PTPRC OR CD45) LEUKOCYTE COMMON ANTIGEN PRECURSOR (EC 3.1.3.48) (L-CA) (CD45 ANTIGEN) (T200). | 1.48 | 1.58 | 0.55 | 0.18 | 0.77 | |
| 12690 | CRIP1: (CRIP1 OR CRIP) CYSTEINE-RICH PROTEIN 1 (CYSTEINE-RICH INTESTINAL PROTEIN) (CRIP) (CYSTEINE-RICH HEART PROTEIN) (HCRHP). | 0.37 | 0.29 | 0.1 | 0.1 | 0.06 | |
| 12704 | S100A11: (S100A11 OR S100C) CALGIZZARIN (ENDOTHELIAL MONOCYTE-ACTIVATING POLYPEPTIDE) (EMAP). | 0.27 | 0.58 | 0.35 | 0.81 | 0.97 | |
| 12710 | CD44_EX11-13_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTE | 1.04 | 1.71 | 1.23 | 1.11 | 2 | |
| 12809 | CD44_EX8-10_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEO | 1.21 | 2.79 | 0.77 | 1.74 | 1.76 | |
| | EGFR-SHORT: (EGFR OR ERBB1) EPIDERMAL GROWTH FACTOR RECEPTOR | | 0.88 | 2.09 | 1.44 | 2.03 | |

Fig 3-25

| | | | | | | |
|---|---|---|---|---|---|---|
| 12917 | PRECURSOR (EC 2.7.1.112) (RECEPTOR PROTEIN-TYROSINE KINASE ERBB-1). | | | | | |
| 12920 | PRKCM: (PRKCM) PROTEIN KINASE C, MU TYPE (EC 2.7.1.-) (NPKC-MU). | | | | 7.74 | |
| | PRKCQ: (PRKCQ OR PRKCT) PROTEIN KINASE C, THETA TYPE (EC 2.7.1.-) (NPKC-THETA). | 1.22 | 1.48 | 1.04 | 0.8 | 1.01 |
| 12956 | BEX2-BEX1: (BEX2) BRAIN EXPRESSED X-LINKED PROTEIN 2 (BEX1) (BRAIN-EXPRESSED PROTEIN BEX1) (REX3 OR BEX1) (BRAIN EXPRESSED X-LINKED PROTEIN 1). | 1.45 | 1.19 | 3.18 | 1.3 | 2.7 |
| 13004 | ELAVL2: (ELAVL2 OR HUB) ELAV-LIKE PROTEIN 2 (HU-ANTIGEN B) (HUB) (ELAV-LIKE NEURONAL PROTEIN 1) (NERVOUS SYSTEM-SPECIFIC RNA BINDING PROTEIN HEL-N1). | | 1.24 | 16.57 | 2.38 | 0.98 |
| 13106 | NTF3: (NTF3) NEUROTROPHIN-3 PRECURSOR (NT-3) (NEUROTROPHIC FACTOR) (HDNF) (NERVE GROWTH FACTOR 2) (NGF-2). | | 1.05 | | 1.63 | |
| 13118 | PMX2B: (PMX2B) PAIRED MESODERM HOMEOBOX PROTEIN 2B (PAIRED-LIKE HOMEOBOX 2B) (PHOX2B HOMEODOMAIN PROTEIN) (NEUROBLASTOMA PHOX) (NBPHOX). | 1.07 | 0.96 | 0.94 | 1.47 | 0.91 |
| 13124 | POU6F1: (POU6F1 OR MPOU OR BRN5 OR TCFB1) POU DOMAIN, CLASS 6, TRANSCRIPTION FACTOR 1 (MPOU HOMEOBOX PROTEIN) (BRAIN-SPECIFIC HOMEOBOX/POU DOMAIN PROTEIN 5) (BRN-5 PROTEIN). | 1.3 | 2.48 | 0.96 | 0.92 | 1.26 |
| 13163 | SYP: (SYP) SYNAPTOPHYSIN (MAJOR SYNAPTIC VESICLE PROTEIN P38). | 1.03 | 1.84 | 1.14 | 0.85 | 1.14 |
| 13234 | BDNF: (BDNF) BRAIN-DERIVED NEUROTROPHIC FACTOR PRECURSOR (BDNF). | 0.32 | 0.17 | 0.13 | 4.43 | 0.18 |
| 13249 | CACNA1B: (CACNA1B OR CACNL1A5 OR CACH5) VOLTAGE-DEPENDENT N-TYPE CALCIUM CHANNEL ALPHA-1B SUBUNIT (CALCIUM CHANNEL, L TYPE, ALPHA-1 POLYPEPTIDE ISOFORM 5) (BRAIN CALCIUM CHANNEL III) (BIII). | | 0.69 | 1.07 | 1.27 | 1.59 |
| 13258 | CDC42_1: (CDC42) G25K GTP-BINDING PROTEIN, PLACENTAL ISOFORM (GP) (CDC42 HOMOLOG). | 2.9 | 3.69 | 1.01 | 1.97 | 1.1 |
| 13309 | GABRA1: (GABRA1) GAMMA-AMINOBUTYRIC-ACID RECEPTOR ALPHA-1 SUBUNIT PRECURSOR (GABA(A) RECEPTOR). | | | | | 0.69 |
| 13591 | STX1A: (STX1A OR STX1) SYNTAXIN 1A (NEURON-SPECIFIC ANTIGEN HPC-1). | 1.45 | 0.87 | 0.43 | 1.62 | 0.63 |
| 14615 | CLCN3: (CLCN3) CHLORIDE CHANNEL PROTEIN 3 (CLC-3). | 1.44 | 4.25 | 1.24 | 2.12 | 0.73 |
| 14618 | CLCN7: (CLCN7) CHLORIDE CHANNEL PROTEIN 7 (CLC-7). | 1.01 | 1.73 | 2.3 | 1.27 | 2.38 |
| 14716 | COL9A1_2: (COL9A1) COLLAGEN ALPHA 1(IX) CHAIN PRECURSOR. | 1.19 | 1.44 | 0.95 | 0.84 | 1.01 |
| 14734 | PRKCB_3: (PRKCB1 OR PRKCB OR PKCB) PROTEIN KINASE C, BETA TYPE (EC 2.7.1.37) (PKC-BETA) (PKC-B). | 0.64 | 0.63 | 0.42 | 0.09 | 0.42 |
| 14749 | VEGF_2: (VEGF OR VEGFA) VASCULAR ENDOTHELIAL GROWTH FACTOR PRECURSOR (VEGF) (VASCULAR PERMEABILITY FACTOR) (VPF)(VEGF A). | 0.73 | 0.94 | 0.74 | 1.69 | 0.65 |
| 14752 | VGR1: (FLT1 OR FLT OR FRT) VASCULAR ENDOTHELIAL GROWTH FACTOR RECEPTOR 1 PRECURSOR (EC 2.7.1.112) (VEGFR-1) (TYROSINE-PROTEIN KINASE | | | | | 2.45 |

Fig 3-26

| | | | | | | | |
|---|---|---|---|---|---|---|---|
| 14773 | RECEPTOR FLT) (FLT-1) (TYROSINE-PROTEIN KINASE FRT). | | | 1.37 | | 1.08 | 1 | 1.22 |
| 14809 | AKT2: (AKT2) RAC-BETA SERINE/THREONINE PROTEIN KINASE (EC 2.7.1.-) (RAC-PK-BETA) (PROTEIN KINASE AKT-2) (PROTEIN KINASE B, BETA) (PKB BETA). | | 1.95 | | | | |
| | BUB1: (BUB1 OR BUB1L) MITOTIC CHECKPOINT SERINE/THREONINE-PROTEIN KINASE BUB1 (EC 2.7.1.-) (HBUB1) (BUB1A). | 3.29 | | 7.28 | | 7.1 |
| 15028 | MAPK13: (MAPK13 OR PRKM13 OR SAPK4) MITOGEN-ACTIVATED PROTEIN KINASE 13 (EC 2.7.1.-) (STRESS-ACTIVATED PROTEIN KINASE-4) (MITOGEN-ACTIVATED PROTEIN KINASE P38 DELTA) (MAP KINASE P38 DELTA). | 1.86 | 1.64 | 0.77 | 2.24 | 3.09 |
| 15092 | EPHA1: (EPHA1 OR EPHT1 OR EPHT OR EPH) EPHRIN TYPE-A RECEPTOR 1 PRECURSOR (EC 2.7.1.112) (TYROSINE-PROTEIN KINASE RECEPTOR EPH). | 0.84 | 0.81 | 0.64 | 0.26 | 0.6 |
| 15116 | EPHB4: (EPHB4 OR HTK) EPHRIN TYPE-B RECEPTOR 4 PRECURSOR (EC 2.7.1.112) (TYROSINE-PROTEIN KINASE RECEPTOR HTK). | 0.87 | 0.74 | 1.2 | 1.89 | 0.63 |
| 15194 | PAK1: (PAK1) SERINE/THREONINE-PROTEIN KINASE PAK 1 (EC 2.7.1.-) (P21-ACTIVATED KINASE 1) (PAK-1) (P65-PAK) (ALPHA-PAK). | 0.56 | 1.08 | 0.91 | 0.37 | 0.67 |
| 15492 | MAP3K3: (MAP3K3 OR MAPKKK3 OR MEKK3) MITOGEN-ACTIVATED PROTEIN KINASE KINASE KINASE 3 (EC 2.7.1.-) (MAPK/ERK KINASE KINASE 3) (MEK KINASE 3) (MEKK 3). | | 1.85 | 0.64 | 1.05 | 0.54 |
| 15750 | DLX2: (DLX2) HOMEOBOX PROTEIN DLX-2. | | 1.58 | 1.11 | 1.13 | 1.13 |
| 15762 | DLX5: (DLX5) HOMEOBOX PROTEIN DLX-5 (DLX-5 BETA). | | | | 5.74 | 2.05 |
| 15783 | EN1: (EN1) HOMEOBOX PROTEIN ENGRAILED-1 (HU-EN-1). | | 1.28 | 0.91 | 6.04 | 0.83 |
| 15915 | POU2F2: (POU2F2 OR OTF2 OR OCT2) OCTAMER-BINDING TRANSCRIPTION FACTOR 2 (OTF-2) (LYMPHOID-RESTRICTED IMMUNOGLOBULIN OCTAMER BINDING PROTEIN NF-A2) (OCT-2 FACTOR). | 0.91 | 0.93 | 0.7 | 0.59 | 0.69 |
| 15918 | POU5F_1: (POU5F1 OR OTF3 OR OCT3 OR OCT4) OCTAMER-BINDING TRANSCRIPTION FACTOR 3A (OCT-3A) (OCT-4) (POU5FLC20) (POU 5 DOMAIN PROTEIN) (POU5FLC8) (OTF3C) (OCTAMER-BINDING TRANSCRIPTION FACTOR 3C) (OCT-3C) (POU5FLC1) (POU5FLC12). | 1.11 | 1.41 | 0.94 | 0.89 | 0.96 |
| 15945 | TCF2_1: (TCF2 OR HNF1B) HEPATOCYTE NUCLEAR FACTOR 1-BETA (HNF-1B) (VARIANT HEPATIC NUCLEAR FACTOR 1) (VHNF1) (HOMEOPROTEIN LFB3) (TRANSCRIPTION FACTOR 2) (TCF-2). | 0.89 | 0.74 | 0.76 | 0.83 | 1.01 |
| 16074 | ISL1: (ISL1) INSULIN GENE ENHANCER PROTEIN ISL-1 (ISLET-1). | | 2.19 | | 2.25 | |
| 16116 | NKX2-2: (NKX2-2 OR NKX2B OR NKX2.2) HOMEOBOX PROTEIN NKX-2.2 (HOMEOBOX PROTEIN NK-2 HOMOLOG B). | 1.61 | 1.79 | 1.23 | 0.76 | 0.72 |
| 16138 | OTX2: (OTX2) HOMEOBOX PROTEIN OTX2. | | 0.59 | 0.76 | | |
| 16534 | AIF1: (AIF1 OR IBA1) ALLOGRAFT INFLAMMATORY FACTOR-1 (AIF-1) (IONIZED CALCIUM-BINDING ADAPTER MOLECULE 1). | 0.3 | 0.48 | 0.43 | 0.07 | 0.59 |
| 16555 | CALU: (CALU) CALUMENIN PRECURSOR. | 0.77 | 0.08 | 0.38 | 4.8 | 0.32 |
| 16675 | MYL4: (MYL4 OR MLC1) MYOSIN LIGHT CHAIN 1, EMBRYONIC MUSCLE/ATRIAL | 1.65 | 6.62 | 0.78 | 1.07 | 0.95 |

Fig 3-27

| | | | | | | | |
|---|---|---|---|---|---|---|---|
| 16826 | ISOFORM (PRO1957). MYOSIN LIGHT CHAIN ALKALI, GT-1 ISOFORM (FRAGMENT). | 0.66 | | | | 3.15 | 0.82 |
| 16888 | ANKRD17_1: (4933425K22RIK or GTAR) GENE TRAP ANKYRIN REPEAT CONTAINING PROTEIN (KIAA0697) (ANKYRIN REPEAT DOMAIN 17) (ANKRD17) (SEROLOGICALLY DEFINED BREAST CANCER ANTIGEN NY-BR-16) (FLJ22206) (DKFZP547D039). | | | | 1.46 | | |
| 16891 | RTN4: (RTN4 OR NOGO OR ASY OR KIAA0886) RETICULON 4 (NEURITE OUTGROWTH INHIBITOR) (NOGO PROTEIN) (FOOCEN) (NEUROENDOCRINE-SPECIFIC PROTEIN) (NSP) (NEUROENDOCRINE SPECIFIC PROTEIN C HOMOLOG) (RTN-X) (RETICULON 5) (MY043 PROTEIN). | 0.25 | 0.26 | 0.55 | 0.5 | 0.3 |
| 16897 | S100A10: (S100A10 OR CAL1L OR ANX2LG OR CLP11) CALPACTIN I LIGHT CHAIN (P10 PROTEIN) (P11) (CELLULAR LIGAND OF ANNEXIN II). | 1.34 | 0.24 | 0.16 | 0.82 | 0.66 |
| 16924 | SEMA3C: (SEMA3C OR SEMAE) SEMAPHORIN 3C PRECURSOR (SEMAPHORIN E) (SEMA E). | 1.18 | 0.55 | 1.24 | 0.87 | 1.02 |
| 17161 | SOX20: (SOX20 OR SOX15 OR SOX-15) SOX-20 PROTEIN. | 0.97 | 1.4 | 1.18 | | |
| 17641 | IGHA1-IGHA2_HUMAN: (IGHA1) IG ALPHA-1 CHAIN C REGION (IGHA2) IG ALPHA-2 CHAIN C REGION. | 0.72 | 2 | 0.77 | 1.06 | 0.83 |
| 17674 | TNNC1: (TNNC1 OR TNNC) TROPONIN C, SLOW SKELETAL AND CARDIAC MUSCLES (TN-C). | 0.13 | 0.88 | 0.87 | 0.51 | 0.76 |
| 17843 | SERPINA1_2_HUMAN: (SERPINA1 OR PI OR AAT) ALPHA-1-ANTITRYPSIN PRECURSOR (ALPHA-1 PROTEASE INHIBITOR) (ALPHA-1-ANTIPROTEINASE). | 0.24 | 0.7 | 0.24 | 0.06 | 0.28 |
| 17848 | DLK1: (DLK1 OR DLK OR PREF1 OR SCP-1) DELTA-LIKE PROTEIN PRECURSOR (DLK) (PREADIPOCYTE FACTOR 1) (PREF-1) (ADIPOCYTE DIFFERENTIATION INHIBITOR PROTEIN) (ZOG) ZOG. | 1.77 | 0.45 | 1.36 | 1.27 | |
| 17857 | DNMT1: (DNMT1 OR DNMT OR AIM) DNA (CYTOSINE-5)-METHYLTRANSFERASE HSAI (EC 2.1.1.37) (DNA METHYLTRANSFERASE HSAI) (DNA MTASE HSAI) (MCMT) (M.HSAI). | 0.95 | 1.17 | 3.09 | 0.76 | 1.78 |
| 17920 | DNMT3B: (DJ1085F17.1 OR DNMT3B) MODIFICATION METHYLASE ISOFORM 1 (EC 2.1.1.73) (CYTOSINE-SPECIFIC METHYLTRANSFERASE). | 1.07 | 0.93 | 0.93 | 1.63 | 0.95 |
| 17935 | HDC: (HDC) HISTIDINE DECARBOXYLASE (EC 4.1.1.22) (HDC). | 0.32 | 1.36 | 2.89 | 1.03 | 5.39 |
| 18160 | IFNGR2: (IFNGR2 OR IFNGT1) INTERFERON-GAMMA RECEPTOR BETA CHAIN PRECURSOR (INTERFERON-GAMMA RECEPTOR ACCESSORY FACTOR-1) (AF-1) (INTERFERON-GAMMA TRANSDUCER-1). | 1.28 | 0.61 | 0.43 | 0.67 | 0.65 |
| 18164 | HDAC2: (HDAC2) HISTONE DEACETYLASE 2 (HD2). | 1.25 | 2.85 | 1.57 | 1.1 | 0.82 |
| 18379 | HMGIY: (HMGIY OR HMGA1 OR HMGI) HIGH MOBILITY GROUP PROTEIN HMG-Y (HIGH MOBILITY GROUP AT-HOOK 1). | 1.5 | 1.04 | 2.09 | 0.79 | 1.23 |
| 18385 | HSPC150: (HSPC150) (UBIQUITIN-CONJUGATING ENZYME E2) (CDNA FLJ20497 FIS, CLONE KAT08890) (HSPC150 PROTEIN SIMILAR TO UBIQUITIN-CONJUGATING ENZYME) (2700084L22RIK). | 0.54 | 0.88 | 10.41 | 1.73 | 3.41 |
| | IGFBP2: (IGFBP2 OR BP2) INSULIN-LIKE GROWTH FACTOR BINDING PROTEIN 2 | | 0.26 | 3.85 | 20.42 | 4.96 |

Fig 3-28

| | | | | | | |
|---|---|---|---|---|---|---|
| 19048 | PRECURSOR (IGFBP-2) (IBP-2) (IGF-BINDING PROTEIN 2). | 1.37 | 1.33 | 1.64 | 0.83 | 0.85 |
| | ALB: (ALB OR ALB1 OR ALB-1) SERUM ALBUMIN PRECURSOR. | | | | | |
| 19408 | RNF138: (RNF138) RING FINGER PROTEIN 138 (STRIN) (TRIF) (RSD-4) (FLJ13517) (HSD-4) (DKFZP434I1714) (2410015A17RIK). | 1.41 | 1.21 | 1.73 | 0.38 | 0.88 |
| | EPRS: (EPRS OR QPRS OR GLNS OR PARS) BIFUNCTIONAL AMINOACYL-TRNA SYNTHETASE [INCLUDES: GLUTAMYL-TRNA SYNTHETASE (EC 6.1.1.17) (GLUTAMATE--TRNA LIGASE); PROLYL-TRNA SYNTHETASE (EC 6.1.1.15) (PROLINE--TRNA LIGASE)]. | 0.98 | 0.54 | 1.8 | 2.81 | 0.98 |
| 19669 | RPLP0: (RPLP0) 60S ACIDIC RIBOSOMAL PROTEIN P0 (L10E). | 1.72 | 1.19 | 1.34 | 0.52 | 1.23 |
| 19690 | F7: (F7) COAGULATION FACTOR VII PRECURSOR (EC 3.4.21.21) (SERUM PROTHROMBIN CONVERSION ACCELERATOR) (EPTACOG ALFA). | 1.79 | 7.29 | | | 1.12 |
| 19759 | GATA6: (GATA6) TRANSCRIPTION FACTOR GATA-6 (GATA BINDING FACTOR-6)(DNA BINDINGPROTEIN GATA-GT2). | 1.16 | 0.94 | 1.33 | 3.05 | 0.98 |
| 20039 | SEM2: (SEM2) SEMAPHORIN SEM2. | 1.12 | 1.99 | 1.59 | 0.8 | 1.04 |
| 20526 | SEMA3B: (SEMA3B OR SEMA5) SEMAPHORIN 3B PRECURSOR (SEMAPHORIN V) (SEMA V). (SEMA3B OR SEMAA OR SEMA) SEMAPHORIN 3B PRECURSOR (SEMAPHORIN A) (SEMA A). | | | | 33.04 | |
| 20532 | SEMA4C: (SEMA4C OR KIAA1739) SEMAPHORIN 4C PRECURSOR (SEMAI) (SEMACL1) (SEMAPHORIN C-LIKE 1) KIAA1739 PROTEIN (FRAGMENT). | 1.18 | 1.13 | 1.2 | 1.45 | 1 |
| 20586 | ASPIC1: (ASPIC1 OR CEP-68) ASPIC PRECURSOR (CHONDROCYTE EXPRESSED PROTEIN 68 KDA) ((2810454P21RIK OR CRTAC1) (CRTAC1-B PROTEIN) (CARTILAGE ACIDIC PROTEIN 1) (FLJ10320). | 1.15 | 0.92 | 1.22 | 2.15 | 0.8 |
| 20616 | VIM: (VIM) VIMENTIN. | 0.36 | 0.42 | 0.2 | 0.99 | 0.79 |
| 21478 | VTN: (VTN) VITRONECTIN PRECURSOR (SERUM SPREADING FACTOR) (S-PROTEIN). | 0.98 | 0.85 | 1.1 | 2.03 | 1.32 |
| 21481 | KRAS2A-KRAS2B: (KRAS2A-2B OR RASK2) TRANSFORMING PROTEIN P21A (K-RAS 2A) TRANSFORMING PROTEIN P21B (K-RAS 2B) (KI-RAS) (C-K-RAS). | 0.71 | 0.42 | 1 | 1.36 | 0.8 |
| 21835 | TC10-PIGF: (RHOQ OR ARHQ OR TC10) RHO-RELATED GTP-BINDING PROTEIN RHOQ (RAS-RELATED GTP-BINDING PROTEIN TC10) (RHO-LIKE GTP-BINDING PROTEIN TC10) (PIGF) (PHOSPHATIDYLINOSITOL-GLYCAN BIOSYNTHESIS, CLASS F PROTEIN) (PIG-F). | 0.39 | 0.41 | 0.61 | 1.57 | 0.94 |
| 22015 | GPS1_3PRIME: (GPS1 OR COPS1) COP9 SIGNALOSOME COMPLEX SUBUNIT 1 (G PROTEIN PATHWAY SUPPRESSOR 1) (GPS1 PROTEIN) (MFH PROTEIN). | 0.89 | 0.56 | 1.18 | 1.01 | 0.76 |
| 22039 | HBZ: (HBZ OR HBZ2) HEMOGLOBIN ZETA CHAIN. | 20.2 | 122.8 | 3.26 | | |
| 22114 | GAL: (GAL OR GAL1 OR GALN OR GLNN) GALANIN PRECURSOR. | 1.87 | 1.17 | 2.54 | 1.09 | 1.21 |
| 22441 | KCNQ3: (KCNQ3) VOLTAGE-GATED POTASSIUM CHANNEL PROTEIN KQT-LIKE 3. | | 2.35 | | | 1.44 |
| 22453 | RAMP1: (RAMP1) RECEPTOR ACTIVITY MODIFYING PROTEIN 1. | 0.36 | 0.09 | 0.23 | 0.37 | 0.12 |
| 22462 | RAMP3: (RAMP3) RECEPTOR ACTIVITY MODIFYING PROTEIN 3. | 1.19 | 0.66 | 1.46 | 0.83 | 0.92 |

Fig 3-29

| 22584 | E2IG3: (E2IG3) E2IG3 (FLJ14608) (NUCLEOSTEMIN) (NS OR C77032). | 1.35 | | 2.62 | 1.48 | 0.91 |
| --- | --- | --- | --- | --- | --- | --- |
| 22644 | GBP2_HUMAN: (GBP2) INTERFERON-INDUCED GUANYLATE-BINDING PROTEIN 2 (GUANINE NUCLEOTIDE-BINDING PROTEIN 2) (MGBP-2). | 0.95 | 0.68 | 0.26 | 0.35 | 0.3 |
| 22663 | HNRPA1: (HNRPA1) HETEROGENEOUS NUCLEAR RIBONUCLEOPROTEIN A1 (HELIX-DESTABILIZING PROTEIN) (SINGLE-STRAND BINDING PROTEIN) (HNRNP CORE PROTEIN A1). | 1.2 | 0.82 | 1.96 | 0.5 | 1.14 |
| 22693 | MYH7: (MYH7 OR MYHCB) MYOSIN HEAVY CHAIN, CARDIAC MUSCLE BETA ISOFORM (MYHC-BETA). | 1.01 | 0.89 | 1.27 | 1.16 | 1.45 |
| 22801 | RPL6: (RPL6) 60S RIBOSOMAL PROTEIN L6 (TAX-RESPONSIVE ENHANCER ELEMENT BINDING PROTEIN 107) (TAXREB107) (NEOPLASM-RELATED PROTEN C140). | 1.47 | 1.14 | 0.98 | 0.59 | 0.74 |
| 22935 | DDX21: (DDX21) NUCLEOLAR RNA HELICASE II (NUCLEOLAR RNA HELICASE GU) (RH II/GU) (DEAD BOX PROTEIN 21). | 0.93 | 0.94 | 1.16 | 1.48 | 1.22 |
| 23212 | KCNJ3: (KCNJ3 OR GIRK1) G PROTEIN-ACTIVATED INWARD RECTIFIER POTASSIUM CHANNEL 1 (GIRK1) (POTASSIUM CHANNEL, INWARDLY RECTIFYING, SUBFAMILY J, MEMBER 3) (INWARD RECTIFIER K+ CHANNEL KIR3.1). | | 1.32 | 1.54 | 0.78 | 0.95 |
| 23215 | KCNJ6: (KCNJ6 OR KCNJ7 OR GIRK2 OR KATP2) G PROTEIN-ACTIVATED INWARD RECTIFIER POTASSIUM CHANNEL 2 (GIRK2) (POTASSIUM CHANNEL, INWARDLY RECTIFYING, SUBFAMILY J, MEMBER 6) (INWARD RECTIFIER K+ CHANNEL KIR3.2) (KATP-2) (BIR1). | 0.96 | 1.23 | 1.1 | | 1.42 |
| 23218 | KCNJ9: (KCNJ9 OR GIRK3) G PROTEIN-ACTIVATED INWARD RECTIFIER POTASSIUM CHANNEL 3 (GIRK3) (POTASSIUM CHANNEL, INWARDLY RECTIFYING, SUBFAMILY J, MEMBER 9) (INWARDLY RECTIFIER K+ CHANNEL KIR3.3). | | 1.21 | 1.43 | | |
| 23248 | SOX2: (SOX2) TRANSCRIPTION FACTOR SOX-2. | | 1.57 | 1.6 | | 0.93 |
| 23322 | CLDN1: (CLDN1 OR CLD1 OR SEMP1) CLAUDIN-1 (SENESCENCE-ASSOCIATED EPITHELIAL MEMBRANE PROTEIN). | 0.57 | 1.09 | 0.48 | 0.88 | 0.77 |
| 23325 | CLDN10: (CLDN10) CLAUDIN-10 (OSP LIKE PROTEIN). | 1.09 | 1.07 | 2.8 | 0.92 | 1.25 |
| 23364 | CLDN5: (CLDN5 OR TMVCF) CLAUDIN-5 (TRANSMEMBRANE PROTEIN DELETED IN VCFS) (TMDVCF). | 3.26 | | | | |
| 23367 | CLDN6: (CLDN6) CLAUDIN-6 (SKULLIN 2). | 0.87 | 0.58 | 0.7 | 1.75 | 0.64 |
| 24438 | ELAVL4: (ELAVL4 OR HUD OR PNEM) ELAV-LIKE PROTEIN 4 (PARANEOPLASTIC ENCEPHALOMYELITIS ANTIGEN HUD) (HU-ANTIGEN D). | 0.52 | 1.13 | 0.7 | 0.94 | 0.72 |
| 24570 | MSI2_1: (MSI2H OR MSI2) RNA-BINDING PROTEIN MUSASHI HOMOLOG 2 (MUSASHI-2) (RNA-BINDING PROTEIN MUSASHI2). | 1.15 | 1.5 | 0.89 | 0.73 | 1.17 |
| 24645 | CDH4: (CDH4) CADHERIN-4 PRECURSOR (RETINAL-CADHERIN) (R-CADHERIN) (R-CAD) (BA489M19.1). | | | 1.14 | | 1.52 |
| 24938 | C20ORF1: (C20ORF1 OR C20ORF2 OR DIL2 OR TPX2) RESTRICTED EXPRESSION PROLIFERATION ASSOCIATED PROTEIN 100 (P100) (DIFFERENTIALLY EXPRESSED IN LUNG CELLS 2) (DIL-2) (TARGETING PROTEIN FOR XKLP2) (C20ORF1 PROTEIN) | 1.14 | 1.48 | 8.52 | | 5.39 |

Fig 3-30

| ID | Description | | | | | | |
|---|---|---|---|---|---|---|---|
| 24965 | (C20ORF2 PROTEIN) (PROTEIN FLS353). | | | | | | |
|  | DPYSL3: (DPYSL3 OR ULIP OR DRP3 OR CRMP4) DIHYDROPYRIMIDINASE RELATED PROTEIN-3 (DRP-3) (UNC-33-LIKE PHOSPHOPROTEIN) (ULIP PROTEIN) (COLLAPSIN RESPONSE MEDIATOR PROTEIN 4) (CRMP-4). | | 0.96 | | | 5.67 | 1.19 |
| 25040 | PUM2: (PUM2 OR PUMH2 OR KIAA0235) PUMILIO HOMOLOG 2 (PUMILIO2) (PUMM2) (PUMILIO 2) (TRANSLATIONAL REPRESSOR PUMILIO). | 0.98 | 1.65 | 0.8 | 0.65 | 0.89 |
| 25052 | KITLG: (KITLG OR MGF OR SCF) KIT LIGAND PRECURSOR (C-KIT LIGAND) (STEM CELL FACTOR) (SCF) (MAST CELL GROWTH FACTOR) (MGF). | | | | | | 1.46 |
| 25324 | KCNA4: (KCNA4) VOLTAGE-GATED POTASSIUM CHANNEL PROTEIN KV1.4 (HK1) (HPCN2) (HBK4) (HUKII) (RCK4) (RHK1) (RK4). | 0.92 | 1.26 | 1.33 | 1.07 | 1.66 |
| 25333 | KCNA7: (KCNA7) POTASSIUM VOLTAGE-GATED CHANNEL, SHAKER-RELATED SUBFAMILY, MEMBER 7) (KCNC7). | | | | | | 1.5 |
| 25360 | KCNH2: (KCNH2 OR HERG OR HERG1 OR ERG OR ERG1) POTASSIUM VOLTAGE-GATED CHANNEL SUBFAMILY H MEMBER 2 (ETHER-A-GO-GO RELATED GENE POTASSIUM CHANNEL 1) (H-ERG) (ERG1) (ETHER-A-GO-GO RELATED PROTEIN 1) (EAG RELATED PROTEIN 1) (EAG HOMOLOG) (MERG) (MERG1) (R-E | 1.37 | 1.9 | 4.38 | | 1.77 |
| 25363 | KCNJ1: (KCNJ1 OR ROMK1) ATP-SENSITIVE INWARD RECTIFIER POTASSIUM CHANNEL 1 (POTASSIUM CHANNEL,INWARDLY RECTIFYING, SUBFAMILY J, MEMBER 1) (ATP-REGULATED POTASSIUM CHANNEL ROM-K) (KIR1.1) ROM-K POTASSIUM CHANNEL PROTEIN ISOFORM ROMK2 (KAB-1). | | | 1.06 | 1.02 | 1.16 |
| 25372 | KCNJ15: (KCNJ15 OR KCNJ14) ATP-SENSITIVE INWARD RECTIFIER POTASSIUM CHANNEL 15 (POTASSIUM CHANNEL, INWARDLY RECTIFYING, SUBFAMILY J, MEMBER 15) (INWARD RECTIFIER K+ CHANNEL KIR4.2) (KIR1.3). | | 0.7 | 1.24 | | 1.01 |
| 25384 | KCNJ8: (KCNJ8) ATP-SENSITIVE INWARD RECTIFIER POTASSIUM CHANNEL 8 (POTASSIUM CHANNEL,INWARDLY RECTIFYING, SUBFAMILY J, MEMBER 8) (INWARDLY RECTIFIER K+CHANNEL KIR6.1) (UKATP-1). | 1.13 | 0.8 | 1.64 | 1.29 | 1.11 |
| 25390 | KCNK1: (KCNK1 OR TWIK1 OR HOHO1 OR KCNO1) POTASSIUM CHANNEL SUBFAMILY K MEMBER 1 (INWARD RECTIFYING POTASSIUM CHANNEL PROTEIN TWIK-1) (POTASSIUM CHANNEL KCNO1) PUTATIVE POTASSIUM CHANNEL TWIK. | 1.17 | 0.9 | 0.78 | 1.55 | 1.08 |
| 25411 | KCNK2: (KCNK2 OR TREK1 OR TREK) POTASSIUM CHANNEL SUBFAMILY K MEMBER 2 (OUTWARD RECTIFYING POTASSIUM CHANNEL PROTEIN TREK-1) (TREK-1 K+ CHANNEL SUBUNIT) (TWO-PORE POTASSIUM CHANNEL TPKC1) 2P DOMAIN POTASSIUM CHANNEL KCNK2. | | 0.74 | 1.41 | 2.53 | 0.9 |
| 25417 | KCNK4: (KCNK4 OR TRAAK) POTASSIUM CHANNEL SUBFAMILY K MEMBER 4 (TWIK-RELATED ARACHIDONIC ACID-STIMULATED POTASSIUM CHANNEL PROTEIN) (TRAAK) MECHANOSENSITIVE TANDEM PORE POTASSIUM CHANNEL. | 0.81 | 0.86 | 0.69 | 1.08 | 0.83 |
| 25420 | KCNK5: (KCNK5 OR TASK2) POTASSIUM CHANNEL SUBFAMILY K MEMBER 5 (ACID-SENSITIVE POTASSIUM CHANNEL PROTEIN TASK-2) (TWIK-RELATED ACID- | 1.09 | 0.93 | 1.43 | | 1.48 |

Fig 3-31

| | | | | | | | |
|---|---|---|---|---|---|---|---|
| 25441 | SENSITIVE K+ CHANNEL 2). KCNQ4: (KCNQ4) VOLTAGE-GATED POTASSIUM CHANNEL PROTEIN KQT-LIKE 4. | 1.48 | 1.32 | 1.01 | 0.92 | 0.94 |
| 25444 | KCNQ5: (KCNQ5) VOLTAGE-GATED POTASSIUM CHANNEL PROTEIN KQT-LIKE 5. | 0.85 | 0.89 | 0.86 | 1.44 | 0.97 |
| 25468 | KIR2.4: (KIR2.4 OR KCNJ14) INWARD RECTIFIER POTASSIUM CHANNEL (INWARDLY RECTIFYING POTASSIUM CHANNEL KIR2.4). | 1 | 0.71 | 1.13 | 1.03 | 1.27 |
| 25583 | CLCN4: (CLCN4) CHLORIDE CHANNEL PROTEIN 4 (CLC-4) (CLCN4-2) PUTATIVE CHLORIDE CHANNEL (SIMILAR TO MM CLCN4-2). | 0.83 | 0.69 | 2.1 | 1.24 | 1.88 |
| 25586 | CLCN5: (CLCN5 OR CLCK2) CHLORIDE CHANNEL PROTEIN 5 (CLC-5). | 7.55 | 18.09 | 1.22 | 0.76 | 0.97 |
| 25932 | HIST1H2AC: (HIST1H2AC OR H2AFL) HISTONE H2A.L (H2A/L). | 1.63 | 0.84 | 0.25 | 0.68 | 0.25 |
| 25941 | PBXIP1: (PBXIP1 OR 4732463H20RIK) PRE-B-CELL LEUKEMIA TRANSCRIPTION FACTOR INTERACTING PROTEIN 1 (HEMATOPOIETIC PBX-INTERACTING PROTEIN) (HPIP) (FLJ12435) (FLJ13157) (HPBXIP). | 2.57 | 1.41 | 0.52 | 0.96 | 0.51 |
| 26175 | GPC4: (GPC4) GLYPICAN-4 PRECURSOR (K-GLYPICAN). | 0.97 | 1.02 | 1.2 | 2.93 | 1.05 |
| 26188 | KCNQ2_2: (KCNQ2) VOLTAGE-GATED POTASSIUM CHANNEL PROTEIN KQT-LIKE 2 (NEUROBLASTOMA-SPECIFIC POTASSIUM CHANNEL PROTEIN). | 3.33 | 1.03 | 2.1 | | 1.24 |
| 26268 | VAP-A: (VAP-A OR VAP33) VAMP-ASSOCIATED PROTEIN A (VAPA). | 0.83 | 0.7 | 1.36 | 0.89 | 1.22 |
| 26503 | KCNE3: (KCNE3) MINIMUM POTASSIUM ION CHANNEL-RELATED PEPTIDE 2 (MIRP2) (MINK-RELATED PEPTIDE 2). | 0.71 | 0.8 | 0.77 | 0.5 | 0.91 |
| 26951 | NME2: (NME2 OR NM23B) NUCLEOSIDE DIPHOSPHATE KINASE B (EC 2.7.4.6) (NDK B) (NDP KINASE B) (P18). | 0.82 | 0.31 | 1.37 | 1.28 | 1.05 |
| 27246 | PTN: (PTN OR NEGF1 OR HBNF1) PLEIOTROPHIN PRECURSOR (PTN) (HEPARIN-BINDING GROWTH-ASSOCIATED MOLECULE) (HB-GAM) (HEPARIN-BINDING GROWTH FACTOR 8) (HBGF-8) (OSTEOBLAST SPECIFIC FACTOR 1) (OSF-1) (HEPARIN-BINDING NEURITE OUTGROWTH PROMOTING FACTOR 1) (HBNF-PTTG_HUMAN; (PTTG) PITUITARY TUMOR TRANSFORMING GENE, PITUITARY | 1.02 | 0.84 | 0.97 | 1.45 | 0.98 |
| 27251 | TUMOR TRANSFORMING GENE PROTEIN 1 (SECURIN HOMOLOG) (HPTTG OR PTTG1 OR TUTR1) (PTTG2) PITUITARY TUMOR TRANSFORMING GENE 2 PROTEIN (PTTG3) PITUITARY TUMOR TRANSFORMING GENE PROTEIN 3. | 1.62 | 2.01 | 13.29 | 0.72 | 6.43 |
| 27255 | RPS24: (RPS24 OR RPS19) 40S RIBOSOMAL PROTEIN S24 (S19). | 1.46 | 0.71 | 1.21 | 0.39 | 0.53 |
| 27501 | ALPL: (ALPL) ALKALINE PHOSPHATASE, TISSUE-NONSPECIFIC ISOZYME PRECURSOR (EC 3.1.3.1) (AP-TNAP) (LIVER/BONE/KIDNEY ISOZYME) (TNSALP) (AKP2 OR AKP-2). | 1.04 | 0.77 | 0.6 | 2.16 | 0.58 |
| 27579 | PTHLH: (PTHLH OR PTHRP) PARATHYROID HORMONE-RELATED PROTEIN PRECURSOR (PTH-RP) (PTHRP) [CONTAINS: OSTEOSTATIN (PTHRP[107-139])] PARATHYROID HORMONE-LIKE HORMONE. | 1.65 | 1.68 | 1.61 | 1.64 | |
| 27741 | MAD2L1: (MAD2L1 OR MAD2 OR MAD2A) MITOTIC SPINDLE ASSEMBLY CHECKPOINT PROTEIN MAD2A (MAD2-LIKE 1). | 1.73 | 1.06 | 8.77 | 1.03 | 4.08 |

Fig 3-32

| | | | | | | | |
|---|---|---|---|---|---|---|---|
| 27831 | CITED2: (CITED2 OR MRG1) CBP/P300-INTERACTING TRANSACTIVATOR 2 (MSG-RELATED PROTEIN 1) (MRG1 PROTEIN) (P35SRJ). | 0.9 | 0.6 | 1.08 | 1.35 | 1.21 |
| 27873 | ANGPT2: (ANGPT2) ANGIOPOIETIN-2 PRECURSOR (ANG-2). | 1.41 | | | | |
| 28292 | CHI3L2_HUMAN: (CHI3L2) CHITINASE 3-LIKE PROTEIN 2 PRECURSOR (YKL-39) (CHONDROCYTE PROTEIN 39). | 3.9 | 1.58 | 0.81 | 0.54 | 0.83 |
| 28320 | KPNA2: (KPNA2 OR RCH1 OR SRP1) IMPORTIN ALPHA-2 SUBUNIT (KARYOPHERIN ALPHA-2 SUBUNIT) (SRP1-ALPHA) (RAG COHORT PROTEIN 1). | 0.74 | 0.63 | 3.46 | 0.9 | 1.97 |
| 28475 | LAPTM4B: (LAPTM4B OR LAPTM4BETA OR DKFZP586E1124) LYSOSOMAL-ASSOCIATED TRANSMEMBRANE PROTEIN 4 BETA (NT2RM1000066) (LC27) (INTEGRAL MEMBRANE TRANSPORTER) (HYPOTHETICAL PROTEIN PSEC0001). | 0.97 | 0.98 | 1.95 | 1.12 | 1.76 |
| 28604 | NPPA: (NPPA OR PND) ATRIAL NATRIURETIC FACTOR PRECURSOR (ANF) (ATRIAL NATRIURETIC PEPTIDE) (ANP) (PREPRONATRIODILATIN). | 1.35 | 1.01 | 2.76 | 0.92 | 2.09 |
| 28658 | RPL24: (RPL24) 60S RIBOSOMAL PROTEIN L24 (L30). | 1.31 | 0.71 | 0.93 | 0.56 | 0.7 |
| 28891 | DAB1: (DAB1) DISABLED HOMOLOG 1. | 1.59 | 0.67 | 1.23 | 0.7 | 0.76 |
| 28915 | OLIG1: (OLIG1) OLIGODENDROCYTE TRANSCRIPTION FACTOR 1 (OLIGO1) (OLIGODENDROCYTE-SPECIFIC BHLH TRANSCRIPTION FACTOR 1). | 0.24 | 0.41 | 0.23 | 0.2 | 0.24 |
| 28921 | RELN: (RELN OR RL) REELIN PRECURSOR (EC 3.4.21.-) (REELER PROTEIN). | | | | 1.43 | |
| 28937 | TUBB4_HUMAN: (TUBB4) TUBULIN BETA-4 CHAIN (TUBULIN BETA-III). | 0.82 | 0.55 | 0.7 | 1.97 | 0.77 |
| 29197 | LEFTA_HUMAN: (EBAF OR TGFB4 OR LEFTA OR LEFTYA) TRANSFORMING GROWTH FACTOR BETA 4 PRECURSOR (TGF-BETA 4) (ENDOMETRIAL BLEEDING-ASSOCIATED FACTOR) (LEFT-RIGHT DETERMINATION FACTOR A) (LEFTY-A PROTEIN). | 2.01 | 0.93 | 1.99 | | |
| 29221 | NCAM2: (NCAM2 OR NCAM21) NEURAL CELL ADHESION MOLECULE 2 PRECURSOR (N-CAM 2). | 1.81 | 0.82 | 2.11 | 0.64 | 0.88 |
| 29310 | SNAI2: (SNAI2 OR SLUG OR SLUGH) ZINC FINGER PROTEIN SLUG (NEURAL CREST TRANSCRIPTION FACTOR SLUG) (SNAIL HOMOLOG 2). | 0.74 | 0.78 | 1.05 | 0.65 | 0.82 |
| 29322 | SST: (SST OR SMST) SOMATOSTATIN PRECURSOR [CONTAINS: ANTRIN; SOMATOSTATIN-28; SOMATOSTATIN-14]. | 0.83 | 0.63 | 1.34 | 1.78 | 0.81 |
| 29328 | TH: (TH OR TYH) TYROSINE 3-MONOOXYGENASE (EC 1.14.16.2) (TYROSINE 3-HYDROXYLASE) (TH). | 0.64 | 0.82 | 0.81 | 1.19 | 1.08 |
| 29371 | DLX1: (DLX1) HOMEOBOX PROTEIN DLX-1. | 1.09 | 0.85 | 1.48 | 0.47 | 1.35 |
| 29475 | CEBPA_3: (CEBPA) CCAAT/ENHANCER BINDING PROTEIN ALPHA (C/EBP ALPHA). | 0.22 | 0.33 | 1.6 | 0.96 | 0.92 |
| 29909 | IGHA1-IGHA2_M_HUMAN: (IGHA1) IG ALPHA-1 CHAIN C REGION (IGHA2) (IG ALPHA-2 CHAIN C REGION). | 1.06 | 0.7 | 1.34 | 0.15 | 0.88 |
| 30025 | CD133: (PROM1 OR PROML1 OR PROM OR CD133 OR AC133) PROMININ 1 PRECURSOR (PROMININ-LIKE PROTEIN 1) (ANTIGEN AC133) (CD133 ANTIGEN). | 1.18 | 0.91 | 1.56 | 0.56 | 1.01 |
| 30155 | L30: (L30) 60S RIBOSOMAL PROTEIN L30 ISOLOG (MY024 PROTEIN) (RPL24). | 1.1 | 0.74 | 1.82 | 0.86 | 0.79 |

Fig 3-33

| | | | | | | |
|---|---|---|---|---|---|---|
| 30231 | (CHROMOSOME 15 OPEN READING FRAME 15). | | | | | 1.63 |
| | SNRPF: (SNRPF OR PBSCF) SMALL NUCLEAR RIBONUCLEOPROTEIN F (SNRNP-F) (SM PROTEIN F) (SM-F) (SMF). | 1.12 | 0.5 | 3.81 | 0.63 | |
| 30327 | ACTC: (ACTC OR ACTC1) ACTIN, ALPHA, CARDIAC. | | 1.23 | | 96.81 | 0.79 |
| 30346 | MMRN: (MMRN OR ECM) ENDOTHELIAL CELL MULTIMERIN PRECURSOR. | 1.82 | 0.54 | 1.14 | 0.95 | 1.08 |
| 30353 | ROBO4: (ROBO4 OR 1200012D01RIK) MAGIC ROUNDABOUT (FLJ14946) (FLJ00236) (FLJ20798) (FLJ21542). | 1.44 | 1.89 | 1.51 | 0.97 | |
| 30355 | TEAD1: (TEAD1 OR TEF1 OR TEF-1 OR TCF13) TRANSCRIPTIONAL ENHANCER FACTOR TEF-1 (TEA DOMAIN FAMILY MEMBER 1) (TEAD-1) (PROTEIN GT-IIC) (TRANSCRIPTION FACTOR 13) (NTEF-1). | 1.34 | 0.56 | 1.25 | 0.65 | 0.66 |
| 30362 | TNNT2: (TNNT2) TROPONIN T, CARDIAC MUSCLE ISOFORMS (TNTC). | 1.35 | 1.42 | 1.31 | 0.79 | 1.03 |
| 30433 | ITGAX: (ITGAX OR CD11C) INTEGRIN ALPHA-X PRECURSOR (LEUKOCYTE ADHESION GLYCOPROTEIN P150,95 ALPHA CHAIN) (LEUKOCYTE ADHESION RECEPTOR P150,95) (CD11C) (LEU M5). | 0.18 | 0.78 | 0.13 | | 0.73 |
| 30459 | PF4-PF4V1_HUMAN: (SCYB4 OR PF4) PLATELET FACTOR 4 PRECURSOR (PF-4) (ONCOSTATIN A) (IROPLACT) (PF4V1 OR SCYB4V1) (PLATELET FACTOR 4 VARIANT PRECURSOR) (PF4VAR1) (PF4ALT) (CXCL4). | 2.42 | 0.22 | 0.37 | 0.03 | 0.03 |
| 30546 | FGF20: (FGF20) FIBROBLAST GROWTH FACTOR-20 (FGF-20). | 1.19 | 0.98 | 1.18 | 0.66 | 1.1 |
| 30615 | SDF2: (SDF2) STROMAL CELL-DERIVED FACTOR 2 PRECURSOR (SDF-2). | 0.65 | 0.44 | 0.82 | 1.21 | 0.78 |
| 30624 | BMP11: (GDF11 OR BMP11) GROWTH/DIFFERENTIATION FACTOR 11 PRECURSOR (BONE MORPHOGENETIC PROTEIN 11). | 0.98 | 0.63 | 0.93 | 1.33 | 0.84 |
| 30637 | FGF4: (FGF4 OR HST OR HSTF1 OR KS3) FIBROBLAST GROWTH FACTOR-4 PRECURSOR (FGF-4) (HEPARIN SECRETORY TRANSFORMING PROTEIN) (HST-1) (HST) (TRANSFORMING PROTEIN KS3) (HBGF-4). | 1.22 | 0.81 | 1.45 | 0.74 | 0.95 |
| 30671 | RARA1_HUMAN: (RARA OR NR1B1) RETINOIC ACID RECEPTOR ALPHA (RAR-ALPHA). | 0.87 | 1.23 | 0.98 | 0.93 | 0.6 |
| 30686 | FN1_REPEAT-A: (FN1 OR FN) FIBRONECTIN PRECURSOR (FN) (COLD-INSOLUBLE GLOBULIN) (CIG). | 0.74 | 0.17 | 0.17 | 2.73 | 0.16 |
| 30689 | FN1_REPEAT-B: (FN1 OR FN) FIBRONECTIN PRECURSOR (FN) (COLD-INSOLUBLE GLOBULIN) (CIG). | 0.62 | 0.09 | 0.08 | 3 | 0.09 |
| 30808 | CNTFR: (CNTFR) CILIARY NEUROTROPHIC FACTOR RECEPTOR ALPHA PRECURSOR (CNTFR ALPHA). | 1.12 | 0.69 | 1.17 | 0.61 | 0.73 |
| 30815 | GATA5: (GATA5) TRANSCRIPTION FACTOR GATA-5 (GATA BINDING FACTOR-5). | 1.24 | 1.04 | 1.65 | 1.12 | 0.99 |
| 30954 | ACRP: (ACRP OR CTNNAL1) ALPHA-CATENIN-LIKE PROTEIN. | 0.82 | 1.68 | 1.59 | 2.32 | 0.71 |
| 30957 | ADH4: (ADH4) ALCOHOL DEHYDROGENASE CLASS II PI CHAIN PRECURSOR (EC 1.1.1.1). | 0.63 | 0.82 | 0.72 | 1.03 | 0.87 |
| 30963 | ARHGAP9: (ARHGAP9) RHO-GTPASE ACTIVATING PROTEIN (FLJ35444) (RGL1). | 0.86 | 1 | 0.63 | 0.05 | 0.53 |

Fig 3-34

| | | | | | | | |
|---|---|---|---|---|---|---|---|
| | (DKFZP667F149) (AU043488). | | | | | | |
| 30969 | BUB1B: (BUB1B OR MAD3L OR BUBR1) MITOTIC CHECKPOINT SERINE/THREONINE-PROTEIN KINASE BUB1 BETA (EC 2.7.1.-) (HBUBR1) (MAD3/BUB1-RELATED PROTEIN KINASE) (MITOTIC CHECKPOINT KINASE MAD3L). | 1.17 | 0.86 | 3.85 | | 1.65 |
| 30972 | BUB3: (BUB3) MITOTIC CHECKPOINT PROTEIN BUB3. | 1.44 | 0.65 | 2.35 | 0.81 | 1.36 |
| 30978 | CCCAP: (SDCCAG8 OR CCCAP) CENTROSOMAL COLON CANCER AUTOANTIGEN PROTEIN (HSPC085) (NY-CO-8) (2700048G21RIK) (5730470G24RIK) (SLINKY). | 1.05 | 0.65 | 1.05 | 1.19 | 0.92 |
| 30981 | CDO1: (CDO1) CYSTEINE DIOXYGENASE TYPE I (EC 1.13.11.20) (CDO) (CDO-I). | 1.28 | 0.95 | 1.08 | 0.65 | 0.95 |
| 30984 | CHI3L1: (CHI3L1) CHITINASE-3 LIKE PROTEIN 1 PRECURSOR (CARTILAGE GLYCOPROTEIN-39) (GP-39) (39 KDA SYNOVIAL PROTEIN) (YKL-40). | 0.3 | 0.08 | 0.03 | 0.11 | 0.06 |
| 30987 | CPN2: (CPN2) CARBOXYPEPTIDASE N 83 KDA CHAIN (CARBOXYPEPTIDASE N REGULATORY SUBUNIT) (CARBOXYPEPTIDASE N POLYPEPTIDE 2). | 1.17 | 1.47 | 1.05 | 0.88 | 1.03 |
| 30990 | CRM1: (CRM1) CRM1 PROTEIN (XPO1) (EXPORTIN 1) (EXPRESSED SEQUENCE AA420417) (NUCLEAR EXPORT FACTOR CRM1). | 1.04 | 0.59 | 2.13 | 1.06 | 1.1 |
| 30993 | CRYL1: (CRYL1) LAMBDA-CRYSTALLIN HOMOLOG. | 0.88 | 0.57 | 1.22 | 1.07 | 0.84 |
| 30999 | CTNNA2: (CTNNA2 OR CAPR) ALPHA-2 CATENIN (ALPHA-CATENIN RELATED PROTEIN) (ALPHA N-CATENIN). | 1.08 | 0.67 | 0.89 | 1.28 | 0.69 |
| 31002 | DJ924G13.1: (DJ924G13.1 OR KIAA1221) DJ924G13.1 (KIAA1221) (PUTATIVE ZINC FINGER PROTEIN) (BM-005) (FLJ10725) (FLJ13534) (FLJ13964) (D5ERTD689E OR MKIAA1221) (1110068L01RIK). | 1.16 | 0.79 | 0.84 | 1.39 | 0.69 |
| 31006 | DPPA5: (DPPA5) DEVELOPMENTAL PLURIPOTENCY ASSOCIATED 5 (EMBRYONAL STEM CELL SPECIFIC GENE 1) (2410024L16RIK) (LOC340168). | 1.62 | 1.58 | 0.96 | 0.94 | 1.01 |
| 31008 | DTYMK: (DTYMK OR TYMK OR TMPK OR CDC8) THYMIDYLATE KINASE (EC 2.7.4.9) (DTMP KINASE). | 1.33 | 0.91 | 3.88 | 1.01 | 2.09 |
| 31014 | EED: (EED) EMBRYONIC ECTODERM DEVELOPMENT PROTEIN HOMOLOG (WAIT1). | 1.06 | 0.59 | 2.06 | 1.15 | 1.14 |
| 31020 | F11R: (F11R OR JAM1 OR JCAM) JUNCTIONAL ADHESION MOLECULE 1 PRECURSOR (JAM) (PLATELET ADHESION MOLECULE 1) (PAM-1) (PLATELET F11 RECEPTOR) (UNQ264/PRO301). | 1.09 | 1.73 | 1.82 | 0.52 | 2.39 |
| 31032 | FLJ10884: (DKFZP434B1629) HYPOTHETICAL PROTEIN FLJ10884 (FLJ1111). | 1.47 | 0.83 | 1.06 | 0.98 | 0.77 |
| 31035 | FLJ21190: HYPOTHETICAL PROTEIN FLJ21190 (CDA03) (RS21C6) (TDRG-TL1 OR 2410015N17RIK) (RS21-C6). | 1.45 | 0.89 | 2.23 | 0.76 | 1.2 |
| 31047 | FBXL13: (FBXL13) F-BOX AND LEUCINE-RICH REPEAT PROTEIN 13 (FLJ38068) (4921539K22RIK) (MGC21636) (FLJ40218) (DKFZP434L2422). | 1.03 | 0.71 | 1.41 | 1.04 | 1.07 |
| 31050 | GGH: (GGH) GAMMA-GLUTAMYL HYDROLASE PRECURSOR (EC 3.4.19.9) (GAMMA-GLU-X CARBOXYPEPTIDASE) (CONJUGASE) (GH). | 1.23 | 0.89 | 2.74 | 1.01 | 1.74 |
| 31066 | HSCDGF: (HSCDGF OR PDGFC) SECRETORY GROWTH FACTOR-LIKE PROTEIN FALLOTEIN (SPINAL CORD-DERIVED GROWTH FACTOR) (PLATELET-DERIVED GROWTH FACTOR C). | 0.8 | 0.6 | 0.8 | 2.23 | 0.56 |

Fig 3-35

| | | | | | | |
|---|---|---|---|---|---|---|
| 31069 | ICSBP1: (ICSBP1) INTERFERON CONSENSUS SEQUENCE BINDING PROTEIN (ICSBP). | 0.82 | 0.93 | 1.01 | 0.57 | 0.84 |
| 31075 | JAM2: (JAM2 OR VEJAM OR C21ORF43) JUNCTIONAL ADHESION MOLECULE 2 PRECURSOR (VASCULAR ENDOTHELIAL JUNCTION-ASSOCIATED MOLECULE) (VE-JAM). | 0.9 | 1.07 | 1.1 | 1.89 | 0.99 |
| 31093 | KS: (KS) KIDNEY-SPECIFIC PROTEIN (XENOBIOTIC/MEDIUM-CHAIN FATTY ACID:COA LIGASE) (FLJ26434) (FLJ38720). | 1.03 | 0.83 | 1.11 | 1.99 | 1.21 |
| 31096 | MAD1: (MAD1L1 OR MAD1) MITOTIC CHECKPOINT PROTEIN (MAD1 (MITOTIC ARREST DEFICIENT, YEAST, HOMOLOG)-LIKE 1) (TXBP181) (MAD1A) (MAD1B). | 2.4 | 1.02 | 1.11 | 0.68 | 0.45 |
| 31099 | MAD2L2: (MAD2L2 OR MAD2B OR REV7) MITOTIC SPINDLE ASSEMBLY CHECKPOINT PROTEIN MAD2B (MAD2-LIKE 2) (HREV7) (2310033C13RIK). | 0.8 | 0.66 | 2 | 0.79 | 1.19 |
| 31102 | MAT1A: (MAT1A OR MATA1 OR AMS1) S-ADENOSYLMETHIONINE SYNTHETASE ALPHA AND BETA FORMS (EC 2.5.1.6) (METHIONINE ADENOSYLTRANSFERASE) (ADOMET SYNTHETASE) (MAT-I/III). | 1 | 2.27 | 0.88 | 1.22 | 0.97 |
| 31105 | MAWBP: (MAWBP) MAWD BINDING PROTEIN (UNKNOWN PROTEIN 32 FROM 2D-PAGE OF LIVER TISSUE) (PROBABLE OXIDOREDUCTASE 0610038K03RIK) (PROBABLE OXIDOREDUCTASE 3110049J23RIK). | | 1.29 | 1.9 | 1.28 | 1.28 |
| 31114 | NOP5: (NOP5) NUCLEOLAR PROTEIN NOP5 (NUCLEOLAR PROTEIN 5) (NOP58) (HSPC120) (NOL5) (SIK SIMILAR PROTEIN). | 1.41 | 0.77 | 3.38 | 0.72 | 1.37 |
| 31117 | NUMB: (NUMB) NUMB PROTEIN HOMOLOG (H-NUMB) (PROTEIN S171). | 0.74 | 0.81 | 0.74 | 0.68 | 0.8 |
| 31129 | PPP2R1B_1: (PPP2R1B) SERINE/THREONINE PROTEIN PHOSPHATASE 2A, 65 KDA REGULATORY SUBUNIT A,BETA ISOFORM (PP2A, SUBUNIT A, PR65-BETA ISOFORM) (PP2A, SUBUNIT A,R1-BETA ISOFORM) (TRANSCRIPT VARIANT 1). | 1.19 | 1.31 | 1.6 | | 1.57 |
| 31135 | PROX1: (PROX1) HOMEOBOX PROSPERO-LIKE PROTEIN PROX1 (PROX 1). | 0.63 | 9.68 | | | |
| 31144 | RPL13A: (RPL13A) 60S RIBOSOMAL PROTEIN L13A (23 KDA HIGHLY BASIC PROTEIN). | 1.85 | 1.14 | 0.94 | 0.54 | 0.48 |
| 31147 | SALL2: (SALL2 OR SAL2 OR KIAA0360) SAL-LIKE PROTEIN 2 (ZINC FINGER PROTEIN SALL2) (HSAL2). | 0.56 | 1.16 | 0.6 | 0.5 | 0.54 |
| 31153 | SNAI1: (SNAI1 OR SNAH) ZINC FINGER PROTEIN SNAI1 (SNAIL PROTEIN HOMOLOG) (SNA PROTEIN). | 0.46 | 0.35 | 0.23 | 1.51 | 0.2 |
| 31171 | SOX6: (SOX6) TRANSCRIPTION FACTOR SOX-6. | 1.67 | 3.94 | 0.92 | 0.94 | 0.92 |
| 31177 | TFPI: (TFPI OR TFPI1 OR LACI) TISSUE FACTOR PATHWAY INHIBITOR PRECURSOR (TFPI) (LIPOPROTEIN-ASSOCIATED COAGULATION INHIBITOR) (LACI) (EXTRINSIC PATHWAY INHIBITOR) (EPI). | 1.12 | 0.74 | 0.94 | 1 | 0.65 |
| 31186 | TREM1: (TREM1) TRIGGERING-RECEPTOR TREM1. | 0.87 | 1.63 | 0.92 | 0.65 | 0.91 |
| 31192 | ZFP42: (ZFP42 OR REX1 OR REX-1) ZINC FINGER PROTEIN 42 (ZFP-42) (REX-1) PROTEIN) (REDUCED EXPRESSION-1 PROTEIN). | 1.74 | 2.25 | 1.03 | 0.87 | 1.31 |
| 31460 | KIAA0152_1: (KIAA0152) HYPOTHETICAL PROTEIN KIAA0152 (2410014A08RIK). | 1.01 | 0.89 | 1.89 | 1.8 | 1.23 |
| 31466 | KIAA0152_3: (KIAA0152) HYPOTHETICAL PROTEIN KIAA0152 (2410014A08RIK). | 2.34 | 2.09 | 1.37 | 0.84 | 1 |

Fig 3-36

| ID | Description | | | | | | |
|---|---|---|---|---|---|---|---|
| 32031 | TFRC_3PRIME: (TFRC) TRANSFERRIN RECEPTOR PROTEIN (TFR1) (TR) (TFR) (TRFR) (CD71 ANTIGEN) (T9) (P90). | 1.33 | 2.26 | 14.63 | 1.63 | 4.79 |
| 32034 | TFRC_5PRIME: (TFRC) TRANSFERRIN RECEPTOR PROTEIN (TFR1) (TR) (TFR) (TRFR) (CD71 ANTIGEN) (T9) (P90). | 1.51 | 0.96 | 1.68 | 0.67 | 0.81 |
| 32488 | NPM1: (NPM1 OR NPM) NUCLEOPHOSMIN (NPM) (NUCLEOLAR PHOSPHOPROTEIN B23) (NUMATRIN) (NUCLEOLAR PROTEIN NO38). | 1.68 | 0.77 | 2.29 | 0.98 | 1.31 |
| 32647 | TREM2: TRIGGERING RECEPTOR EXPRESSED ON MYELOID CELLS 2. | 1.03 | 1.08 | 1.01 | 0.87 | 1.77 |
| 32676 | ARL8: (ARL8) ADP-RIBOSYLATION FACTOR-LIKE PROTEIN 8. | 1.67 | 1.93 | 1.58 | 1.34 | 1.35 |
| 32679 | BRIX: (BRIX) RIBOSOME BIOGENESIS PROTEIN BRIX. | 1.21 | 0.94 | 1.63 | 1.01 | 1.2 |
| 32688 | EIF4A1: (EIF4A1 OR EIF4A OR DDX2A) EUKARYOTIC INITIATION FACTOR 4A-I (EIF4A-I) (EIF-4A-I). | 0.93 | 0.8 | 1.39 | 0.81 | 1.61 |
| 32691 | IDH1: (IDH1 OR PICD) ISOCITRATE DEHYDROGENASE CYTOPLASMIC (EC 1.1.1.42) (OXALOSUCCINATE DECARBOXYLASE) (IDH) (NADP+-SPECIFIC ICDH) (IDP). | 0.44 | 0.26 | 3 | 2.05 | 4.41 |
| 32694 | IMPDH2: (IMPDH2 OR IMPD2) INOSINE-5'-MONOPHOSPHATE DEHYDROGENASE 2 (EC 1.1.1.205) (IMP DEHYDROGENASE 2) (IMPDH-II) (IMPD 2). | 1.18 | 1.61 | 1.87 | 1.17 | 1.19 |
| 32700 | KIAA1573: (KIAA1573) HYPOTHETICAL PROTEIN KIAA1573 (B430218L07RIK) (DKFZP686L04115) (FLJ12509) (FLJ14194). | 1.19 | 1.48 | 1.67 | 1.35 | 1.33 |
| 32703 | KIF4A: (KIF4A OR KIF4) CHROMOSOME-ASSOCIATED KINESIN KIF4A (CHROMOKINESIN). | 0.97 | 1.19 | 1.45 | 1.02 | 1.12 |
| 32706 | LIN-28: (LIN28 OR LIN-28) HYPOTHETICAL PROTEIN FLJ12457 (RNA-BINDING PROTEIN LIN-28). | 1.22 | 1.31 | 2.32 | 1.07 | 1.41 |
| 32709 | LRRN1: (LRRN1 OR NLRR-1) LEUCINE RICH REPEAT PROTEIN 1, NEURONAL (KIAA1497) (NLRR). | 1.65 | 2.02 | 1.74 | 1.09 | 1.15 |
| 32712 | MTHFD1: (MTHFD1 OR MTHFD OR MTHFC) C-1-TETRAHYDROFOLATE SYNTHASE, CYTOPLASMIC (C1-THF SYNTHASE). | 1.43 | 0.88 | 4.27 | 1 | 2.13 |
| 32715 | NBR2_HUMAN: (NBR2) NBR2 PROTEIN (NEXT TO BRCA1 GENE 2 PROTEIN). | 1.33 | 1.64 | 1.56 | 0.76 | 1.12 |
| 32716 | PPAT: (PPAT OR GPAT) AMIDOPHOSPHORIBOSYLTRANSFERASE PRECURSOR (EC 2.4.2.14) (GLUTAMINE PHOSPHORIBOSYLPYROPHOSPHATE AMIDOTRANSFERASE) (ATASE) (GPAT). | 1.62 | 1.85 | 2.85 | 1.31 | 1.54 |
| 32719 | RPL4: (RPL4 OR RPL1) 60S RIBOSOMAL PROTEIN L4 (L1). | 2.05 | 0.97 | 1.65 | 0.41 | 0.84 |
| 32722 | SMS: (SMS) SPERMINE SYNTHASE (EC 2.5.1.22) (SPERMIDINE AMINOPROPYLTRANSFERASE) (SPMSY). | 1.1 | 0.64 | 1.48 | 0.68 | 0.71 |
| 32725 | ZNF117_HUMAN: (ZNF117) ZINC FINGER PROTEIN 117 (ZINC FINGER PROTEIN HPF9). | 0.77 | 1.38 | 1.5 | 1.33 | 1.08 |
| 32726 | ZNF257-MGC12518-ZNF92-ZNF43-ZNF273-FLJ90430_HUMAN: (ZNF257 OR BMZF4) ZINC FINGER PROTEIN 257 (BONE MARROW ZINC FINGER 4) (BMZF-4) (MGC12518) (FLJ34299) (ZNF43 OR ZNF39 OR KOX27) ZINC FINGER PROTEIN 43 (ZINC PROTEIN HTF6) (ZINC FINGER PROTEIN KOX27) (ZNF27) | 1.28 | 1.03 | 1.45 | 0.81 | 1.02 |

…

MULTI-LINEAGE PROGENITOR CELLS

CROSS-REFERENCE TO RELATED APPLICATION

This application is a continuation-in-part and claims benefit under 35 U.S.C. §120 of U.S. application Ser. No. 11/110,299, filed Apr. 20, 2005, which claims benefit under 35 U.S.C. §119(e) of U.S. Application No. 60/564,687, filed on Apr. 23, 2004, both of which are incorporated by reference herein in their entirety.

TECHNICAL FIELD

The invention relates to multi-lineage progenitor cells (MLPC) from human blood and more particularly, to MLPC with the potential to differentiate into multiple tissue lineages and use of such cells for regenerative therapies.

BACKGROUND

Progenitor cells capable of hematopoietic reconstitution after myeloablative therapy have been identified in a number of sources including the bone marrow, umbilical cord and placental blood, and in the peripheral blood of subjects treated with stem cell-mobilizing doses of granulocyte-colony stimulation factor. These cells, often referred to as hematopoietic stem cells (HSC), are identified by the presence of cell surface glycoproteins such as CD34 and CD133. HSC represent a very small percentage of the total population of cells given as part of a 'bone marrow transplant' and are considered to be the life-saving therapeutic portion of this treatment responsible for the restoration of the blood-forming capacity of patients given myeloablative doses of chemotherapy or radiation therapy. Stem cell therapies via bone marrow transplantation have become a standard treatment for a number of intractable leukemias and genetic blood disorders.

Recent studies have suggested the presence of a more primitive cell population in the bone marrow capable of self-renewal as well as differentiation into a number of different tissue types other than blood cells. These multi-potential cells were discovered as a minor component in the CD34-plastic-adherent cell population of adult bone marrow, and are variously referred to as mesenchymal stem cells (MSC) (Pittenger, et al., *Science* 284:143-147 (1999)) or multi-potent adult progenitor cells (MAPC) cells (Furcht, L. T., et al., U.S. patent publication 20040107453 A1). MSC cells do not have a single specific identifying marker, but have been shown to be positive for a number of markers, including CD29, CD90, CD105, and CD73, and negative for other markers, including CD14, CD3, and CD34. Various groups have reported to differentiate MSC cells into myocytes, neurons, pancreatic beta-cells, liver cells, bone cells, and connective tissue. Another group (Wernet et al., U.S. patent publication 20020164794 A1) has described an unrestricted somatic stem cell (USSC) with multi-potential capacity that is derived from a CD45$^-$/CD34$^-$ population within cord blood.

SUMMARY

The invention is based on the identification of a rare undifferentiated cell population from human fetal blood that is capable of self-renewal and has the potential to differentiate into cells representing each of the three embryonic germ layers. These fetal blood-derived cells are referred to as multi-lineage progenitor cells (MLPC). As described herein, fetal blood MLPC are distinguished from bone marrow-derived MSC, HSC, and USSC on the basis of their immunophenotypic characteristics, gene expression profile, morphology, and distinct growth pattern. The invention provides methods for developing monotypic clonal cell lines from individual cells. The invention also provides methods for cryopreserving MLPC (e.g., for cord blood banking) and methods of using MLPC in regenerative therapies.

In one aspect, the invention features a purified population of human fetal blood (e.g., cord blood) MLPC, wherein the MLPC are positive for CD9 and CD45. The MLPC can display a leukocyte morphology. The MLPC can be further positive for SSEA-4 or CD34, as well as CD133, CD41, CD44, CD105, CD29, CD73, CD90, stem cell factor, SSEA-3, and CD13. The MLPC can be negative for CD15, CD38, glycophorin-A, CD2, CD3, CD8, CD19, CD20, CD22, CD5, CD7, CD10, CD14, CD4, HLA-DR, CD16, CD33, and CD61. The MLPC can attain a fibroblast-like morphology over time in culture. The MLPC also can adhere to a plastic surface when cultured. The MLPC are capable of differentiating into cells from all three embryonic germ layers, including, for example, cells having an osteocytic phenotype, cells having an adipocytic phenotype, cells having a neural stem cell phenotype, cells having a myocytic phenotype, cells having an endothelial phenotype, cells having a hepatocytic phenotype, and cells having a pancreatic phenotype. The MLPC can include an exogenous nucleic acid (e.g., an exogenous nucleic acid encoding a polypeptide).

In another aspect, the invention features a purified population of human fetal blood (e.g., cord blood) MLPC, wherein the MLPC are positive for CD9, negative for CD45, negative for CD34, and negative for SSEA-4. The MLPC can display a fibroblast morphology. The MLPC can be further positive for CD13, CD29, CD44, CD73, CD90, and CD105, and can be further negative for CD2, CD3, CD4, CD5, CD7, CD8, CD10, CD14, CD15, CD16, CD19, CD20, CD22, CD33, CD36, CD38, CD41, CD61, CD62E, CD133, glycophorin-A, stem cell factor, SSEA-3, and HLA-DR. The MLPC can adhere to a plastic surface when cultured. The MLPC are capable of differentiating into cells from all three embryonic germ layers, including, for example, cells having an osteocytic phenotype, cells having an adipocytic phenotype, cells having a neural stem cell phenotype, cells having a myocytic phenotype, cells having an endothelial phenotype, cells having a hepatocytic phenotype, and cells having a pancreatic phenotype. The MLPC can include an exogenous nucleic acid (e.g., an exogenous nucleic acid encoding a polypeptide).

The invention also features a clonal line of human fetal blood (e.g., cord blood) MLPC, wherein the MLPC are positive for CD9, negative for CD45, negative for CD34, and negative for SSEA-4. The MLPC can display a fibroblast morphology. The MLPC can be further positive for CD13, CD29, CD44, CD73, CD90, and CD105, and can be further negative for CD2, CD3, CD4, CD5, CD7, CD8, CD10, CD 14, CD15, CD16, CD19, CD20, CD22, CD33, CD36, CD38, CD41, CD61, CD62E, CD133, glycophorin-A, stem cell factor, SSEA-3, and HLA-DR. The MLPC can adhere to a plastic surface when cultured. The MLPC are capable of differentiating into cells from all three embryonic germ layers, including, for example, cells having an osteocytic phenotype, cells having an adipocytic phenotype, cells having a neural stem cell phenotype, cells having a myocytic phenotype, cells having an endothelial phenotype, cells having a hepatocytic phenotype, and cells having a pancreatic phenotype. The MLPC can include an exogenous nucleic acid (e.g., an exogenous nucleic acid encoding a polypeptide). In some embodiments, the clonal line has undergone at least 5 doublings (e.g., at least 8, at least 10, at least 15, or at least 25 doublings) in culture.

The invention also features a method for purifying a population of MLPC from human fetal blood. The method includes contacting a human fetal blood sample (e.g., cord blood) with a composition that includes dextran, anti-glycophorin A antibody, anti-CD15 antibody, and anti-CD9 antibody; allowing the sample to partition into an agglutinate and a supernatant phase; recovering cells from the supernatant phase; and purifying MLPC from the recovered cells by adherence to a solid substrate (e.g., a plastic substrate), wherein the MLPC are positive for CD9 and positive for CD45. The MLPC can be further positive for CD34, CD133, CD41, CD44, CD105, CD29, CD73, CD90, stem cell factor, SSEA-3, SSEA-4, and CD13. The MLPC can be further negative for CD15, CD38, glycophorin-A, CD2, CD3, CD8, CD19, CD20, CD22, CD5, CD7, CD10, CD14, CD4, HLA-DR, CD16, CD33, and CD61. The method further can include testing the MLPC for CD9 or testing for CD9, CD29, CD45, CD73, and CD90.

The method further can include culturing the MLPC such that the MLPC obtain a fibroblast morphology, wherein the MLPC, after obtaining the fibroblast morphology, are positive for CD9, negative for CD45, negative for CD34, and negative for SSEA-4. The MLPC, after obtaining the fibroblast morphology, can be further positive for CD13, CD29, CD44, CD73, CD90, and CD105. The MLPC, after obtaining the fibroblast morphology, can be further negative for CD2, CD3, CD4, CD5, CD7, CD8, CD10, CD14, CD15, CD16, CD19, CD20, CD22, CD33, CD36, CD38, CD41, CD61, CD62E, CD133, glycophorin-A, stem cell factor, SSEA-3, and HLA-DR. The method further can include testing the MLPC for CD9 or testing for CD9, CD29, CD45, CD73, and CD90.

The invention also features a purified population of MLPC or undifferentiated progeny thereof, wherein the MLPC have enhanced expression of mRNA for CXCR4, FLT3, and CD133 relative to a population of MSC. The MLPC further can have an enhanced expression of mRNA for TERT, KIT, and POU5F, or enhanced expression of mRNA for CD34 relative to the population of MSC. The MLPC further can have an enhanced expression of mRNA for CD24, CD44, CD45, CD58, CD68, CD33, CD37, and CD38 relative to the population of MSC, or further have an enhanced expression of the mRNA for ICAM2, ITGAX, TFRC, KIT, IL6R, IL7R, ITGAM, FLT3, PDGFRB, SELE, SELL, TFRC, ITGAL, ITGB2, PECAM1, ITGA2B, ITGA3, ITGA4, ITGA6, and ICAM1 relative to the population of MSC. The MLPC can be obtained from cord blood. The MLPC can be positive for CD9, negative for CD45, negative for CD34, and negative for SSEA-4. The MLPC can be capable of differentiating into cells from all three embryonic germ layers, including, for example, cells having an osteocytic phenotype, cells having an adipocytic phenotype, cells having a neural stem cell phenotype, cells having a myocytic phenotype, cells having an endothelial phenotype, cells having a hepatocytic phenotype, and cells having a pancreatic phenotype. The MLPC can include an exogenous nucleic acid, e.g., an exogenous nucleic acid encoding a polypeptide.

In another aspect, the invention features a clonal line of human fetal blood MLPC and undifferentiated progeny thereof, wherein the MLPC have enhanced expression of mRNA for CXCR4, FLT3, and CD133 relative to that of a population of MSC. The MLPC further can have an enhanced expression of the mRNA for TERT, KIT, and POU5F, or enhanced expression of the mRNA for CD34 relative to the population of MSC. The MLPC further can have an enhanced expression of the mRNA for CD24, CD44, CD45, CD58, CD68, CD33, CD37, and CD38 relative to the population of MSC, or further have an enhanced expression of mRNA for ICAM2, ITGAX, TFRC, KIT, IL6R, IL7R, ITGAM, FLT3, PDGFRB, SELE, SELL, TFRC, ITGAL, ITGB2, PECAM1, ITGA2B, ITGA3, ITGA4, ITGA6, and ICAM1 relative to the population of MSC. The MLPC can be positive for CD9, negative for CD45, negative for CD34, and negative for SSEA-4, and can be obtained from cord blood. The MLPC can include an exogenous nucleic acid, e.g., a nucleic acid encoding a polypeptide. In some embodiments, the clonal line has undergone at least 5 doublings (e.g., at least 8, at least 10, at least 15, or at least 25 doublings) in culture.

The invention also features differentiated progeny of a purified population of MLPC or of a clonal line of MLPC. The progeny can have an osteocytic phenotype, an adipocytic phenotype, a neural stem cell phenotype, a myocytic phenotype, an endothelial phenotype, a hepatocytic phenotype, or a pancreatic phenotype.

In another aspect, the invention features a composition that includes a purified population of MLPC or a clonal line of MLPC and a culture medium. The composition further can include a cryopreservative. In one embodiment, the cryopreservative is dimethylsulfoxide (DMSO) (e.g., 1 to 10% DMSO). In another embodiment, the cryopreservative is fetal bovine serum, human serum, or human serum albumin in combination with one or more of the following: DMSO, trehalose, and dextran. For example, the cryopreservative can be DMSO and trehalose, or fetal bovine serum and DMSO.

In yet an another aspect, the invention features an article of manufacture that includes a purified population of MLPC or a clonal line of MLPC. The purified population of MLPC or the clonal line can be housed within a container (e.g., a vial or a bag). The container further can include a cryopreservative. The article of manufacture further can include a label indicating that the MLPC have enhanced expression of mRNA for CXCR4, FLT3, and CD133 relative to that of a population of MSC. In some embodiments, the article of manufacture further includes a reagent for characterizing the population of MLPC or the clonal MLPC line. The reagent can be selected from the group consisting of a nucleic acid probe for detecting expression of CXCR4, a nucleic acid probe for detecting expression of FLT3, a nucleic acid probe for detecting expression of CD133, a nucleic acid probe for detecting expression of CD34, a nucleic acid probe for detecting expression of TERT, a nucleic acid probe for detecting expression of KIT, a nucleic acid probe for detecting expression of POU5F, an antibody having specific binding affinity for CD9, an antibody having specific binding affinity for CD34, an antibody having specific binding affinity for CD45, and an antibody having specific binding affinity for SSEA-4.

The invention also features a method for purifying a population of MLPC from human fetal blood. The method includes contacting a human fetal blood sample (e.g., cord blood) with a composition that includes dextran, anti-glycophorin A antibody, anti-CD15 antibody, and anti-CD9 antibody; allowing the sample to partition into an agglutinate and a supernatant phase; recovering cells from the supernatant phase; purifying MLPC from the recovered cells by adherence to a solid substrate (e.g., a plastic substrate); and culturing the MLPC such that the MLPC obtain a fibroblast morphology, wherein the MLPC, after obtaining the fibroblast morphology, have enhanced expression of mRNA for CXCR4, FLT3, and CD133 relative to that of a population of MSC. The MLPC further can have an enhanced expression of mRNA for TERT, KIT, and POU5F relative to the population of MSC. In some embodiments, the method further includes testing the MLPC for enhanced expression of mRNA for CXCR4, FLT3, and CD133 relative to the population of MSC. The method also can include testing for CD9 and/or testing for CD29, CD45, CD73, and CD90.

In another aspect, the invention features a method for cryopreserving MLPC. The method includes contacting a purified population of MLPC or clonal line of MLPC with a cryopreservative; and freezing the purified population of MLPC or the clonal line. In one embodiment, the cryopreservative is DMSO (e.g., 1 to 10% DMSO). In another embodiment, the cryopreservative is fetal bovine serum, human serum, or human serum albumin in combination with one or more of the following: DMSO, trehalose, and dextran. For example, the cryopreservative can be DMSO and trehalose, or fetal bovine serum and DMSO. The purified population of MLPC or the clonal line can be suspended in the cryopreservative at a concentration between $1\times10^5$ and $5\times10^7$ cells/mL. The purified population or clonal line can be frozen at a controlled rate (e.g., the freezing rate is controlled electronically) or by placement in an ethanol bath in the vapor phase of a liquid nitrogen cryogenic storage tank.

In yet another aspect, the invention features a method of producing a population of differentiated cells. The method includes culturing a purified population of MLPC or a clonal line of MLPC with an agent effective to induce differentiation of the MLPC. The agent can include insulin, glutamine, dexamethasone, indomethacin, and 3-isobutyl-1-methyl-xanthine; dexamethasone, glutamine, ascorbate, and β-glycerophosphate; epithelial growth factor, insulin, fetuin, dexamethasone, and fibroblast growth factor-basic; fibroblast growth factor-basic, epidermal growth factor, NSF-1, and retinoic acid; heparin, bovine brain extract, epithelial growth factor, and hydrocortisone; or ascorbic acid, hydrocortisone, transferrin, insulin, epidermal growth factor, hepatocyte growth factor, fibroblast growth factor-basic, fibroblast growth factor-4, and stem cell factor.

The invention also features a method of characterizing a population of MLPC. The method includes providing a purified population of MLPC; and assessing expression in the population of MLPC of one or more mRNAs selected from the group consisting of CXCR4, FLT3, CD133, ICAM2, ITGAX, TFRC, KIT, IL6R, IL7R, ITGAM, FLT3, PDGFRB, SELE, SELL, TFRC, ITGAL, ITGB2, PECAM1, ITGA2B, ITGA3, ITGA4, ITGA6, ICAM1, CD24, CD34, CD44, CD45, CD58, CD68, CD33, CD37, CD38, TERT, KIT, and POUF5. In some embodiments, expression of mRNA for CXCR4, FLT3, and CD133 is assessed. In other embodiments, expression of mRNA for TERT, KIT, and POU5F is assessed. In still other embodiments, expression of mRNA for CD34 is assessed.

In another aspect, the invention features a method for characterizing the immaturity of a population of MLPC. The method includes providing a purified population of MLPC; and assessing expression of mRNA for CXCR4, FLT3, and CD133 in the population of MLPC, wherein enhanced expression of CXCR4, FLT3, and CD133 relative to that of a population of MSC is indicative of an immature phenotype.

The invention also features a method of making a clonal line of MLPC. The method includes providing a population of MLPC, culturing a single MLPC in a culture vessel lacking other cells until a plurality of progeny are produced; and culturing the progeny to obtain the clonal line.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2A-2D are photomicrographs depicting the morphology of developing MLPC. FIG. 2A shows an early culture of MLPC isolated from umbilical cord blood demonstrating the cells in the leukocyte morphology phase. FIG. 2B shows a culture of MLPC beginning to change their morphology from leukocyte to fibroblast morphology. FIG. 2C shows a later culture of MLPC in logarithmic growth phase. FIG. 2D shows a fully confluent culture of MLPC.

FIG. 3 is a table that lists the 631 genes that had >1.4 fold differential expression between MLPC and any one or more of the five cell groups. Shaded text refers to over-expression of the gene in the comparative cell group; bold text refers to over-expression of genes in MLPC. The values represent the ratio of the signal intensity for the comparative cell group to the signal intensity of the MLPC, i.e., for uniq ID 43, signal intensity of B/signal intensity of MLPC is 0.68.

DETAILED DESCRIPTION

Figure 1:
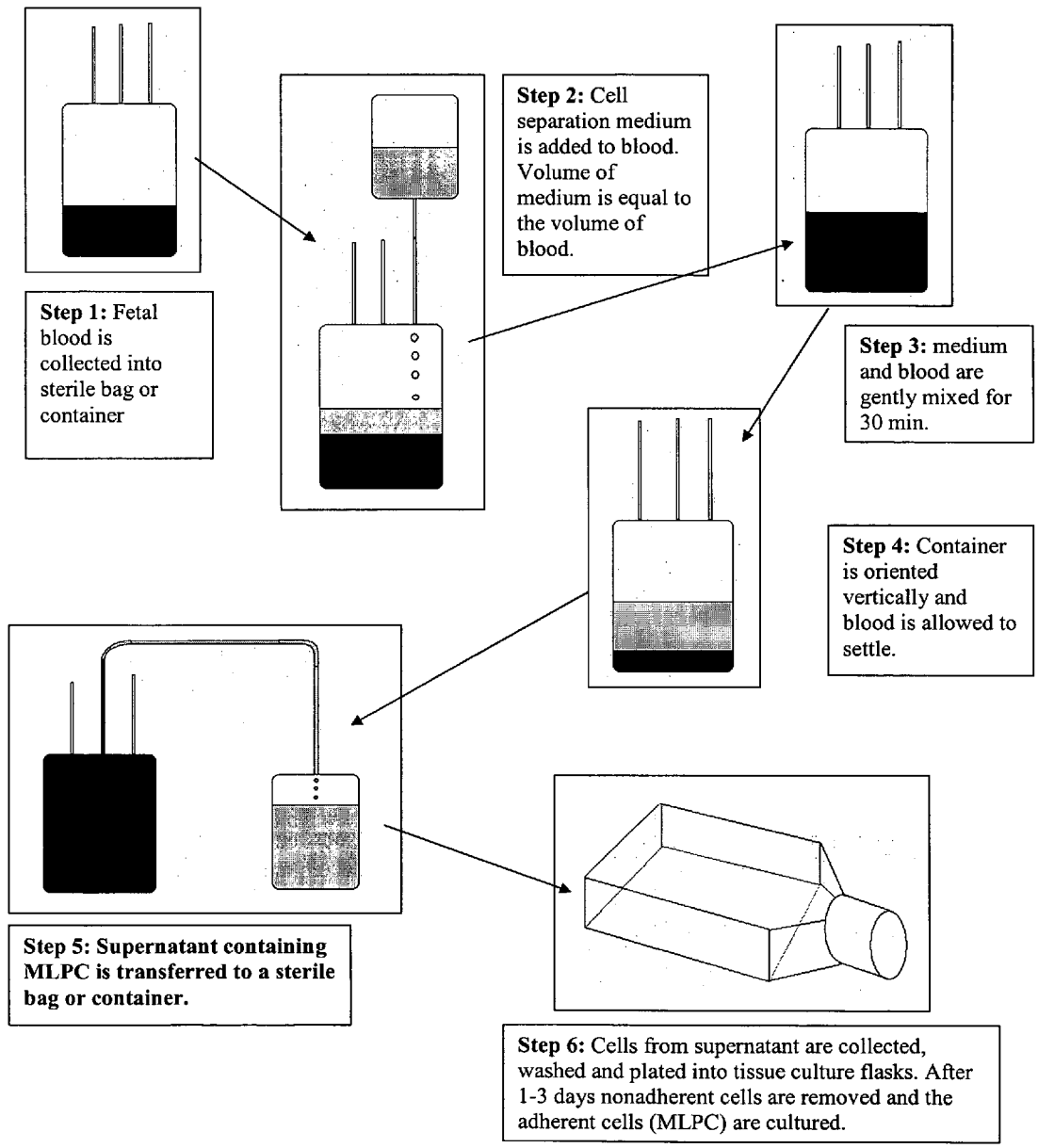
FIG. 1 is a schematic of a cell separation procedure for purifying MLPC from fetal blood.
Figure 4:
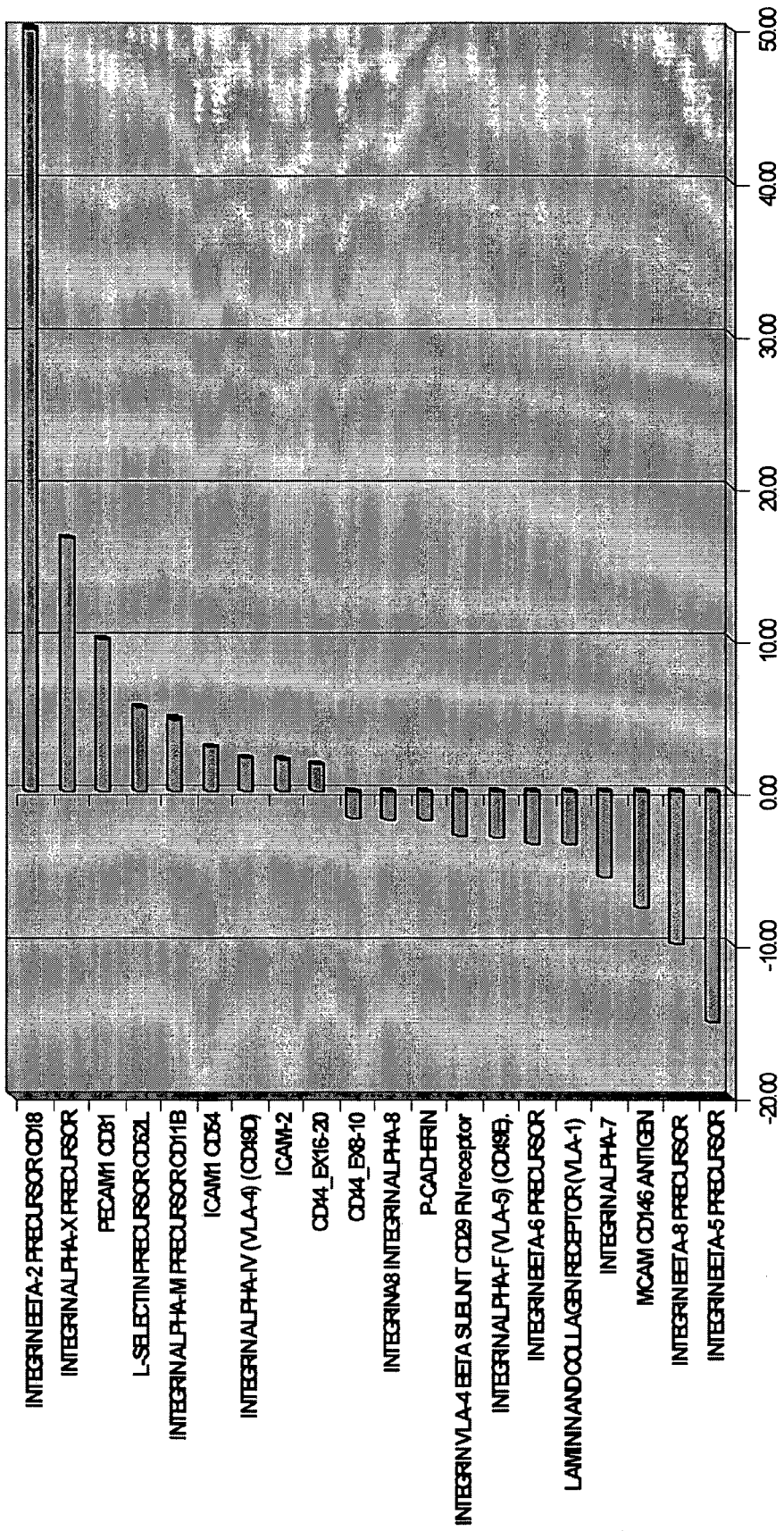
FIG. 4 is a chart that provides examples of the differences between MLPC and MSC in the expression of adhesion molecules.
Figure 5:
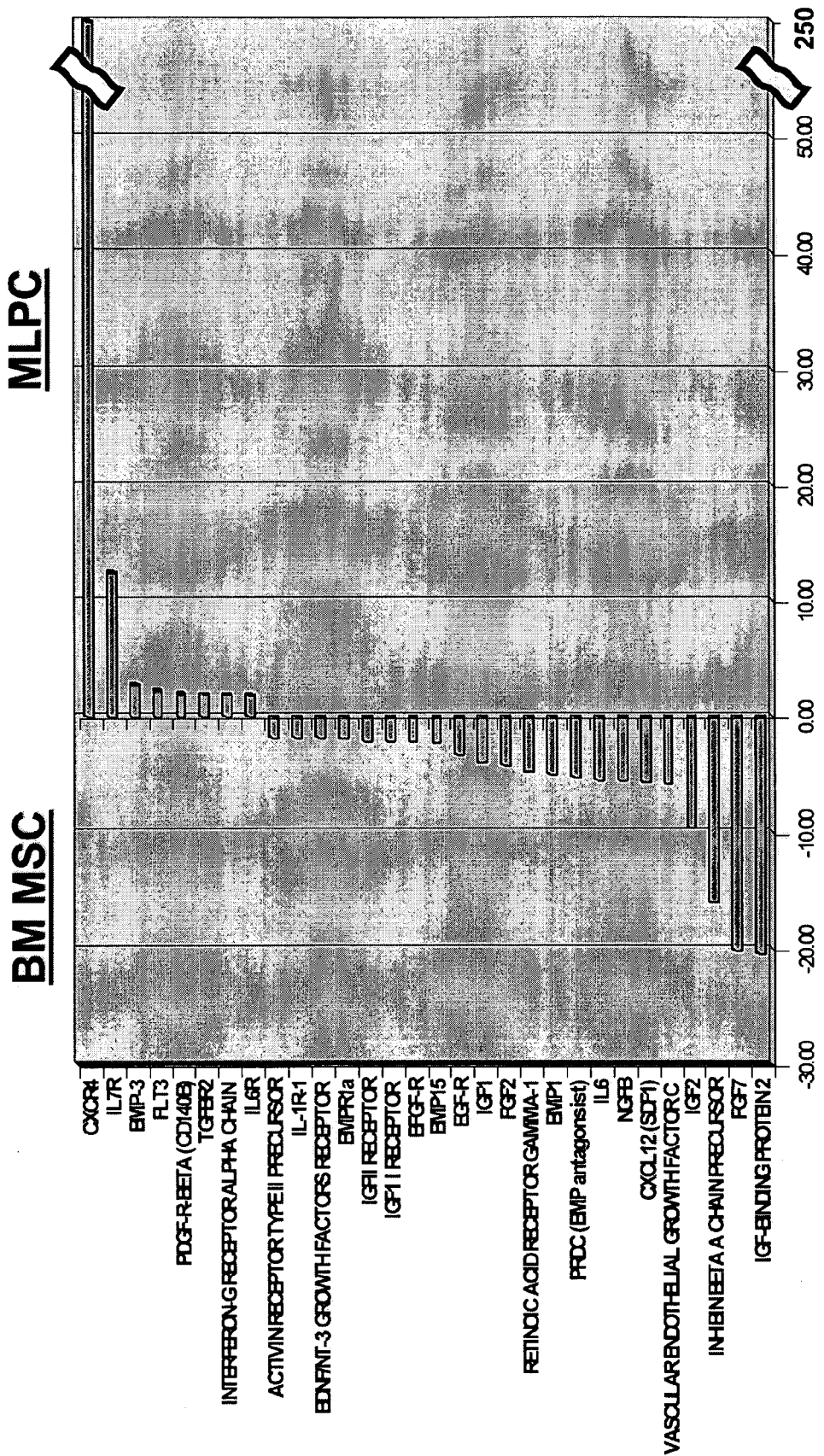
FIG. 5 is a chart that provides examples of the differences between MLPC and MSC in the expression of growth factors and receptors.
Figure 6:
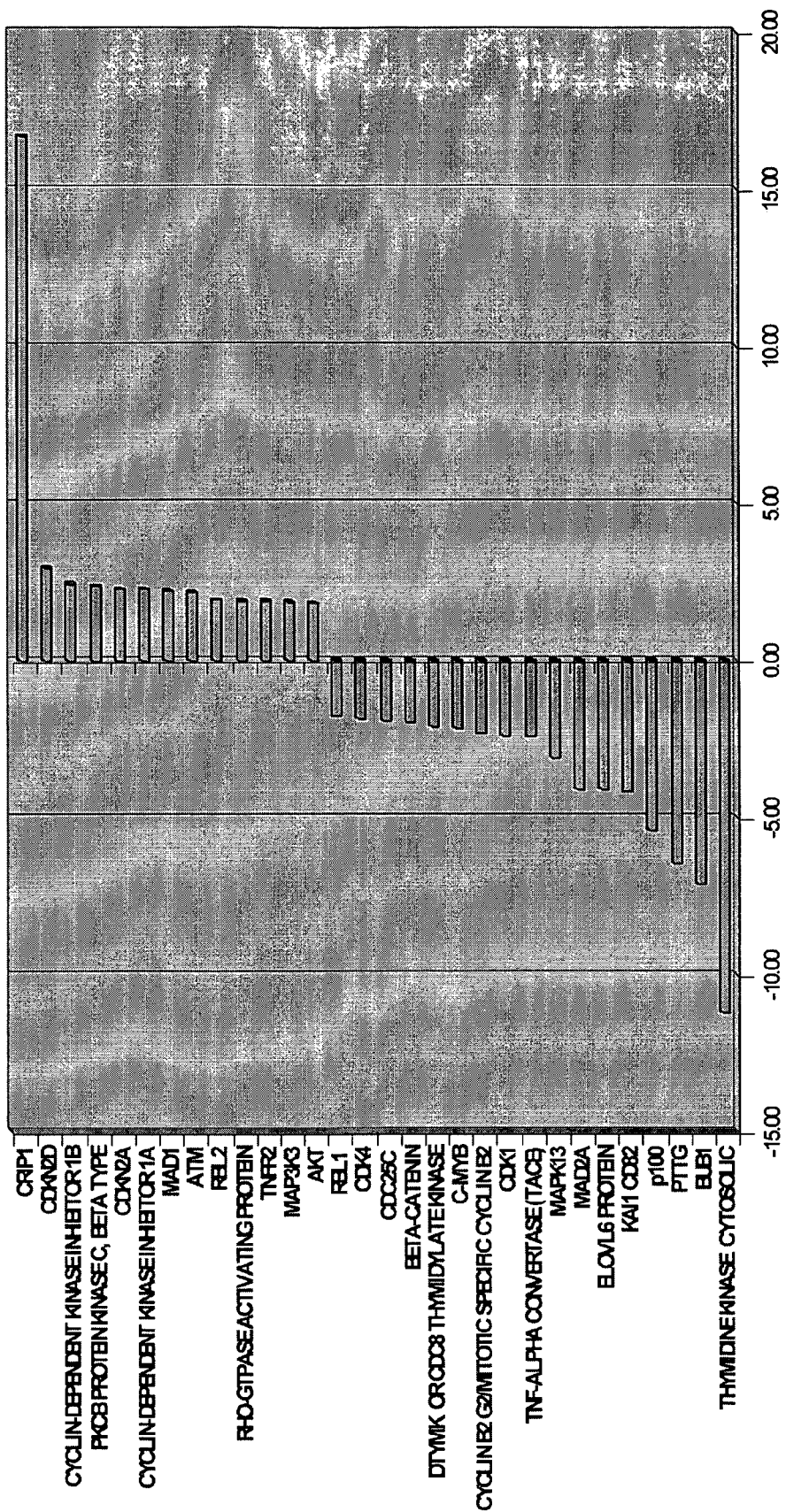
FIG. 6 is a chart that provides examples of the differences between MLPC and MSC in the expression of genes involved in cell cycle, proliferation, and anti-apoptosis.
Figure 7:
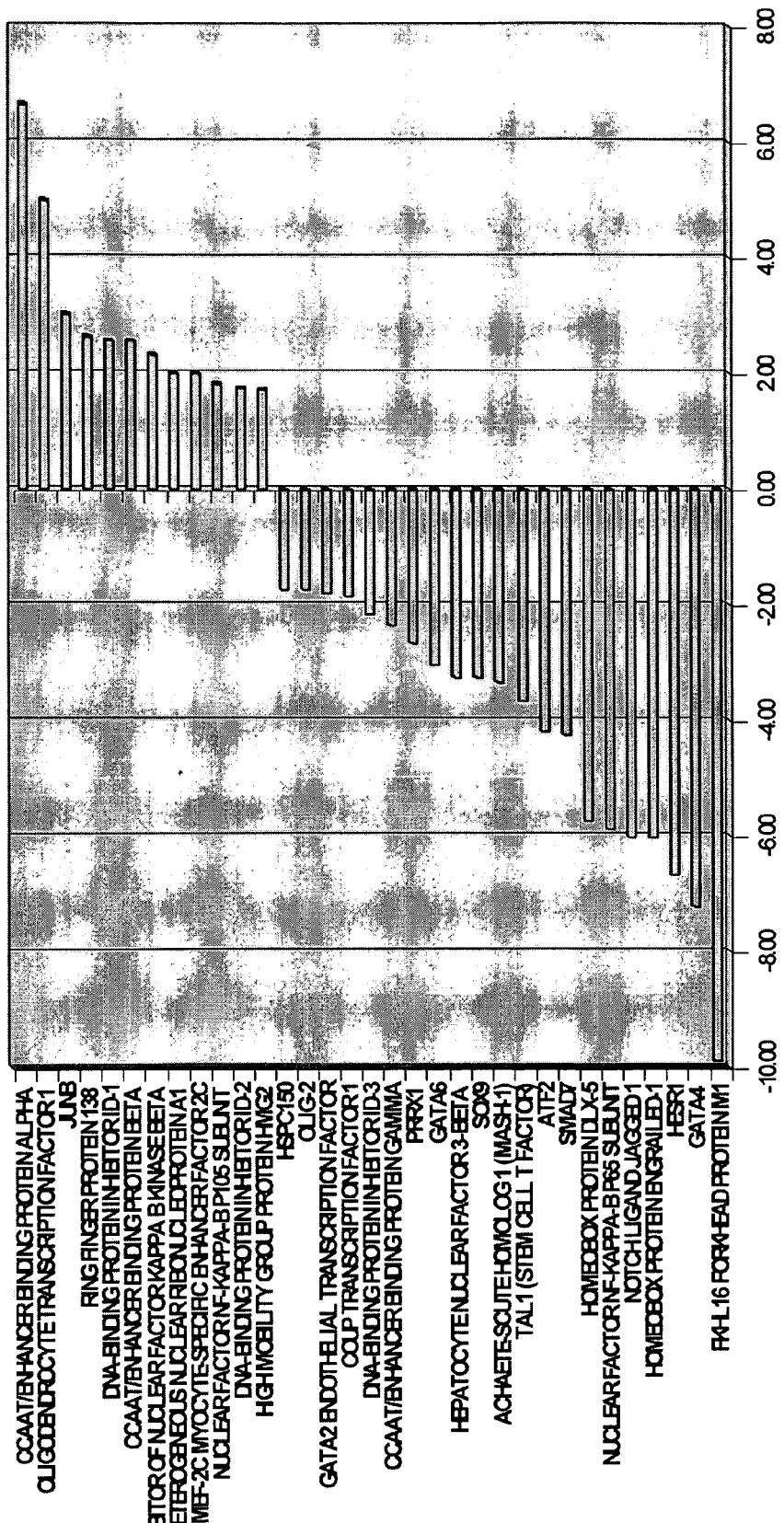
FIG. 7 is a chart that provides examples of the differences between MLPC and MSC in the expression of transcription factors.
Figure 8:
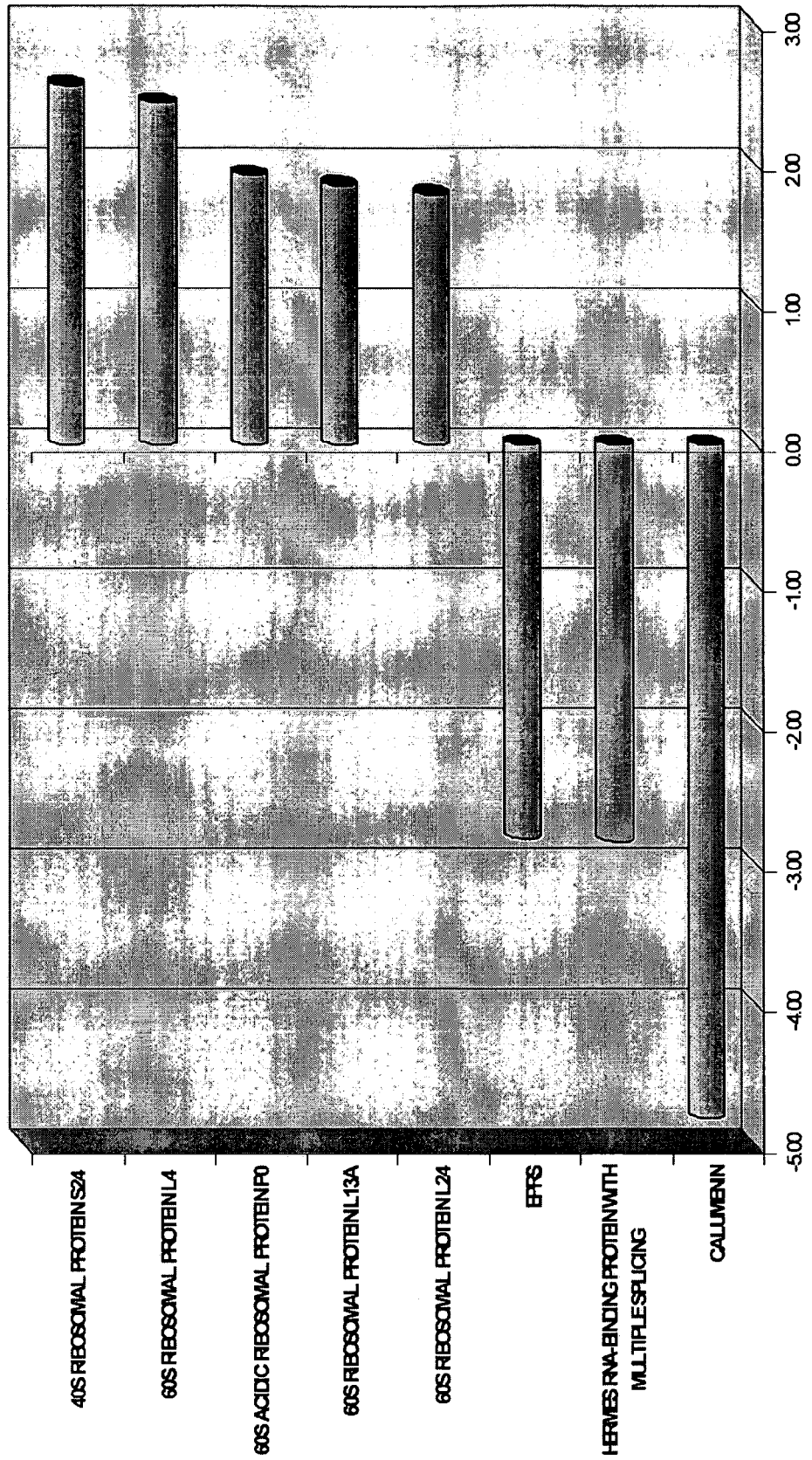
FIG. 8 is a chart that provides examples of the differences between MLPC and MSC in the expression of translation regulators.
Figure 9:
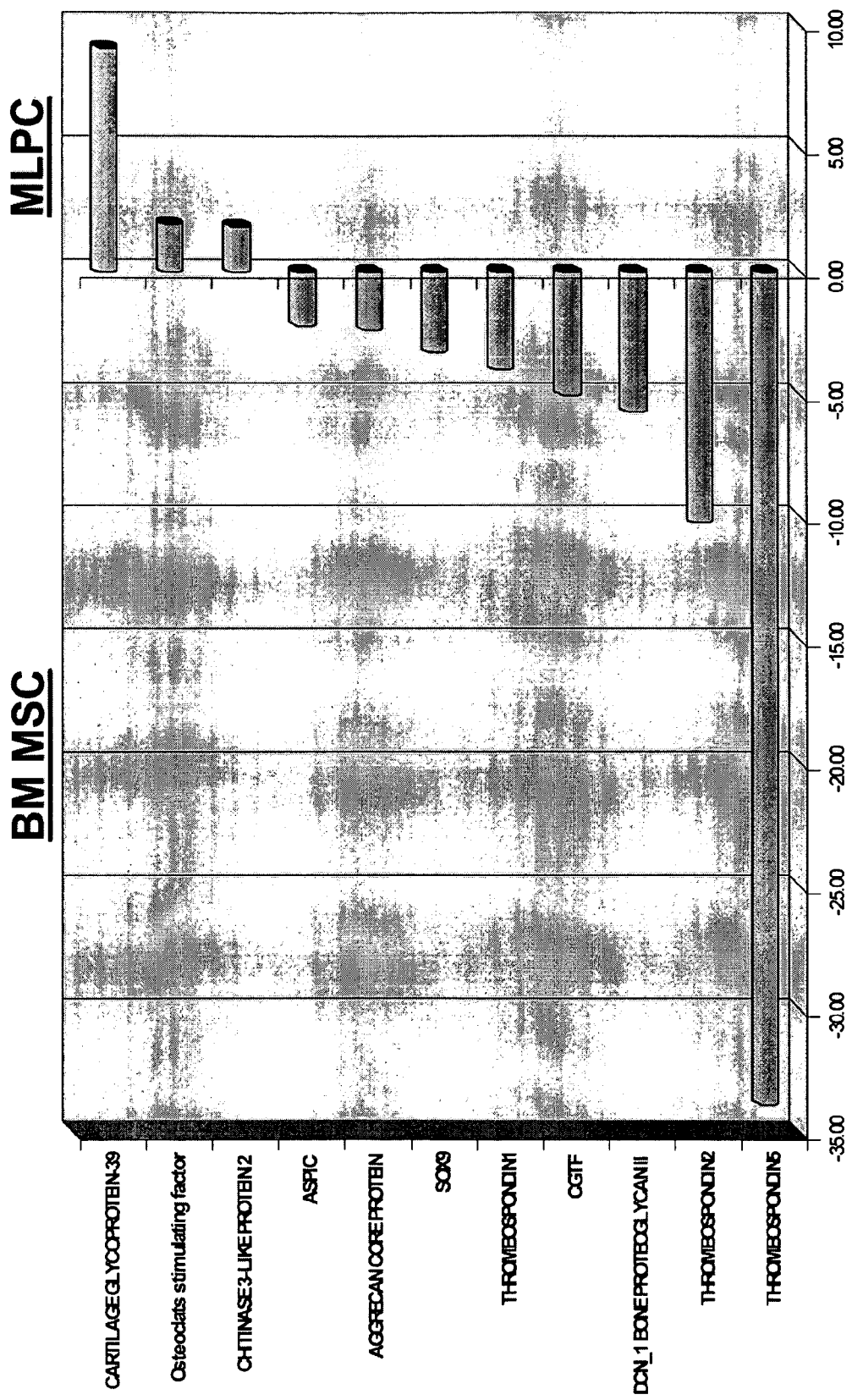
FIG. 9 is a chart that provides examples of the differences between MLPC and MSC in the expression of genes for connective tissue, cartilage, and bone.
Figure 10:
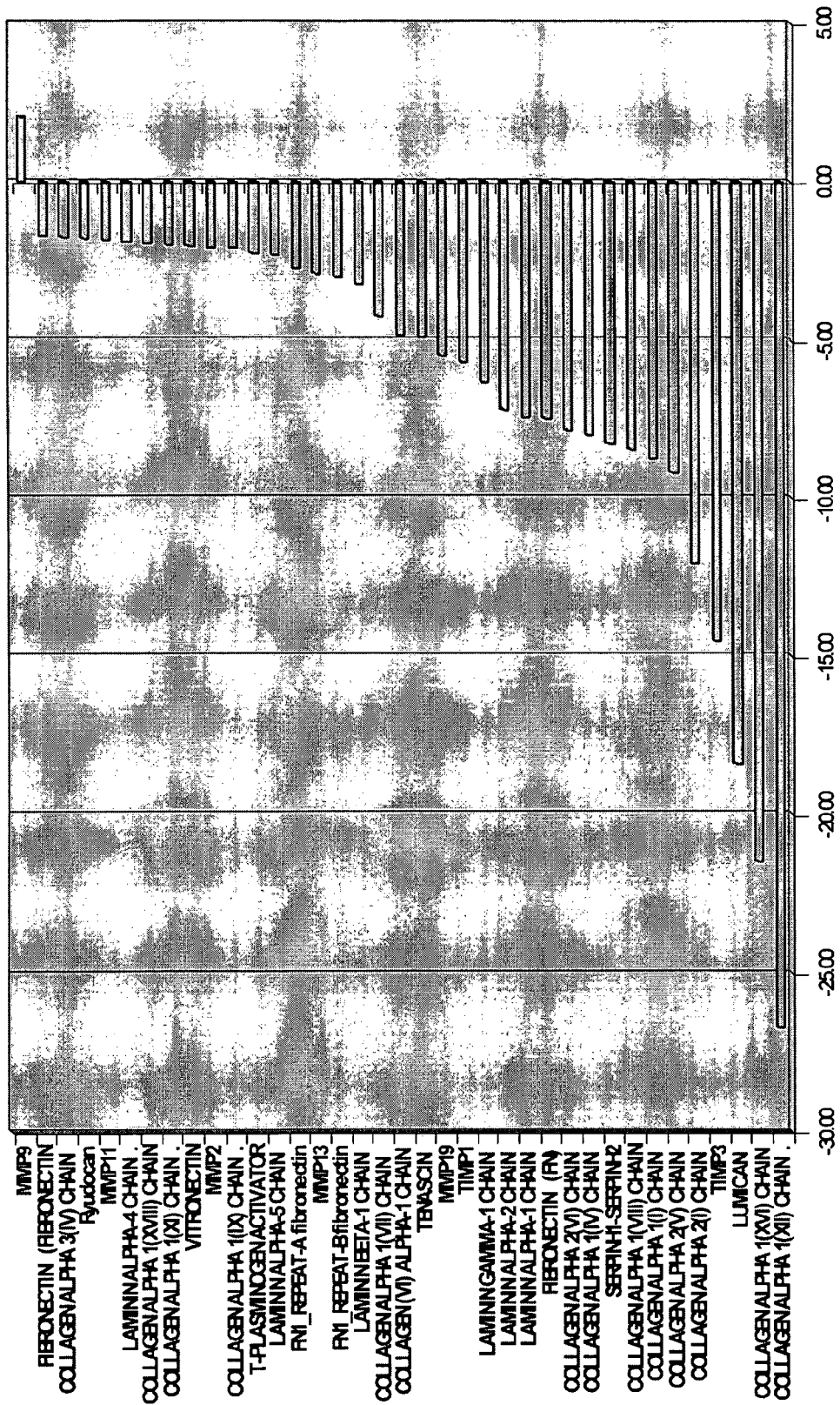
FIG. 10 is a chart that provides examples of the differences between MLPC and MSC in the expression of genes for extracellular matrix.
Figure 11:
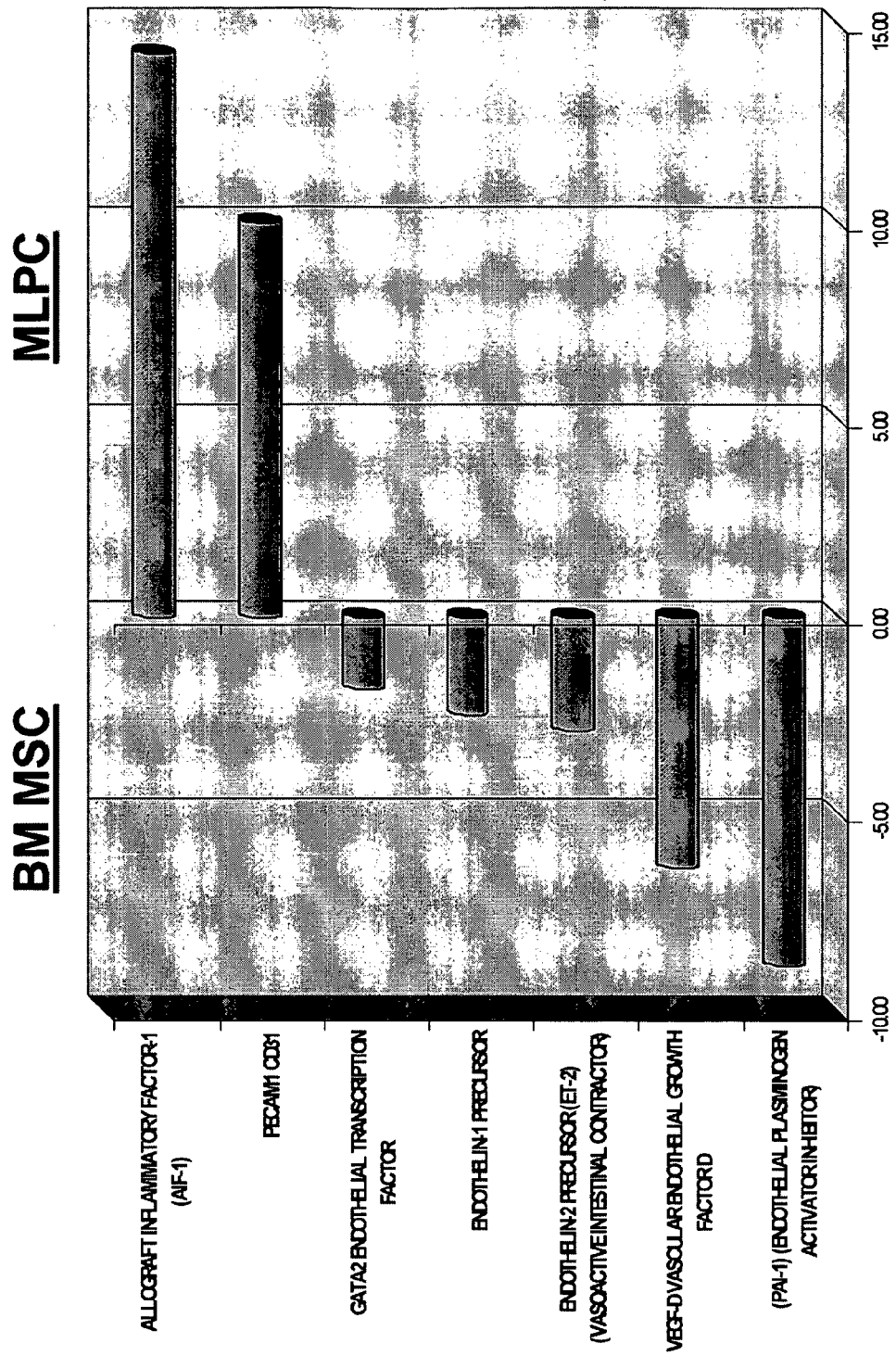
FIG. 11 is a chart that provides examples of the differences between MLPC and MSC in the expression of genes for the endothelium.
Figure 12:
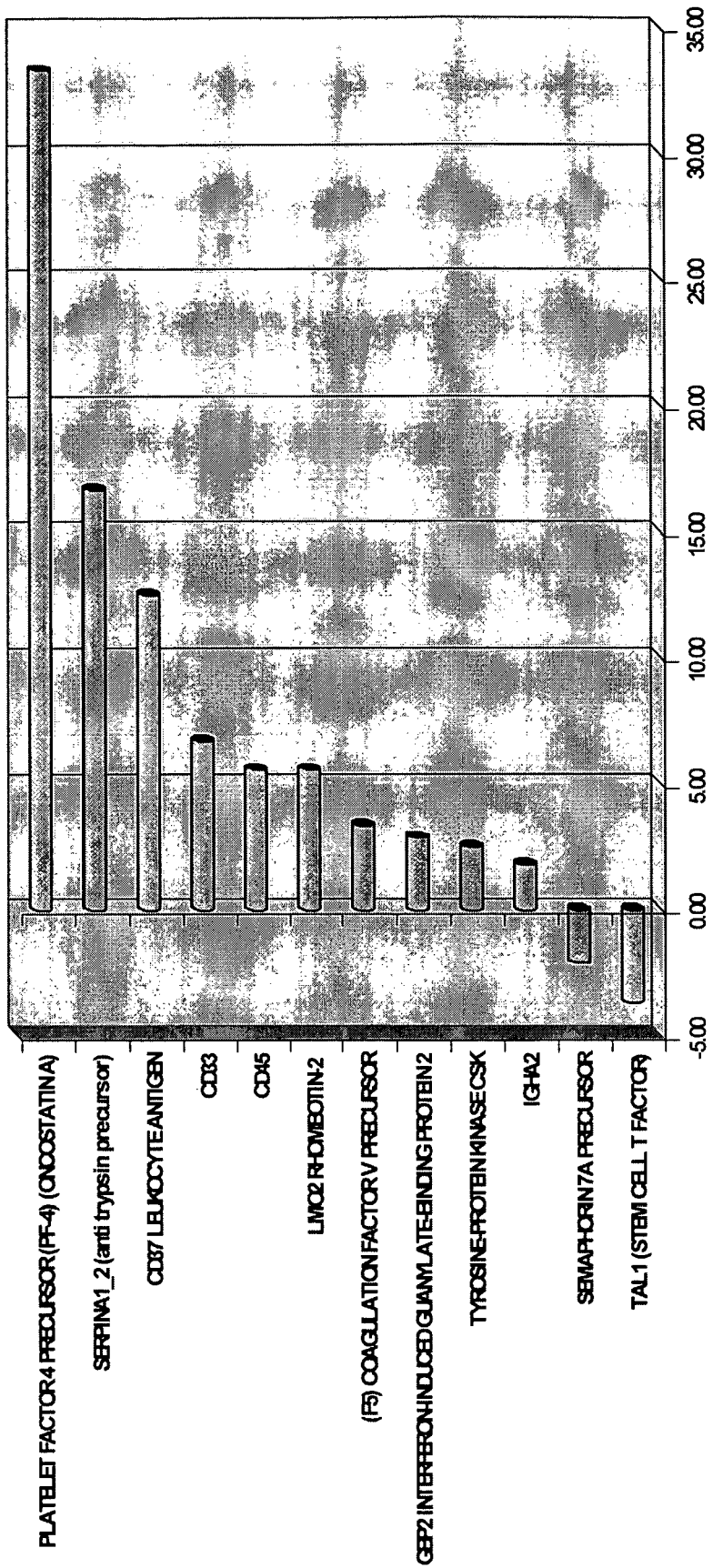
FIG. 12 is a chart that provides examples of the differences between MLPC and MSC in the expression of genes involved in hematopoiesis and the immune response.
Figure 13:
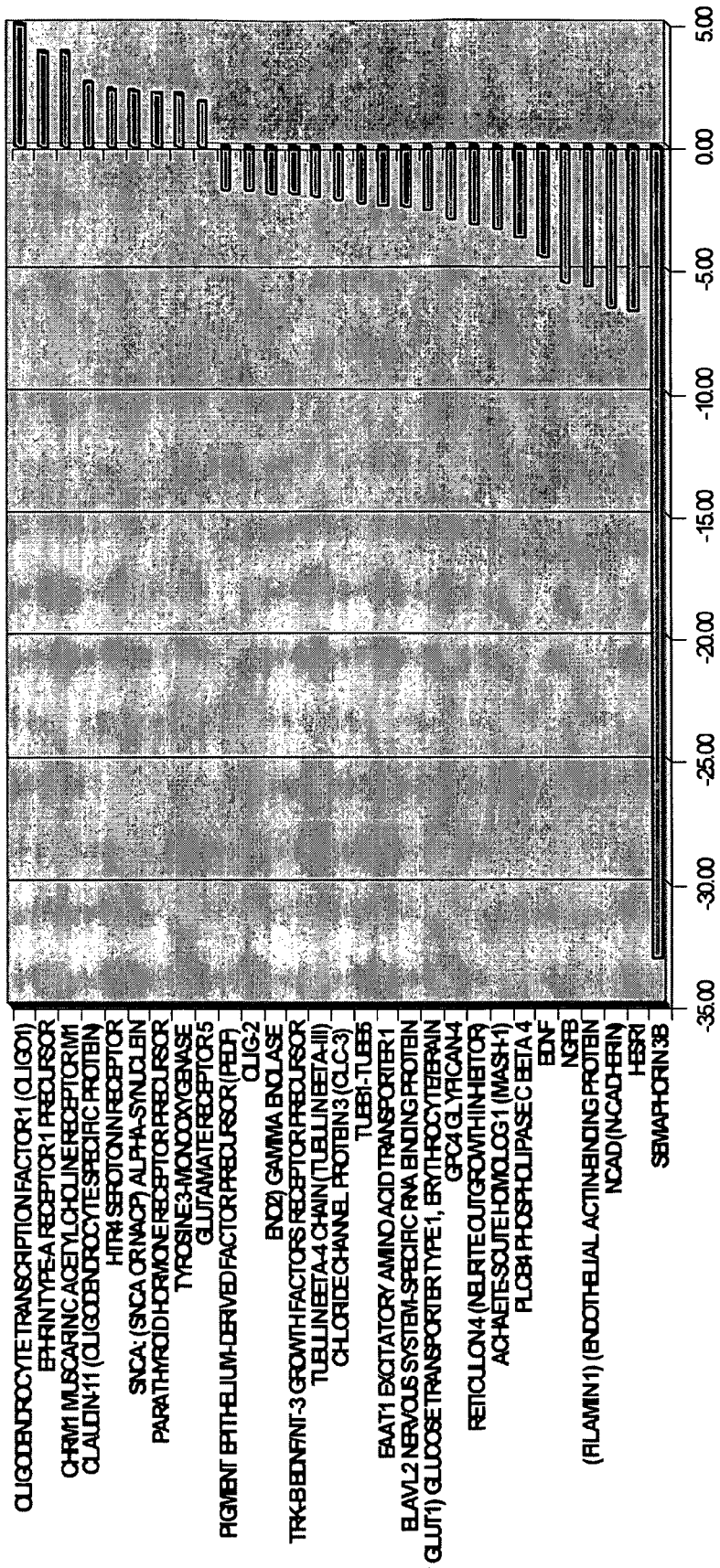
FIG. 13 is a chart that provides examples of the differences between MLPC and MSC in the expression of neural genes.
Figure 14:
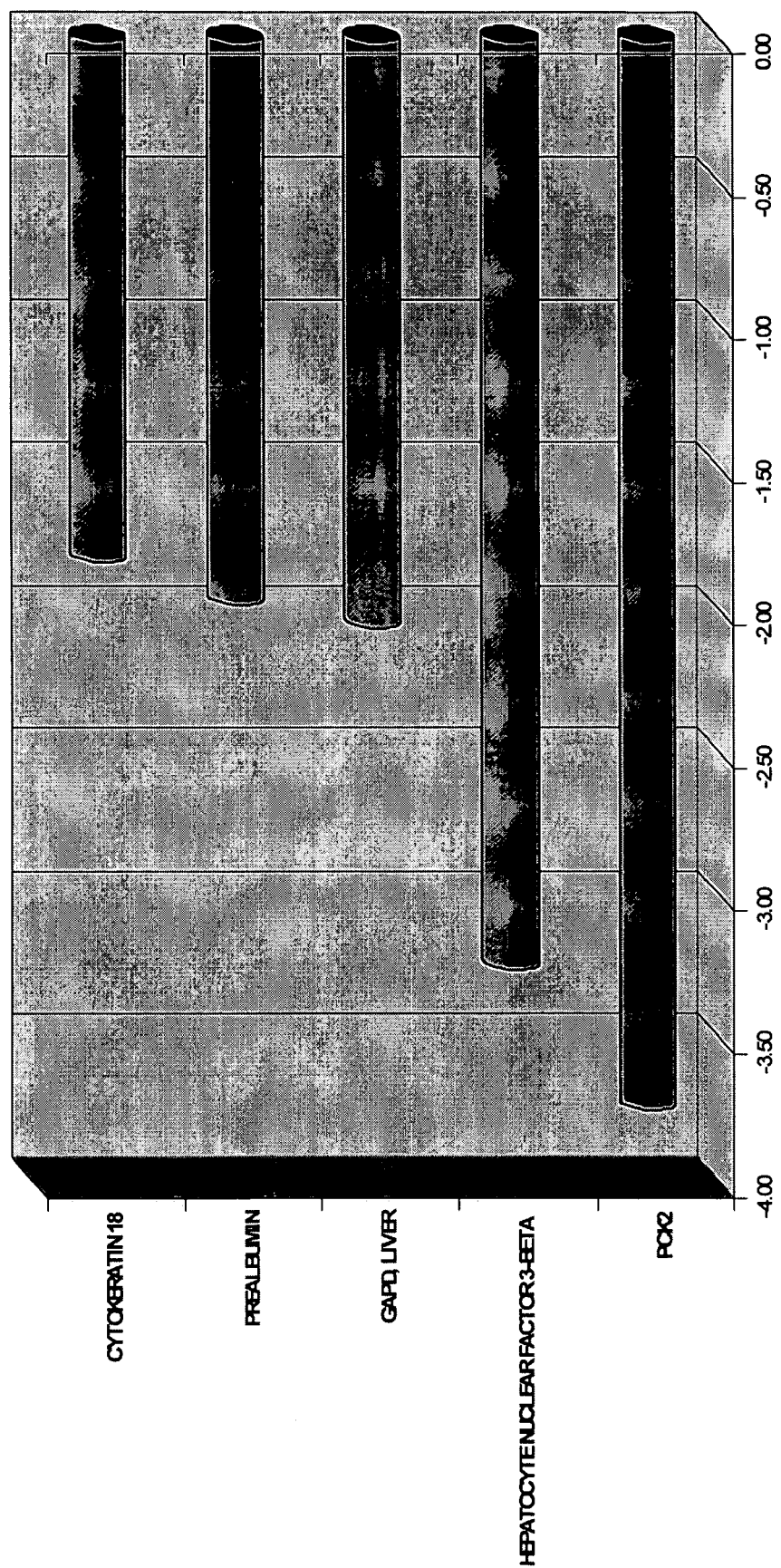
FIG. 14 is a chart that provides examples of the differences between MLPC and MSC in the expression of hepatic genes.
Figure 15:
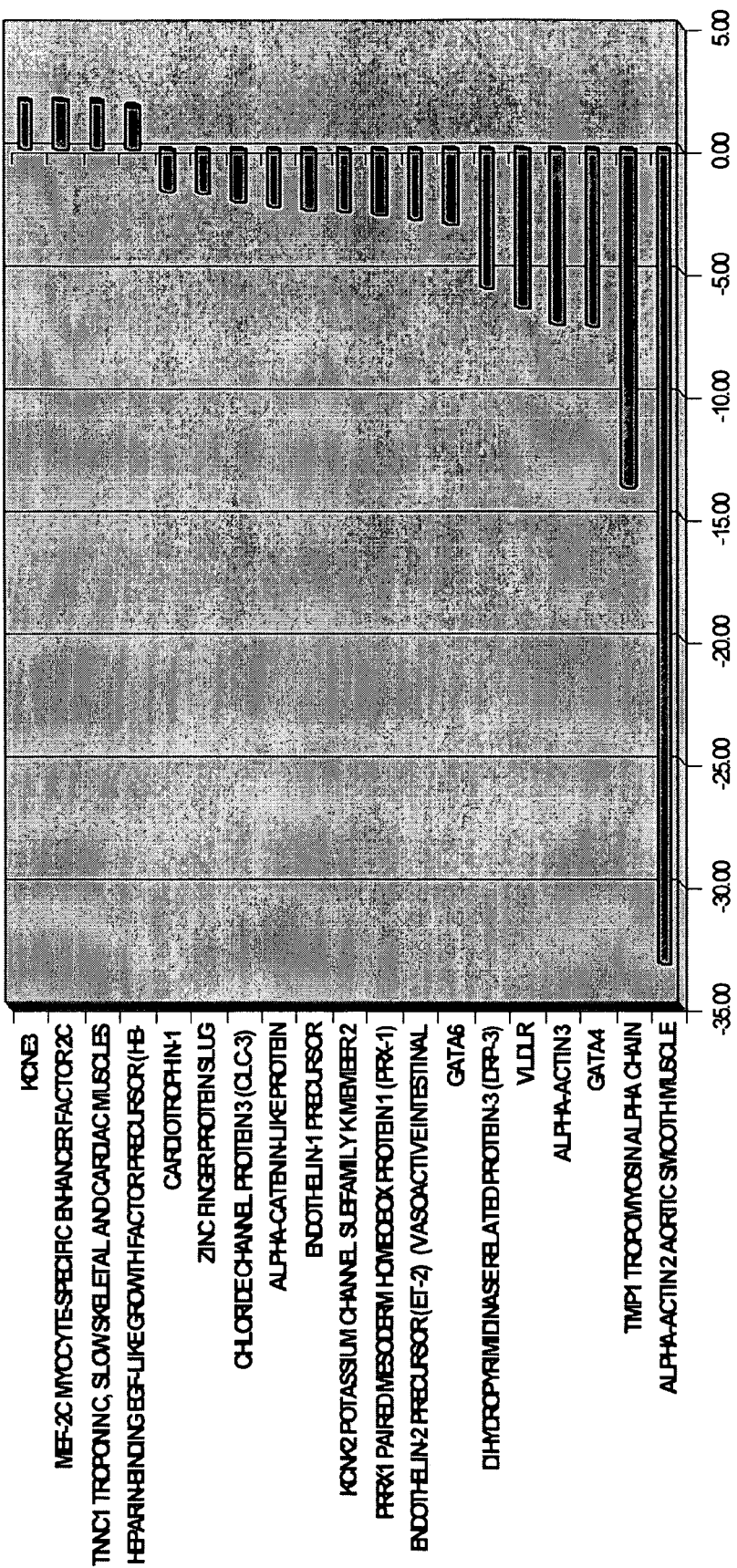
FIG. 15 is a chart that provides examples of the differences between MLPC and MSC in the expression of muscle, smooth muscle, and cardiac genes.
Figure 16:
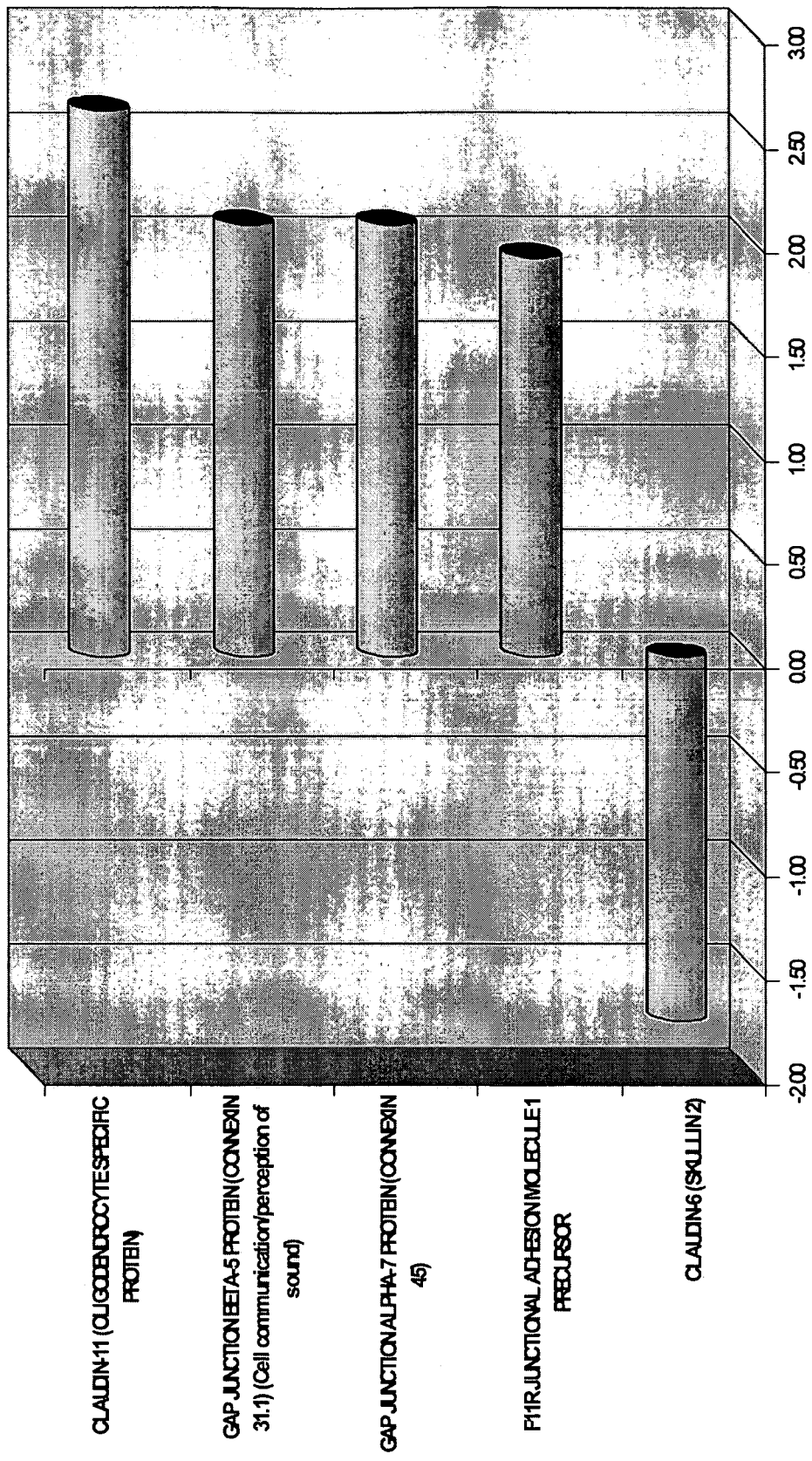
FIG. 16 is a chart that provides examples of the differences between MLPC and MSC in the expression of genes involved in cell-cell communication.
Figure 17:
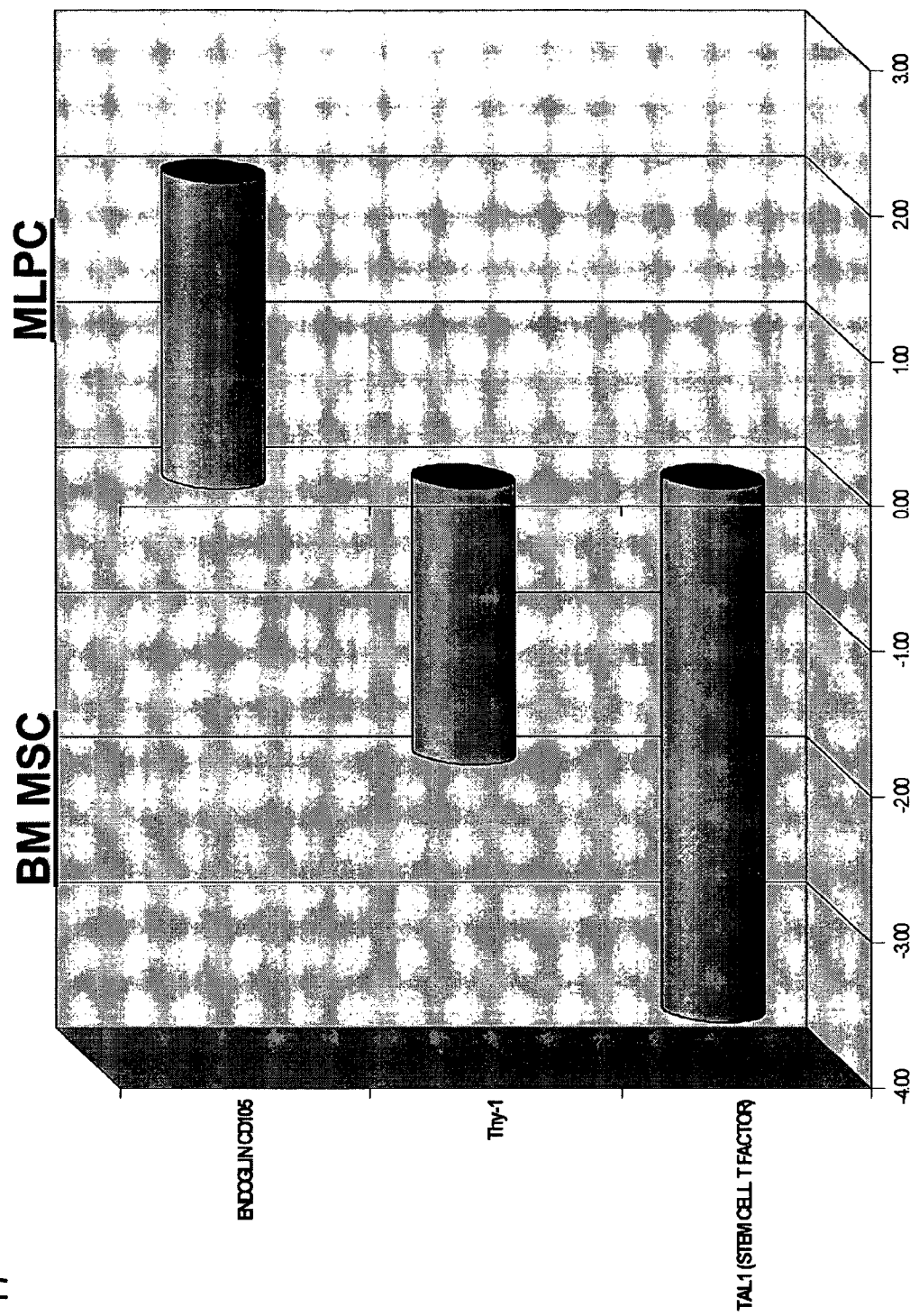
FIG. 17 is a chart that provides examples of the differences between MLPC and MSC in the expression of stem cell markers (hematopoietic and mesenchymal).
Figure 18:
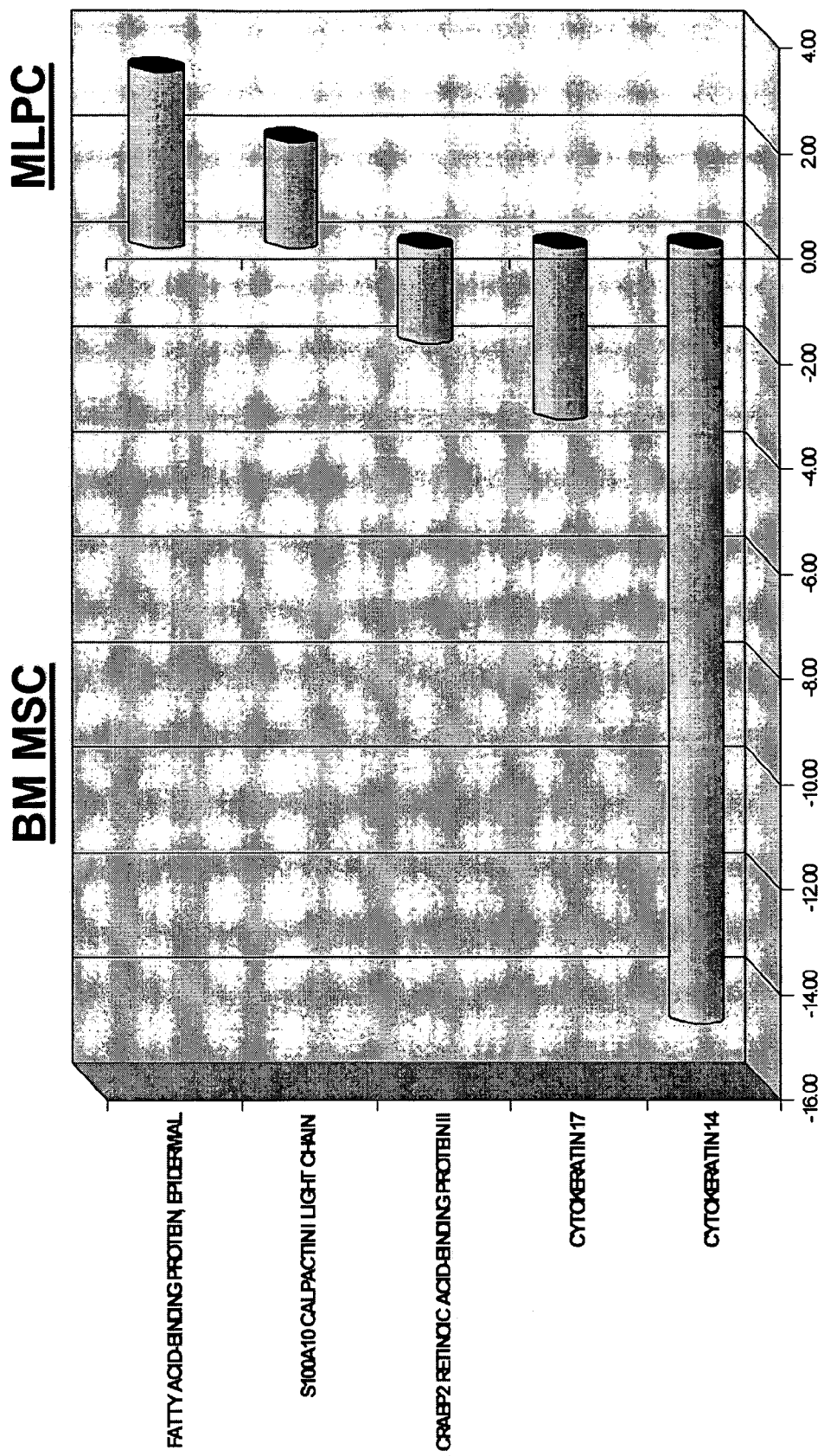
FIG. 18 is a chart that provides examples of the differences between MLPC and MSC in the expression of epidermal genes.
Figure 19:
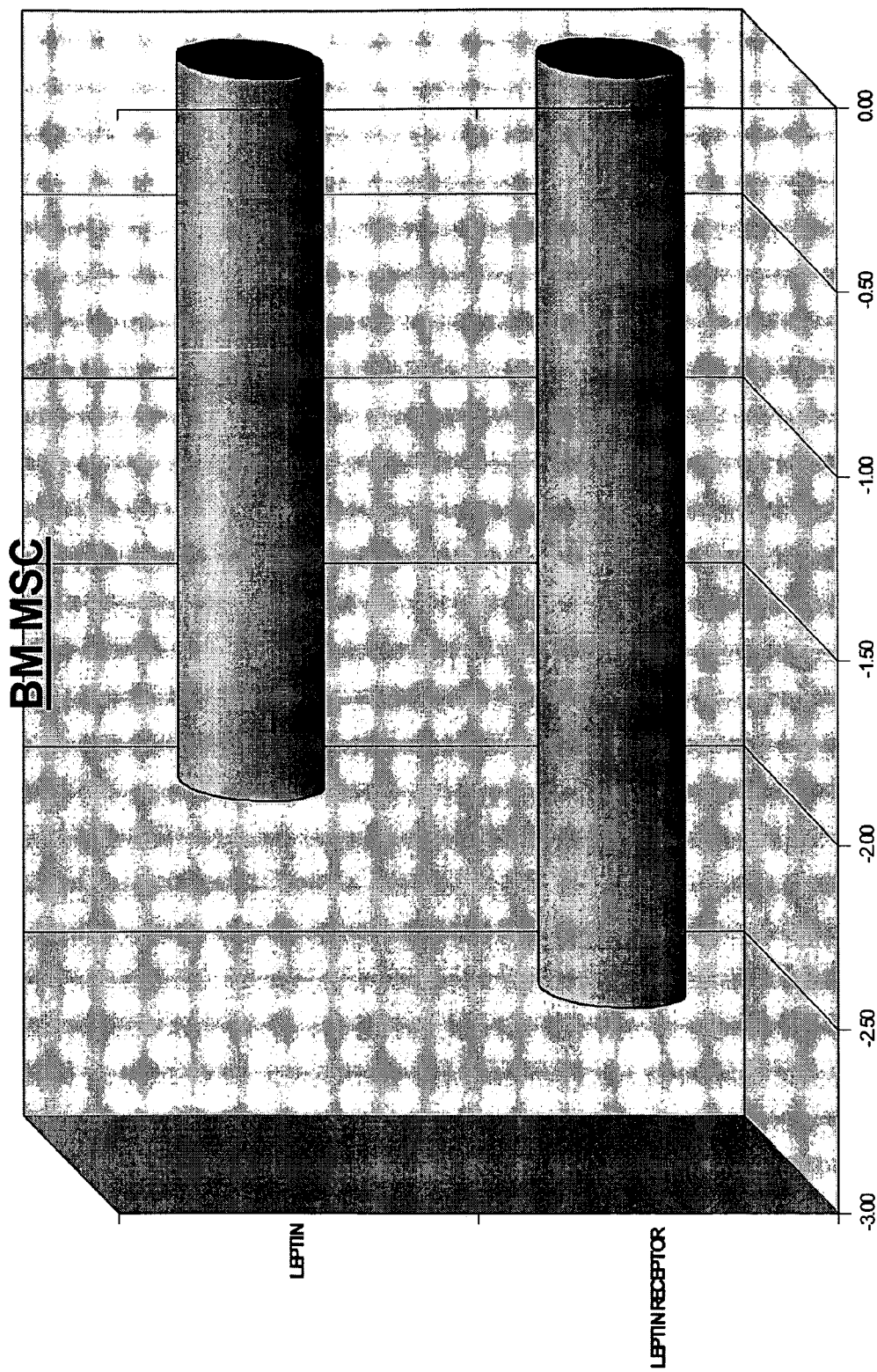
FIG. 19 is a chart that provides examples of the differences between MLPC and MSC in the expression of adipocytic genes.
Figure 20:
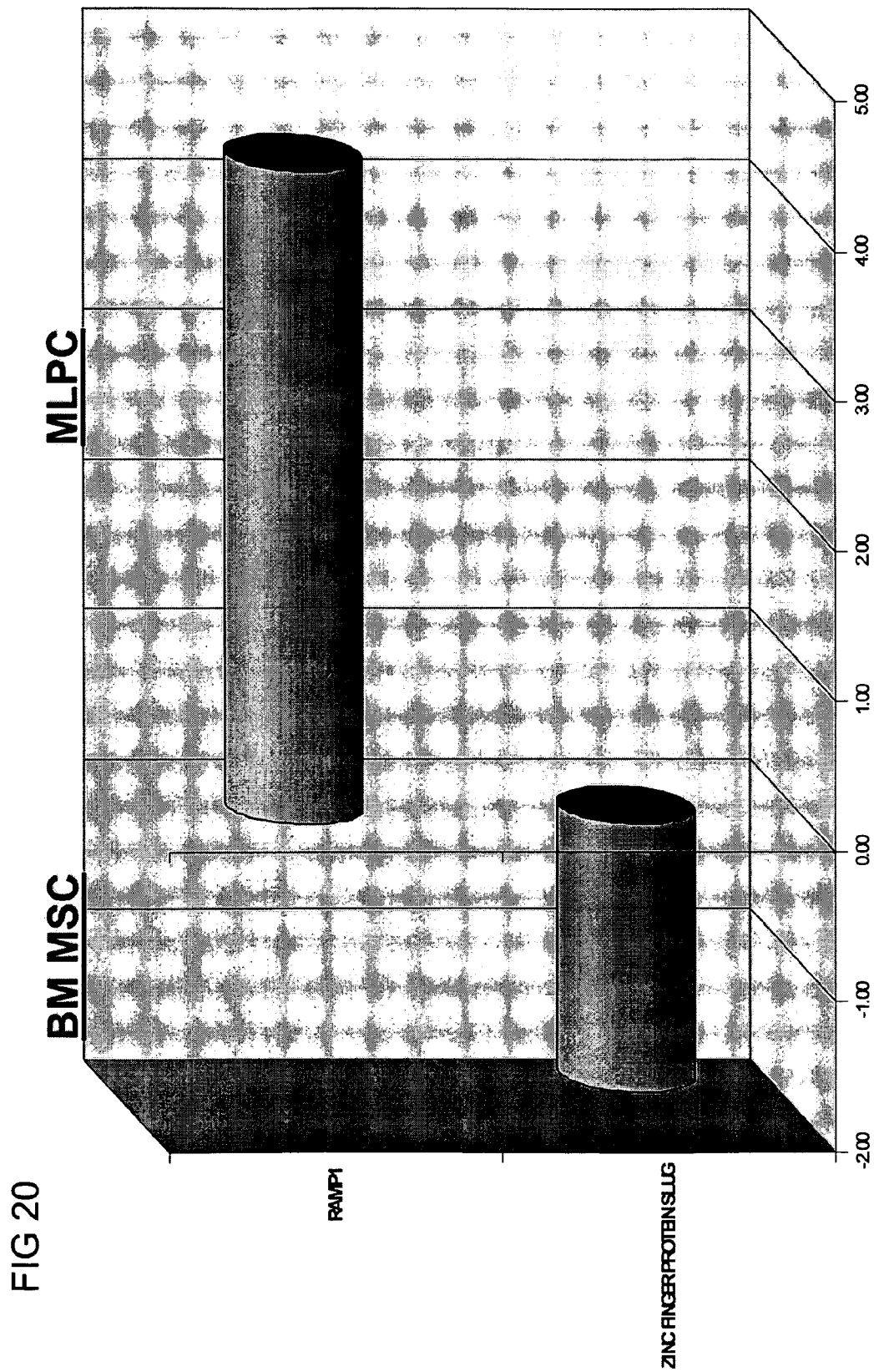
FIG. 20 is a chart that provides examples of the differences between MLPC and MSC in the expression of pancreatic genes
Figure 21:
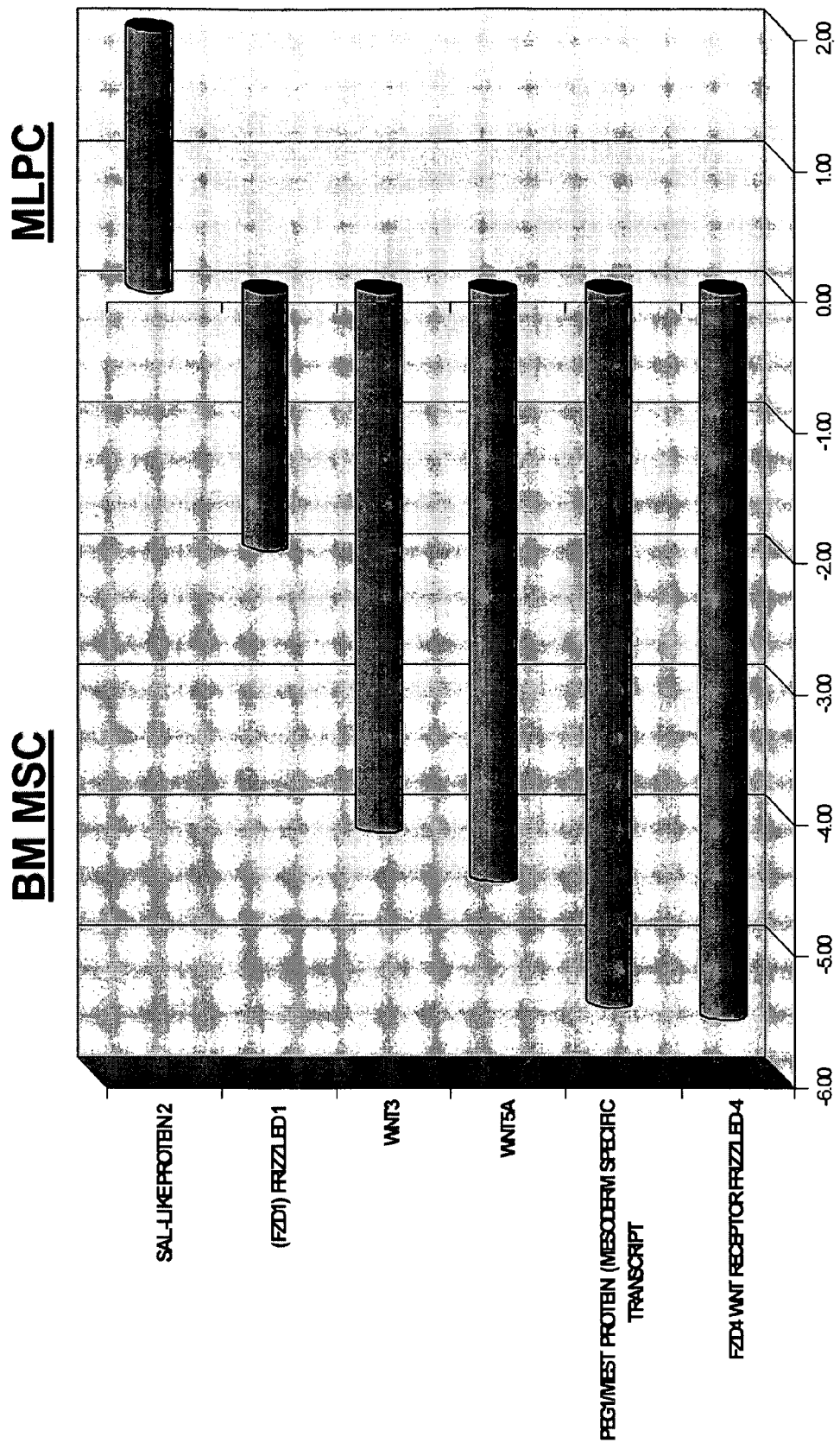
FIG. 21 is a chart that provides examples of the differences between MLPC and MSC in the expression of genes involved in development/morphogenesis.

In general, the invention provides purified populations of MLPC from human fetal blood (e.g., umbilical cord blood ("cord blood"), placental blood, or the blood from a fetus) and clonal MLPC lines derived from individual MLPC. Fetal blood provides a source of cells that is more immature than adult bone marrow and has a higher percentage of cells bearing immature cell surface markers. Consequently, there may be advantages in the expansion and differentiation capacity of the progenitor cells from fetal blood. As described herein, MLPC have immunophenotypic characteristics and a gene expression profile distinct from bone marrow derived MSC's, bone marrow-derived HSC, and umbilical cord blood-derived HSC and USSC. The cells described herein have the capacity to self renew and differentiate into diverse tissue types similar to the bone marrow-derived MSC and MAPC cells. MLPC can be used to develop cellular therapies and establish cryopreserved cell banks for future regenerative medicine procedures. MLPC also can be modified such that the cells can produce one or more polypeptides or other therapeutic compounds of interest.

Cell Separation Compositions

MLPC can be isolated from fetal blood (e.g., cord blood) using the negative selection process and cell separation compositions disclosed in U.S. Patent Publication No. 2003-0027233-A1. Such cell compositions can include dextran and one or more antibodies against (i.e., that have binding affinity for) a cell surface antigen.

Dextran is a polysaccharide consisting of glucose units linked predominantly in alpha (1 to 6) mode. Dextran can cause stacking of erythrocytes (i.e., rouleau formation) and thereby facilitate the removal of erythroid cells from solution. Antibodies against cell surface antigens can facilitate the removal of blood cells from solution via homotypic agglutination (i.e., agglutination of cells of the same cell type) and/or heterotypic agglutination (i.e., agglutination of cells of different cell types).

For example, a cell separation composition can include dextran and antibodies against glycophorin A, CD15, and CD9. Cell separation compositions also can contain antibodies against other blood cell surface antigens including, for example, CD2, CD3, CD4, CD8, CD72, CD16, CD41a, HLA Class I, HLA-DR, CD29, CD11a, CD11b, CD11c, CD19, CD20, CD23, CD39, CD40, CD43, CD44, CDw49d, CD53, CD54, CD62L, CD63, CD66, CD67, CD81, CD82, CD99, CD100, Leu-13, TPA-1, surface Ig, and combinations thereof. Thus, cell separation compositions can be formulated to selectively agglutinate particular types of blood cells.

Typically, the concentration of anti-glycophorin A antibodies in a cell separation composition ranges from 0.1 to 15 mg/L (e.g., 0.1 to 10 mg/L, 1 to 5 mg/L, or 1 mg/L). Anti-glycophorin A antibodies can facilitate the removal of red cells from solution by at least two mechanisms. First, anti-glycophorin A antibodies can cause homotypic agglutination of erythrocytes since glycophorin A is the major surface glycoprotein on erythrocytes. In addition, anti-glycophorin A antibodies also can stabilize dextran-mediated rouleau formation. Exemplary monoclonal anti-glycophorin A antibodies include, without limitation, 107FMN (Murine IgG1 isotype), YTH89.1 (Rat IgG2b isotype), 2.2.2.E7 (Murine IgM isotype; BioE, St. Paul, Minn.), and E4 (Murine IgM isotype). See e.g., M. Vanderlaan et al., *Molecular Immunology* 20:1353 (1983); Telen M. J. and Bolk, T. A., *Transfusion* 27: 309 (1987); and Outram S. et al., *Leukocyte Research*. 12:651 (1988).

The concentration of anti-CD 15 antibodies in a cell separation composition can range from 0.1 to 15 mg/L (e.g., 0.1 to 10, 1 to 5, or 1 mg/L). Anti-CD15 antibodies can cause homotypic agglutination of granulocytes by crosslinking CD15 molecules that are present on the surface of granulocytes. Anti CD15 antibodies also can cause homotypic and heterotypic agglutination of granulocytes with monocytes, NK-cells and B-cells by stimulating expression of adhesion molecules (e.g., L-selectin and beta-2 integrin) on the surface of granulocytes that interact with adhesion molecules on monocytes, NK-cells and B-cells. Heterotypic agglutination of these cell types can facilitate the removal of these cells from solution along with red cell components. Exemplary monoclonal anti-CD15 antibodies include, without limitation, AHN1.1 (Murine IgM isotype), FMC-10 (Murine IgM isotype), BU-28 (Murine IgM isotype), MEM-157 (Murine IgM isotype), MEM-158 (Murine IgM isotype), 324.3.B9 (Murine IgM isotype; BioE, St. Paul, Minn.), and MEM-167 (Murine IgM isotype). See e.g., *Leukocyte typing IV* (1989); *Leukocyte typing II* (1984); *Leukocyte typing VI* (1995); Solter D. et al., *Proc. Natl. Acad. Sci. USA* 75:5565 (1978); Kannagi R. et al., *J. Biol. Chem.* 257:14865 (1982); Magnani, J. L. et al., *Arch. Biochem. Biophys* 233:501 (1984); Eggens I. et al., *J. Biol. Chem.* 264:9476 (1989).

The concentration of anti-CD9 antibodies in a cell separation composition can range from 0.1 to 15, 0.1 to 10, 1 to 5, or 1 mg/L. Anti-CD9 antibodies can cause homotypic agglutination of platelets. Anti-CD9 antibodies also can cause heterotypic agglutination of granulocytes and monocytes via platelets that have adhered to the surface of granulocytes and monocytes. CD9 antibodies can promote the expression of platelet p-selectin (CD62P), CD41/61, CD31, and CD36, which facilitates the binding of platelets to leukocyte cell surfaces. Thus, anti-CD9 antibodies can promote multiple cell-cell linkages and thereby facilitate agglutination and removal from solution. Exemplary monoclonal anti-CD9 antibodies include, without limitation, MEM-61 (Murine IgG1 isotype), MEM-62 (Murine IgG1 isotype), MEM-192 (Murine IgM isotype), FMC-8 (Murine IgG2a isotype), SN4 (Murine IgG1 isotype), 8.10.E7 (Murine IgM isotype; BioE, St. Paul, Minn.), and BU-16 (Murine IgG2a isotype). See e.g., *Leukocyte typing VI* (1995); *Leukocyte typing II* (1984); Von dem Bourne A. E. G. Kr. and Moderman P. N. (1989) In *Leukocyte typing IV* (ed. W. Knapp, et al), pp. 989-92, Oxford University Press, Oxford; Jennings, L. K., et al. In *Leukocyte typing V*, ed. S. F. Schlossmann et al., pp. 1249-51, Oxford University Press, Oxford (1995); Lanza F. et al., *J. Biol. Chem.* 266:10638 (1991); Wright et al., *Immunology Today*

15:588 (1994); Rubinstein E. et al., *Seminars in Thrombosis and Hemostasis* 21:10 (1995).

In some embodiments, a cell separation composition contains antibodies against CD41, which can selectively agglutinate platelets. In some embodiments, a cell separation composition contains antibodies against CD3, which can selectively agglutinate T-cells. In some embodiments, a cell separation composition contains antibodies against CD2, which can selectively agglutinate T-cells and NK cells. In some embodiments, a cell separation composition contains antibodies against CD72, which can selectively agglutinate B-cells. In some embodiments, a cell separation composition contains antibodies against CD16, which can selectively agglutinate NK cells and neutrophilic granulocytes. The concentration of each of these antibodies can range from 0.01 to 15 mg/L. Exemplary anti-CD41 antibodies include, without limitation, PLT-1 (Murine IgM isotype), CN19 (Murine $IgG_1$ isotype), and 8.7.C3 (Murine IgG1 isotype). Non-limiting examples of anti-CD3 antibodies include OKT3 (Murine $IgG_1$), HIT3a (Murine IgG2a isotype), SK7 (Murine $IgG_1$) and BC3 (Murine $IgG_{2a}$). Non-limiting examples of anti-CD2 antibodies include 7A9 (Murine IgM isotype), T11(Murine $IgG_1$ isotype), and Leu5b (Murine $IgG_{2a}$ Isotype). Non-limiting examples of anti-CD72 antibodies include BU-40 (Murine $IgG_1$ isotype) and BU-41 (Murine $IgG_1$ isotype). Non-limiting examples of anti-CD16 antibodies include 3G8 (Murine IgG).

As mentioned above, cell separation compositions can be formulated to selectively agglutinate particular blood cells. As an example, a cell separation composition containing antibodies against glycophorin A, CD15, and CD9 can facilitate the agglutination of erythrocytes, granulocytes, NK cells, B cells, and platelets. T cells, NK cells and rare precursor cells such as MLPC then can be recovered from solution. If the formulation also contained an antibody against CD3, T cells also could be agglutinated, and NK cells and rare precursors such as MLPC could be recovered from solution.

Cell separation compositions can contain antibodies against surface antigens of other types of cells (e.g., cell surface proteins of tumor cells). Those of skill in the art can use routine methods to prepare antibodies against cell surface antigens of blood, and other, cells from humans and other mammals, including, for example, non-human primates, rodents (e.g., mice, rats, hamsters, rabbits and guinea pigs), swine, bovines, and equines.

Typically, antibodies used in the composition are monoclonal antibodies, which are homogeneous populations of antibodies to a particular epitope contained within an antigen. Suitable monoclonal antibodies are commercially available, or can be prepared using standard hybridoma technology. In particular, monoclonal antibodies can be obtained by techniques that provide for the production of antibody molecules by continuous cell lines in culture, including the technique described by Kohler, G. et al., *Nature*, 1975, 256:495, the human B-cell hybridoma technique (Kosbor et al., *Immunology Today* 4:72 (1983); Cole et al., *Proc. Natl. Acad. Sci. USA* 80:2026 (1983)), and the EBV-hybridoma technique (Cole et al., "Monoclonal Antibodies and Cancer Therapy," Alan R. Liss, Inc., pp. 77-96 (1983)).

Antibodies can be of any immunoglobulin class including IgG, IgM, IgE, IgA, IgD, and any subclass thereof. Antibodies of the IgG and IgM isotypes are particularly useful in cell separation compositions of the invention. Pentameric IgM antibodies contain more antigen binding sites than IgG antibodies and can, in some cases (e.g., anti-glycophorin A and anti-CD15), be particularly useful for cell separation reagents. In other cases (e.g., anti-CD9 antibodies), antibodies of the IgG isotype are particularly useful for stimulating homotypic and/or heterotypic agglutination.

Antibodies against cell surface antigens can be provided in liquid phase (i.e., soluble). Liquid phase antibodies typically are provided in a cell separation composition at a concentration between about 0.1 and about 15 mg/l (e.g., between 0.25 to 10, 0.25 to 1, 0.5 to 2, 1 to 2, 4 to 8, 5 to 10 mg/l).

Antibodies against cell surface antigens also can be provided in association with a solid phase (i.e., substrate-bound). Antibodies against different cell surface antigens can be covalently linked to a solid phase to promote crosslinking of cell surface molecules and activation of cell surface adhesion molecules. The use of substrate-bound antibodies can facilitate cell separation (e.g., by virtue of the mass that the particles contribute to agglutinated cells, or by virtue of properties useful for purification).

In some embodiments, the solid phase with which a substrate-bound antibody is associated is particulate. In some embodiments, an antibody is bound to a latex microparticle such as a paramagnetic bead (e.g., via biotin-avidin linkage, covalent linkage to COO groups on polystyrene beads, or covalent linkage to $NH_2$ groups on modified beads). In some embodiments, an antibody is bound to an acid-etched glass particle (e.g., via biotin-avidin linkage). In some embodiments, an antibody is bound to an aggregated polypeptide such as aggregated bovine serum albumin (e.g., via biotin-avidin linkage, or covalent linkage to polypeptide COO groups or $NH_2$ groups). In some embodiments, an antibody is covalently linked to a polysaccharide such as high molecular weight (e.g., $>1,000,000$ $M_r$) dextran sulfate. In some embodiments, biotinylated antibodies are linked to avidin particles, creating tetrameric complexes having four antibody molecules per avidin molecule. In some embodiments, antibodies are bound to biotinylated agarose gel particles (One Cell Systems, Cambridge, Mass., U.S.A.) via biotin-avidin-biotinylated antibody linkages. Such particles typically are about 300-500 microns in size, and can be created in a sonicating water bath or in a rapidly mixed water bath.

Cell-substrate particles (i.e., particles including cells and substrate-bound antibodies) can sediment from solution as an agglutinate. Cell-substrate particles also can be removed from solution by, for example, an applied magnetic field, as when the particle is a paramagnetic bead. Substrate-bound antibodies typically are provided in a cell separation composition at a concentration between about 0.1 and about $50.0\times10^9$ particles/l (e.g., between 0.25 to $10.0\times10^9$, 1 to $20.0\times10^9$, 2 to $10.0\times10^9$, 0.5 to $2\times10^9$, 2 to $5\times10^9$, 5 to $10\times10^9$, and 10 to $30\times10^9$ particles/l), where particles refers to solid phase particles having antibodies bound thereto.

Cell separation compositions also can contain divalent cations (e.g., $Ca^{+2}$ and $Mg^{+2}$). Divalent cations can be provided, for example, by a balanced salt solution (e.g., Hank's balanced salt solution). $Ca^{+2}$ ions reportedly are important for selectin-mediated and integrin-mediated cell-cell adherence.

Cell separation compositions also can contain an anticoagulant such as heparin. Heparin can prevent clotting and non-specific cell loss associated with clotting in a high calcium environment. Heparin also promotes platelet clumping. Clumped platelets can adhere to granulocytes and monocytes and thereby enhance heterotypic agglutination more so than single platelets. Heparin can be supplied as a heparin salt (e.g., sodium heparin, lithium heparin, or potassium heparin).

Populations and Clonal Lines of MLPC

MLPC can be purified from human fetal blood using a cell separation composition described above. As used herein, "purified" means that at least 90% (e.g., 91, 92, 93, 94, 95, 96, 97, 98, or 99%) of the cells within the population are MLPC. As used herein, "MLPC" refers to fetal blood cells that are positive for CD9 and typically display a constellation of other markers such as CD13, CD73, and CD105. "MLPC population" refers to the primary culture obtained from the human fetal blood and uncloned progeny thereof. "Clonal line" refers to a cell line derived from a single cell. As used herein, a "cell line" is a population of cells able to renew themselves for extended periods of times in vitro under appropriate culture conditions. The term "line," however, does not indicate that the cells can be propagated indefinitely. Rather, clonal lines described herein typically can undergo 75 to 100 doublings before senescing.

Typically, an MLPC population is obtained by contacting a fetal blood sample with a cell separation composition described above and allowing the sample to partition into an agglutinate and a supernatant phase. For example, the sample can be allowed to settle by gravity or by centrifugation. Preferably, MLPC are purified from an umbilical cord blood sample that is less than 48 hours old (e.g., less than 24, 12, 8, or 4 hours post-partum). After agglutination, unagglutinated cells can be recovered from the supernatant phase. For example, cells in the supernatant phase can be recovered by centrifugation then washed with a saline solution and plated on a solid substrate (e.g., a plastic culture device such as a chambered slide or culture flask), using a standard growth medium with 10% serum (e.g., DMEM with 10% serum; RPMI-1640 with 10% serum, or mesenchymal stem cell growth medium with 10% serum (catalog # PT-3001, Cambrex, Walkersville, Md.). MLPC attach to the surface of the solid substrate while other cells, including T cells, NK cells and $CD34^+$ HSC, do not and can be removed with washing. The MLPC change from the leukocyte morphology to the fibroblastic morphology between 3 days and 2 weeks post initiation of culture after which the cells enter logarithmic growth phase and will continue growing logarithmically as long as cultures are maintained at cell concentrations of less than about $1.5 \times 10^5$ cells/$cm^2$.

Clonal lines can be established by harvesting the MLPC then diluting and re-plating the cells on a multi-well culture plate such that a single cell can be found in a well. Cells can be transferred to a larger culture flask after a concentration of 1 to $5 \times 10^5$ cells/75 $cm^2$ is reached. Cells can be maintained at a concentration between $1 \times 10^5$ and $5 \times 10^5$ cells/75 $cm^2$ for logarithmic growth.

MLPC can be assessed for viability, proliferation potential, and longevity using techniques known in the art. For example, viability can be assessed using trypan blue exclusion assays, fluorescein diacetate uptake assays, or propidium iodide uptake assays. Proliferation can be assessed using thymidine uptake assays or MTT cell proliferation assays. Longevity can be assessed by determining the maximum number of population doublings of an extended culture.

MLPC can be immunophenotypically characterized using known techniques. For example, the cell culture medium can be removed from the tissue culture device and the adherent cells washed with a balanced salt solution (e.g., Hank's balanced salt solution) and bovine serum albumin (e.g., 2% BSA). Cells can be incubated with an antibody having binding affinity for a cell surface antigen such as CD9, CD45, CD13, C73, CD105, or any other cell surface antigen. The antibody can be detectably labeled (e.g., fluorescently or enzymatically) or can be detected using a secondary antibody that is detectably labeled. Alternatively, the cell surface antigens on MLPC can be characterized using flow cytometry and fluorescently labeled antibodies.

As described herein, the cell surface antigens present on MLPC can vary, depending on the stage of culture. Early in culture when MLPC display a leukocyte-like morphology, MLPC are positive for CD9 and CD45, SSEA-4 (stage-specific embryonic antigen-4), CD34, as well as CD13, CD29, CD44, CD73, CD90, CD105, stem cell factor, STRO-1 (a cell surface antigen expressed by bone marrow stromal cells), SSEA-3 (galactosylgloboside), and CD133, and are negative for CD15, CD38, glycophorin A (CD235a), and lineage markers CD2, CD3, CD4, CD5, CD7, CD8, CD10, CD11b, CD16, CD19, CD20, CD21, CD22, CD33, CD36, CD41, CD61, CD62E, CD72, HLA-DR, and CD102. After transition to the fibroblastic morphology, MLPC remain positive for CD9, CD13, CD29, CD73, CD90, and CD105, and become negative for CD34, CD41, CD45, stem cell factor, STRO-1, SSEA-3, SSEA-4, and CD133. At all times during in vitro culture, the undifferentiated MLPC are negative for CD15, CD38, glycophorin A (CD235a), and lineage markers CD2, CD3, CD4, CD5, CD7, CD8, CD10, CD11b, CD16, CD19, CD20, CD21, CD22, CD33, CD36, CD41, CD61, CD62E, CD72, HLA-DR, and CD102.

Bone marrow-derived MSC and MAPC as well as the cord blood-derived USSC have been described as being derived from a $CD45^-/CD34^-$ cell population. MLPC are distinguished from those cell types as being a CD45+/CD34+ derived cell. Additionally, the presence and persistence of CD9 on the fetal blood-derived MLPC at all stages of maturation further distinguishes MLPC from MSC and MAPC, which do not possess CD9 as a marker. CD9 is expressed as a marker on human embryonic stem cells. MLPC, which share the hematopoietic markers CD45, CD133, CD90 and CD34 during their leukocyte morphology phase, can be distinguished from HSC by their obligate plastic adherence and the presence of mesenchymal associated markers CD105, CD29, CD73, CD13 and embryonic associated markers SSEA-3 and SSEA-4. Additionally using currently available technology, HSC are unable to be cultured in vitro without further differentiation while MLPC can be expanded for many generations without differentiation. MLPC also differ from MSC and USSC by their more gracile in vitro culture appearance, thread-like cytoplasmic projections and their preference for low density culture conditions for optimal growth.

MLPC also can be characterized based on the expression of one or more genes. Methods for detecting gene expression can include, for example, measuring levels of the mRNA or protein of interest (e.g., by Northern blotting, reverse-transcriptase (RT)-PCR, microarray analysis, Western blotting, ELISA, or immunohistochemical staining). As described in Example 12, the gene expression profile of MLPC is significantly different than other cell types. Microarray analysis indicated that the MLPC lines have an immature phenotype that differs from the phenotypes of, for example, CD133+ HSC, lineage negative cells (Forrz et al., *Stem Cells*, 22(1): 100-108 (2004)), and MSC (catalog #PT-2501, Cambrex, Walkersville; Md., U.S. Pat. No. 5,486,359), which demonstrate a significant degree of commitment down several lineage pathways.

Comparison of the gene expression profile of MLPC and MSC demonstrates MSC are more committed to connective tissue pathways. There are 80 genes up-regulated in MSC, and 152 genes up-regulated in MLPC. In particular, the following genes were up-regulated in MLPC when compared with MSC, i.e., expression was decreased in MSC relative to MLPC: ITGB2, ARHGAP9, CXCR4, INTEGRINB7, PECAM1, PRKCB_1, PRKCB_3, IL7R, AIF1, CD45_EX10-11, PLCG2, CD37, PRKCB_2, TCF2_1, RNF138, EAAT4, EPHA1, RPLP0, PTTG, SERPINA12, ITGAX, CD24, F11R, RPL4, ICAM1, LMO2, HMGB2, CD38, RPL7A, BMP3, PTHR2, S100B, OSF, SNCA, GRIK1, HTR4, CHRM1, CDKN2D, HNRPA1, IL6R, MUSLAMR, ICAM2, CSK, ITGA6, MMP9, DNMT1, PAK1, IKKB, TFRC_MIDDLE, CHI3L2, ITGA4, FGF20, NBR2, TNFRSF1B, CEBPA_3, CDO1, NFKB1, GATA2, PDGFRB, ICSBP1, KCNE3, TNNC1, ITGA2B, CCT8, LEFTA, TH, RPS24, HTR1F, TREM1, CCNB2, SELL, CD34, HMGIY, COX7A2, SELE, TNNT2, SEM2, CHEK1, CLCN5, F5, PRKCQ, ITGAL, NCAM2, ZNF257-MGC12518-ZNF92-ZNF43-ZNF273-FLJ90430, CDK1, RPL6, RPL24, IGHA1-IGHA2_M, PUM2, GJA7, HTR7, PTHR1, MAPK14, MSI2_1, KCNJ3, CD133, SYP, TFRC_5PRIME, TDGF1-TDGF3_2, FLT3, HPRT, SEMA4D, ITGAM, KIAA0152_3, ZFP42, SOX20, FLJ21190, CPN2, POU2F2, CASP8_1, CLDN10, TREM2, TERT, OLIG1, EGR2, CD44_EX3-5, CD33, CNTFR, OPN, COL9A1_2, ROBO4, HTR1D1, IKKA, KIT, NPPA, PRKCH, FGF4, CD68, NUMB, NRG3, SALL2, NOP5, HNF4G, FIBROMODULIN, CD58, CALB1, GJB5, GJA5, POU5F_1, GDF5, POU6F1, CD44_EX16-20, BCAN, PTEN1-PTEN2, AGRIN, ALB, KCNQ4, DPPA5, EPHB2, TGFBR2, and ITGA3.

MLPC express a number of genes associated with "stemness," which refers to the ability to self-renew undifferentiated and ability to differentiate into a number of different cell types. Genes associated with "stemness" include the genes known to be over-expressed in human human embryonic stem cells, including, for example, POU5F (October 4), TERT, and ZFP42. For example, 65 genes associated with protein synthesis are down-regulated, 18 genes linked with phosphate metabolism are down-regulated, 123 genes regulating proliferation and cell cycling are down-regulated, 12 different gene clusters associated with differentiation surface markers are down-regulated, e.g., genes associated with connective tissue, including integrin alpha-F, laminin and collagen receptor, ASPIC, thrombospondins, endothelium endothelin-1 and -2 precursors, epidermal CRABP-2, and genes associated with adipocytes, including, for example, the leptin receptor, and 80 genes linked to nucleic acid binding and regulation of differentiation are up-regulated. Thus, the immaturity of a population of MLPC can be characterized based on the expression of one or more genes (e.g., one or more of CXCR4, FLT3, TERT, KIT, POU5F, or hematopoietic CD markers such as CD9, CD34, and CD133).

MLPC can be cryopreserved by suspending the cells (e.g. $5 \times 10^6$ to $2 \times 10^7$ cells/mL) in a cryopreservative such as dimethylsulfoxide (DMSO, typically 1 to 10%) or in fetal bovine serum, human serum, or human serum albumin in combination with one or more of DMSO, trehalose, and dextran. For example, (1) fetal bovine serum containing 10% DMSO; (2) human serum containing 10% DMSO and 1% Dextran; (3) human serum containing 1% DMSO and 5% trehalose; or (4) 20% human serum albumin, 1% DMSO, and 5% trehalose can be used to cryopreserve MLPC. After adding cryopreservative, the cells can be frozen (e.g., to −90° C.). In some embodiments, the cells are frozen at a controlled rate (e.g., controlled electronically or by suspending the cells in a bath of 70% ethanol and placed in the vapor phase of a liquid nitrogen storage tank. When the cells are chilled to −90° C., they can be placed in the liquid phase of the liquid nitrogen storage tank for long term storage. Cryopreservation can allow for long-term storage of these cells for therapeutic use.

Differentiation of MLPC

MLPC are capable of differentiating into a variety of cells, including cells of each of the three embryonic germ layers (i.e., endoderm, ectoderm, and mesoderm). As used herein, "capable of differentiating" means that a given cell, or its progeny, can proceed to a differentiated phenotype under the appropriate culture conditions. For example, MLPC can differentiate into cells having an osteocytic phenotype, cells having an adipocytic phenotype, cells having a neurocytic phenotype, cells having a myocytic phenotype, cells having an endothelial phenotype, cells having a hepatocytic/pancreatic precursor phenotype (also known as an oval cell) as well as other cell types. Differentiation can be induced using one or more differentiation agents, including without limitation, $Ca^{2+}$, an epidermal growth factor (EGF), a platelet derived growth factor (PDGF), a keratinocyte growth factor (KGF), a transforming growth factor (TGF), cytokines such as an interleukin, an interferon, or tumor necrosis factor, retinoic acid, transferrin, hormones (e.g., androgen, estrogen, insulin, prolactin, triiodothyronine, hydrocortisone, or dexamethasone), sodium butyrate, TPA, DMSO, NMF (N-methyl formamide), DMF (dimethylformamide), or matrix elements such as collagen, laminin, heparan sulfate).

Determination that an MLPC has differentiated into a particular cell type can be assessed using known methods, including, measuring changes in morphology and cell surface markers (e.g., by flow cytometry or immunohistochemistry), examining morphology by light or confocal microscopy, or by measuring changes in gene expression using techniques such as polymerase chain reaction (PCR) or gene-expression profiling.

For example, MLPC can be induced to differentiate into cells having an osteocytic phenotype using an induction medium (e.g., Osteogenic Differentiation Medium, catalog # PT-3002, from Cambrex) containing dexamethasone, L-glutamine, ascorbate, and β-glycerophosphate (Jaiswal et al., *J. Biol. Chem.* 64(2):295-312 (1997)). Cells having an osteocytic phenotype contain deposits of calcium crystals, which can be visualized, for example, using Alizarin red stain.

MLPC can be induced to differentiate into cells having an adipocytic phenotype using an induction medium (e.g., Adipogenic Differentiation Medium, catalog # PT-3004, from Cambrex) containing insulin, L-glutamine, dexamethasone, indomethacin, and 3-isobutyl-1-methyl-xanthine. Cells having an adipocytic phenotype contain lipid filled liposomes that can be visualized with Oil Red stain. Such cells also contain trigycerides, which fluoresce green with Nile Red stain (Fowler and Greenspan, *Histochem. Cytochem.* 33:833-836 (1985)).

MLPC can be induced to differentiate into cells having a myocytic phenotype using an induction medium (e.g., SkGM™, catalog # CC-3160, from Cambrex) containing EGF, insulin, Fetuin, dexamethasone, and FGF-basic (Wernet, et al., U.S. patent publication 20020164794 A1). Cells having a myocytic phenotype express fast skeletal muscle myosin and alpha actinin.

MLPC can be induced to differentiate into cells having a neural stem cell phenotype (neurospheres) using an induction medium (e.g., NPMM™—Neural Progenitor Maintenance medium, catalog #CC-3209, from Cambrex) containing human FGF-basic, human EGF, NSF-1, and FGF-4 and a culture device pre-coated with poly-D-lysine and laminin (e.g., from BD Biosciences Discovery Labware, catalog #354688). Once cells have been differentiated into neurospheres, they can be further differentiated into motor neurons with the addition of brain-derived neurotrophic factor (BDNF) and neurotrophin-3 (NT-3), astrocytes with the addition of leukemia inhibitory factor (LIF), retinoic acid and ciliary neurotrophic factor, and oligodendrocytes with the addition of 3,3',5-triiodo-L-thyronine (T3). Neurocytic differentiation can be confirmed by the expression of nestin, class III beta-tubulin (tubulin β-4), glial fibrillary acidic protein (GFAP), and galactocerebroside (GalC). Neurospheres are positive for all such markers while some differentiated cell types are not. Differentiation into oligodendrocytes can be confirmed by positive staining for myelin basic protein (MBP).

MLPC can be induced to differentiate into cells having an endothelial phenotype using an endothelial growth medium (e.g., EGM™-MV, catalog # CC-3125, from Cambrex) containing heparin, bovine brain extract, epithelial growth factor (e.g., human recombinant epithelial growth factor), and hydrocortisone. Endothelial differentiation can be confirmed by expression of E-selectin (CD62E), ICAM-2 (CD102), CD34, and STRO-1.

MLPC can be induced to differentiate into cells having a hepatocyte/pancreatic precursor cell phenotype using an induction medium (e.g., HCM™—hepatocyte culture medium, catalog # CC-3198, from Cambrex) containing ascorbic acid, hydrocortisone, transferrin, insulin, EGF, hepatocyte growth factor, FGF-basic, fibroblast growth factor-4, and stem cell factor. Liver and pancreas cells share a common progenitor. Hepatocyte differentiation can be confirmed by expression of hepatocyte growth factor and human serum albumin. Pancreatic cell differentiation can be confirmed by production of insulin and pro-insulin.

Modified Populations of MLPC

MLPC can be modified such that the cells can produce one or more polypeptides or other therapeutic compounds of interest. To modify the isolated cells such that a polypeptide or other therapeutic compound of interest is produced, the appropriate exogenous nucleic acid must be delivered to the cells. In some embodiments, the cells are transiently transfected, which indicates that the exogenous nucleic acid is episomal (i.e., not integrated into the chromosomal DNA). In other embodiments, the cells are stably transfected, i.e., the exogenous nucleic acid is integrated into the host cell's chromosomal DNA. The term "exogenous" as used herein with reference to a nucleic acid and a particular cell refers to any nucleic acid that does not originate from that particular cell as found in nature. In addition, the term "exogenous" includes a naturally occurring nucleic acid. For example, a nucleic acid encoding a polypeptide that is isolated from a human cell is an exogenous nucleic acid with respect to a second human cell once that nucleic acid is introduced into the second human cell. The exogenous nucleic acid that is delivered typically is part of a vector in which a regulatory element such as a promoter is operably linked to the nucleic acid of interest.

Cells can be engineered using a viral vector such as an adenovirus, adeno-associated virus (AAV), retrovirus, lentivirus, vaccinia virus, measles viruses, herpes viruses, or bovine papilloma virus vector. See, Kay et al. (1997) *Proc. Natl. Acad. Sci. USA* 94:12744-12746 for a review of viral and non-viral vectors. A vector also can be introduced using mechanical means such as liposomal or chemical mediated uptake of the DNA. For example, a vector can be introduced into an MLPC by methods known in the art, including, for example, transfection, transformation, transduction, electroporation, infection, microinjection, cell fusion, DEAE dextran, calcium phosphate precipitation, liposomes, LIPOFECTIN™, lysosome fusion, synthetic cationic lipids, use of a gene gun or a DNA vector transporter.

A vector can include a nucleic acid that encodes a selectable marker. Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture.

MLPC also can have a targeted gene modification. Homologous recombination methods for introducing targeted gene modifications are known in the art. To create a homologous recombinant MLPC, a homologous recombination vector can be prepared in which a gene of interest is flanked at its 5' and 3' ends by gene sequences that are endogenous to the genome of the targeted cell, to allow for homologous recombination to occur between the gene of interest carried by the vector and the endogenous gene in the genome of the targeted cell. The additional flanking nucleic acid sequences are of sufficient length for successful homologous recombination with the endogenous gene in the genome of the targeted cell. Typically, several kilobases of flanking DNA (both at the 5' and 3' ends) are included in the vector. Methods for constructing homologous recombination vectors and homologous recombinant animals from recombinant stem cells are commonly known in the art (see, e.g., Thomas and Capecchi, 1987, *Cell* 51:503; Bradley, 1991, *Curr. Opin. Bio/Technol.* 2:823-29; and PCT Publication Nos. WO 90/11354, WO 91/01140, and WO 93/04169.

Methods of Using MLPC

The MLPC can be used in enzyme replacement therapy to treat specific diseases or conditions, including, but not limited to lysosomal storage diseases, such as Tay-Sachs, Niemann-Pick, Fabry's, Gaucher's, Hunter's, and Hurler's syndromes, as well as other gangliosidoses, mucopolysaccharidoses, and glycogenoses.

In other embodiments, the cells can be used as carriers in gene therapy to correct inborn errors of metabolism, adrenoleukodystrophy, cystic fibrosis, glycogen storage disease, hypothyroidism, sickle cell anemia, Pearson syndrome, Pompe's disease, phenylketonuria (PKU), porphyrias, maple syrup urine disease, homocystinuria, mucoplysaccharidenosis, chronic granulomatous disease and tyrosinemia and Tay-Sachs disease or to treat cancer, tumors or other pathological conditions.

MLPC can be used to repair damage of tissues and organs resulting from disease. In such an embodiment, a patient can be administered a population of MLPC to regenerate or restore tissues or organs which have been damaged as a consequence of disease. For example, a population of MLPC can be administered to a patient to enhance the immune system following chemotherapy or radiation, or to repair heart tissue following myocardial infarction.

The cells also can be used in tissue regeneration or replacement therapies or protocols, including, but not limited to treatment of corneal epithelial defects, cartilage repair, facial dermabrasion, mucosal membranes, tympanic membranes, intestinal linings, neurological structures (e.g., retina, auditory neurons in basilar membrane, olfactory neurons in olfactory epithelium), burn and wound repair for traumatic injuries of the skin, or for reconstruction of other damaged or diseased organs or tissues.

MLPC also can be used in therapeutic transplantation protocols, e.g., to augment or replace stem or progenitor cells of the liver, pancreas, kidney, lung, nervous system, muscular system, bone, bone marrow, thymus, spleen, mucosal tissue, gonads, or hair.

Compositions and Articles of Manufacture

The invention also features compositions and articles of manufacture containing purified populations of MLPC or clonal lines of MLPC. In some embodiments, the purified population of MLPC or clonal line is housed within a container (e.g., a vial or bag). In some embodiments, the clonal lines have undergone at least 3 doublings in culture (e.g., at least 4, 5, 6, 7, 8, 9, 10, 15, 20, 25, 30, 35, 40, 45, or 50 doublings). In other embodiments, a culture medium (e.g., MSCGM™ medium) is included in the composition or article of manufacture. In still other embodiments, the composition or article of manufacture can include one or more cryopreservatives or pharmaceutically acceptable carriers. For example, a composition can include serum and DMSO, a mixture of serum, DMSO, and trehalose, or a mixture of human serum albumin, DMSO, and trehalose.

Purified populations of MLPC or clonal MLPC lines can be combined with packaging material and sold as a kit. The packaging material included in a kit typically contains instructions or a label describing how the purified populations of MLPC or clonal lines can be grown, differentiated, or used. A label also can indicate that the MLPC have enhanced expression of, for example, CXCR4, FLT3, or CD133 relative to a population of MSC. Components and methods for producing such kits are well known.

An article of manufacture or kit also can include one or more reagents for characterizing a population of MLPC or a clonal MLPC line. For example, a reagent can be a nucleic acid probe or primer for detecting expression of a gene such as CXCR4, FLT3, CD133, CD34, TERT, KIT, POU5F, ICAM2, ITGAX, TFRC, KIT, IL6R, IL7R, ITGAM, FLT3, PDGFRB, SELE, SELL, TFRC, ITGAL, ITGB2, PECAM1, ITGA2B, ITGA3, ITGA4, ITGA6, ICAM1, CD24, CD44, CD45, CD58, CD68, CD33, CD37, or CD38. Such a nucleic acid probe or primer can be labeled, (e.g., fluorescently or with a radioisotope) to facilitate detection. A reagent also can be an antibody having specific binding affinity for a cell surface marker such as CD9, CD45, SSEA-4, CD34, CD13, CD29, CD41, CD44, CD73, CD90, CD105, stem cell factor, STRO-1, SSEA-3, CD133, CD15, CD38, glycophorin A (CD235a), CD2, CD3, CD4, CD5, CD7, CD8, CD10, CD11b, CD13, CD16, CD19, CD20, CD21, CD22, CD29, CD33, CD36, CD41, CD61, CD62E, CD72, CD73, CD90, HLA-DR, CD102, or CD105. An antibody can be detectably labeled (e.g., fluorescently or enzymatically).

The invention is further described in the following examples, which do not limit the scope of the invention described in the claims.

EXAMPLES

Example 1

Separating Blood Cells

This example describes the general method by which cells were separated using the cell separation reagents described below. Equal volumes of a cell separation reagent (see Table 1) and an acid citrate dextrose (ACD), CPDA (citrate, phosphate, dextrose, adenine) or heparinized umbilical cord blood sample were combined (25 ml each) in a sterile closed container (e.g., a 50 ml conical tube). Samples containing white blood cell counts greater than $20 \times 10^6$ cells/ml were combined one part blood with two parts cell separation reagent. Tubes were gently mixed on a rocker platform for 20 to 45 minutes at room temperature. Tubes were stood upright in a rack for 30 to 50 minutes to permit agglutinated cells to partition away from unagglutinated cells, which remained in solution. A pipette was used to recover unagglutinated cells from the supernatant without disturbing the agglutinate. Recovered cells were washed in 25 ml PBS and centrifuged at 500×g for 7 minutes. The cell pellet was resuspended in 4 ml PBS+2% human serum albumin.

TABLE 1

| Cell Separation Reagent | |
| --- | --- |
| Dextran (average molecular weight 413,000) | 20 g/l |
| Dulbecco's phosphate buffered saline (10×) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Cells also were recovered from the agglutinate using a hypotonic lysing solution containing EDTA and ethylene glycol-bis(2-aminoethylether)-N,N,N',N'-tetraacetic acid (EGTA). Agglutinated cells were treated with 25 ml VitaLyse® (BioE, St. Paul, Minn.) and vortexed. After 10 minutes, cells were centrifuged at 500×g for 7 minutes and the supernatant was removed. Cells were resuspended in 4 ml PBS.

Recoveries of erythrocytes, leukocytes, lymphocytes, monocytes, granulocytes, T cells, B cells, NK cells, hematopoietic stem cells, and non-hematopoietic stem cells were determined by standard flow cytometry and immunophenotyping. Prior to flow cytometry, leukocyte recovery (i.e., white blood cell count) was determined using a Coulter Onyx Hematology Analyzer. Cell types were identified and enumerated by combining hematology analysis with flow cytometry analysis, identifying cells on the basis of light scattering properties and staining by labeled antibodies.

As shown in Table 2, 99.9% of erythrocytes were removed, 99.8% monocytes and granulocytes, 74% of B cells, 64.9% of NK cells, and 99.4% of the platelets were removed from the cord blood.

TABLE 2

| | Recovery of Cells | |
| --- | --- | --- |
| | Before separation | After separation |
| Erythrocytes per ml | $4.41 \times 10^9$ | $0.006 \times 10^9$ |
| Leukocytes per ml | $5.9 \times 10^6$ | $1.53 \times 10^6$ |
| Lymphocytes (%) | 28.7 | 99.0 |
| Monocytes (%) | 8.69 | 0.12 |
| Granulocytes (%) | 62.5 | .083 |
| T Cells (CD3+) | 19.7 | 83.2 |
| B Cells (CD19+) | 4.46 | 8.10 |
| NK Cells (CD16+) | 3.15 | 8.43 |
| Platelets per ml | $226 \times 10^6$ | $1.4 \times 10^6$ |

Example 2

Purification of MLPC

The cell separation reagent of Table 3 was used to isolate MLPC from the non-agglutinated supernatant phase. See FIG. 1 for a schematic of the purification.

TABLE 3

| Cell Separation Reagent | |
|---|---|
| Dextran (average molecular weight 413,000) | 20 g/l |
| Dulbecco's phosphate buffered saline (10×) | 100 ml/l |
| Sodium Heparin (10,000 units/ml) | 1 ml/l |
| Hank's balanced salt solution (pH 7.2-7.4) | 50 ml/l |
| Anti-human glycophorin A (murine IgM monoclonal antibody, clone 2.2.2.E7) | 0.1-15 mg/L (preferably about 0.25 mg/L) |
| Anti-CD15 (murine IgM monoclonal antibody, clone 324.3.B9) | 0.1-15 mg/L (preferably about 2.0 mg/L) |
| Anti-CD9 (murine IgM monoclonal antibody, clone 8.10.E7) | 0.1-15 mg/L (preferably about 2.0 mg/L) |

Briefly, 50-150 ml of CPDA anti-coagulated umbilical cord blood (<48 hours old) was gently mixed with an equal volume of cell separation composition described in Table 3 for 30 minutes. After mixing was complete, the container holding the blood/cell separation composition mixture was placed in an upright position and the contents allowed to settle by normal 1×g gravity for 30 minutes. After settling was complete, the non-agglutinated cells were collected from the supernatant. The cells were recovered from the supernatant by centrifugation then washed with PBS. Cells were resuspended in complete MSCGM™ (Mesenchymal stem cell growth medium, catalog # PT-3001, Cambrex, Walkersville, Md.) and adjusted to $2-9 \times 10^6$ cells/ml with complete MSCGM™. Cells were plated in a standard plastic tissue culture flask (e.g., Corning), chambered slide, or other culture device and allowed to incubate overnight at 37° C. in a 5% $CO_2$ humidified atmosphere. All subsequent incubations were performed at 37° C. in a 5% $CO_2$ humidified atmosphere unless otherwise noted. MLPC attached to the plastic during this initial incubation. Non-adherent cells (T-cells, NK-cells and CD34+ hematopoietic stem cells) were removed by vigorous washing of the flask or well with complete MSCGM™.

MLPC cultures were fed periodically by removal of the complete MSCGM™ and addition of fresh complete MSCGM™. Cell were maintained at concentrations of $1 \times 10^5 - 1 \times 10^6$ cells/75 cm² by this method. When cell cultures reached a concentration of $8 \times 10^5 - 1 \times 10^6$ cells/75 cm², cells were cryopreserved using 10% DMSO and 90% serum or expanded into new flasks. Cells were recovered from the adherent cultures by removal of the complete MSCGM™ and replacement with PBS+0.1% EGTA. Cells were incubated for 15-60 minutes at 37° C. then collected from the flask and washed in complete MSCGM™. Cells were then replated at $1 \times 10^5$ cells/mL. Cultures that were allowed to achieve confluency where found to have diminished capacity for both proliferation and differentiation. Subsequent to this finding, cultures were not allowed to achieve higher densities than $1 \times 10^6$ cells/75 cm².

Example 3

Morphology of MLPC and Development to Fibroblastic Morphology

Cord blood derived MLPC isolated and cultured according to Examples 1 and 2 were cultured in standard MSCGM™ until confluency. Depending on the donor, MLPC cultures achieved confluency in 2-8 weeks. The morphology of these cells during growth and cultural maturation is shown in FIG. 2A-2D.

In the early stage shown in FIG. 2A, the cells are dividing very slowly and resemble circulating leukocytes but with dendritic cytoplasmic extensions. Many cells still exhibit the small round cell morphology that these cells would exhibit in circulation. As culture continues, the leukocyte-like cells start to change their morphology from the leukocyte-like appearance to a flatter, darker more fibroblast-like appearance (see FIG. 2B). When cells are dividing, they round up, divide, and then reattach to the culture vessel surface and spread out again. This slowly continues until the cells fill the available surface. FIG. 2C shows the morphology of cell cultures during logarithmic growth. FIG. 2D shows the morphology of a fully confluent culture of MLPC. With the exception of the two cells in active division seen in the lower left corner of the picture, all of the cells have a fibroblast-like morphology.

In summary, early during culture, cells appeared small and round, but had cytoplasmic projections, both finger-like and highly elongate projections, which help distinguish them from the other blood cells. Shortly after the initiation of the culture, the cells began to spread and flatten, taking on a morphology consistent with fibroblasts. Eventually, upon confluency, the cells grew in largely parallel orientation. Repeated growth of cultures to confluency resulted in their having diminished proliferation and differentiating capacity.

Example 4

Immunophenotyping of Cells by Immunofluorescent Microscopy

In order to determine the surface markers present on MLPC, freshly isolated cells were plated in 16 well chamber slides and grown to confluency. At various times during the culture (from 3 days post plating to post confluency), cells were harvested and stained for the following markers: CD45-FITC (BD/Pharmingen), CD34-PE (BD/Pharmingen), CD4-PE (BioE), CD8-PE (BioE), anti-HLA-DR-PE (BioE), CD41-PE (BioE), CD9-PE (Ancell), CD105-PE (Ancell), CD29-PE (Coulter), CD73-PE (BD/Pharmingen), CD90-PE (BD/Pharmingen), anti-hu Stem Cell Factor-FITC (R&D Systems), CD14-PE (BD/Pharmingen), CD 15-FITC (Ancell), CD38-PE (BD/Pharmingen), CD2-PE (BD/Pharmingen), CD3-FITC (BD/Pharmingen), CD5-PE (BD/Pharmingen), CD7-PE (BD/Pharmingen), CD16-PE (BD/Pharmingen), CD20-FITC (BD/Pharmingen), CD22-FITC (BD/Pharmingen), CD19-PE (BD/Pharmingen), CD33-PE (BD/Pharmingen), CD10-FITC (BD/Pharmingen), CD61-FITC (BD/Pharmingen), CD133-PE (R&D Systems), anti-STRO-1 (R&D Systems) and Goat anti-mouse IgG(H+L)-PE (BioE), SSEA-3 (R&D Systems) and goat anti-rat IgG (H+L)-PE (BioE), SSEA-4 (R&D Systems) and goat anti-mouse IgG(H+L)-PE (BioE). The cell surface markers also were assessed in bone marrow MSC (Cambrex, Walkersville, Md.) and cord blood HSC (obtained from the non-adherent cells described above).

Briefly, cell culture medium was removed from the wells and the cells were washed 3× with Hank's Balanced Salt Solution +2% BSA. Cells were then stained with the antibodies for 20 minutes in the dark at room temperature. After incubation, the cells were washed 3× with Hank's Balanced Salt Solution +2% BSA and the cells were directly observed for fluorescence by fluorescent microscopy. Results obtained comparing cord blood derived MLPC with bone marrow-derived MSC's and cord blood derived hematopoietic stem cells (HSC) are outlined in Table 4.

TABLE 4

| Cell Marker | Early MLPC (Leukocyte morphology) | Mature MLPC (Fibroblast morphology) | Cord Blood HSC | Bone Marrow MSC |
|---|---|---|---|---|
| CD2 | Negative | Negative | Negative | Negative |
| CD3 | Negative | Negative | Negative | Negative |
| CD4 | Negative | Negative | Negative | Negative |
| CD5 | Negative | Negative | Negative | Negative |
| CD7 | Negative | Negative | Negative | Negative |
| CD8 | Negative | Negative | Negative | Negative |
| CD9 | Positive | Positive | Negative | Negative |
| CD10 | Negative | Negative | Negative | Negative |
| CD13 | Positive | Positive | Negative | Positive |
| CD14 | Negative | Negative | Negative | Negative |
| CD15 | Negative | Negative | Negative | Negative |
| CD16 | Negative | Negative | Negative | Negative |
| CD19 | Negative | Negative | Negative | Negative |
| CD20 | Negative | Negative | Negative | Negative |
| CD22 | Negative | Negative | Negative | Negative |
| CD29 | Positive | Positive | Positive | Positive |
| CD33 | Negative | Negative | Variable | Negative |
| CD34 | Positive | Negative | Positive | Negative |
| CD36 | Negative | Negative | Negative | Negative |
| CD38 | Negative | Negative | Variable | Negative |
| CD41 | Negative | Negative | Negative | Negative |
| CD45 | Positive | Negative | Positive | Negative |
| CD61 | Negative | Negative | Variable | Negative |
| CD73 | Positive | Positive | Negative | Positive |
| Anti-HLA-DR | Negative | Negative | Variable | Negative |
| CD90 | Positive | Positive | Positive | Positive |
| CD105 | Positive | Positive | Negative | Positive |
| STRO-1 | Positive | Negative | Negative | Negative |
| SSEA-3 | Positive | Negative | Negative | Negative |
| SSEA-4 | Positive | Negative | Negative | Negative |
| SCF | Positive | Negative | Negative | Negative |
| Glycophorin A | Negative | Negative | Negative | Negative |
| CD133 | Positive | Negative | Positive | Negative |

Example 5

Clonal MLPC Cell Lines

After the second passage of MLPC cultures from Example 2, the cells were detached from the plastic surface of the culture vessel by substituting PBS containing 0.1% EGTA (pH 7.3) for the cell culture medium. The cells were diluted to a concentration of 1.3 cells/ml in complete MSCGM™ and distributed into a 96 well culture plate at a volume of 0.2 ml/well, resulting in an average distribution of approximately 1 cell/3 wells. After allowing the cells to attach to the plate by overnight incubation at 37° C., the plate was scored for actual distribution. Only the wells with 1 cell/well were followed for growth. As the cells multiplied and achieved concentrations of $1\text{-}5\times10^5$ cells/75 cm$^2$, they were transferred to a larger culture vessel in order to maintain the cells at a concentration between $1\times10^5$ and $5\times10^5$ cells/75 cm$^2$ to maintain logarithmic growth. Cells were cultured at 37° C. in a 5% $CO_2$ atmosphere.

At least 52 clonal cell lines have been established using this procedure and were designated: UM081704-1-E2, UM081704-1-B6, UM081704-1-G11, UM081704-1-G9, UM081704-1-E9, UM081704-1-E11, UM081704-1-G8, UM081704-1-H3, UM081704-1-D6, UM081704-1-H11, UM081704-1-B4, UM081704-1-H4, UM081704-1-C2, UM081704-1-G1, UM081704-1-E10, UM081704-1-B7, UM081704-1-G4, UM081704-1-F12, UM081704-1-H1, UM081704-1-D3, UM081704-1-A2, UM081704-1-B11, UM081704-1-D5, UM081704-1-E4, UM081704-1-C10, UM081704-1-A5, UM081704-1-E8, UM081704-1-C12, UM081704-1-E5, UM081704-1-A12, UM081704-1-C5, UM081704-1-A4, UM081704-1-A3, MH091404-2 #1-1.G10, UM093004-1-A3, UM093004-1-B7, UM093004-1-F2, UM093004-1-A12, UM093004-1-G11, UM093004-1-G4, UM093004-1-B12, UM093004-2-A6, UM093004-2-A9, UM093004-2-B9, UM093004-2-C5, UM093004-2-D12, UM093004-2-H3, UM093004-2-H11, UM093004-2-H4, UM093004-2-A5, UM093004-2-C3, and UM093004-2-C10. The surface markers of clonal cell line UM081704-1-E8 were assessed according to the procedure outlined in Example 4 and found to be the same as the "mature MLPC" having fibroblast morphology, as shown in Table 4.

Example 6

Osteocytic Differentiation of MLPC

A population of MLPC and clonal cell line UM081704-1-E8 each were cultured in complete MSCGM™ and grown under logarithmic growth conditions outlined above. Cells were harvested by treatment with PBS+0.1% EGTA and replated at $5\times10^3$ to $2\times10^4$/ml in complete MSCGM™. The cells were allowed to adhere overnight and then the medium was replaced with Osteogenic Differentiation Medium (catalog # PT-3002, Cambrex) consisting of complete MSCGM™ supplemented with dexamethasone, L-glutamine, ascorbate, and β-glycerophosphate. Cells were cultured at 37° C. in a 5% $CO_2$ atmosphere and fed every 3-4 days for 2-3 weeks. Deposition of calcium crystals was demonstrated by using a modification of the Alizarin red procedure and observing red staining of calcium mineralization by phase contrast and fluorescent microscopy.

Example 7

Adipocytic Differentiation of MLPC

A population of MLPC and clonal cell line UM081704-1-E8 each were plated in complete MSCGM™ at a concentration of $1\times10^4$ to $2\times10^5$ cells/mL medium and cultured at 37° C. in a 5% $CO_2$ atmosphere. Cells were allowed to re-adhere to the culture plate and were fed every 3-4 days until the cultures reached confluency. At 100% confluency, cells were differentiated by culture in Adipogenesis differentiation medium (catalog #PT-3004, Cambrex) consisting of complete MSCGM™ supplemented with hu-insulin, L-glutamine, dexamethasone, indomethacin, and 3-isobutyl-1-methyl-xanthine, for at least 14 days.

To assess differentiation, the cells were stained with Oil Red stain specific for lipid. Confluent cultures of MLPC display a fibroblast-like morphology and do not display any evidence of liposome development as assessed by Oil Red staining. In contrast, MLPC differentiated with Adipogenic medium for 3 weeks exhibit liposomes that are characteristic of adipocytes (i.e., bright white vessels in cytoplasm) and that stain red with the Oil Red stain. MLPC differentiated with Adipogenic medium also fluoresce green with Nile Red stain specific for trigycerides. Undifferentiated cells retain their fibroblast-like morphology and do not stain.

Example 8

Myocytic Differentiation of MLPC

MLPC (both a population and clonal cell line UM081704-1-E8) were plated in complete MSCGM™ at a concentration of $1.9\times10^4$ cells/well within a 4-chamber fibronectin pre-coated slide and allowed to attach to the plate for 24-48 hr at 37° C. in a 5% $CO_2$ atmosphere. Medium was removed and replaced with 10 µM 5-azacytidine (catalog #A1287, Sigma Chemical Co.) and incubated for 24 hours. Cells were washed twice with PBS and fed with SkGM™ Skeletal Muscle Cell Medium (catalog # CC-3160, Cambrex) containing recombinant human epidermal growth factor (huEGF), human insulin, Fetuin, dexamethasone, and recombinant human basic fibroblast growth factor (100 ng/mL) (huFGF-basic, catalog # F0291, Sigma Chemical Co., St. Louis, Mo.). Cells were fed every 2-3 days for approximately 21 days. Control wells were fed with MSCGM™ while experimental wells were fed with SkGM™ (as described above).

Cultures were harvested 7 days post initiation of myocytic culture. Culture supernatant was removed and cells were fixed for 2 hours with 2% buffered formalin. Cells were permeabilized with PermaCyte™ (BioE, St. Paul, Minn.) and stained with mouse monoclonal antibody specific for human fast skeletal myosin (MY-32, catalog #ab7784, Abcam, Cambridge, Mass.) or mouse monoclonal antibody specific for alpha actinin (BM 75.2, catalog #ab11008, Abcam). Cells were incubated with the primary antibody for 20 minutes, washed with PBS and counter stained with goat anti-mouse IgG (H+L)-PE (BioE, St. Paul, Minn.). The myocytic culture contained fast skeletal muscle myosin and alpha actinin, which is indicative of the transdifferentiation of MLPC to skeletal muscle cells.

Example 9

Neurocytic Differentiation of MLPC

Bone marrow derived hMSC (Cambrex), cord blood MLPC, and MLPC clonal cell line were grown under logarithmic growth conditions described above. Cells were harvested as described above and replated at $0.8 \times 10^4$ cells per chamber in 4-chamber slides that were pre-coated with poly-D-lysine and laminin (BD Biosciences Discovery Labware, catalog #354688) in 0.5 mL of NPMM™ (catalog #CC-3209, Cambrex) containing huFGF-basic, huEGF, brain-derived neurotrophic factor, neural survival factor-1, fibroblast growth factor-4 (20 ng/mL), and 200 mM GlutaMax I Supplement (catalog #35050-061, Invitrogen, Carlsbad, Calif.). The medium was changed every 2-3 days for 21 days. Neurospheres developed after 4 to 20 days. Transformation of MLPC to neural lineage was confirmed by positive staining for nestin (monoclonal anti-human nestin antibody, MAB1259, clone 196908, R&D Systems), class III beta-tubulin (tubulin b-4) (monoclonal anti-neuron-specific class III beta-tubulin antibody, MAB 1195, Clone TuJ-1, R&D Systems), glial fibrillary acidic protein (GFAP) (monoclonal anti-human GFAP, HG2b-GF5, clone GF5, Advanced immunochemical, Inc.), and galactocerebroside (GalC) (mouse anti-human GalC monoclonal antibody MAB342, clone mGalC, Chemicon).

Cells were further differentiated into neurons by the addition of 10 ng/mL BDNF (catalog #B3795, Sigma Chemical Co.) and 10 ng/mL NT3 (catalog #N1905, Sigma Chemical Co.) to the neural progenitor maintenance medium and further culturing for 10-14 days. Neurospheres were further differentiated into astrocytes by the addition of $10^{-6}$ M retinoic acid (catalog #R2625, Sigma Chemical Co.), 10 ng/mL LIF (catalog #L5158, Sigma Chemical Co.) and 10 ng/mL CNTF (catalog #C3710, Sigma Chemical Co.) to the neural progenitor maintenance medium and further culturing for 10-14 days. Neurospheres were further differentiated into oligodendrocytes by the addition of $10^{-6}$ M T3 (catalog #T5516, Sigma Chemical Co.) to the neural progenitor maintenance medium and further culturing for 10-14 days. Differentiation to oligodendrocytes was confirmed by positive staining for myelin basic protein (MBP) (monoclonal anti-MBP, catalog #ab8764, clone B505, Abcam).

Example 10

Endothelial Differentiation of MLPC

MLPC were plated at $1.9 \times 10^4$ cells per well within a 4-chamber slide (2 $cm^2$). Cells were fed with 1 ml of endothelial growth medium-microvasculature (EGM™-MV, catalog #CC-3125, Cambrex) containing heparin, bovine brain extract, human recombinant epithelial growth factor and hydrocortisone. The cells were fed by changing the medium every 2-3 days for approximately 21 days. Morphological changes occurred within 7-10 days. Differentiation of MLPC's to endothelial lineage was assessed by staining for CD62E [E-selectin, mouse anti-human CD62E monoclonal antibody, catalog #551145, clone 68-5H11, BD Pharmingen] and CD102 [ICAM-2, monoclonal anti-human ICAM-2, MAB244, clone 86911, R&D Systems], CD34 [BD Pharmingen] and STRO-1 (R&D Systems]. Control MLPC cultures grown in MSCGM for 14 days were negative for CD62E staining and CD102, CD34 and STRO-1, while differentiated cultures were positive for both CD62E, CD102, CD34, and STRO-1.

Example 11

Differentiation of MLPC into Hepatocyte/Pancreatic Precursor Cells

MLPC were plated at a concentration of $1 \times 10^5$ cells/$cm^2$ in vitro in HCM™ medium (catalog #CC-3198, Cambrex) containing ascorbic acid, hydrocortisone, transferrin, insulin, huEGF, recombinant human hepatocyte growth factor (40 ng/mL), huFGF-basic (20 ng/mL), recombinant human fibroblast growth factor-4 (20 ng/mL), and stem cell factor (40 ng/mL). Cells were cultured for 29 or more days to induce differentiation to precursor cells of both hepatocytes and pancreatic cells lineage. MLPC changed from a fibroblast morphology to a hepatocyte morphology, expressed cell surface receptors for Hepatocyte Growth Factor, and produced both human serum albumin, a cellular product of hepatocytes, and insulin, a cellular product of pancreatic islet cells, both confirmed by intracellular antibody staining on day 30.

Example 12

Comparative Gene Expression of MLPC

In order to determine the relationship between MLPC and various other cell types at various stages of lineage commitment, the relative expression of 942 genes associated with "stemness" and differentiating capacity was assessed by high definition microarray. The phenotype of MLPC (E8 clone, passage 8, see Example 5) was compared to human umbilical cord mononuclear cells (MNC), PrepaCyte®-MLPC isolated cord blood cells, CD133+ positively selected cord blood progenitor cells, lineage negative cord blood cells, and bone marrow-derived mesenchymal stem cells (MSC, Cambrex, Walkersville, Md.). The MNC were isolated by density gradient centrifugation method on Ficoll. Cells were mature terminally differentiated lymphocytes and monocytes with some minor contamination with platelets and granulocytes.

The PrepaCyte isolated cells were human umbilical cord blood cells isolated by PrepaCyte-MLPC method. Cells were mainly lymphocytes, hematopoietic stem cells, and MLPC with some minor contamination with monocytes, granulocytes, and platelets. CD133+ selected cells were human umbilical cord blood cells separated by Ficoll density gradient separation then positively selected using anti-CD133 coated paramagnetic particles (Miltenyi). These cells are consistent with hematopoietic stem cells. Lineage Negative cells were isolated from human umbilical cord blood cells by Ficoll density gradient separation then negatively selected by depletion with anti-CD45, anti-CD7, and anti-glycophorin A-coated paramagnetic particles. These cells have been demonstrated to have some multi-lineage differentiating capacity. See, Forrz et al., Stem Cells, 22(1):100-108 (2004). MSC were purchased from Cambrex (catalog # PT-2501).

Methods: Total RNA was extracted from each cell population using the Qiagen RNeasy Mini Kit (Qiagen, Valencia, Calif.). Complementary DNAs (cDNA) were derived from the total RNA samples and the cDNA labeled with Cy3 (MLPC) or Cy5 (other cell types) according to the PIQOR™ Instruction Manual. The labeled samples then were hybridized to the PIQOR™ 942 gene Stem Cell Human Antisense Microarray platform (Miltenyi Biotec) according to the PIQOR™ Instruction Manual. Thus, a total of five hybridizations were done: MLPC and PrepaCyte cells (designated hybridization B), MLPC and MNC (designated hybridization C), MLPC and CD133+ selected cells (designated hybridization D), MLPC and MSC (designated hybridization E), and MLPC and LinNeg cells (designated hybridization F). After hybridization, the intensity of the Cy3 and Cy5 labels was assessed on each microarray. Comparative over-expression of genes in MLPC resulted in a green spot, over-expression of genes in the comparative cell group resulted in a red spot. Equal expression resulted in a yellow spot. The ratio of green to red fluorescence allowed the determination of over- or under-expression. Analysis of the microarrays was performed by the Memorec division of Miltenyi Biotec in a blinded analysis.

Genes that did not reach an at least 1.4-fold differential expression in at least one experiment were excluded from further analyses. The resulting dataset included 631 genes that were >1.4 fold up- or down-regulated between MLPC and any one or more of the other five cell groups (see FIG. 3; shaded text refers to over-expression of the gene in the comparative cell group; bold text refers to over-expression of genes in MLPC; the values represent the ratio of the signal intensity for the comparative cell group to the signal intensity of the MLPC, i.e., for uniq ID 43, signal intensity of B/signal intensity of MLPC is 0.68). To identify the discriminatory genes, genes were selected that had their maximum expression value in hybridizations B, C, D, E, or F. Genes were removed where the 'maximum expression' was just due to a less pronounced down-regulation relative to the other experiments. The difference between the highest and the second-best expression value was determined for each gene and used as an indicated for its suitability to separate between the different conditions. A corresponding procedure was performed to identify the down-regulated genes most suitable for the discrimination of the different cell populations.

Pathway and signal network analysis delineated numerous biological pathways characterizing MLPCs unique features. During this procedure, each group was screened for significant enrichment of genes belonging to a common pathway or sharing other biological properties.

MLPC vs. PrepaCyte Cells

Sixty-five (65) genes were up-regulated in the PrepaCyte cells relative to the MLPC: PF4-PF4V1, CLDN5, IL7R, CHI3L2, CD38, RBL2, MAD1, INTEGRINB7, CD7, DRD3, HIST1H2AC, PBXIP1, ITGAL, FKHR, CDKN2B, RPL13A, MMRN, KCNQ2_2, MFHI, BMP6, ABCC8, MUSLAMR, ALCAM, CDKN1B, ANGPT2, RPL24, FLJ10884, ICAM2, FOXG1A-FOXG1B, PLCG1, ERBB2, DAB1, RPL6, RPLP0, MMP21-22-23, RPL4, RPL7A, SMAD2, RPS24, ATM, CDO1, SELE, SELL, GRIK1, VEGFB, KCNQ4, TGFBR1, TFP1, KIAA0152_3, COL4A5, MAP-2, FAST1, TBX3, PRKCH, HNF4A, SEMA3C, TEAD1, NFKB2, COL4A6, HNF4G, DPPA5, LEFTA, FGF20, OSF, RPSA, and ITGA2B. Among the 65 genes, 8 were annotated as ribosomal subunits (RPLP0 (genno. 19690), RPL6 (genno. 22801), RPS24 (genno. 27255), RPL24 (genno. 28658), RPL13A (genno. 31144), RPL4 (genno. 32719), RPSA (genno. 3929), and RPL7A (genno. 7951). This enrichment may point to an enhancement of protein synthesis relative to the MLPC and also shows that the PrepaCyte cells are a heterogeneous group of cells, many of which are mature.

Fifty-five (55) genes were down-regulated relative to MLPC, including PROX1, DLK1, CRABP1, HNF3G, CSPG2_1, TIMP2, CD44_EX10-12, ANPEP, ZNF117, IFNGR1, COL4A3_1, ATF4, LAMB3, ELAVL4, IFNGR2, CTNNA1, CDC25C, S100A11, CRABP2, MMP11, PAFAH1B1, MTHFD2, BRACHYURY, BMPRIA, KCNA4, TUBA, TTR, ACVR2B, KCNJ6, ADH4, VLDLR, GAPD, RACK17, MCAM, HNF3B, TNFR1, JAM2, IL3RA, FGF1, VGR3, ORP150, SNA12, GPC4, KIF4A, TC10-PIGF, RAC1, CYP3A4, THBD, CHEK2, VEGF 1, AMBP, TCF3, KCNQ5, DDX21, and LAPTM4B. Thus, MLPC and Prepa-Cyte cells have different profiles.

MLPC vs. MNC

MLPC and MNC also have different profiles. One hundred and eight (108) genes were up-regulated in the MNC, including: PROX1, KCNJ15, IL1R2, SNCA, HBZ, F7, MYL4, CDKN2D, BMPR1B, TCF2_1, RXRA, CLCN5, SOX6, SLC2A1, TAL1, CLCN3, SALL2, POU6F1, IGHA1-IGHA2, MAT1A, EGR2, HDAC2, FGFR3, TREM1, MAP3K3, PRKCZ, PUM2, BMP4, PTEN1-PTEN2, KCNQ3, SYP, CD44_EX8-10, IL4R, ACVRL1, CDC25B, ODC1, SLC16A1, PGH2, EDNRA, TRK-C, CDH5, COL10A1, PIK3CG, NEUROG1, AKT2, ITGA3, CXCR4, DLX2, IL6R, KCNJ1, SLIT-1, IKKA, GDF5, ITGB3, CASP8_1, FIBROMODULIN, AGRIN, TENASCINX, KIT, CD44_EX7-9, TERT, ZFP42, MS12_1, ACVR2B, CDC42_1, POU5F_1, CPN2, RARA1, TNFSF4, ROBO4, SEM2, CLDN1, TDGF1-TDGF3_2, PRKCQ, COL9A1_2, ELAVL4, EPHB2, ELOVL6, PAK1, SOX20, BRACHYURY, NOTCH1, LRRN1, SEMA4D, ARL8, HGF, PRKCB_2, BMP3, WNT10B, BCRP, NKX2-2, FGFR2, HAND1, PLAUR, CSK, PDGFRB, COL18A1_1, CCNG2, ITGA3-5PRIME, CD45_EX10-11, PTHR1, SEMAL, MAPK3, TNNT2, NBR2, APC3, PTHLH, and HTR6. Table 5 lists the 23 genes identified as belonging to a particular pathway or family ("A" refers to a kinase and "B" refers to phosphate metabolism).

Eighteen genes were identified as belonging to the family of protein kinases (ACVR2B, ACVRL1, BMPR1B, EPHB2, PRKCZ, PRKCQ, MAPK3, AKT2, PPKCB, PAK1, MAP3K3, CSK, KIT, PDGFRB, IKKA, FGFR2, NTRK3, and FGFR3). Five genes (CD45, PIK3CG, PTEN1-PTEN2, CDC25B, and TDGF1-TDGF3) were identified as being involved in phosphate metabolism in general, e.g., as phosphatases. The PIQOR probes PTEN1-PTEN2 or TDGF1-TDGF3 are specific for two different, highly similar genes each. Among these kinases, growth factor receptors like, e.g., FGFR2, FGFR3, PDGFRB, KIT, and NTRK3, and two activin receptors, ACVR2B and ACVRL1 can be found.

TABLE 5

Pathway analysis for up-regulated genes in MNC

| genno. | Description | | |
|---|---|---|---|
| 11328 | TDGF1-TDGF3_2_HUMAN: (TDGF1 OR CRIPTO) TERATOCARCINOMA-DERIVED GROWTH FACTOR 1 (EPIDERMAL GROWTH FACTOR-LIKE CRIPTO PROTEIN CR1) (CRIPTO-1 GROWTH FACTOR) (CRGF) (TDGF3 OR TDGF2) TERATOCARCINOMA-DERIVED GROWTH FACTOR 2 (EPIDERMAL GROWTH FACTOR-LIKE CRIPTO PROTEIN CR3) (CRIPTO-3 GROWTH FACTOR). | | B |
| 11644 | ACVR2B: (ACVR2B) ACTIVIN RECEPTOR TYPE IIB PRECURSOR (EC 2.7.1.—) (ACTR-IIB). | A | B |
| 11647 | ACVRL1: (ACVRL1 OR ACVRLK1 OR ALK1) SERINE/THREONINE-PROTEIN KINASE RECEPTOR R3 PRECURSOR (EC 2.7.1.37) (SKR3) (ACTIVIN RECEPTOR-LIKE KINASE 1) (ALK-1) (TGF-B SUPERFAMILY RECEPTOR TYPE I) (TSR-I). | A | B |
| 11689 | BMPR1B: (BMPR1B OR ACVRLK6) BONE MORPHOGENETIC PROTEIN RECEPTOR TYPE IB PRECURSOR (EC 2.7.1.37) (SERINE/THREONINE-PROTEIN KINASE RECEPTOR R6) (SKR6) (ACTIVIN RECEPTOR-LIKE KINASE 6) (ALK-6). | A | B |
| 11767 | EPHB2: (EPHB2 OR EPTH3 OR ERK OR DRT OR HEK5) EPHRIN TYPE-B RECEPTOR 2 PRECURSOR (EC 2.7.1.112) (TYROSINE-PROTEIN KINASE RECEPTOR EPH-3) (DRT) (RECEPTOR PROTEIN-TYROSINE KINASE HEK5) (ERK). | A | B |
| 12034 | PRKCZ: (PRKCZ OR PKC2) PROTEIN KINASE C, ZETA TYPE (EC 2.7.1.—) (NPKC-ZETA). | A | B |
| 12452 | CD45_EX10-11: (PTPRC OR CD45) LEUKOCYTE COMMON ANTIGEN PRECURSOR (EC 3.1.3.48) (L-CA) (CD45 ANTIGEN) (T200). | | B |
| 12920 | PRKCQ: (PRKCQ OR PRKCT) PROTEIN KINASE C, THETA TYPE (EC 2.7.1.—) (NPKC-THETA). | A | B |
| 139 | MAPK3: (MAPK3 OR PRKM3 OR ERK1) MITOGEN-ACTIVATED PROTEIN KINASE 3 (EC 2.7.1.—) (EXTRACELLULAR SIGNAL-REGULATED KINASE 1) (ERK-1) (INSULIN-STIMULATED MAP2 KINASE) (MAP KINASE 1) (MAPK 1) (P44-ERK1) (ERT2) (P44-MAPK) (MICROTUBULE-ASSOCIATED PROTEIN-2 KINASE). | A | B |
| 14773 | AKT2: (AKT2) RAC-BETA SERINE/THREONINE PROTEIN KINASE (EC 2.7.1.—) (RAC-PK-BETA) (PROTEIN KINASE AKT-2) (PROTEIN KINASE B, BETA) (PKB BETA). | A | B |
| 1499 | PRKCB_2: (PRKCB1 OR PRKCB OR PKCB) PROTEIN KINASE C, BETA TYPE (EC 2.7.1.37) (PKC-BETA) (PKC-B). | A | B |
| 15194 | PAK1: (PAK1) SERINE/THREONINE-PROTEIN KINASE PAK 1 (EC 2.7.1.—) (P21-ACTIVATED KINASE 1) (PAK-1) (P65-PAK) (ALPHA-PAK). | A | B |
| 15492 | MAP3K3: (MAP3K3 OR MAPKKK3 OR MEKK3) MITOGEN-ACTIVATED PROTEIN KINASE KINASE KINASE 3 (EC 2.7.1.—) (MAPK/ERK KINASE KINASE 3) (MEK KINASE 3) (MEKK 3). | A | B |
| 1915 | CSK: (CSK) TYROSINE-PROTEIN KINASE CSK (EC 2.7.1.112) (C-SRC KINASE) (PROTEIN-TYROSINE KINASE CYL). | A | B |
| 1953 | PIK3CG: (PIK3CG) PHOSPHATIDYLINOSITOL 3-KINASE CATALYTIC SUBUNIT, GAMMA ISOFORM (EC 2.7.1.137) (PI3-KINASE P110 SUBUNIT GAMMA) (PTDINS-3-KINASE P110) (PI3K). | | B |
| 322 | KIT: (KIT OR SL) MAST/STEM CELL GROWTH FACTOR RECEPTOR PRECURSOR (EC 2.7.1.112) (SCFR) (PROTO-ONCOGENE TYROSINE-PROTEIN KINASE KIT) (C-KIT) (CD117 ANTIGEN) (C-KIT RECEPTOR TYROSINE KINASE). | A | B |
| 357 | PDGFRB: (PDGFRB OR PDGFR) BETA PLATELET-DERIVED GROWTH FACTOR RECEPTOR PRECURSOR (EC 2.7.1.112) (PDGF-R-BETA) (CD140B ANTIGEN). | A | B |
| 4042 | IKKA: (IKK ALPHA OR CHUK) INHIBITOR OF NUCLEAR FACTOR KAPPA-B KINASE ALPHA SUBUNIT (EC 2.7.1.—) (I KAPPA-B KINASE ALPHA) (IKBKA) (IKK-ALPHA) (IKK-A) (IKAPPAB KINASE) (I-KAPPA-B KINASE 1) (IKK1) (CONSERVED HELIX-LOOP-HELIX UBIQUITOUS KINASE) (NUCLEAR FACTOR NFKAPPAB INHIBITOR KINASE ALPHA) (NFKBIKA). | A | B |
| 5042 | PTEN1-PTEN2: (PTEN OR MMAC1 OR TEP1) PROTEIN-TYROSINE PHOSPHATASE PTEN (EC 3.1.3.48) (MUTATED IN MULTIPLE ADVANCED CANCERS 1). (PTEN2) HYPOTHETICAL 39.9 KDA PROTEIN (EC 3.1.3.48). | | B |
| 5209 | FGFR2: (FGFR2 OR ECT1 OR BEK) FIBROBLAST GROWTH FACTOR RECEPTOR 2 PRECURSOR (FGFR-2) (EC 2.7.1.112) (KERATINOCYTE GROWTH FACTOR RECEPTOR). (K-SAM). (BFR2) FIBROBLAST GROWTH FACTOR RECEPTOR BFR-2 PRECURSOR (EC 2.7.1.112). | A | B |
| 5225 | NTRK3: (NTRK3 OR TRKC) NT-3 GROWTH FACTOR RECEPTOR PRECURSOR (EC 2.7.1.112) (TRKC TYROSINE KINASE) (GP145-TRKC) (TRK-C). | A | B |
| 7088 | CDC25B: (CDC25B OR CDC25HU2) M-PHASE INDUCER PHOSPHATASE 2 (EC 3.1.3.48). | | B |
| 9099 | FGFR3: (FGFR3 OR JTK4) FIBROBLAST GROWTH FACTOR RECEPTOR 3 PRECURSOR (FGFR-3) (EC 2.7.1.112). | A | B |

The following genes were down-regulated in MNC relative to MLPC: ID1, EDN1, CALU, UPA, CDK4, CTNNB1, NME2, SERPINH1-SERPINH2, PSMA3, HSPA4_1, TIMP1, FGF2_1, KRT14, RTN4, LAMG1, HSPA9, PCK2, IGFBP2, GFAP_1, ANXA2, EPRS, EED, ITGA5, OB_2, COL4A5, CRM1, HSPC150, PAX5, IDH1, KRAS2A-KRAS2B, TUBB1-TUBB5, ATF2, MMP6, NMYC, EGFR-SHORT, FGF19, PEG1-MEST, CEBPG, KRT18, GRIA1, CACNA1B, BAMACAN, CITED2, FKHL16, SDF2, CRYL1, MGST1, MMRN, VCAM1, FBXL13, IGF1, LAMB1, TFCOUP1, CCCAP, KIR2.4, KCNJ8, BUB1B, GPS1_3PRIME, PSMA2, VEGFB, FGF7, RAMP1, BMP11, SST, IL1R1, PAI2, ENG, NGN3, OTX2, SMAD2, COL9A1_1, NPM1, TUBB4, ID2, SNRPF, RAMP3, CD164, COL14A1, BUB3, KS, DPYSL3, RARG1, FLN1, KCNK2, CLCN4, INTEGRINB5, SEMA3C, MAD2L2, VAP-A, KPNA2, KCNK5, TEAD1, PTN, VTN, AKT, MTHFD1, GGH, KIAA0152_1, MYH7, OSP, WNT5A, ITGB1, DTYMK, CLDN6, FGF5, GADi_1, MAPK6, DLX1, CD47, BRIX, FABE, L30, FAB1, SMS, VEGC, NFATCB_1, DAB1, GATA6, SELPLG, CTNNA2, ISL1, ENO2, and EIF4A1.

MLPC vs. CD133

The following genes were up-regulated in CD133+ cells relative to MLPC: ELAVL2, FZD3, TFRC_3PRIME, HSPC150, CDK4, TFRC MIDDLE, KCNH2, NOP5, SNRPF, BUB1B, CLDN10, MAD2L1, PTTG, MTHFD1, CNTF-ZFP91_1, CRM1, HMGB2, LMO2, BAMACAN, DTYMK, FLT3, TK1, CEBPA 3, MGST1, EED, E21G3, HTR7, KPNA2, DNMT1, FGF19, MAD2L2, HMGIY, FGF16, MAP3K5, MYB, PLCB4, L30, NMYC, LIN-28, FABE, HNRPA1, BUB3, ENOS, C200RF1, GGH, PSMA3, PPAT, FLJ21190, CCNB2, SELPLG, CDK1, CDC25C, HSPA4_1, HOXA2, CHEK2, MAWBP, ANKRD17_1, OB_2, CCNE2, CCT8, NPM1, GAL, DLX1, BRIX, SMS, CHEK1, TUBB1-TUBB5, GATA5, TUBA, EAAT2_1, CD133, NPPA, FBXL13, HPRT, KCNJ8, IGHA1-IGHA2_M, RBL1, NGN3, RNF138, RAMP3, KIF4A, ITGA6, PSMA2, ALB, FGF4, KCNJ9, BEX2-BEX1, ILIRI, GPS1_3PRIME, KCNJ3, NCAM2, LDHB, IMPDH2, P53, TNFSF11, CRYL1, ZNF257-MGC12518-ZNF92-ZNF43-ZNF273-FLJ90430, GRIA1, KIAA1573, SST, CLCN4, VAP-A, TFRC_5PRIME, LAPTM4B, SCARB1, ZNF117, ICSBP1, HNF3G, DLK1, CD164, NME2, NFKB1, COL9A1_1, KIAA0152_1, CNTFR, EAAT4, BCAN, EGFR-SHORT, PAI2, HSPA9, BUB1, SOX2, PPP2R1B_1, TCF4, ATF4, TRK-B, LIF, and NRG3. Table 6 lists 42 genes identified as belonging to a particular pathway or family. In Table 6, "A" refers to cell cycle, DNA repair, DNA metabolism, as determined by Memorec's annotation system (ME), "B" refers to M phase as determined by gene ontology (GO), "C" refers to cell cycle as determined by GO, "F" refers to regulation of mitosis as determined by GO, "H" refers to mitotic cell cycle as determined by GO, "I" refers to cell cycle checkpoint as determined by GO, "L" refers to nucleotide synthesis as determined by GO, "P" refers to nucleotide/nucleoside metabolism as determined by GO, and "S" refers to microtubule cytoskeleton as determined by GO.

TABLE 6

Pathway analysis for up-regulated genes in CD133+ cells

| genno. | Description | | | | | | | | |
|---|---|---|---|---|---|---|---|---|---|
| 10934 | CHEK1: (CHEK1 OR CHK1) SERINE/THREONINE-PROTEIN KINASE CHK1 (EC 2.7.1.—) CHECKPOINT KINASE 1. | A | B | C | | | H | I | |
| 10937 | CHEK2: (CHEK2 OR CHK2) SERINE/THREONINE-PROTEIN KINASE CHK2 (EC 2.7.1.—) (CDS1). | A | | C | | | | I | |
| 10985 | HMGB2: (HMGB2 OR HMG2) HIGH MOBILITY GROUP PROTEIN HMG2 (HMG-2). | A | | | | | | | |
| 118 | CCNB2: (CCNB2) CYCLIN B2 G2/MITOTIC SPECIFIC CYCLIN B2. | A | B | C | | | H | | |
| 13004 | ELAVL2: (ELAVL2 OR HUB) ELAV-LIKE PROTEIN 2 (HU-ANTIGEN B) (HUB) (ELAV-LIKE NEURONAL PROTEIN 1) (NERVOUS SYSTEM-SPECIFIC RNA BINDING PROTEIN HEL-N1). | A | | | | | | | |
| 138 | CCNE2: (CCNE2) G1/S-SPECIFIC CYCLIN E2. | A | | C | | | H | I | |
| 14809 | BUB1: (BUB1 OR BUB1L) MITOTIC CHECKPOINT SERINE/THREONINE-PROTEIN KINASE BUB1 (EC 2.7.1.—) (HBUB1) (BUB1A). | A | B | C | F | | H | I | S |
| 17848 | DNMT1: (DNMT1 OR DNMT OR AIM) DNA (CYTOSINE-5)-METHYLTRANSFERASE HSAI (EC 2.1.1.37) (DNA METHYLTRANSFERASE HSAI) (DNA MTASE HSAI) (MCMT) (M.HSAI). | A | | | | | | | |
| 18164 | HMGIY: (HMGIY OR HMGA1 OR HMGI) HIGH MOBILITY GROUP PROTEIN HMG-Y (HIGH MOBILITY GROUP AT-HOOK 1). | A | | | | | | | |
| 22039 | GPS1_3PRIME: (GPS1 OR COPS1) COP9 SIGNALOSOME COMPLEX SUBUNIT 1 (G PROTEIN PATHWAY SUPPRESSOR 1) (GPS1 PROTEIN) (MFH PROTEIN). | A | | | | | | | |
| 22663 | HNRPA1: (HNRPA1) HETEROGENEOUS NUCLEAR RIBONUCLEOPROTEIN A1 (HELIX-DESTABILIZING PROTEIN) (SINGLE-STRAND BINDING PROTEIN) (HNRNP CORE PROTEIN A1). | A | | | | | | | |
| 2429 | BAMACAN: (BAM OR SMCD OR HCAP OR CSPG6 OR SMC3 OR SMC3L1 OR BMH) STRUCTURAL MAINTENANCE OF CHROMOSOME 3 (CHONDROITIN SULFATE PROTEOGLYCAN 6) (CHROMOSOME SEGREGATION PROTEIN SMCD) (BAMACAN) BASEMENT MEMBRANE-ASSOCIATED CHONDROITIN PROTEOGLYCAN) (HCAP). | | B | | | | H | | S |
| 24938 | C20ORF1: (C20ORF1 OR C20ORF2 OR DIL2 OR TPX2) RESTRICTED EXPRESSION PROLIFERATION ASSOCIATED PROTEIN 100 (P100) (DIFFERENTIALLY EXPRESSED IN LUNG CELLS 2) (DIL-2) (TARGETING PROTEIN FOR XKLP2) (C20ORF1 PROTEIN) (C20ORF2 PROTEIN) (PROTEIN FLS353). | A | B | | | | H | | S |
| 26268 | VAP-A: (VAP-A OR VAP33) VAMP-ASSOCIATED PROTEIN A (VAPA). | | | | | | | | S |
| 26951 | NME2: (NME2 OR NM23B) NUCLEOSIDE DIPHOSPHATE KINASE B (EC 2.7.4.6) (NDK B) (NDP KINASE B) (P18). | | | | | L | | | P |
| 27251 | PTTG_HUMAN: (PTTG) PITUITARY TUMOR TRANSFORMING GENE, PITUITARY TUMOR TRANSFORMING GENE PROTEIN 1 (SECURIN HOMOLOG) (HPTTG OR PTTG1 OR TUTR1) (PTTG2) PITUITARY TUMOR TRANSFORMING | A | B | | | | H | | |

TABLE 6-continued

Pathway analysis for up-regulated genes in CD133+ cells

| genno. | Description | | | | | | | | | |
|---|---|---|---|---|---|---|---|---|---|---|
| | GENE 2 PROTEIN (PTTG3) PITUITARY TUMOR TRANSFORMING GENE PROTEIN 3. | | | | | | | | | |
| 27741 | MAD2L1: (MAD2L1 OR MAD2 OR MAD2A) MITOTIC SPINDLE ASSEMBLY CHECKPOINT PROTEIN MAD2A (MAD2-LIKE 1). | A | B | C | F | H | I | | | S |
| 28320 | KPNA2: (KPNA2 OR RCH1 OR SRP1) IMPORTIN ALPHA-2 SUBUNIT (KARYOPHERIN ALPHA-2 SUBUNIT) (SRP1-ALPHA) (RAG COHORT PROTEIN 1). | | B | | | H | | | | |
| 28475 | LAPTM4B: (LAPTM4B OR LAPTM4BETA OR DKFZP586E1124) LYSOSOMAL-ASSOCIATED TRANSMEMBRANE PROTEIN 4 BETA (NT2RM1000066) (LC27) (INTEGRAL MEMBRANE TRANSPORTER) (HYPOTHETICAL PROTEIN PSEC0001). | | | | | | | | P | |
| 3018 | HPRT: (HPRT1 OR HPRT) HYPOXANTHINE-GUANINE PHOSPHORIBOSYLTRANSFERASE (EC 2.4.2.8) (HGPRT) (HGPRTASE). | A | | | | | | L | | |
| 30231 | SNRPF: (SNRPF OR PBSCF) SMALL NUCLEAR RIBONUCLEOPROTEIN F (SNRNP-F) (SM PROTEIN F) (SM-F) (SMF). | A | | | | | | | | |
| 30969 | BUB1B: (BUB1B OR MAD3L OR BUBR1) MITOTIC CHECKPOINT SERINE/THREONINE-PROTEIN KINASE BUB1 BETA (EC 2.7.1.—) (HBUBR1) (MAD3/BUB1-RELATED PROTEIN KINASE) (MITOTIC CHECKPOINT KINASE MAD3L). | A | B | C | F | H | I | | | |
| 30972 | BUB3: (BUB3) MITOTIC CHECKPOINT PROTEIN BUB3. | A | B | C | F | H | I | | | |
| 31008 | DTYMK: (DTYMK OR TYMK OR TMPK OR CDC8) THYMIDYLATE KINASE (EC 2.7.4.9) (DTMP KINASE). | | | | | | | L | P | |
| 31099 | MAD2L2: (MAD2L2 OR MAD2B OR REV7) MITOTIC SPINDLE ASSEMBLY CHECKPOINT PROTEIN MAD2B (MAD2-LIKE 2) (HREV7) (2310033C13RIK). | A | B | C | F | H | I | | | |
| 31129 | PPP2R1B_1: (PPP2R1B) SERINE/THREONINE PROTEIN PHOSPHATASE 2A, 65 KDA REGULATORY SUBUNIT A, BETA ISOFORM (PP2A, SUBUNIT A, PR65-BETA ISOFORM) (PP2A, SUBUNIT A, R1-BETA ISOFORM) (TRANSCRIPT VARIANT 1). | | | | | | | | | S |
| 32488 | NPM1: (NPM1 OR NPM) NUCLEOPHOSMIN (NPM) (NUCLEOLAR PHOSPHOPROTEIN B23) (NUMATRIN) (NUCLEOLAR PROTEIN NO38). | A | B | | | | | | | S |
| 32694 | IMPDH2: (IMPDH2 OR IMPD2) INOSINE-5'-MONOPHOSPHATE DEHYDROGENASE 2 (EC 1.1.1.205) (IMP DEHYDROGENASE 2) (IMPDH-II) (IMPD 2). | | | | | | | L | P | |
| 32700 | KIAA1573: (KIAA1573) HYPOTHETICAL PROTEIN KIAA1573 (B430218L07RIK) (DKFZP686L04115) (FLJ12509) (FLJ14194). | | | | | | | | | |
| 32703 | KIF4A: (KIF4A OR KIF4) CHROMOSOME-ASSOCIATED KINESIN KIF4A (CHROMOKINESIN). | A | | | | | | | | S |
| 32706 | LIN-28: (LIN28 OR LIN-28) HYPOTHETICAL PROTEIN FLJ12457 (RNA-BINDING PROTEIN LIN-28). | | | | | | | | | |
| 32712 | MTHFD1: (MTHFD1 OR MTHFD OR MTHFC) C-1-TETRAHYDROFOLATE SYNTHASE, CYTOPLASMIC (C1-THF SYNTHASE). | | | | | | | L | | |
| 32716 | PPAT: (PPAT OR GPAT) AMIDOPHOSPHORIBOSYLTRANSFERASE PRECURSOR (EC 2.4.2.14) (GLUTAMINE PHOSPHORIBOSYLPYROPHOSPHATE AMIDOTRANSFERASE) (ATASE) (GPAT). | A | | | | | | L | P | |
| 49 | TUBA_HUMAN: (TUBA3) (TUBA6) TUBULIN ALPHA-UBIQUITOUS CHAIN (ALPHA-TUBULIN UBIQUITOUS) (TUBULIN K-ALPHA-1) (TUBULIN ALPHA-6 CHAIN) (ALPHA-TUBULIN 6) (TUBULIN ALPHA-3 CHAIN) (ALPHA-TUBULIN 3) (TUBULIN B-ALPHA-1). | | | | | | | | | S |
| 5036 | MYB: (MYB) MYB PROTO-ONCOGENE PROTEIN (C-MYB). | | | | | H | | | | |
| 5131 | CDK1: (CDC2) CELL DIVISION CONTROL PROTEIN 2 HOMOLOG (EC 2.7.1.—) (P34 PROTEIN KINASE) (CYCLIN-DEPENDENT KINASE 1) (CDK1). | A | B | C | F | H | I | | | |
| 5137 | CDK4: (CDK4) CELL DIVISION PROTEIN KINASE 4 (EC 2.7.1.—) (CYCLIN-DEPENDENT KINASE4) (PSK-J3). | A | | C | | H | | | | |
| 55 | TUBB1-TUBB5_HUMAN: (TUBB1) TUBULIN BETA-1 CHAIN. (TUBB5) TUBULIN BETA-5 CHAIN. | A | | | | | | | | S |
| 7091 | CDC25C: (CDC25C) M-PHASE INDUCER PHOSPHATASE 3 (EC 3.1.3.48). | A | B | C | F | H | | | | |
| 7996 | TK1: (TK1) THYMIDINE KINASE, CYTOSOLIC (EC 2.7.1.21). | | | | | | | | P | |
| 91 | P53: (TP53 OR P53) CELLULAR TUMOR ANTIGEN P53 (TUMOR SUPPRESSOR P53) (PHOSPHOPROTEIN P53). | A | | C | | | I | | | |
| 9386 | RBL1: (RBL1) RETINOBLASTOMA-LIKE PROTEIN 1 (107 KDA RETINOBLASTOMA-ASSOCIATED PROTEIN) (PRB1) (P107). | A | | C | | | | | | |

Many of the genes up-regulated in the CD133+ cells belong to different protein families that are involved in cell cycle regulation, indicating that the CD133+ cell population was in strong proliferation before harvesting. Among the up-regulated genes are cyclin-dependent kinases (CDK2 and CDK4), checkpoint proteins (CHEK1, BUB1, MAD2L1, BUB1B, BUB3, and MAD2L2), cyclins (CCNB2 and CCNE2), enzymes involved in nucleotide metabolism (NME2, HPRT, DTYMK, IMPDH2, MTHFD1, PPAT, and DNMT1), P53 and proteins involved in re-modelling of the cytoskeleton (BAMACAN, C200RF1, VAP-A, PPP2R1B_1, NPM1, KIF4A, TUBA_HUMAN, and TUBB1-TUBB5_HUMAN).

The following genes were down-regulated in CD133+ cells relative to MLPC: CDKN1A, MAPK13, ALCAM, CHI3L1, BMP6, VIM, COL15A1, COL7A1, LAMA2, CD44_EX8-10, CD9, IL6, THROMBOSPONDIN1, S100A10, CDKN2A_1, STX1A, TPA, EDNRA, CEBPB, LAMA3, MAP-2, ACTB, IL4R, SMAD7, COL1A1, BDNF, INHBA, RXRA, MAPK3, WISP3, M6PR, CCNG2, ITGA1_2, PLCG1, MYL4, VEGFD, ABCC8, COL4A1, CD44_EX13-15, SLIT-1, LAMA4, CLDN1, KCNK4, KRT8, LXR-ALPHA, INTEGRINA8, KCNK1, COL11A1, GBP2, CDH5, CTGF, PAI1, NT5, CD7, TRK-C, FN1_REPEAT-B, ACVR1, ITGB3, SLC2A1, PDGFRA, RHOA, SOX9, MAT1A, GCK, THY1, DRD3, IGHA1-IGHA2, PRRX1, AGGRECAN1, MMP2, IL6ST, COL16A1, HAND1, FOXG1A-FOXG1B, ASCL1, FN1, HB-EGF, SMAD5, BMP1_1, MMP12, INTEGRINB6, and CD44_EX7-9. Table 7 lists the 38 genes identified as belonging to a particular pathway or family. In Table 7, "B" refers to extracellular matrix as determined by ME, "C" refers to LAM_G_DOMAIN as determined by PS, "D" refers to cell adhesion as determined by GO, and "E" refers to structural protein as determined by ME.

TABLE 7

Pathway analysis for down-regulated genes in CD133+ cells

| genno. | Description | | | | |
|---|---|---|---|---|---|
| 11204 | KRT8: (KRT8 OR CYK8) KERATIN, TYPE II CYTOSKELETAL 8 (CYTOKERATIN 8) (K8) (CK 8) (KRT2-8). | | | | E |
| 11704 | CD44_EX13-15_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | | | D | |
| 11710 | CD44_EX7-9_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | | | D | |
| 12710 | CD44_EX8-10_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | | | D | |
| 1294 | CTGF: (CTGF OR HCS24) CONNECTIVE TISSUE GROWTH FACTOR PRECURSOR (HYPERTROPHIC CHONDROCYTE-SPECIFIC PROTEIN 24). | | | D | |
| 1447 | SLIT1: (SLIT1 or KIAA0813 or MEGF4) Slit homolog 1 protein precursor (Slit-1) (Multiple epidermal growth factor-like domains 4). | | C | D | |
| 16675 | MYL4: (MYL4 OR MLC1) MYOSIN LIGHT CHAIN 1, EMBRYONIC MUSCLE/ATRIAL ISOFORM (PRO1957). MYOSIN LIGHT CHAIN ALKALI, GT-1 ISOFORM (FRAGMENT). | | | | E |
| 1691 | ACTB: (ACTB) BETA1, CYTOPLASMIC (BETA-ACTIN) ACTIN, CYTOPLASMIC 1. | | | | E |
| 21478 | VIM: (VIM) VIMENTIN. | | | | E |
| 2260 | COL1A1: (COL1A1) COLLAGEN ALPHA 1(I) CHAIN PRECURSOR. | B | | | E |
| 2264 | COL11A1: (COL11A1) COLLAGEN ALPHA 1(XI) CHAIN PRECURSOR. | B | C | D | E |
| 2275 | COL15A1: (COL15A1) COLLAGEN ALPHA 1(XV) CHAIN PRECURSOR. | B | C | D | E |
| 2277 | COL16A1: (COL16A1) COLLAGEN ALPHA 1(XVI) CHAIN PRECURSOR. | B | C | D | E |
| 2289 | COL4A1: (COL4A1) COLLAGEN ALPHA 1(IV) CHAIN PRECURSOR (ARRESTEN). | B | | | E |
| 2295 | COL7A1: (COL7A1) COLLAGEN ALPHA 1(VII) CHAIN PRECURSOR (LONG-CHAIN COLLAGEN) (LC COLLAGEN). | B | | D | E |
| 2326 | ITGA8: (ITGA8) INTEGRIN ALPHA-8 (INTEGRINA8). | B | | D | |
| 2332 | ITGB6: (ITGB6) INTEGRIN BETA-6 PRECURSOR (INTEGRINB6). | B | | D | |
| 23322 | CLDN1: (CLDN1 OR CLD1 OR SEMP1) CLAUDIN-1 (SENESCENCE-ASSOCIATED EPITHELIAL MEMBRANE PROTEIN). | | | D | E |
| 2338 | PAI1: (SERPINE1 OR PAI1 OR PLANH1) PLASMINOGEN ACTIVATOR INHIBITOR-1 PRECURSOR (PAI-1) (ENDOTHELIAL PLASMINOGEN ACTIVATOR INHIBITOR) (PAI). | B | | | |
| 2352 | TPA: (PLAT) TISSUE-TYPE PLASMINOGEN ACTIVATOR PRECURSOR (EC 3.4.21.68) (TPA) (T-PA) (T-PLASMINOGEN ACTIVATOR) (ALTEPLASE) (RETEPLASE). | B | | | |
| 2362 | LAMA2: (LAMA2 OR LAMM) LAMININ ALPHA-2 CHAIN PRECURSOR (LAMININ M CHAIN) (MEROSIN HEAVY CHAIN). | B | C | D | E |
| 2364 | LAMA3: (LAMA3) LAMININ ALPHA-3 CHAIN PRECURSOR (EPILIGRIN 170 KDA SUBUNIT) (E170). | B | C | D | E |
| 2366 | LAMA4: (LAMA4) LAMININ ALPHA-4 CHAIN PRECURSOR. | B | C | D | E |
| 2423 | AGGRECAN1: (AGC1 OR CSPG1 OR AGC) AGGRECAN CORE PROTEIN PRECURSOR (CARTILAGE-SPECIFIC PROTEOGLYCAN CORE PROTEIN) (CSPCP) (CHONDROITIN SULFATE PROTEOGLYCAN CORE PROTEIN 1). | B | | D | E |
| 2433 | BMP1_1: (BMP1 OR PCP-3) BONE MORPHOGENETIC PROTEIN 1 PRECURSOR (EC 3.4.24.—) (BMP-1) PROCOLLAGEN C-PROTEINASE 3. | B | | | |
| 2453 | FN1: (FN1 OR FN) FIBRONECTIN PRECURSOR (FN) (COLD-INSOLUBLE GLOBULIN) (CIG). | B | | D | E |
| 2491 | MMP12: (MMP12 OR HME) MACROPHAGE METALLOELASTASE PRECURSOR (EC 3.4.24.65) (HME) (MATRIX METALLOPROTEINASE-12) (MMP-12). | B | | | |
| 2501 | MMP2: (MMP2 OR CLG4A) 72 KDA TYPE IV COLLAGENASE PRECURSOR (EC 3.4.24.24) (72 KDA GELATINASE) (MATRIX METALLOPROTEINASE-2) (MMP-2) (GELATINASE A) (TBE-1). | B | | | |
| 2555 | THBS1: (THBS1 OR TSP1 OR TSP) THROMBOSPONDIN 1 PRECURSOR (THROMBOSPONDIN1). | B | C | D | E |
| 30689 | FN1_REPEAT-B: (FN1 OR FN) FIBRONECTIN PRECURSOR (FN) (COLD-INSOLUBLE GLOBULIN) (CIG). | B | | D | E |
| 365 | CDH5: (CDH5) VASCULAR ENDOTHELIAL-CADHERIN PRECURSOR (VE-CADHERIN) (CADHERIN-5) (7B4 ANTIGEN) (CD144 ANTIGEN) (CDH5). | | | D | |

TABLE 7-continued

Pathway analysis for down-regulated genes in CD133+ cells

| genno. | Description | | | |
|---|---|---|---|---|
| 3676 | FOXG1A-FOXG1B: (FOXG1B OR FKHL1) FORKHEAD PROTEIN G1B (FORKHEAD-RELATED PROTEIN FKHL1) (TRANSCRIPTION FACTOR BF-1) (BRAIN FACTOR 1) (BF1) (HFK1) (FOXG1A OR FKHL2) FORKHEAD BOX PROTEIN G1A (FORKHEAD-RELATED PROTEIN FKHL2) (TRANSCRIPTION FACTOR BF-2). | | D | |
| 387 | ALCAM: (ALCAM) CD166 ANTIGEN PRECURSOR (ACTIVATED LEUKOCYTE-CELL ADHESION MOLECULE) (ALCAM) (MEMD PROTEIN) (HB2) (KG-CAM) (MEMD PROTEIN) (HB2) (KG-CAM). | | D | |
| 3919 | MAP-2: (MAP2) MICROTUBULE-ASSOCIATED PROTEIN 2 (MAP2B) [CONTAINS: MAP2C]. | | | E |
| 401 | ITGB3: (ITGB3 OR GP3A) INTEGRIN BETA-3 PRECURSOR (PLATELET MEMBRANE GLYCOPROTEIN IIIA) (GPIIIA) (CD61 ANTIGEN). | B | D | |
| 549 | ITGA1_2: (ITGA1) INTEGRIN ALPHA-1 (LAMININ AND COLLAGEN RECEPTOR) (VLA-1) (CD49A). | B | D | |
| 573 | CD9: (CD9 OR MIC3) CD9 ANTIGEN (P24) (LEUKOCYTE ANTIGEN MIC3) (MOTILITY-RELATED PROTEIN) (MRP-1). | | D | |
| 7939 | RHOA: (ARHA OR ARH12 OR RHOA OR RHO12) TRANSFORMING PROTEIN RHOA (H12). | | D | |

Many extracellular matrix genes were down-regulated in the CD133+ cells, including collagens (COL11A1, COL15A1, COL16A1, COL1A1, COL4A1, and COL7A1), laminins (LAMA2, LAMA3, and LAMA4), and integrins (ITGA1_2, ITGA8, ITGB3, ITGB6). Interestingly, this subset of genes overlaps with those up-regulated in the MSC cells (see below).

MLPC vs. MSC

The following genes were up-regulated in MSC cells relative to MLPC: ACTC, ACTA2, SEMA3B, COL16A1, LUMICAN, COL12A1, COL8A1, COL5A2, FGF7, COL1A2, INHBA, DCN_1, TPM1, THROMBOSPONDIN5, TIMP3, ITGB8, THROMBOSPONDIN2, BDNF, LAMA2, INTEGRINB5, SERPINH1-SERPINH2, COL6A2_1, COL6A1, FKHL16, LAMA1, LAMG1, GATA4, COL1A1, KRT14, CTGF, HESR1, FN1, PAI1, NCAD, FLN1, COL4A1, PRKCM, INTEGRINA7, TNC, CXCL12, NFKB3, MCAM, BMP1_1, CALU, VLDLR, PRRX1, IL6, SMAD7, ACTG2, PRDC, ID3, LAMA4, FN1_REPEAT-B, DPYSL3, RARG1, EN1, ANXA2, INTEGRINB6, ITGA1_2, FZD4, VEGC, WNT3, IGFBP2, EDN1, PEG1-MEST, LAMB1, THROMBOSPONDIN1, ITGB1, COL7A1, FGF21, CDKN1A, RTN4, WNT5A, FN1_REPEAT-A, KRT18, MAPK6, EGFR-LONG, IGF2_1, COL11A1, HERMES, SNAI1, ATF2, VEGFD, ITGA5, NGFB, HJ1, EDN2, HNF3B, SOX9, DLX5, HSCDGF, MMP2, FN1_EIIIA, CRABP2, COL15A1, GPC4, THY1, COL14A1, TUBB4, CTNNA1, FZD1_2, COL4A3_1, WISP3, GATA6, HIF1A, SMAD5, CDKN2A_1, BMP15, ISL1, EBCTF, NRG1, PCK2, M6PR, EAAT1, RARB2_1, ALPL, RXRG, MMP13, CLDN6, TFCOUP1, AGGRECAN1, MMP19, EDN3, ENO2, BFGFR_1, KRT17, ASCL1, BMPR1A, VEGF_2, KCNK2, ASPIC1, JAM2, DNMT3B, SNAI2, TC10-PIGF, KS, MMP11, ENG, FGF6, LEPR, EPHB4, CEBPG, TCF3, EPRS, NTF3, VTN, MYH11, VEGF_1, TTR, PLCE, KRT8, CDH1, CNP, KCNQ5, INTEGRINA8, SDF2, FGF5, TIMP1, RELN, TPA, PTN, FGF1, SMAD3, IL6ST, ACRP, PMX2B, IGF1R, KRAS2A-KRAS2B, BMP11, IGF1, KCNK1, SMAD1, ORP150, NFATCB_1, LXR-ALPHA, ACVR1, KCNK4, PAFAHIB1, RACK17, BMP7, DDX21, SEMA4C, DJ924G13.1, VCAM1, CTNNA2, ADH4, RHOA, ACVR2, FABI, TRF1, LAMB3, CCCAP, MAPT, EMX-2, ACTB, AKT, VGR3, CYP3A4, STX1A, CITED2, PDGB, PDGFRA, LAMA5, GAPD, RYUDOCAN, SHH, AMBP, and GFAP_1. The MSC had a high amount of strongly up-regulated genes. Table 8 lists the genes identified as belonging to a particular pathway or family. In Table 8, "A" refers to extracellular matrix as determined by GO, "C" refers to structural protein as determined by ME/GO, "D" refers to extracellular matrix as determined by ME, "E" refers to extracellular region as determined by GO, "I" refers to histogenesis as determined by GO, "J" refers to collagen as determined by ME, "K" refers to laminin as determined by ME, "L" refers to adherens junction as determined by the Kegg pathway (KE), and "R" refers to hormone, growth factor, secreted factor as determined by ME.

TABLE 8

Pathway analysis for genes up-regulated in MSC

| genno. | description | | | |
|---|---|---|---|---|
| 11181 | KRT18: (KRT18 OR CYK18) KERATIN, TYPE I CYTOSKELETAL 18 (CYTOKERATIN 18) (K18) (CK 18). | C | | |
| 11204 | KRT8: (KRT8 OR CYK8) KERATIN, TYPE II CYTOSKELETAL 8 (CYTOKERATIN 8) (K8) (CK 8) (KRT2-8). | C | | |
| 11334 | TPM1: (TPM1 OR TPMA OR TMSA) TROPOMYOSIN ALPHA CHAIN. | C | | |
| 11641 | ACVR2: (ACVR2) ACTIVIN RECEPTOR TYPE II PRECURSOR (EC 2.7.1.—) (ACTR-II) (ACTRIIA). | | E | |
| 11683 | BMP15: (BMP15 OR GDF9B) BONE MORPHOGENETIC PROTEIN 15 PRECURSOR (BMP-15) (GROWTH/DIFFERENTIATION FACTOR 9B) (GDF-9B). | | E | R |

TABLE 8-continued

Pathway analysis for genes up-regulated in MSC

| genno. | description | | | | | | | |
|---|---|---|---|---|---|---|---|---|
| 11686 | BMPR1A: (BMPR1A OR ACVRLK3) BONE MORPHOGENETIC PROTEIN RECEPTOR TYPE IA PRECURSOR (EC 2.7.1.—) (SERINE/THREONINE-PROTEIN KINASE RECEPTOR R5) (SKR5) (ACTIVIN RECEPTOR-LIKE KINASE 3) (ALK-3). | | | | E | I | | |
| 11804 | GATA4_HUMAN: (GATA4) TRANSCRIPTION FACTOR GATA-4 (GATA BINDING FACTOR-4). | | | | | | | |
| 12091 | SHH: (SHH) SONIC HEDGEHOG PROTEIN PRECURSOR (SHH) (HHG-1). | | | | E | I | | R |
| 1210 | FZD4: (FZD4) WNT RECEPTOR FRIZZLED-4, FRIZZLED 4 PRECURSOR (FRIZZLED-4) (FZ-4) (HFZ4) (FZE4) (MFZ4) (RFZ4). | | | | E | | | |
| 12917 | PRKCM: (PRKCM) PROTEIN KINASE C, MU TYPE (EC 2.7.1.—) (NPKC-MU). | | | | E | | | |
| 1294 | CTGF: (CTGF OR HCS24) CONNECTIVE TISSUE GROWTH FACTOR PRECURSOR (HYPERTROPHIC CHONDROCYTE-SPECIFIC PROTEIN 24). | A | | | E | I | | R |
| 13106 | NTF3: (NTF3) NEUROTROPHIN-3 PRECURSOR (NT-3) (NEUROTROPHIC FACTOR) (HDNF) (NERVE GROWTH FACTOR 2) (NGF-2). | | | | E | I | | R |
| 13234 | BDNF: (BDNF) BRAIN-DERIVED NEUROTROPHIC FACTOR PRECURSOR (BDNF). | | | | E | | | R |
| 1350 | PDGB: (PDGFB OR C-SIS OR PDGF2 OR SIS) PLATELET-DERIVED GROWTH FACTOR, B CHAIN PRECURSOR (PDGF B-CHAIN) (PDGF-2) (BECAPLERMIN) (C-SIS). | | | | E | | | R |
| 143 | MAPK6: (MAPK6 OR PRKM6 OR ERK3) MITOGEN-ACTIVATED PROTEIN KINASE 6 (EC 2.7.1.—) (EXTRACELLULAR SIGNAL-REGULATED KINASE 3) (ERK3) (P55-MAPK). | | | | | | L | |
| 1436 | VEGF_1: (VEGF OR VEGFA) VASCULAR ENDOTHELIAL GROWTH FACTOR PRECURSOR (VEGF) (VASCULAR PERMEABILITY FACTOR) (VPF)(VEGF A). | A | | | E | I | | R |
| 1442 | WISP3: (WISP3 OR CCN6 OR DJ142L7.3 OR LIBC) WNT1 INDUCIBLE SIGNALING PATHWAY PROTEIN 3 PRECURSOR (WISP-3) (CONNECTIVE TISSUE GROWTH FACTOR (NOV, GIG) LIKE PROTEIN (WISP3) (CONNECTIVE TISSUE GROWTH FACTOR RELATED PROTEIN WISP-3) (LOST IN INFLAMMATORY BREAST CANCER TUMOR SUPPRESSOR PROTEIN). | | | | E | | | R |
| 1465 | VEGFD: (FIGF OR VEGF-D) VASCULAR ENDOTHELIAL GROWTH FACTOR D (C-FOS INDUCED GROWTH FACTOR). | | | | E | | | |
| 14749 | VEGF_2: (VEGF OR VEGFA) VASCULAR ENDOTHELIAL GROWTH FACTOR PRECURSOR (VEGF) (VASCULAR PERMEABILITY FACTOR) (VPF) (VEGF A). | A | | | E | I | | R |
| 15116 | EPHB4: (EPHB4 OR HTK) EPHRIN TYPE-B RECEPTOR 4 PRECURSOR (EC 2.7.1.112) (TYROSINE-PROTEIN KINASE RECEPTOR HTK). | | | | E | | | |
| 1691 | ACTB: (ACTB) BETA1, CYTOPLASMIC (BETA-ACTIN) ACTIN, CYTOPLASMIC 1. | | C | | | | L | |
| 1710 | MAPT: (MAPT OR MTBT1 OR TAU) MICROTUBULE-ASSOCIATED PROTEIN TAU (NEUROFIBRILLARY TANGLE PROTEIN) (PAIRED HELICAL FILAMENT-TAU) (PHF-TAU). | | C | | | | | |
| 18385 | IGFBP2: (IGFBP2 OR BP2) INSULIN-LIKE GROWTH FACTOR BINDING PROTEIN 2 PRECURSOR (IGFBP-2) (IBP-2) (IGF-BINDING PROTEIN 2). | | | | E | | | R |
| 20532 | SEMA3B: (SEMA3B OR SEMA5) SEMAPHORIN 3B PRECURSOR (SEMAPHORIN V) (SEMA V). (SEMA3B OR SEMAA OR SEMA) SEMAPHORIN 3B PRECURSOR (SEMAPHORIN A) (SEMA A). | | | | E | | | |
| 20586 | SEMA4C: (SEMA4C OR KIAA1739) SEMAPHORIN 4C PRECURSOR (SEMAI) (SEMACL1) (SEMAPHORIN C-LIKE 1) KIAA1739 PROTEIN (FRAGMENT). | | | | E | | | |
| 20616 | ASPIC1: (ASPIC1 OR CEP-68) ASPIC PRECURSOR (CHONDROCYTE EXPRESSED PROTEIN 68 KDA) ((2810454P21RIK OR CRTAC1) (CRTAC1-B PROTEIN) (CARTILAGE ACIDIC PROTEIN 1) (FLJ10320). | | | D | | | | |
| 2108 | INHBA: (INHBA) INHIBIN BETA A CHAIN PRECURSOR (ACTIVIN BETA-A CHAIN) (ERYTHROID DIFFERENTIATION PROTEIN) (EDF). | | | | E | I | | R |
| 21481 | VTN: (VTN) VITRONECTIN PRECURSOR (SERUM SPREADING FACTOR) (S-PROTEIN). | | C | | E | | | |
| 2183 | VEGC: (VEGFC) VASCULAR ENDOTHELIAL GROWTH FACTOR C PRECURSOR (VEGF-C) (VASCULAR ENDOTHELIAL GROWTH FACTOR RELATED PROTEIN) (VRP) (FLT4 LIGAND) (FLT4-L). | | | | E | | | R |
| 2260 | COL1A1: (COL1A1) COLLAGEN ALPHA 1(I) CHAIN PRECURSOR. | A | C | D | E | I | J | |
| 2264 | COL11A1: (COL11A1) COLLAGEN ALPHA 1(XI) CHAIN PRECURSOR. | A | C | D | E | I | J | |
| 2266 | COL12A1: (COL12A1) COLLAGEN ALPHA 1(XII) CHAIN PRECURSOR. | A | C | D | E | | J | |
| 2271 | COL14A1: (COL14A1) EXTRACELLULAR MATRIX PROTEIN COLLAGEN TYPE XIV, C-TERMINUS (FRAGMENT) (UNDULIN). | | C | D | | | J | |
| 2275 | COL15A1: (COL15A1) COLLAGEN ALPHA 1(XV) CHAIN PRECURSOR. | A | C | D | E | | J | |
| 2277 | COL16A1: (COL16A1) COLLAGEN ALPHA 1(XVI) CHAIN PRECURSOR. | A | C | D | E | | J | |
| 2289 | COL4A1: (COL4A1) COLLAGEN ALPHA 1(IV) CHAIN PRECURSOR (ARRESTEN). | A | C | D | E | | J | |
| 2293 | COL6A1: (COL6A1) COLLAGEN (VI) ALPHA-1 CHAIN (FRAGMENT) COLLAGEN ALPHA 1(VI) CHAIN PRECURSOR. | A | C | D | E | | J | |
| 2295 | COL7A1: (COL7A1) COLLAGEN ALPHA 1(VII) CHAIN PRECURSOR (LONG-CHAIN COLLAGEN) (LC COLLAGEN). | A | C | D | E | I | J | |
| 2297 | COL8A1: (COL8A1) COLLAGEN ALPHA 1(VIII) CHAIN PRECURSOR (ENDOTHELIAL COLLAGEN). | A | C | D | E | | J | |
| 2301 | COL1A2: (COL1A2) COLLAGEN ALPHA 2(I) CHAIN PRECURSOR. | A | C | D | E | | J | |
| 2307 | COL5A2: (COL5A2) COLLAGEN ALPHA 2(V) CHAIN PRECURSOR. | A | C | D | E | | J | |
| 2309 | COL6A2_1: (COL6A2) COLLAGEN ALPHA 2(VI) CHAIN PRECURSOR. COLLAGEN VI ALPHA-2 C-TERMINAL GLOBULAR DOMAIN (FRAGMENT). (DKFZP586E1322). | A | C | D | E | | J | |
| 2315 | COL4A3_1: (COL4A3) COLLAGEN ALPHA 3(IV) CHAIN PRECURSOR. | A | C | D | E | | J | |

TABLE 8-continued

Pathway analysis for genes up-regulated in MSC

| genno. | description | | | | | | | |
|---|---|---|---|---|---|---|---|---|
| 2324 | ITGA7: (ITGA7) INTEGRIN ALPHA-7 (INTEGRIN ALPHA 7 CHAIN) (INTEGRIN ALPHA-7) (INTEGRINA7). | | | D | E | | | |
| 2326 | ITGA8: (ITGA8) INTEGRIN ALPHA-8 (INTEGRINA8). | | | D | | | | |
| 2330 | ITGB5: (ITGB5) INTEGRIN BETA-5 PRECURSOR (INTEGRINB5). | | | D | E | | | |
| 2332 | ITGB6: (ITGB6) INTEGRIN BETA-6 PRECURSOR (INTEGRINB6). | | | D | | | | |
| 2336 | ITGB8: (ITGB8) INTEGRIN BETA-8 PRECURSOR. | | | D | | | | |
| 23367 | CLDN6: (CLDN6) CLAUDIN-6 (SKULLIN 2). | | C | | | | | |
| 2338 | PAI1: (SERPINE1 OR PAI1 OR PLANH1) PLASMINOGEN ACTIVATOR INHIBITOR-1 PRECURSOR (PAI-1) (ENDOTHELIAL PLASMINOGEN ACTIVATOR INHIBITOR) (PAI). | | | D | E | | | |
| 2344 | TIMP1: (TIMP1 OR TIMP OR CLGI) METALLOPROTEINASE INHIBITOR 1 PRECURSOR (TIMP-1) (ERYTHROID POTENTIATING ACTIVITY) (EPA) (TISSUE INHIBITOR OF METALLOPROTEINASES) (FIBROBLAST COLLAGENASE INHIBITOR) (COLLAGENASE INHIBITOR). | A | | D | E | | | |
| 2348 | TIMP3: (TIMP3) METALLOPROTEINASE INHIBITOR 3 PRECURSOR (TIMP-3) (TISSUE INHIBITOR OF METALLOPROTEINASES-3) (MIG-5 PROTEIN). | A | | D | E | | | |
| 2352 | TPA: (PLAT) TISSUE-TYPE PLASMINOGEN ACTIVATOR PRECURSOR (EC 3.4.21.68) (TPA) (T-PA) (T-PLASMINOGEN ACTIVATOR) (ALTEPLASE) (RETEPLASE). | | | D | E | | | |
| 2356 | BMP7: (BMP7 OR BMP-7 OR OP1) BONE MORPHOGENETIC PROTEIN 7 PRECURSOR (BMP-7) (OSTEOGENIC PROTEIN 1) (OP-1). | | | D | E | | | R |
| 2360 | LAMA1: (LAMA1 OR LAMA) LAMININ ALPHA-1 CHAIN PRECURSOR (LAMININ A CHAIN). | A | C | D | E | I | K | |
| 2362 | LAMA2: (LAMA2 OR LAMM) LAMININ ALPHA-2 CHAIN PRECURSOR (LAMININ M CHAIN) (MEROSIN HEAVY CHAIN). | A | C | D | E | | K | |
| 2366 | LAMA4: (LAMA4) LAMININ ALPHA-4 CHAIN PRECURSOR. | A | C | D | E | | K | |
| 2368 | LAMA5: (KIAA0533 OR LAMA5) KIAA0533 PROTEIN (LAMININ ALPHA 5 CHAIN) (FRAGMENT). | A | C | D | E | | K | |
| 2370 | LAMB1: (LAMB1) LAMININ BETA-1 CHAIN PRECURSOR (LAMININ B1 CHAIN). | A | C | D | E | | K | |
| 2375 | LAMB3: (LAMB3) LAMININ BETA-3 CHAIN PRECURSOR (LAMININ B1K CHAIN) (KALININ B1 CHAIN). | A | C | D | E | I | K | |
| 2377 | LAMG1: (LAMC1 OR LAMB2) LAMININ GAMMA-1 CHAIN PRECURSOR (LAMININ B2 CHAIN). | A | C | D | E | I | K | |
| 2423 | AGGRECAN1: (AGC1 OR CSPG1 OR AGC) AGGRECAN CORE PROTEIN PRECURSOR (CARTILAGE-SPECIFIC PROTEOGLYCAN CORE PROTEIN) (CSPCP) (CHONDROITIN SULFATE PROTEOGLYCAN CORE PROTEIN 1). | A | C | D | E | I | | R |
| 2433 | BMP1_1: (BMP1 OR PCP-3) BONE MORPHOGENETIC PROTEIN 1 PRECURSOR (EC 3.4.24.—) (BMP-1) PROCOLLAGEN C-PROTEINASE 3. | | | D | E | I | | |
| 2453 | FN1: (FN1 OR FN) FIBRONECTIN PRECURSOR (FN) (COLD-INSOLUBLE GLOBULIN) (CIG). | A | C | D | E | | | R |
| 2473 | LUMICAN: (LDC) LUMICAN PRECURSOR (LUM) (KERATAN SULFATE PROTEOGLYCAN). | A | C | D | E | | | |
| 2489 | MMP11: (MMP11 OR STMY3) STROMELYSIN-3 PRECURSOR (EC 3.4.24.—) (MATRIX METALLOPROTEINASE-11) (MMP-11) (ST3) (SL-3). | A | | D | E | | | |
| 2493 | MMP13: (MMP13) COLLAGENASE 3 PRECURSOR (EC 3.4.24.—) (MATRIX METALLOPROTEINASE-13) (MMP-13). | A | | D | E | J | | |
| 2501 | MMP2: (MMP2 OR CLG4A) 72 KDA TYPE IV COLLAGENASE PRECURSOR (EC 3.4.24.24) (72 KDA GELATINASE) (MATRIX METALLOPROTEINASE-2) (MMP-2) (GELATINASE A) (TBE-1). | A | | D | E | | | |
| 2527 | DCN_1: (DCN) BONE PROTEOGLYCAN II PRECURSOR (PG-S2) (DECORIN) (PG40) (PGS2). | A | C | D | E | | | |
| 2531 | RYUDOCAN: (SDC4) SYNDECAN-4 PRECURSOR (AMPHIGLYCAN) (SYND4) (RYUDOCAN CORE PROTEIN). | | C | D | E | | | |
| 2541 | TNC: (TNC OR HXB) TENASCIN PRECURSOR (TN) (HEXABRACHION) (CYTOTACTIN) (NEURONECTIN) (GMEM) (JI) (MIOTENDINOUS ANTIGEN) (GLIOMA-ASSOCIATED-EXTRACELLULAR MATRIX ANTIGEN) (GP 150-225) (TENASCIN-C) (TN-C). | A | C | D | E | | | |
| 25417 | KCNK4: (KCNK4 OR TRAAK) POTASSIUM CHANNEL SUBFAMILY K MEMBER 4 (TWIK-RELATED ARACHIDONIC ACID-STIMULATED POTASSIUM CHANNEL PROTEIN) (TRAAK) MECHANOSENSITIVE TANDEM PORE POTASSIUM CHANNEL. | | | | E | | | |
| 2549 | THBS2: (THBS2 OR TSP2) THROMBOSPONDIN 2 PRECURSOR (THROMBOSPONDIN2). | A | C | D | E | | | |
| 2555 | THBS1: (THBS1 OR TSP1 OR TSP) THROMBOSPONDIN 1 PRECURSOR (THROMBOSPONDIN1). | | C | D | E | | | |
| 2557 | COMP: (COMP) CARTILAGE OLIGOMERIC MATRIX PROTEIN PRECURSOR (COMP) (THROMBOSPONDIN5). | A | C | D | E | | | |
| 2560 | MMP19: (MMP19 OR MMP18 OR RASI) MATRIX METALLOPROTEINASE-19 PRECURSOR (EC 3.4.24.—) (MMP-19) (MATRIX METALLOPROTEINASE RASI) (MMP-18). | A | | D | E | | | |
| 26175 | GPC4: (GPC4) GLYPICAN-4 PRECURSOR (K-GLYPICAN). | A | | | E | | | |

TABLE 8-continued

Pathway analysis for genes up-regulated in MSC

| genno. | description | A | C | D | E | I | L | R |
|---|---|---|---|---|---|---|---|---|
| 27246 | PTN: (PTN OR NEGF1 OR HBNF1) PLEIOTROPHIN PRECURSOR (PTN) (HEPARIN-BINDING GROWTH-ASSOCIATED MOLECULE) (HB-GAM) (HEPARIN-BINDING GROWTH FACTOR 8) (HBGF-8) (OSTEOBLAST SPECIFIC FACTOR 1) (OSF-1) (HEPARIN-BINDING NEURITE OUTGROWTH PROMOTING FACTOR 1) (HBNF-1). | A | | | E | | | R |
| 27501 | ALPL: (ALPL) ALKALINE PHOSPHATASE, TISSUE-NONSPECIFIC ISOZYME PRECURSOR (EC 3.1.3.1) (AP-TNAP) (LIVER/BONE/KIDNEY ISOZYME) (TNSALP) (AKP2 OR AKP-2). | | | | E | | | |
| 28921 | RELN: (RELN OR RL) REELIN PRECURSOR (EC 3.4.21.—) (REELER PROTEIN). | A | | | E | | | R |
| 28937 | TUBB4_HUMAN: (TUBB4) TUBULIN BETA-4 CHAIN (TUBULIN BETA-III). | | C | | | | | |
| 29310 | SNAI2: (SNAI2 OR SLUG OR SLUGH) ZINC FINGER PROTEIN SLUG (NEURAL CREST TRANSCRIPTION FACTOR SLUG) (SNAIL HOMOLOG 2). | | | | | I | L | |
| 2936 | IL6: (IL6 OR IFNB2 OR IL-6) INTERLEUKIN-6 PRECURSOR (IL-6) (B-CELL STIMULATORY FACTOR 2) (BSF-2) (INTERFERON BETA-2) (HYBRIDOMA GROWTH FACTOR). | | | | E | | | R |
| 30327 | ACTC: (ACTC OR ACTC1) ACTIN, ALPHA CARDIAC. | | C | | | | | |
| 3058 | PRDC: (PRDC) PRDC (FLJ21195). | | | | | | | R |
| 30615 | SDF2: (SDF2) STROMAL CELL-DERIVED FACTOR 2 PRECURSOR (SDF-2). | | | | E | | | R |
| 30624 | BMP11: (GDF11 OR BMP11) GROWTH/DIFFERENTIATION FACTOR 11 PRECURSOR (BONE MORPHOGENETIC PROTEIN 11). | | | | E | I | | R |
| 30686 | FN1_REPEAT-A: (FN1 OR FN) FIBRONECTIN PRECURSOR (FN) (COLD-INSOLUBLE GLOBULIN) (CIG). | A | C | D | E | | | R |
| 30689 | FN1_REPEAT-B: (FN1 OR FN) FIBRONECTIN PRECURSOR (FN) (COLD-INSOLUBLE GLOBULIN) (CIG). | A | C | D | E | | | R |
| 309 | ENG: (ENG OR END) ENDOGLIN PRECURSOR (CD105 ANTIGEN) (CELL SURFACE MJ7/18 ANTIGEN). | | | | E | | | |
| 30999 | CTNNA2: (CTNNA2 OR CAPR) ALPHA-2 CATENIN (ALPHA-CATENIN RELATED PROTEIN) (ALPHA N-CATENIN). | | C | | | | L | |
| 31066 | HSCDGF: (HSCDGF OR PDGFC) SECRETORY GROWTH FACTOR-LIKE PROTEIN FALLOTEIN (SPINAL CORD-DERIVED GROWTH FACTOR) (PLATELET-DERIVED GROWTH FACTOR C). | | | | | | | R |
| 311 | VCAM1: (VCAM1 OR L1CAM OR VCAM-1) VASCULAR CELL ADHESION PROTEIN 1 PRECURSOR (V-CAM 1) (CD106 ANTIGEN) (INCAM-100). | | | | E | | | |
| 31153 | SNAI1: (SNAI1 OR SNAH) ZINC FINGER PROTEIN SNAI1 (SNAIL PROTEIN HOMOLOG) (SNA PROTEIN). | | | | | I | L | |
| 343 | IL6ST: (IL6ST) INTERLEUKIN-6 RECEPTOR BETA CHAIN PRECURSOR (IL-6R-BETA) (INTERLEUKIN 6 SIGNAL TRANSDUCER) (MEMBRANE GLYCOPROTEIN 130) (GP130) (ONCOSTATIN M RECEPTOR) (CDW130) (CD130 ANTIGEN). | | | | E | | | |
| 355 | PDGFRA: (PDGFRA) ALPHA PLATELET-DERIVED GROWTH FACTOR RECEPTOR PRECURSOR (EC 2.7.1.112) (PDGF-R-ALPHA) (CD 140A ANTIGEN). | | | | E | | | |
| 4528 | CXCL12: (CXCL12 OR SDF1) STROMAL CELL-DERIVED FACTOR 1 PRECURSOR (SDF-1) (CXCL12) (PRE-B CELL GROWTH STIMULATING FACTOR) (PBSF) (12-O-TETRADECANOYLPHORBOL 13-ACETATE REPRESSED PROTEIN 1) (TPAR1) (THYMIC LYMPHOMA CELL STIMULATING FACTOR) (TLSF). | | | | E | | | R |
| 4683 | BFGFR_1_HUMAN: (FGFR1 OR FLG OR FGFBR OR FLT2) BASIC FIBROBLAST GROWTH FACTOR RECEPTOR 1 PRECURSOR (BFGF-R) EC 2.7.1.112 (FMS-LIKE TYROSINE KINASE-2) (C-FGR). | | | | E | | L | |
| 4693 | EGFR-LONG: (EGFR OR ERBB1) EPIDERMAL GROWTH FACTOR RECEPTOR PRECURSOR (EC 2.7.1.112) (RECEPTOR PROTEIN-TYROSINE KINASE ERBB-1). | | | | | | L | |
| 4695 | FN1_EIIIA: (FN1 OR FN) FIBRONECTIN PRECURSOR (FIBRONECTIN EIIIA DOMAIN). | A | C | D | E | | | R |
| 4699 | EDN1: (EDN1) ENDOTHELIN-1 PRECURSOR (ET-1). | | | | E | | | |
| 47 | ACTA2: (ACTA2 OR ACTSA OR ACTVS) AORTIC SMOOTH MUSCLE (ALPHA-ACTIN 2). | | C | | | | | |
| 4701 | EDN2: (EDN2) ENDOTHELIN-2 PRECURSOR (ET-2) (VASOACTIVE INTESTINAL CONTRACTOR) (VIC). | | | | E | | | |
| 4705 | GFAP_1_HUMAN: (GFAP) GLIAL FIBRILLARY ACIDIC PROTEIN, ASTROCYTE (GFAP). | | C | | | | | |
| 4715 | SERPINH1-SERPINH2: (SERPINH1 OR CBP1 OR HSP47) HEAT SHOCK PROTEIN 47 COLLAGEN BINDING PROTEIN 1 (CBP1) (COLLIGIN 1) (SERPINH2 OR CBP2) (COLLAGEN-BINDING PROTEIN 2 PRECURSOR) (COLLIGIN 2) (RHEUMATOID ARTHRITIS RELATED ANTIGEN RA-A47). | | | D | E | | | |
| 4727 | IGF1R: (IGF1R) INSULIN-LIKE GROWTH FACTOR I RECEPTOR PRECURSOR (EC 2.7.1.112) (CD221 ANTIGEN). | | | | E | | L | |
| 4747 | M6PR_HUMAN: (IGF2R OR MPRI) CATION-INDEPENDENT MANNOSE-6-PHOSPHATE RECEPTOR PRECURSOR (CI MAN-6-P RECEPTOR) (CI-MPR) (INSULIN-LIKE GROWTH FACTOR II RECEPTOR) (300 KDA MANNOSE 6-PHOSPHATE RECEPTOR) (MPR 300) (MPR300) (CD222 ANTIGEN). | | | | E | | | |
| 4767 | SMAD3_HUMAN: (MADH3 OR SMAD3 OR MAD33) MOTHERS AGAINST DECAPENTAPLEGIC HOMOLOG 3 (SMAD 3) (MOTHERS AGAINST DPP HOMOLOG 3) (MAD3) (HMAD-3) (MMAD3) (JV15-2). | | | | | | L | |
| 499 | ITGB1: (ITGB1 OR FNRB) INTEGRIN BETA-1 PRECURSOR (FIBRONECTIN RECEPTOR BETA SUBUNIT) (CD29 ANTIGEN) (INTEGRIN VLA-4 BETA SUBUNIT). | | | D | E | | | |

TABLE 8-continued

Pathway analysis for genes up-regulated in MSC

| genno. | description | A | C | D | E | I | L | R |
|---|---|---|---|---|---|---|---|---|
| 4990 | NRG1: (NRG1 OR HGL OR NDF OR HRGA OR GGF OR SMDF) PRO-NEUREGULIN-1 PRECURSOR (PRO-NRG1) [CONTAINS: NEUREGULIN-1 (NEU DIFFERENTIATION FACTOR) (HEREGULIN) (HRG) (BREAST CANCER CELL DIFFERENTIATION FACTOR P45) (ACETYLCHOLINE RECEPTOR INDUCING ACTIVITY) (ARIA) (SENSORY AND MOTOR NEURON-DERIVED FACTOR) (GLIAL GROWTH FACTOR)]. | | | | E | | | |
| 5056 | IGF1: (IGF-I OR IGF1) INSULIN-LIKE GROWTH FACTOR I PRECURSOR (SOMATOMEDIN). (IGF1 OR IBP1) INSULIN-LIKE GROWTH FACTOR IA PRECURSOR (IGF-IA) (SOMATOMEDIN C). INSULIN-LIKE GROWTH FACTOR IB PRECURSOR (IGF-IB) (SOMATOMEDIN C). | | | | E | | | R |
| 5149 | CDKN2A_1_HUMAN: (CDKN2A OR CDKN2) CYCLIN-DEPENDENT KINASE 4 INHIBITOR A (CDK4I) (P16-INK4) (P16-INK4A) (MULTIPLE TUMOR SUPPRESSOR 1) (MTS1) (P14ARF OR ARF) (CELL CYCLE REGULATOR). | | | | | I | | |
| 5177 | FGF1: (FGF1 OR FGFA) HEPARIN-BINDING GROWTH FACTOR 1 PRECURSOR (HBGF-1) (ACIDIC FIBROBLAST GROWTH FACTOR) (AFGF) (BETA-ENDOTHELIAL CELL GROWTH FACTOR) (ECGF-BETA). | | | | E | | | R |
| 5199 | FGF5: (FGF5) FIBROBLAST GROWTH FACTOR-5 PRECURSOR (FGF-5) (HBGF-5). | | | | E | | | R |
| 5201 | FGF6: (FGF6 OR HST2) FIBROBLAST GROWTH FACTOR-6 PRECURSOR (FGF-6) (HBGF-6) (HST-2). | | | | E | | | R |
| 5203 | FGF7: (FGF7 OR KGF) KERATINOCYTE GROWTH FACTOR PRECURSOR (KGF) (FIBROBLAST GROWTH FACTOR-7) (FGF-7) (HBGF-7). | | | | E | I | | R |
| 5211 | IGF2_1: (IGF2) INSULIN-LIKE GROWTH FACTOR II PRECURSOR (IGF-II) (SOMATOMEDIN A). | | | | E | | | R |
| 5213 | LEPR: (OBR OR LEPR OR DB OR FA) LEPTIN RECEPTOR PRECURSOR (LEP-R) (OB RECEPTOR) (OB-R) (B219RECEPTOR). | | | | E | | | |
| 5219 | NGFB: (NGFB) BETA-NERVE GROWTH FACTOR PRECURSOR (BETA-NGF). | | | | E | | | R |
| 5231 | VGR3: (FLT4) VASCULAR ENDOTHELIAL GROWTH FACTOR RECEPTOR 3 PRECURSOR (EC 2.7.1.112) (VEGFR-3) (TYROSINE-PROTEIN KINASE RECEPTOR FLT4). | | | | E | | | |
| 5233 | CDH1: (CDH1 OR UVO OR CDHE) EPITHELIAL-CADHERIN PRECURSOR (E-CADHERIN) (UVOMORULIN) (CAM 120/80). | | | | E | | L | |
| 5434 | EDN3: (EDN3) ENDOTHELIN-3 PRECURSOR (ET-3). | | | | E | | | R |
| 5456 | FGF2_1: (FGF2 OR FGFB) HEPARIN-BINDING GROWTH FACTOR 2 PRECURSOR (HBGF-2) (BASIC FIBROBLAST GROWTH FACTOR) (BFGF) (PROSTATROPIN). | | | | E | | | R |
| 549 | ITGA1_2: (ITGA1) INTEGRIN ALPHA-1 (LAMININ AND COLLAGEN RECEPTOR) (VLA-1) (CD49A). | | | D | | | | |
| 5498 | VLDLR: (VLDLR OR LDVR) VERY LOW-DENSITY LIPOPROTEIN RECEPTOR PRECURSOR (VLDL RECEPTOR). | | | | E | | | |
| 556 | ITGA5: (ITGA5 OR FNRA) INTEGRIN ALPHA-5 PRECURSOR (FIBRONECTIN RECEPTOR ALPHA SUBUNIT) (INTEGRIN ALPHA-F) (VLA-5) (CD49E). | | | D | E | | | |
| 6204 | PCK2: (PCK2 OR PEPCK2) PHOSPHOENOLPYRUVATE CARBOXYKINASE, MITOCHONDRIAL PRECURSOR [GTP] (EC 4.1.1.32) (PHOSPHOENOLPYRUVATE CARBOXYLASE) (PEPCK-M). | | | | | | | |
| 6515 | AMBP: (AMBP OR ITIL OR HCP) AMBP PROTEIN PRECURSOR [CONTAINS: ALPHA-1-MICROGLOBULIN (PROTEIN HC) (COMPLEX-FORMING GLYCOPROTEIN HETEROGENEOUS IN CHARGE); INTER-ALPHA-TRYPSIN INHIBITOR LIGHT CHAIN (ITI-LC) (BIKUNIN) (HI-30)]. | | | | E | | | R |
| 7010 | TTR: (TTR OR PALB) TRANSTHYRETIN PRECURSOR (PREALBUMIN) (TBPA) (TTR) (ATTR). | | | | E | | | R |
| 7804 | KRT14: (KRT14) KERATIN, TYPE I CYTOSKELETAL 14 (CYTOKERATIN 14) (K14) (CK 14). | | C | | | I | | |
| 7807 | KRT17: (KRT17) KERATIN, TYPE I CYTOSKELETAL 17 (CYTOKERATIN 17) (K17) (CK 17) (39.1) (VERSION 1). | | C | | | I | | |
| 7837 | NCAD: (CDH2 OR CDHN OR NCAD) NEURAL-CADHERIN PRECURSOR (N-CADHERIN) (CADHERIN-2). | A | | | E | | | |
| 7939 | RHOA: (ARHA OR ARH12 OR RHOA OR RHO12) TRANSFORMING PROTEIN RHOA (H12). | | | | | | L | |
| 8071 | CTNNA1: (CTNNA1) ALPHA-1 CATENIN (CADHERIN-ASSOCIATED PROTEIN) (ALPHA E-CATENIN) | | C | | | | L | |
| 9037 | HJ1: (JAG1) JAGGED 1 PRECURSOR (JAGGED1) (HJ1) NOTCH LIGAND JAGGED 1). | | | | E | | | |
| 9060 | ACTG2: (ACTG2 OR ACTA3 OR ACTSG) ACTIN, GAMMA-ENTERIC SMOOTH MUSCLE (ALPHA-ACTIN 3). | | C | | | | | |
| 9102 | FLN1: (FLNA OR FLN1 OR FLN) FILAMIN A (ALPHA-FILAMIN) (FILAMIN 1) (ENDOTHELIAL ACTIN-BINDING PROTEIN) (ABP-280) (NONMUSCLE FILAMIN). | | C | | | | | |
| 9132 | MYH11: (MYH11) MYOSIN HEAVY CHAIN, SMOOTH MUSCLE ISOFORM (SMMHC) (FRAGMENT). | | C | | | | | |
| 9314 | CRABP2: (CRABP2) RETINOIC ACID-BINDING PROTEIN II, CELLULAR (CRABP-II). | | | | | I | | |
| 9407 | SOX9: (SOX9) TRANSCRIPTION FACTOR SOX-9. | | | | | I | | |
| 9443 | WNT3: (WNT3 OR WNT-3 OR INT4) WNT-3 PROTO-ONCOGENE PROTEIN PRECURSOR. | A | | | E | | | R |
| 9452 | WNT5A: (WNT5A OR WNT-5A) WNT-5A PROTEIN PRECURSOR. | | | | E | | | R |

Characteristic for the MSC population is the high enrichment of genes whose protein products are located within the extracellular matrix, e.g. keratins (KRT18, KRT8, KRT14, KRT17), collagens (COL1A1, COL11A1, COL12A1, COL14A1, COL15A1, COL16A1, COL4A1, COL6A1, COL7A1, COL8A1, COL1A2, COL5A2, COL6A2_1, and COL4A3_1), laminins (LAMA1, LAMA2, LAMA4, LAMA5, LAMB1, LAMB3, and LAMG1), integrins (ITGA7, ITGA8, ITGB5, ITGB6, ITGB8, ITGA1_2, ITGA5), matrix-metalloproteases (BMP1_1, MMP1, MMP13, MMP2, and MMP19) and their inhibitors (TIMP1, TIMP3). Furthermore, a conspicuous enrichment of growth factors (BMP15, NTF3, BDNF, PDGB, VEGF_1, VEGFD, VEGF_2, INHBA, VEGC, BMP7, BMP1_1, PTN, IL6, BMP11, HSCDGF, NRG1, IGF1, FGFI, FGF5, FGF6, FGF7, IGF2_1, NGFB, and FGF2_1) and growth factor receptors (ACVR2, BMPR1A, IL6ST, PDGFRA, BFGFR_1_HUMAN, EGFR-LONG, IGF1R, M6PR_HUMAN, LEPR, and VGR3) was observed.

The following genes were down-regulated in the MSC relative to the MLPC: ITGB2, ARHGAP9, CXCR4, INTEGRINB7, PECAM1, PRKCB_1, PRKCB_3, IL7R, AIF1, CD45_EX10-11, PLCG2, CD37, PRKCB_2, TCF2_1, RNF138, EAAT4, EPHA1, RPLP0, PTTG, SERPINA1_2, ITGAX, CD24, F11R, RPL4, ICAM1, LMO2, HMGB2, CD38, RPL7A, BMP3, PTHR2, S100B, OSF, SNCA, GRIK1, HTR4, CHRM1, CDKN2D, HNRPA1, IL6R, MUSLAMR, ICAM2, CSK, ITGA6, MMP9, DNMT1, PAK1, IKKB, TFRC_MIDDLE, CHI3L2, ITGA4, FGF20, NBR2, TNFRSF1B, CEBPA_3, CDO1, NFKB1, GATA2, PDGFRB, ICSBP1, KCNE3, TNNC1, ITGA2B, CCT8, LEFTA, TH, RPS24, HTR1F, TREM1, CCNB2, SELL, CD34, HMGIY, COX7A2, SELE, TNNT2, SEM2, CHEK1, CLCN5, F5, PRKCQ, ITGAL, NCAM2, ZNF257-MGC12518-ZNF92-ZNF43-ZNF273-FLJ90430, CDK1, RPL6, RPL24, IGHA1-IGHA2_M, PUM2, GJA7, HTR7, PTHR1, MAPK14, MSI2_1, KCNJ3, CD133, SYP, TFRC_5PRIME, TDGF1-TDGF3_2, FLT3, HPRT, SEMA4D, ITGAM, KIAA0152_3, ZFP42, SOX20, FLJ21190, CPN2, POU2F2, CASP8_1, CLDN10, TREM2, TERT, OLIG1, EGR2, CD44_EX3-5, CD33, CNTFR, OPN, COL9A1_2, ROBO4, HTR1D_1, IKKA, KIT, NPPA, PRKCH, FGF4, CD68, NUMB, NRG3, SALL2, NOP5, HNF4G, FIBROMODULIN, CD58, CALB1, GJB5, GJA5, POU5F_1, GDF5, POU6F1, CD44_EX16-20, BCAN, PTEN1-PTEN2, AGRIN, ALB, KCNQ4, DPPA5, EPHB2, TGFBR2, and ITGA3. Table 9 lists the genes identified as belonging to a particular pathway or family. In Table 9, "A" refers to CD as determined by ME, "B" refers to ribonucleoprotein complex as determined by GO, "C" refers to ligand/surface marker as determined by ME "D" refers to ribosome as determined by ME/GO/KE, "J" refers to external side of plasma membrane as determined by GO, and "K" refers to calcium signaling pathway as determined by KE.

TABLE 9

Pathway analysis for genes down-regulated in MSC

| genno. | description | | | | |
|---|---|---|---|---|---|
| 11074 | TERT: (TERT OR TRT OR EST2 OR TCS1) TELOMERASE REVERSE TRANSCRIPTASE (EC 2.7.7.—) (TELOMERASE CATALYTIC SUBUNIT) (HEST2). | | B | | |
| 11701 | CD44_EX16-20_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | A | | C | J |
| 11707 | CD44_EX3-5_HUMAN: (CD44 OR LHR) CD44 ANTIGEN PRECURSOR (PHAGOCYTIC GLYCOPROTEIN I) (PGP-1) (HUTCH-I (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | A | | C | J |
| 11767 | EPHB2: (EPHB2 OR EPTH3 OR ERK OR DRT OR HEK5) EPHRIN TYPE-B RECEPTOR 2 PRECURSOR (EC 2.7.1.112) (TYROSINE-PROTEIN KINASE RECEPTOR EPH-3) (DRT) (RECEPTOR PROTEIN-TYROSINE KINASE HEK5) (ERK). | | | C | |
| 118 | CCNB2: (CCNB2) CYCLIN B2 G2/MITOTIC SPECIFIC CYCLIN B2. | | | | K |
| 12085 | SEMA4D: (SEMA4D OR CD100) SEMAPHORIN 4D PRECURSOR (LEUKOCYTE ACTIVATION ANTIGEN CD100) (BB18) (A8) (GR3). (SEMA4D OR SEMAJ OR SEMACL2) SEMAPHORIN 4D PRECURSOR (SEMAPHORIN J) (SEMA J) (SEMAPHORIN C-LIKE 2) (M-SEMA G). | A | | C | |
| 12452 | CD45_EX10-11: (PTPRC OR CD45) LEUKOCYTE COMMON ANTIGEN PRECURSOR (EC 3.1.3.48) (L-CA) (CD45 ANTIGEN) (T200). | A | | C | J |
| 12920 | PRKCQ: (PRKCQ OR PRKCT) PROTEIN KINASE C, THETA TYPE (EC 2.7.1.—) (NPKC-THETA). | | | | K |
| 14734 | PRKCB_3: (PRKCB1 OR PRKCB OR PKCB) PROTEIN KINASE C, BETA TYPE (EC 2.7.1.37) (PKC-BETA) (PKC-B). | | | | K |
| 1497 | PRKCB_1: (PRKCB1 OR PRKCB OR PKCB) PROTEIN KINASE C, BETA TYPE (EC 2.7.1.37) (PKC-BETA) (PKC-B). | | | | K |
| 1499 | PRKCB_2: (PRKCB1 OR PRKCB OR PKCB) PROTEIN KINASE C, BETA TYPE (EC 2.7.1.37) (PKC-BETA) (PKC-B). | | | | K |
| 1507 | PRKCH: (PRKCH OR PKCL) PROTEIN KINASE C, ETA TYPE (EC 2.7.1.—) (NPKC-ETA) (PKC-L). | | | | K |
| 17641 | TNNC1: (TNNC1 OR TNNC) TROPONIN C, SLOW SKELETAL AND CARDIAC MUSCLES (TN-C). | | | | K |
| 19690 | RPLP0: (RPLP0) 60S ACIDIC RIBOSOMAL PROTEIN P0 (L10E). | | B | | D |
| 20526 | SEM2: (SEM2) SEMAPHORIN SEM2. | | | C | |
| 211 | CASP8_1: (MCH5 OR CASP8) CASPASE 8 PRECURSOR (EC 3.4.22.—) (ICE-LIKE APOPTOTIC PROTEASE 5) (MORT1-ASSOCIATED CED-3 HOMOLOG) (MACH) (FADD HOMOLOGOUS ICE/CED-3-LIKE PROTEASE) (FLICE) (APOPTOTIC CYSTEINE PROTEASE) (APOPTOTIC PROTEASE MCH-5) (CAP4). | | B | | |

TABLE 9-continued

Pathway analysis for genes down-regulated in MSC

| genno. | description | | | | |
|---|---|---|---|---|---|
| 22663 | HNRPA1: (HNRPA1) HETEROGENEOUS NUCLEAR RIBONUCLEOPROTEIN A1 (HELIX-DESTABILIZING PROTEIN) (SINGLE-STRAND BINDING PROTEIN) (HNRNP CORE PROTEIN A1). | | B | | |
| 22801 | RPL6: (RPL6) 60S RIBOSOMAL PROTEIN L6 (TAX-RESPONSIVE ENHANCER ELEMENT BINDING PROTEIN 107) (TAXREB107) (NEOPLASM-RELATED PROTEIN C140). | | B | D | |
| 251 | TNFRSF1B: (TNFRSF1B OR TNFR2 OR TNFBR OR TNFR-2) TUMOR NECROSIS FACTOR RECEPTOR SUPERFAMILY MEMBER 1B PRECURSOR (TUMOR NECROSIS FACTOR RECEPTOR 2) (TUMOR NECROSIS FACTOR BINDING PROTEIN 2) (TBPII) (P80) (TNF-R2) (P75) (CD120B) (ETANERCEPT). | A | | C | |
| 27255 | RPS24: (RPS24 OR RPS19) 40S RIBOSOMAL PROTEIN S24 (S19). | | B | D | |
| 28604 | NPPA: (NPPA OR PND) ATRIAL NATRIURETIC FACTOR PRECURSOR (ANF) (ATRIAL NATRIURETIC PEPTIDE) (ANP) (PREPRONATRIODILATIN). | | | C | |
| 28658 | RPL24: (RPL24) 60S RIBOSOMAL PROTEIN L24 (L30). | | B | D | |
| 29221 | NCAM2: (NCAM2 OR NCAM21) NEURAL CELL ADHESION MOLECULE 2 PRECURSOR (N-CAM 2). | | | C | |
| 29909 | IGHA1-IGHA2__M__HUMAN: (IGHA1) IG ALPHA-1 CHAIN C REGION (IGHA2) (IG ALPHA-2 CHAIN C REGION). | | | C | |
| 30025 | CD133: (PROM1 OR PROML1 OR PROM OR CD133 OR AC133) PROMININ 1 PRECURSOR (PROMININ-LIKE PROTEIN 1) (ANTIGEN AC133) (CD133 ANTIGEN). | A | | C | |
| 303 | ICAM2: (ICAM2 OR ICAM-2) INTERCELLULAR ADHESION MOLECULE-2 PRECURSOR (ICAM-2) (CD102) (LYMPHOCYTE FUNCTION-ASSOCIATED AG-1 COUNTER-RECEPTOR). | A | | C | |
| 30433 | ITGAX: (ITGAX OR CD11C) INTEGRIN ALPHA-X PRECURSOR (LEUKOCYTE ADHESION GLYCOPROTEIN P150,95 ALPHA CHAIN) (LEUKOCYTE ADHESION RECEPTOR P150,95) (CD11C) (LEU M5). | A | | C | |
| 31020 | F11R: (F11R OR JAM1 OR JCAM) JUNCTIONAL ADHESION MOLECULE 1 PRECURSOR (JAM) (PLATELET ADHESION MOLECULE 1) (PAM-1) (PLATELET F11 RECEPTOR) (UNQ264/PRO301). | | | C | |
| 31114 | NOP5: (NOP5) NUCLEOLAR PROTEIN NOP5 (NUCLEOLAR PROTEIN 5) (NOP58) (HSPC120) (NOL5) (SIK SIMILAR PROTEIN). | | B | | |
| 32034 | TFRC__5PRIME: (TFRC) TRANSFERRIN RECEPTOR PROTEIN (TFR1) (TR) (TFR) (TRFR) (CD71 ANTIGEN) (T9) (P90). | A | | C | |
| 322 | KIT: (KIT OR SL) MAST/STEM CELL GROWTH FACTOR RECEPTOR PRECURSOR (EC 2.7.1.112) (SCFR) (PROTO-ONCOGENE TYROSINE-PROTEIN KINASE KIT) (C-KIT) (CD117 ANTIGEN) (C-KIT RECEPTOR TYROSINE KINASE). | A | | C | J |
| 32719 | RPL4: (RPL4 OR RPL1) 60S RIBOSOMAL PROTEIN L4 (L1). | | B | D | |
| 337 | IL6R: (L6RA OR IL6R) INTERLEUKIN-6 RECEPTOR ALPHA CHAIN PRECURSOR (IL-6R-ALPHA) (CD126 ANTIGEN) (IL-6R 1). | A | | C | |
| 339 | IL7R: (IL7R) INTERLEUKIN-7 RECEPTOR ALPHA CHAIN PRECURSOR (IL-7R-ALPHA) (CDW127) (CD127 ANTIGEN). | A | | C | J |
| 3454 | ITGAM: (ITGAM OR CR3A OR CD11B) INTEGRIN ALPHA-M PRECURSOR (CELL SURFACE GLYCOPROTEIN MAC-1 ALPHA SUBUNIT) (CR-3 ALPHA CHAIN) (CD11B) (LEUKOCYTE ADHESION RECEPTOR MO1) (INTEGRIN ALPHA-M) (NEUTROPHIL ADHERENCE RECEPTOR). | A | | C | J |
| 349 | FLT3: (FLT3 OR STK1 OR FLT-3 OR FLK-2) FL CYTOKINE RECEPTOR PRECURSOR (EC 2.7.1.112) (TYROSINE-PROTEIN KINASE RECEPTOR FLT3) (STEM CELL TYROSINE KINASE 1) (STK-1) (CD135 ANTIGEN) (TYROSINE-PROTEIN KINASE RECEPTOR FLK-2) (FETAL LIVER KINASE 2). | A | | C | |
| 357 | PDGFRB: (PDGFRB OR PDGFR) BETA PLATELET-DERIVED GROWTH FACTOR RECEPTOR PRECURSOR (EC 2.7.1.112) (PDGF-R-BETA) (CD140B ANTIGEN). | A | | C | K |
| 3929 | RPSA: (RPSA OR LAMR1 OR LAMBR OR P40-8) 40S RIBOSOMAL PROTEIN SA (P40) (34/67 KDA LAMININ RECEPTOR) (COLON CARCINOMA LAMININ-BINDING PROTEIN) (NEM/1CHD4) (MULTIDRUG RESISTANCE-ASSOCIATED PROTEIN MGR1-AG) (MUSLAMR). | | B | D | |
| 399 | CD58__HUMAN: (CD58 OR LFA3) LYMPHOCYTE FUNCTION-ASSOCIATED ANTIGEN 3 PRECURSOR (AG3) (ANTIGEN CD58) (SURFACE GLYCOPROTEIN LFA-3). | A | | C | |
| 403 | SELE: (SELE OR ELAM1 OR ELAM-1) E-SELECTIN PRECURSOR (ENDOTHELIAL LEUKOCYTE ADHESION MOLECULE 1) (ELAM-1) (LEUKOCYTE-ENDOTHELIAL CELL ADHESION MOLECULE 2) (LECAM2) (CD62E). | A | | C | |
| 405 | SELL: (SELL OR LYAM1 OR LNHR OR LY-22) L-SELECTIN PRECURSOR (LYMPH NODE HOMING RECEPTOR) (LEUKOCYTE ADHESION MOLECULE-1) (LAM-1) (LEUKOCYTE SURFACE ANTIGEN LEU-8) (TQ1) (GP90-MEL) (LEUKOCYTE-ENDOTHELIAL CELL ADHESION MOLECULE 1) (LECAM1) (CD62L) (LY-22) (LYMPHOCYTE SURFACE MEL-14 ANTIGEN). | A | | C | J |
| 4068 | NFKB1: (NFKB1) NUCLEAR FACTOR NF-KAPPA-B P105 SUBUNIT (DNA-BINDING FACTOR KBF1) (EBP-1) [CONTAINS: NUCLEAR FACTOR NF-KAPPA-B P50 SUBUNIT]. | | | | K |
| 416 | CD68: (CD68) MACROSIALIN PRECURSOR (CD68 ANTIGEN) (GP110). | A | | C | |
| 422 | TFRC__MIDDLE: (TFRC) TRANSFERRIN RECEPTOR PROTEIN (TFR1) (TR) (TFR) (TRFR) (CD71 ANTIGEN) (T9) (P90). | A | | C | |

TABLE 9-continued

Pathway analysis for genes down-regulated in MSC

| genno. | description | | | | |
|---|---|---|---|---|---|
| 466 | ITGAL: (ITGAL OR CD11A OR LFA-1) INTEGRIN ALPHA-L PRECURSOR (LEUKOCYTE ADHESION GLYCOPROTEIN LFA-1 ALPHA CHAIN) (LEUKOCYTE FUNCTION ASSOCIATED MOLECULE 1, ALPHA CHAIN) (CD11A) (INTEGRIN ALPHA-L). | A | C | | |
| 475 | ITGB2: (ITGB2 OR CD18) INTEGRIN BETA-2 PRECURSOR (CELL SURFACE ADHESION GLYCOPROTEINS LFA-1/CR3/P150, 95 BETA-SUBUNIT) (CD18) (COMPLEMENT RECEPTOR C3 BETA-SUBUNIT). | A | C | | |
| 489 | CD24: (CD24 OR CD24A) SIGNAL TRANSDUCER CD24 PRECURSOR (M1/69-J11D HEAT STABLE ANTIGEN) (HSA) (NECTADRIN) (LY-52) (X62 HEAT STABLE ANTIGEN) (R13-AG). | A | C | J | |
| 4995 | NRG3: (NRG3) PRO-NEUREGULIN-3 PRECURSOR (PRO-NRG3) [CONTAINS: NEUREGULIN-3 (NRG-3)]. | | C | | |
| 501 | PECAM1: (PECAM1 OR PECAM-1 OR PECAM) PLATELET ENDOTHELIAL CELL ADHESION MOLECULE PRECURSOR (PECAM-1) (CD31 ANTIGEN) (ENDOCAM) (GPIIA'). | A | C | | |
| 505 | CD33: (CD33) MYELOID CELL SURFACE ANTIGEN CD33 PRECURSOR (GP67) (SIGLEC-3). | A | C | | |
| 506 | CD34: (CD34) HEMATOPOIETIC PROGENITOR CELL ANTIGEN CD34 PRECURSOR. | A | C | J | |
| 512 | CD37: (CD37) LEUKOCYTE ANTIGEN CD37. | A | C | | |
| 5131 | CDK1: (CDC2) CELL DIVISION CONTROL PROTEIN 2 HOMOLOG (EC 2.7.1.—) (P34 PROTEIN KINASE) (CYCLIN-DEPENDENT KINASE 1) (CDK1). | | | | K |
| 514 | CD38: (CD38) ADP-RIBOSYL CYCLASE 1 (EC 3.2.2.5) (CYCLIC ADP-RIBOSE HYDROLASE 1) (CADPR HYDROLASE 1) (LYMPHOCYTE DIFFERENTIATION ANTIGEN CD38) (T10) (ACUTE LYMPHOBLASTIC LEUKEMIA CELLS ANTIGEN CD38) (NIM-R5 ANTIGEN) (I-19) (CD38 HOMOLOG) (CD38H). | A | C | | K |
| 526 | ITGA2B: (ITGA2B OR ITGAB OR GP2B) PLATELET MEMBRANE GLYCOPROTEIN IIB PRECURSOR (GPIIB) (GPALPHA IIB) (INTEGRIN ALPHA-IIB) (CD41). | A | C | J | |
| 552 | ITGA3: (ITGA3) INTEGRIN ALPHA-3 PRECURSOR (GALACTOPROTEIN B3) (GAPB3) (VLA-3 ALPHA CHAIN) (CD49C). | A | C | | |
| 554 | ITGA4: (ITGA4 OR VLA-4) INTEGRIN ALPHA-4 PRECURSOR (INTEGRIN ALPHA-IV) (VLA-4) (CD49D) (LYMPHOCYTE-PEYER'S PATCH ADHESION MOLECULES ALPHA SUBUNIT) (LPAM ALPHA SUBUNIT). | A | C | | |
| 558 | ITGA6: (ITGA6) INTEGRIN ALPHA-6 PRECURSOR (VLA-6) (CD49F) (INTA6) (INTEGRIN ALPHA 6 SUBCHAIN). | A | C | | |
| 563 | ICAM1: (ICAM1 OR ICAM-1) INTERCELLULAR ADHESION MOLECULE 1 PRECURSOR (ICAM-1) (MAJOR GROUP RHINOVIRUS RECEPTOR) (CD54) (MALA-2). | A | C | | |
| 606 | HTR4: (HTR4) 5-HYDROXYTRYPTAMINE 4 RECEPTOR (5-HT-4) (SEROTONIN RECEPTOR) (5-HT) (FRAGMENT). | | | | K |
| 632 | CHRM1: (CHRM1) MUSCARINIC ACETYLCHOLINE RECEPTOR M1. | | | | K |
| 7951 | RPL7A: (RPL7A OR SURF3 OR SURF-3) 60S RIBOSOMAL PROTEIN L7A (SURFEIT LOCUS PROTEIN 3) (PLA-X POLYPEPTIDE). | B | | D | |

A significant portion of the genes (33 out of 82) down-regulated in MSC belongs to the group of CD surface markers (CD44_EX16-20_HUMAN, CD44_EX3-5_HUMAN, SEMA4D, CD45_EX10-11, TNFRSF1B, CD133, ICAM2, ITGAX, TFRC_5PRIME, KIT, IL6R, IL7R, ITGAM, FLT3, PDGFRB, CD58_HUMAN, SELE, SELL, CD68, TFRC_MIDDLE, ITGAL, ITGB2, CD24, PECAM1, CD33, CD34, CD37, CD38, ITGA2B, ITGA3, ITGA4, ITGA6, and ICAM1). Nearly the same set of ribosomal proteins up-regulated in the PrepaCyte cells is down-regulated in the MSC (RPLP0, RPL6, RPS24, RPL24, RPL4, RPSA, and RPL7A).

Based on the profile of up- and down-regulated genes relative to MLPC, MSC are more committed towards the mesenchymal pathways, particularly bone and cartilage as shown by strong up-regulation of keratins, collagens, integrins, matrix-metalloproteases, growth factors, and receptors. Markers of particular interest that are down-regulated in the MSC relative to MLPC are CXCR4, FLT3, TERT, hematopoietic CD markers such as CD133 and CD34, KIT, and embryonic stem cell marker POU5F (October 4). See also FIGS. 4-21, which illustrate the differences in expression between MLPC and MSC of different groups of genes (e.g., adhesion molecules; growth factors and receptors; genes involved in cell cycle, proliferation, and anti-apoptosis; transcription factors; translation regulators; connective tissue, cartilage, and bone; extracellular matrix; endothelium; hematopoiesis and the immune response; neural genes; hepatic genes; muscle, smooth muscle, and cardiac genes; genes involved in cell-cell communication; stem cell markers (hematopoietic and mesenchymal); epidermal genes; adipocytic genes; pancreatic genes; and genes involved in development/morphogenesis).

MLPC vs. LinNeg cells

The following genes were up-regulated in LinNeg cells relative to MLPC: OPN, IL3RA, CD68, CTNNB1, CALB1, PPARG, VGR1, GJB5, HB-EGF, ITGA4, UPA, HDC, GCK, FABP4, APOE, PAX5, TRK-A, THBD, TH, TREM2, KAI1, LIFRA, HTR4, KCNA7, IDH1, KITLG, CD58, MMP6, MMP12, COL18A1_2, GDNF, MAPK13, GAD1_1, LAMA3, MMP9, CDH4, F11R, ID2, TACE, HTR1D_1, CACNA1B, KCNA4, PTHR2, S100B, CD47, CD44_EX13-15, GJA5, ANPEP, CD44_EX16-20, CD44_EX11-13, EIF4A1, KCNJ6, MYH7, TIMP2, NEUROD1, KIR2.4, HNF3A, MAPK14, HTR1F, CD24, GATA2, COX7A2, CD44_EX10-12, CYPA, KCNK5, CLCN7, MTHFD2, CD34, CD44_EX3-5, and CRABP1. Table 10 lists the genes identified as belonging to a particular pathway or family. In Table 10, "A" refers to CD (cluster of differentiation) as determined by ME, "B" refers to external side of plasma membrane as determined by GO, and "C" refers to tube morphogenesis as determined by GO.

TABLE 10

Pathway analysis for genes up-regulated in Lineage Negative Cells

| genno. | description | | | |
|---|---|---|---|---|
| 11701 | CD44_EX16-20_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | A | B | C |
| 11704 | CD44_EX13-15_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | A | B | C |
| 11707 | CD44_EX3-5_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | A | B | C |
| 12704 | CD44_EX11-13_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44). | A | B | C |
| 14752 | VGR1: (FLT1 OR FLT OR FRT) VASCULAR ENDOTHELIAL GROWTH FACTOR RECEPTOR 1 PRECURSOR (EC 2.7.1.112) (VEGFR-1) (TYROSINE-PROTEIN KINASE RECEPTOR FLT) (FLT-1) (TYROSINE-PROTEIN KINASE FRT). | | | C |
| 2342 | TACE: (ADAM17 OR TACE OR CSVP) ADAM 17 PRECURSOR (EC 3.4.24.—) (A DISINTEGRIN AND METALLOPROTEINASE DOMAIN 17) (TNF-ALPHA CONVERTING ENZYME) (TNF-ALPHA CONVERTASE) (SNAKE VENOM-LIKE PROTEASE) (CD156B ANTIGEN). | A | | |
| 332 | IL3RA: ((IL3RAX OR IL3RA OR IL3R OR IL3RX) AND (IL3RAY OR IL3RA OR IL3R OR IL3RY)) INTERLEUKIN-3 RECEPTOR ALPHA CHAIN PRECURSOR (IL-3R-ALPHA) (CD123 ANTIGEN). | A | | |
| 359 | THBD: (THBD OR THRM) THROMBOMODULIN PRECURSOR (FETOMODULIN) (TM) (CD141 ANTIGEN). | A | | |
| 399 | CD58_HUMAN: (CD58 OR LFA3) LYMPHOCYTE FUNCTION-ASSOCIATED ANTIGEN 3 PRECURSOR (AG3) (ANTIGEN CD58) (SURFACE GLYCOPROTEIN LFA-3). | A | | |
| 416 | CD68: (CD68) MACROSIALIN PRECURSOR (CD68 ANTIGEN) (GP110). | A | | |
| 438 | KAI1: (KAI1 OR CD82 OR SAR2) CD82 ANTIGEN (INDUCIBLE MEMBRANE PROTEIN R2) (C33 ANTIGEN) (IA4) (METASTASIS SUPPRESSOR KANGAI 1) (SUPPRESSOR OF TUMORIGENICITY-6). | A | | |
| 469 | ANPEP: (ANPEP OR PEPN OR APN OR CD13 OR LAP1 OR LAP-1) AMINOPEPTIDASE N (EC 3.4.11.2) (MICROSOMAL AMINOPEPTIDASE) (GP150) (MYELOID PLASMA MEMBRANE GLYCOPROTEIN CD13) (P161 MEMBRANE PROTEIN) (MAPN) (RAPN) (ALANYL AMINOPEPTIDASE) (AMINOPEPTIDASE M) (APM) (KIDNEY ZN PEPTIDASE) (KZP). | A | | |
| 489 | CD24: (CD24 OR CD24A) SIGNAL TRANSDUCER CD24 PRECURSOR (M1/69-J11D HEAT STABLE ANTIGEN) (HSA) (NECTADRIN) (LY-52) (X62 HEAT STABLE ANTIGEN) (R13-AG). | A | B | |
| 5018 | CTNNB1: (CTNNB1 OR CTNNB) BETA-CATENIN. | | | C |
| 506 | CD34: (CD34) HEMATOPOIETIC PROGENITOR CELL ANTIGEN CD34 PRECURSOR. | A | B | |
| 538 | CD44_EX10-12_HUMAN: (CD44 OR LHR) CD44 ANTIGEN PRECURSOR (PHAGOCYTIC GLYCOPROTEIN I) (PGP-1) (HUTCH-I) (EXTRACELLULAR MATRIX RECEPTOR-III) (ECMR-III) (GP90 LYMPHOCYTE HOMING/ADHESION RECEPTOR) (HERMES ANTIGEN) (HYALURONATE RECEPTOR) (HEPARAN SULFATE PROTEOGLYCAN) (EPICAN) (CDW44) (LY-24). | A | B | C |
| 543 | CD47: (CD47 OR IAP) LEUKOCYTE SURFACE ANTIGEN CD47 PRECURSOR (ANTIGENIC SURFACE DETERMINANT PROTEIN OA3) (INTEGRIN ASSOCIATED PROTEIN) (IAP) (MER6) (ITGP) (INTEGRIN-ASSOCIATED PROTEIN PRECURSOR). | A | | |
| 554 | ITGA4: (ITGA4 OR VLA-4) INTEGRIN ALPHA-4 PRECURSOR (INTEGRIN ALPHA-IV) (VLA-4) (CD49D) (LYMPHOCYTE-PEYER'S PATCH ADHESION MOLECULES ALPHA SUBUNIT) (LPAM ALPHA SUBUNIT). | A | | |

Among the 70 genes up-regulated in the Lineage Negative cells are twelve different CD (cluster of differentiation) surface markers, including CD44 represented by five non-overlapping PIQOR probes, each specific for different adjacent exons and thus detecting various transcript variants of the CD44 gene. Most of the surface markers (CD13, CD34, CD44, CD47, CD49D, CD58, and CD141), are known to be expressed predominantly on epithelial and endothelial cells.

The following genes were down-regulated in the Lineage Negative cells relative to MLPC: RXRG, CCNE2, CDC25B, MEF-2C, ERBB2, CLCN3, EBCTF, SOX2, CRIP1, HERMES, TAL1, NFKB3, TPM1, NEUROG1, MAD1, FZD4, TNFSF11, E2IG3, RARA1, GABRA1, SMAD3, HDAC2, FN1_EIIIA, IL1R2, HGF, RARB2_1, ELAVL2, BMP4, SERPINF1, EDN3, TCF4, ACTG2, GATA4, ACTA2, CDKN1B, THROMBOSPONDIN2, CNP, LAMA1, MAP3K3, BFGFR_1, EPHB4, NCAD, FZD1_2, NRG1, EGFRLONG, ACRP, ASPIC1, SNAI1, DJ924G13.1, TFP1, HIF1A, JUNB, RPL13A, VEGF_2, TBX3, SLC16A1, HESR1, ITGB8, INTEGRINA7, ATM, P53, EN1, TRK-B, SMAD1, FLJ10884, TNC, PGH2, HSCDGF, JUN, FN1_REPEAT-A, NKX2-2, GATA5, CXCL12, ALPL, PMX2B, TIMP3, TENASCINX, PBXIP1, MMP21-22-23, and DCN_1. Table 11 lists the genes identified as belonging to a particular pathway or family. In Table 11, "A" refers to transcription factor activity as determined by GO, "B" refers to transcription factor as determined by ME, and "C" refers to tube nucleic acid binding as determined by GO.

TABLE 11

Pathway analysis for genes down-regulated in Lineage Negative Cells

| genno. | Description | | | |
|---|---|---|---|---|
| 11804 | GATA4_HUMAN: (GATA4) TRANSCRIPTION FACTOR GATA-4 (GATA BINDING FACTOR-4). | A | B | C |
| 12627 | CRIP1: (CRIP1 OR CRIP) CYSTEINE-RICH PROTEIN 1 (CYSTEINE-RICH INTESTINAL PROTEIN) (CRIP) (CYSTEINE-RICH HEART PROTEIN) (HCRHP). | | B | |
| 13004 | ELAVL2: (ELAVL2 OR HUB) ELAV-LIKE PROTEIN 2 (HU-ANTIGEN B) (HUB) (ELAV-LIKE NEURONAL PROTEIN 1) (NERVOUS SYSTEM-SPECIFIC RNA BINDING PROTEIN HEL-N1). | | | C |
| 13118 | PMX2B: (PMX2B) PAIRED MESODERM HOMEOBOX PROTEIN 2B (PAIRED-LIKE HOMEOBOX 2B) (PHOX2B HOMEODOMAIN PROTEIN) (NEUROBLASTOMA PHOX) (NBPHOX). | A | B | C |
| 15783 | EN1: (EN1) HOMEOBOX PROTEIN ENGRAILED-1 (HU-EN-1). | A | B | C |
| 16116 | NKX2-2: (NKX2-2 OR NKX2B OR NKX2.2) HOMEOBOX PROTEIN NKX-2.2 (HOMEOBOX PROTEIN NK-2 HOMOLOG B). | A | B | C |
| 18160 | HDAC2: (HDAC2) HISTONE DEACETYLASE 2 (HD2). | A | | C |
| 23248 | SOX2: (SOX2) TRANSCRIPTION FACTOR SOX-2. | A | B | C |
| 30671 | RARA1_HUMAN: (RARA OR NR1B1) RETINOIC ACID RECEPTOR ALPHA (RAR-ALPHA). | A | B | C |
| 30815 | GATA5: (GATA5) TRANSCRIPTION FACTOR GATA-5 (GATA BINDING FACTOR-5). | A | B | C |
| 31002 | DJ924G13.1: (DJ924G13.1 OR KIAA1221) DJ924G13.1 (KIAA1221) (PUTATIVE ZINC FINGER PROTEIN) (BM-005) (FLJ10725) (FLJ13534) (FLJ13964) (D5ERTD689E OR MKIAA1221) (1110068L01RIK). | | B | |
| 31153 | SNAI1: (SNAI1 OR SNAH) ZINC FINGER PROTEIN SNAI1 (SNAIL PROTEIN HOMOLOG) (SNA PROTEIN). | | B | C |
| 3535 | JUN: (JUN) TRANSCRIPTION FACTOR AP-1 (ACTIVATOR PROTEIN 1) (AP1) (PROTO-ONCOGENE C-JUN) (V-JUN AVIAN SARCOMA VIRUS 17 ONCOGENE HOMOLOG) (P39). | A | B | C |
| 3644 | JUNB: (JUNB) TRANSCRIPTION FACTOR JUN-B (G0S3). | A | B | C |
| 4072 | NFKB3: (RELA OR NFKB3) TRANSCRIPTION FACTOR P65 (NUCLEAR FACTOR NF-KAPPA-B P65 SUBUNIT). | A | B | C |
| 4197 | HIF1A: (HIF1A) HYPOXIA-INDUCIBLE FACTOR 1 ALPHA (HIF-1 ALPHA) (ARNT INTERACTING PROTEIN) (MEMBER OF PAS PROTEIN 1) (MOP1) (HIF1 ALPHA). | A | B | C |
| 4237 | NEUROG1: (NEUROG1 OR NGN1 OR NGN OR NEUROD3 OR ATH4C) NEUROGENIN 1 (NEUROGENIC DIFFERENTIATION FACTOR 3) (NEUROD3) (NEUROGENIC BASIC-HELIX-LOOP-HELIX PROTEIN). | A | B | C |
| 4251 | TAL1: (TAL1 OR SCL OR TCL5) T-CELL ACUTE LYMPHOCYTIC LEUKEMIA-1 PROTEIN (TAL-1 PROTEIN) (STEM CELL PROTEIN) (T-CELL LEUKEMIA/LYMPHOMA-5 PROTEIN). | | B | C |
| 4257 | TCF4: (TCF4 OR ITF2 OR SEF2) TRANSCRIPTION FACTOR 4 (IMMUNOGLOBULIN TRANSCRIPTION FACTOR 2) (RITF-2) (ITF-2) (SL3-3 ENHANCER FACTOR 2) (SEF-2) (CLASS A HELIX-LOOP-HELIX TRANSCRIPTION FACTOR ME2). | A | B | C |
| 4275 | EBCTF: (EBF) EARLY B-CELL TRANSCRIPTION FACTOR (FRAGMENT). (COE1 OR OLF1) TRANSCRIPTION FACTOR COE1 (OE-1) (O/E-1) (OLFACTORY NEURONAL TRANSCRIPTION FACTOR) (OLF-1). | A | B | C |
| 4289 | HESR1: (HESR-1 OR CHF2 OR HEY1) HAIRY AND ENHANCER OF SPLIT RELATED-1 (HEY1 PROTEIN). | A | B | C |
| 4418 | MEF-2C: (MEF2C) MYOCYTE-SPECIFIC ENHANCER FACTOR 2C. | A | B | C |
| 4446 | TBX3: (TBX3) T-BOX TRANSCRIPTION FACTOR TBX3 (T-BOX PROTEIN 3). | A | B | C |
| 4764 | RARB2_1: (RARB OR NR1B2 OR HAP) RETINOIC ACID RECEPTOR BETA-2 (RAR-BETA-2) (RAR-EPSILON). | A | B | C |
| 4767 | SMAD3_HUMAN: (MADH3 OR SMAD3 OR MAD33) MOTHERS AGAINST DECAPENTAPLEGIC HOMOLOG 3 (SMAD 3) (MOTHERS AGAINST DPP HOMOLOG 3) (MAD3) (HMAD-3) (MMAD3) (JV15-2). | A | | C |
| 4913 | RXRG: (RXRG OR NR2B3) RETINOIC ACID RECEPTOR RXR-GAMMA. | A | B | C |
| 5004 | SMAD1: (MADH1 OR SMAD1 OR MADR1 OR BSP1) MOTHERS AGAINST DECAPENTAPLEGIC HOMOLOG 1 (SMAD 1) (MOTHERS AGAINST DPP HOMOLOG 1) (MAD-RELATED PROTEIN 1) (TRANSFORMING GROWTH FACTOR-BETA SIGNALING PROTEIN-1) (BSP-1) (HSMAD1) (JV4-1). | A | | C |
| 5016 | ATM: (ATM) SERINE-PROTEIN KINASE ATM (EC 2.7.1.37) (ATAXIA TELANGIECTASIA MUTATED) (A-T, MUTATED) (ATDC). | | | C |
| 91 | P53: (TP53 OR P53) CELLULAR TUMOR ANTIGEN P53 (TUMOR SUPPRESSOR P53) (PHOSPHOPROTEIN P53). | A | | C |
| 9663 | HERMES: (HERMES OR RBPMS) RNA-BINDING PROTEIN WITH MULTIPLE SPLICING (RBP-MS). | | | C |

Surprisingly, among the 80 genes down-regulated, 30 are involved in nucleic acid binding (GO:0003676) and/or exhibit transcription factor activity (GO:0003700, ME: transcription factor) (GATA4_HUMAN, CRIP1, ELAVL2, PMX2B, EN1, NKX2-2, HDAC2, SOX2, RARA1_HUMAN, GATA5, DJ924G13.1, SNAI1, JUN, JUNB, NFKB3, HIFLA, NEUROG1, TAL1, TCF4, EBCTF, HESR1, MEF-2C, TBX3, RARB2_1, SMAD3_HUMAN, RXRG, SMAD1, ATM, P53, and HERMES). Increased expression of TBX3 and SOX2 in MLPC relative to the LinNeg cells is of particular interest.

Surface Marker Pattern

Table 12 provides the expression pattern of defined surface markers of each of the cell populations relative to MLPC. Shaded cells refer to a decrease in expression of the particular marker relative to MLPC whereas an up arrow indicates that expression was increased in that cell population relative to the MLPC.

TABLE 12

Expression pattern of cell surface markers

| CD | PrepaCyte | MNC | CD133 | MSC | LinNeg |
|---|---|---|---|---|---|
| CD100 |  | ↑ |  | ↓ |  |
| CD102 | ↑ |  |  | ↓ |  |
| CD105 |  | ↓ |  | ↑ |  |
| CD106 |  | ↓ |  | ↑ |  |
| CD108 |  | ↑ |  |  |  |
| CD117 |  | ↑ |  | ↓ |  |
| CD119 | ↓ |  |  |  |  |
| CD11A | ↑ |  |  | ↓ |  |
| CD11B |  |  |  | ↓ |  |
| CD11C |  |  |  | ↓ |  |
| CD120A | ↓ |  |  |  |  |
| CD120B |  |  |  | ↓ |  |
| CD121A |  | ↓ | ↑ |  |  |
| CD121B |  | ↑ |  |  | ↓ |
| CD123 | ↓ |  |  |  | ↑ |
| CD124 |  | ↑ | ↓ |  |  |
| CD126 |  | ↑ |  | ↓ |  |
| CD127 |  | ↑ |  | ↓ |  |
| CD13 | ↓ |  |  |  | ↑ |

TABLE 12-continued

Expression pattern of cell surface markers

| CD | PrepaCyte | MNC | CD133 | MSC | LinNeg |
|---|---|---|---|---|---|
| CD130 | | | ↓ | ↑ | |
| CD133 | | | ↑ | ↓ | |
| CD135 | | | ↑ | ↓ | |
| CD140A | | | ↓ | ↑ | |
| CD140B | | ↑ | | ↓ | |
| CD141 | ↓ | | | | ↑ |
| CD144 | | ↑ | ↓ | | |
| CD146 | ↓ | | | ↑ | |
| CD156B | | | | | ↑ |
| CD162 | | ↓ | ↑ | | |
| CD164 | | ↓ | ↑ | | |
| CD166 | ↑ | | ↓ | | |
| CD18 | | | | ↓ | |
| CD184 | | ↑ | | ↓ | |
| CD221 | | | | ↑ | |
| CD222 | | | ↓ | ↑ | |
| CD24 | | | | ↓ | ↑ |
| CD29 | | ↓ | | ↑ | |
| CD31 | | | | ↓ | |
| CD33 | | | | ↓ | |
| CD34 | | | | ↓ | ↑ |
| CD37 | | | | ↓ | |
| CD38 | | ↑ | | ↓ | |
| CD41 | | ↑ | | ↓ | |

TABLE 12-continued

Expression pattern of cell surface markers

| CD | PrepaCyte | MNC | CD133 | MSC | LinNeg |
|---|---|---|---|---|---|
| CD44 ex10-12 | ↓ | | | | ↑ |
| CD44 ex11-13 | | | | | ↑ |
| CD44 ex13-15 | | | ↓ | | ↑ |
| CD44 ex16-20 | | | | ↓ | ↑ |
| CD44 ex3-5 | | | | ↓ | ↑ |
| CD44 ex7-9 | | ↑ | ↓ | | |
| CD44 ex8-10 | | ↑ | ↓ | | |
| CD45 ex10-11 | | ↑ | | ↓ | |
| CD47 | | ↓ | | | ↑ |
| CD49A | | | ↓ | ↑ | |
| CD49C | | ↑ | | ↓ | |
| CD49D | | | | ↓ | ↑ |
| CD49E | | ↓ | | ↑ | |
| CD49F | | | ↑ | ↓ | |
| CD54 | | | | ↓ | |
| CD58 | | | | ↓ | ↑ |
| CD61 | | ↑ | ↓ | | |
| CD62E | ↑ | | | ↓ | |
| CD62L | ↑ | | | ↓ | |
| CD68 | | | | ↓ | ↑ |
| CD7 | ↑ | | ↓ | | |
| CD71 | | | ↑ | ↓ | |
| CD73 | | | ↓ | | |
| CD82 | | | | | ↑ |

TABLE 12-continued

Expression pattern of cell surface markers

| CD | PrepaCyte | MNC | CD133 | MSC | LinNeg |
|---|---|---|---|---|---|
| CD87 | | ↑ | | | |
| CD90 | | | ■ | ↑ | |
| CD9 | | | ■ | | |

Overall, MLPCs demonstrate a high degree of stemness and quiescence: down regulation of 65 genes associated with active protein synthesis (i.e.—ribosomal subunits), 18 genes linked with phosphate metabolism (e.g., kinases and phosphatases), 123 genes regulating proliferation and cell cycling (e.g., cyclins, cyclin-dependent kinases, and checkpoint proteins). MLPCs exhibited a very high degree of differentiation multipotentiality as seen in the down-regulation of 12 different clusters of genes associated with differentiation surface marker genes (e.g., epithelium and endothelium) and up-regulation of 80 genes involved in nucleic acid binding and transcription factors that regulate differentiation of tissues from all three germinal layers. Additionally 10 genes associated with maintenance of stemness in embryonic stem cells were overexpressed in MLPC compared to the other cell groups. In particular, MSCs were shown to over-express genes associated with connective and stromal tissue and were strongly committed to that lineage by array analysis.

Example 13

Karyotypic Analysis of MLPC

The karyotype of MLPC (clone UM081704-1 E8, Example 5) was assessed at 20 doublings and >80 doublings and compared with the karyotype of MSC (Cambrex), normal MNC, and the KG-1 cell line, a myeloid leukemia line. MNCs were the reference cell for the other karyotypes. MLPC have a normal karyotype with complete stability through >80 doublings. No deletions, translocations, or suspicious single nucleotide polymorphisms were observed. MSC had deletions and potential epigenic changes after 20 doublings. KG-1 cells, as expected in their role as a positive neoplastic control, had major deletions and substitutions.

OTHER EMBODIMENTS

While the invention has been described in conjunction with the foregoing detailed description and examples, the foregoing description and examples are intended to illustrate and not to limit the scope of the invention, which is defined by the scope of the appended claims. Other aspects, advantages, and modifications are within the scope of the claims.

What is claimed is:

1. A method of characterizing a population of multi-lineage progenitor cells (MLPC), said method comprising: a) providing a purified population of MLPC, wherein said MLPC are positive for CD9, CD13, CD29, CD44, CD73, CD90 and CD105, and negative for CD10, CD34, CD41, CD45, Stro-1, Stage Specific Embryonic Antigen-3 (SSEA-3) and SSEA-4; and b) assessing expression in said population of MLPC of at least one mRNA selected from the group consisting of CXCR4, FLT3, CD133, ICAM2, ITGAX, TFRC, KIT, IL6R, IL7R, ITGAM, FLT3, PDGFRB, SELE, SELL, TFRC, ITGAL, ITGB2, PECAM1, ITGA2B, ITGA3, ITGA4, ITGA6, ICAM1, CD24, CD34, CD44, CD45, CD58, CD68, CD33, CD37, CD38, TERT and POU5F.

2. The method of claim 1, wherein expression of mRNA for CXCR4, FLT3, and CD133 is assessed.

3. The method of claim 1, wherein expression of mRNA for TERT, KIT, and POU5F is assessed.

4. The method of claim 2 or 3, wherein expression of mRNA for CD34 is assessed.

5. The method of claim 1, wherein said MLPC are further negative for CD2, CD3, CD4, CD5, CD7, CD8, CD14, CD15, CD16, CD19, CD20, CD22, CD33, CD36, CD38, CD61, CD62E, CD133, glycophorin-A, stem cell factor, and HLA-DR.

6. The method of claim 1, wherein expression of at least three mRNAs from said group is assessed.

* * * * *

UNITED STATES PATENT AND TRADEMARK OFFICE
CERTIFICATE OF CORRECTION

PATENT NO. : 7,622,108 B2  Page 1 of 1
APPLICATION NO. : 11/208873
DATED : November 24, 2009
INVENTOR(S) : Collins et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 281 days.

Signed and Sealed this

Twenty-sixth Day of October, 2010

David J. Kappos
*Director of the United States Patent and Trademark Office*